US012790377B2

(12) United States Patent
Kim et al.

(10) Patent No.: US 12,790,377 B2
(45) Date of Patent: Nov. 10, 2026

(54) FUSION POLYPEPTIDE COMPRISING GDF15 AND POLYPEPTIDE REGION CAPABLE OF O-GLYCOSYLATION

(71) Applicant: LG CHEM, LTD., Seoul (KR)

(72) Inventors: Yeonchul Kim, Daejeon (KR); Young Dok Son, Daejeon (KR); Kyubong Na, Daejeon (KR); Ji Ho Hong, Daejeon (KR); Saem Jung, Daejeon (KR); Myung Won Jin, Daejeon (KR); Ji A Park, Daejeon (KR); Soomin Noh, Daejeon (KR); Hyuntaek Park, Daejeon (KR)

(73) Assignee: LG CHEM, LTD., Seoul (KR)

( * ) Notice: Subject to any disclaimer, the term of this patent is extended or adjusted under 35 U.S.C. 154(b) by 1165 days.

(21) Appl. No.: 17/784,634

(22) PCT Filed: Dec. 10, 2020

(86) PCT No.: PCT/KR2020/018053

§ 371 (c)(1),
(2) Date: Jun. 11, 2022

(87) PCT Pub. No.: WO2021/118256

PCT Pub. Date: Jun. 17, 2021

(65) Prior Publication Data

US 2023/0133672 A1 May 4, 2023

(30) Foreign Application Priority Data

Dec. 11, 2019 (KR) ........................ 10-2019-0165052

(51) Int. Cl.
*C07K 14/475* (2006.01)
*A61K 38/00* (2006.01)

(52) U.S. Cl.
CPC ............ *C07K 14/475* (2013.01); *A61K 38/00* (2013.01); *C07K 2317/53* (2013.01); *C07K 2319/31* (2013.01)

(58) Field of Classification Search
None
See application file for complete search history.

(56) References Cited

U.S. PATENT DOCUMENTS

| | | | |
|---|---|---|---|
| 5,416,017 | A | 5/1995 | Burton et al. |
| 9,714,276 | B2 | 7/2017 | Xiong et al. |
| 2006/0247425 | A1 | 11/2006 | Chung et al. |
| 2007/0041967 | A1 | 2/2007 | Jung et al. |
| 2008/0300188 | A1 | 12/2008 | Yang et al. |
| 2011/0177029 | A1 | 7/2011 | DeFrees |
| 2016/0031960 | A1 | 2/2016 | Lindhout et al. |
| 2016/0120999 | A1 | 5/2016 | Shen et al. |
| 2016/0168213 | A1 | 6/2016 | Xiong et al. |
| 2017/0044224 | A1 | 2/2017 | Kim et al. |
| 2017/0327560 | A1 | 11/2017 | Armstrong et al. |
| 2017/0362293 | A1 | 12/2017 | Sung et al. |
| 2021/0275644 | A1 | 9/2021 | Kannicht et al. |

FOREIGN PATENT DOCUMENTS

| | | | |
|---|---|---|---|
| CN | 105198998 | A | 12/2015 |
| CN | 105980400 | A | 9/2016 |
| CN | 106687128 | A | 5/2017 |
| CN | 109152817 | A | 1/2019 |
| JP | H01-287041 | A | 11/1989 |
| JP | H02-000213 | A | 1/1990 |
| JP | 2010-531135 | A | 9/2010 |
| JP | 2016-532690 | A | 10/2016 |
| KR | 10-0545720 | B1 | 1/2006 |
| KR | 10-2008-0094781 | A | 10/2008 |
| KR | 10-1380729 | B1 | 4/2014 |
| KR | 10-2015-0125402 | A | 11/2015 |
| KR | 10-2016-0038896 | A | 4/2016 |
| KR | 10-2017-0074852 | A | 6/2017 |
| KR | 10-1825049 | B1 | 2/2018 |
| KR | 10-2019-0003746 | A | 1/2019 |
| RU | 2530168 | C2 | 10/2014 |
| WO | 2013-113008 | A1 | 8/2013 |
| WO | 2015-017548 | A2 | 2/2015 |
| WO | 2015-017710 | A1 | 2/2015 |
| WO | 2015-197446 | A1 | 12/2015 |
| WO | 2016-069921 | A1 | 5/2016 |
| WO | 2017-198435 | A1 | 11/2017 |
| WO | 2019-048660 | A1 | 3/2019 |

OTHER PUBLICATIONS

Wilkinson and Saldova, J. Proteome Res. 2020, 19, 3890-3905 (Year: 2020).*
Helms and Brodbelt, Cells 2024, 13, 394. https://doi.org/10.3390/cells 13050394 (Year: 2024).*
Strohl, "Fusion Proteins for Half-Life Extension of Biologics as a Strategy to Make Biobetters", BioDrugs, 2015, vol. 29, pp. 215-239.
Hashii et al., "In-depth site-specific O-Glycosylation analysis of therapeutic Fc-fusion protein by electron-transfer/higher-energy collisional dissociation mass spectrometry", Biologicals 58, Mar. 2019, pp. 35-43.
Spahr et al., "O-Glycosylation of glycine-serine linkers in recombinant Fc-fusion proteins", MAbs, Jul. 1, 2014, vol. 6, No. 4, pp. 904-914.

(Continued)

*Primary Examiner* — Christina M Borgeest

(74) *Attorney, Agent, or Firm* — ROTHWELL, FIGG, ERNST & MANBECK, P.C.

(57) ABSTRACT

Disclosed are: a fusion polypeptide comprising growth differentiation factor 15 (GDF15) and a polypeptide region capable of O-glycosylation; a pharmaceutical composition comprising the fusion polypeptide; and a method for increasing the in vivo duration of GDF15, comprising the step of fusing a polypeptide region capable of O-glycosylation.

15 Claims, 13 Drawing Sheets

Specification includes a Sequence Listing.

(56) References Cited

OTHER PUBLICATIONS

Rogers et al., "Molecular characterization of immunoglobulin D in mammals: immunoglobulin heavy constant delta genes in dogs, chimpanzees and four old world monkey species", Immunology, vol. 118, No. 1, May 2006, pp. 88-100.
Lin et al., "Primary structure of the Fc region of human immunoglobulin D: Implications for evolutionary origin and biological function", Proc. Natl. Acad. Sci. USA, vol. 78, No. 1, Jan. 15, 1981, pp. 504-508.
International Search Report issued for International Applciation No. PCT/KR2020/018053 on Apr. 6, 2021, 19 pages.
L. Ilum, et al., "Hyaluronic acid ester microspheres as a nasal delivery system for insulin", J. Controlled Rel., (1994) 29, 133-141.
Chen et al., New insights into the enigma of immunoglobulin D, Immunological Reviews, 2010, vol. 237 (1) : 160-179.
Database GenBank [online], AIC5 9036, Mar. 19, 2015, URL:https://www.ncbi.nlm.nih, gov/protein/AIC59036.1.
Partial supplementary European Search Report dated Mar. 23, 2023, of the corresponding European Patent Application No. 20900221.1, 14 pages.
Plomp et al., "Hinge-Region O-Glycosylation of Human Immunoglobulin G3 (IgG3)", Mol Cell Proteomics, 2015,14(5):1373-84.

* cited by examiner

【FIG. 1】
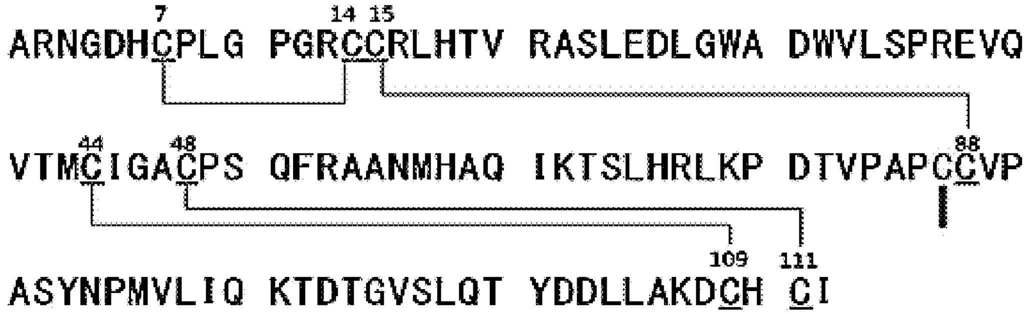
(SEQ ID NO: 3)

【FIG. 2a】
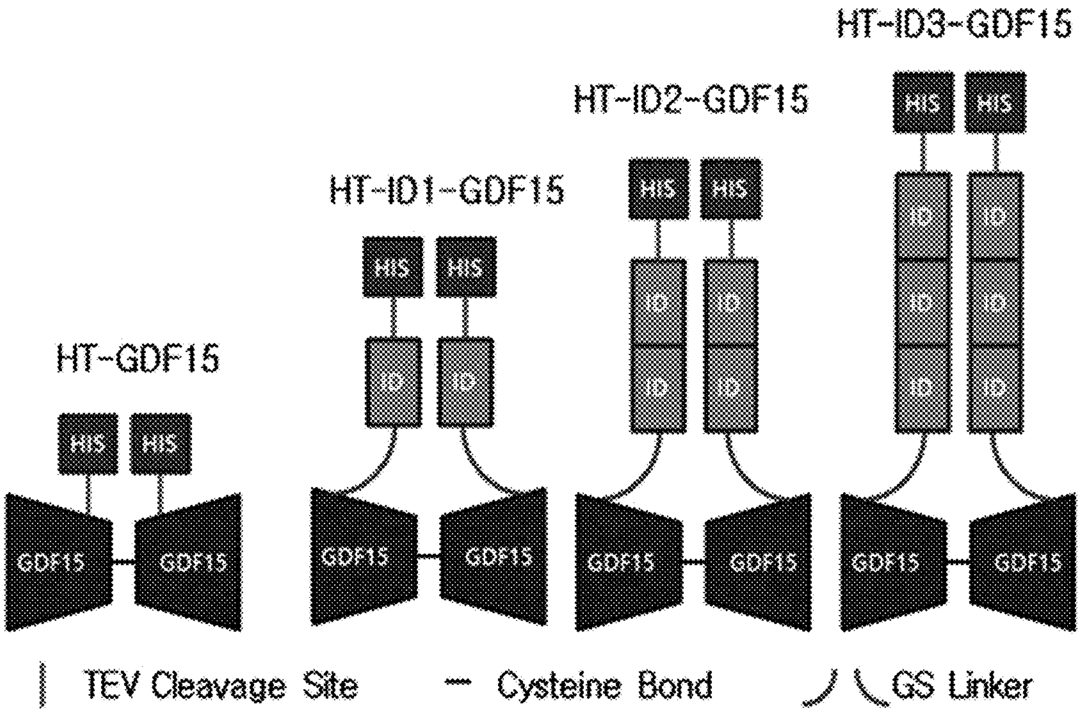
ID: ESPKAQASSVPTAQPQAEGSLAKATTAPATT RNT (SEQ ID NO: 1)
HIS: HHHHHH (SEQ ID NO: 15)
TEV Cleavage Site: ENLYFQG (SEQ ID NO: 16)
GS Linker: GGGGSGGGGS GGGGSGGGGS (SEQ ID NO: 17)
GDF15: SEQ ID NO: 3

【FIG. 2b】
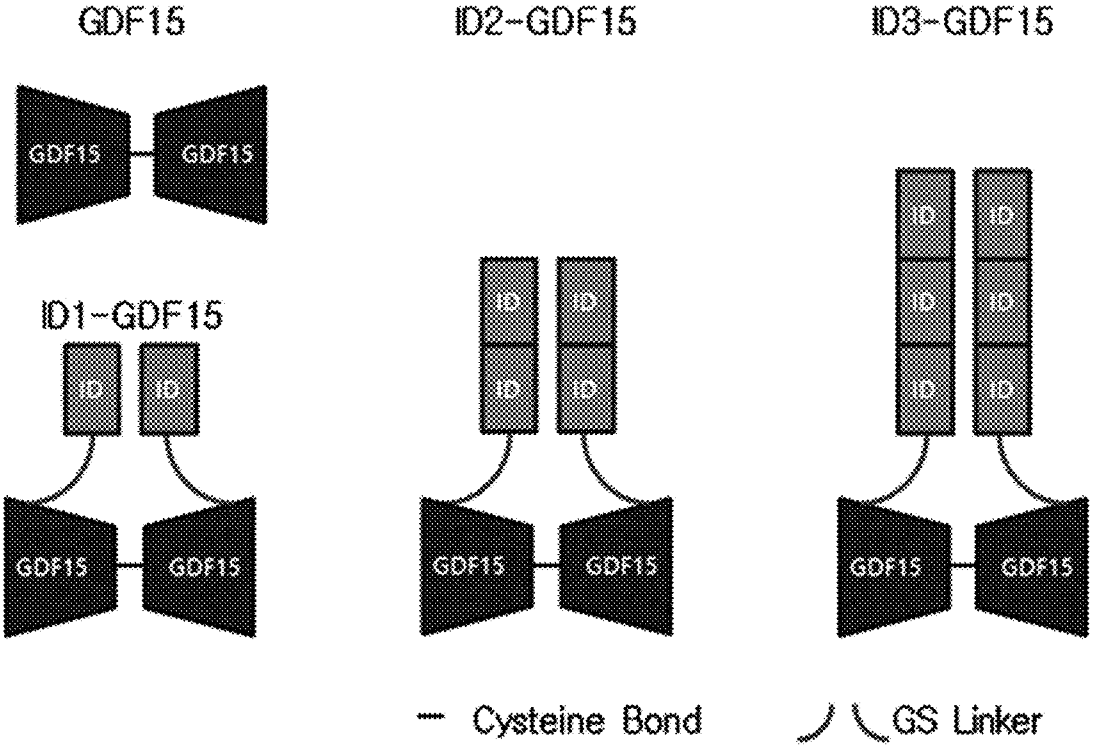
ID: ESPKAQASSVPTAQPQAEGSLAKATTAPATT RNT (SEQ ID NO: 1)
GS Linker: GGGGSGGGGS GGGGSGGGGS (SEQ ID NO: 17)
GDF15: SEQ ID NO: 3

【FIG. 3】
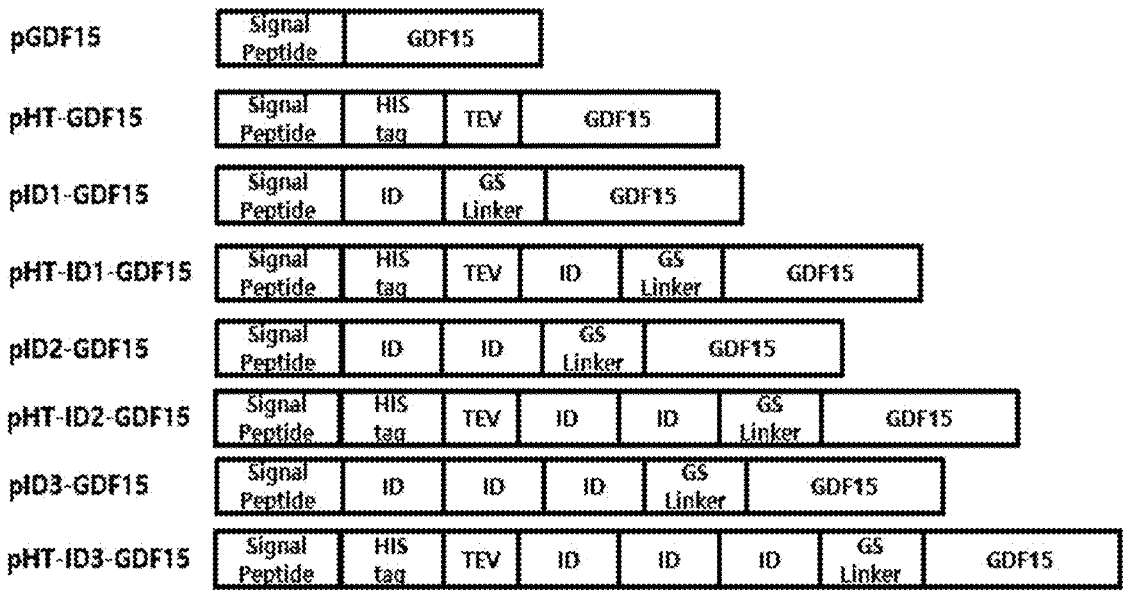

【FIG. 4】
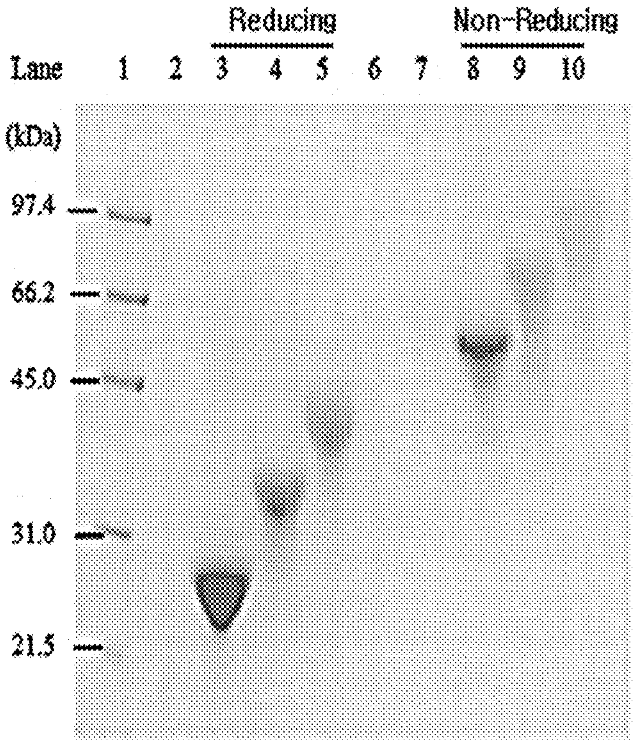
| Lane | Sample |
| --- | --- |
| 1 | Low Range MW Standard |
| 2, 6, 7 | Empty |
| 3 | HT-ID1-GDF15 (R) |
| 4 | HT-ID2-GDF15 (R) |
| 5 | HT-ID3-GDF15 (R) |
| 8 | HT-ID1-GDF15 (NR) |
| 9 | HT-ID2-GDF15 NR) |
| 10 | HT-ID3-GDF15 NR) |

【FIG. 5】
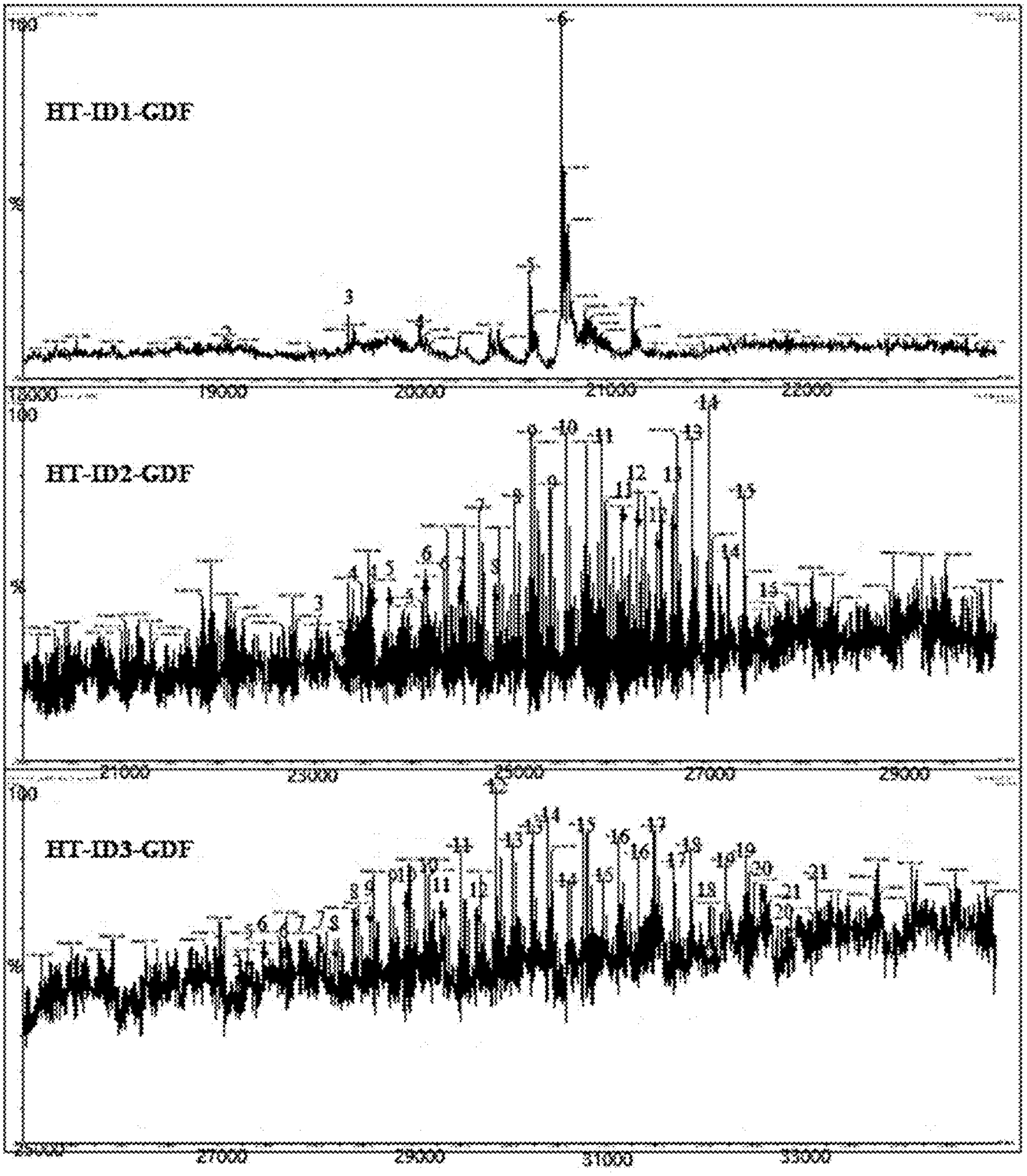

【FIG. 6】
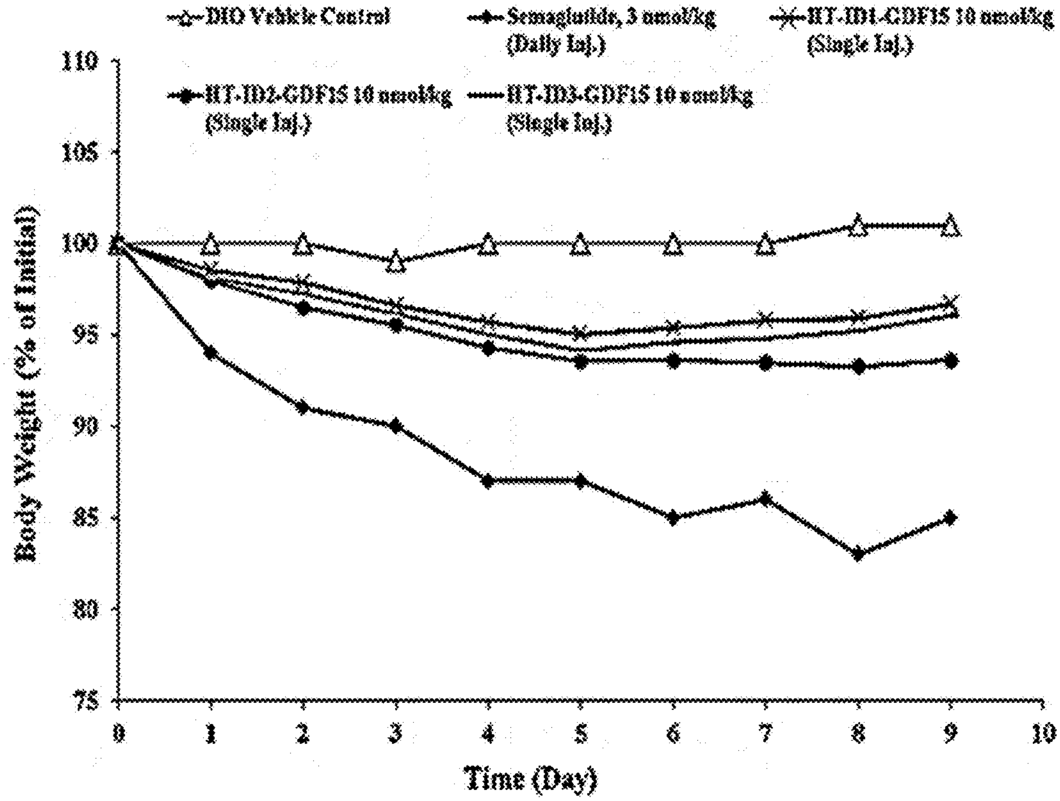

【FIG. 7】
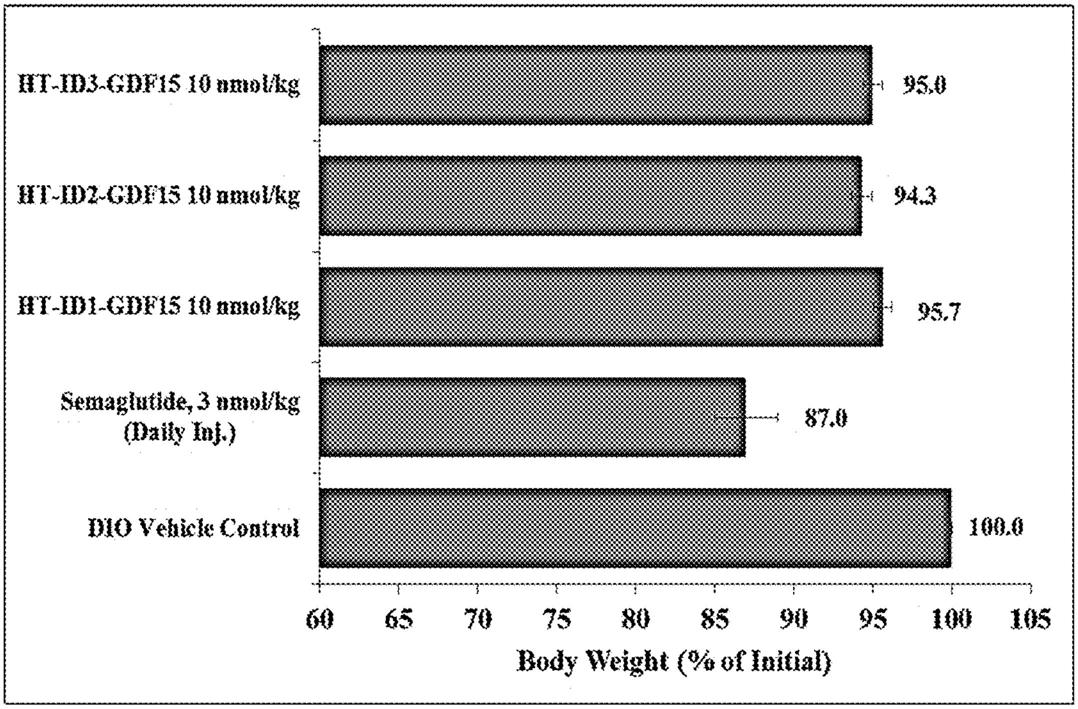
【FIG. 8】
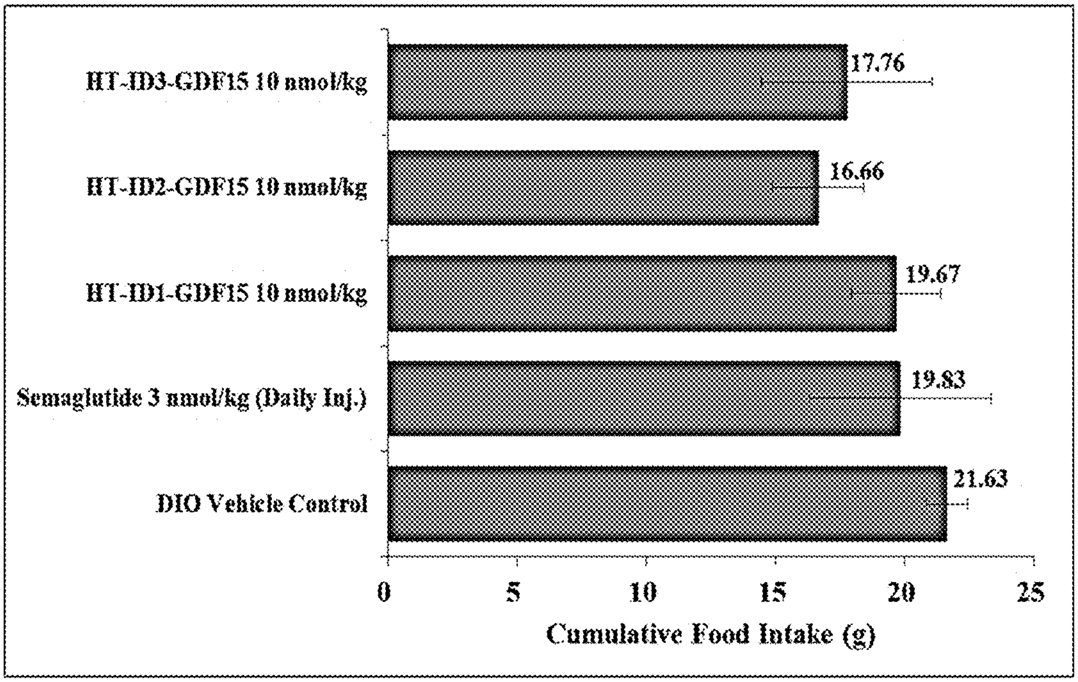

[FIG. 9]
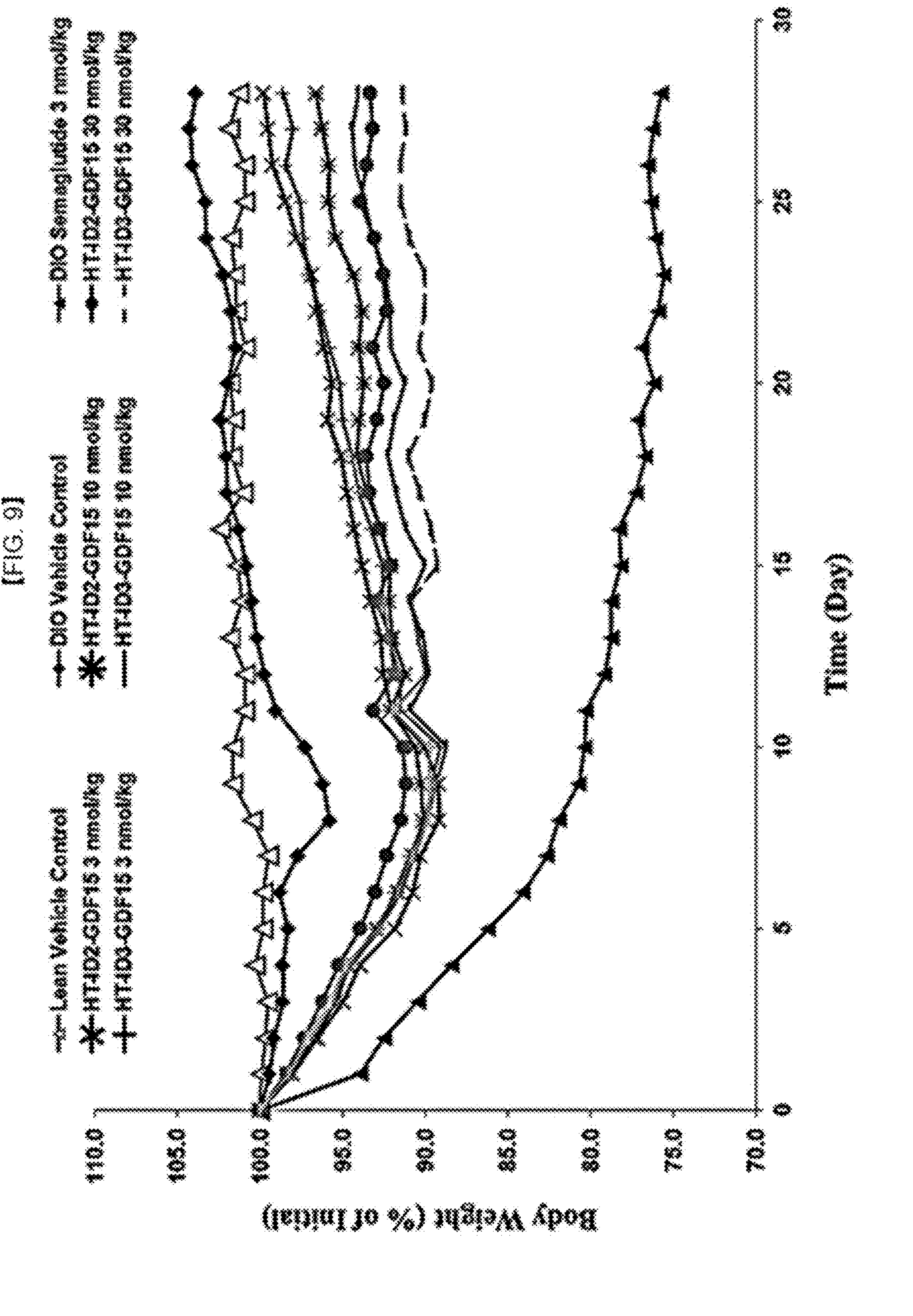

【FIG. 10a】
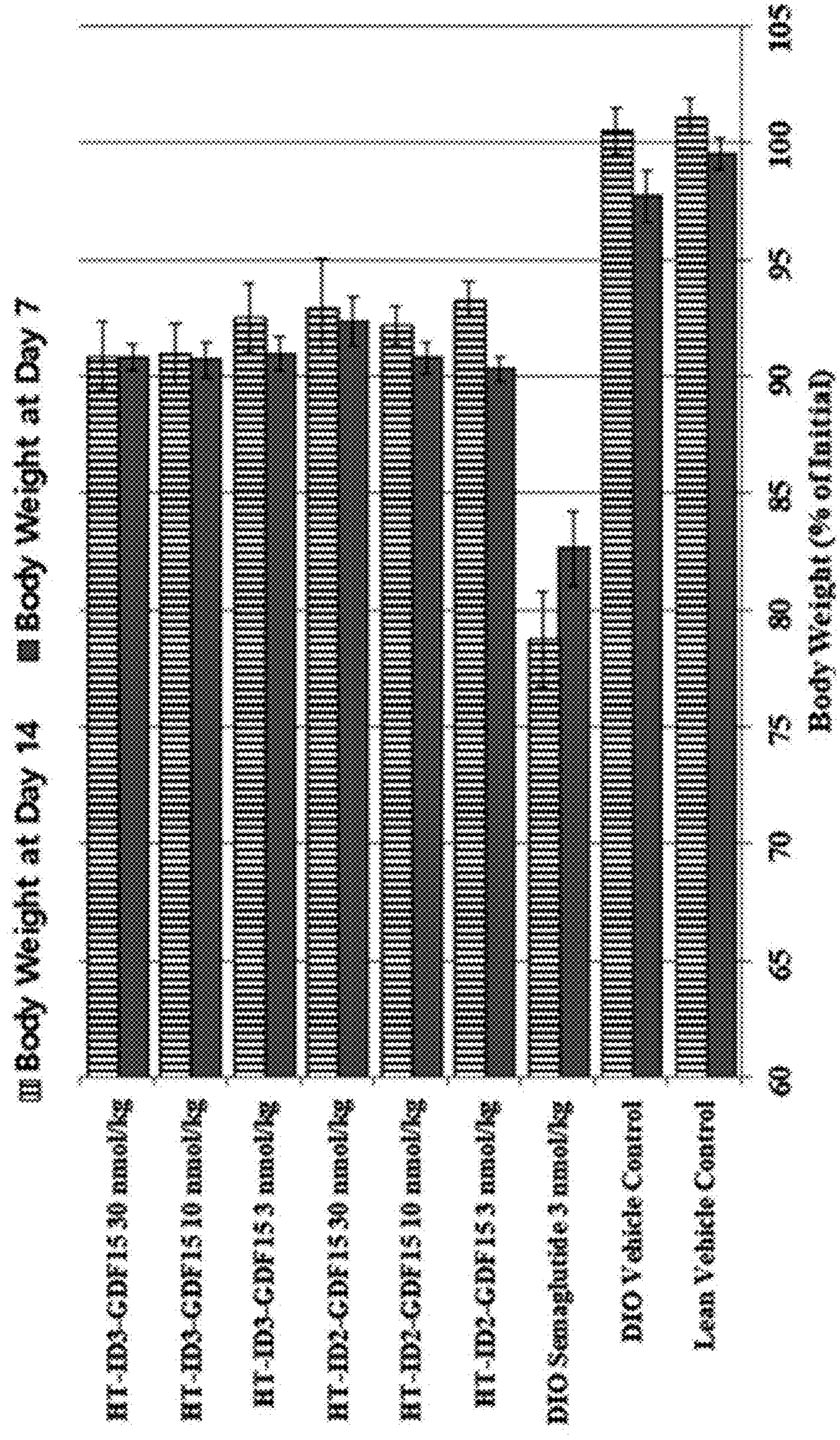

【FIG. 10b】
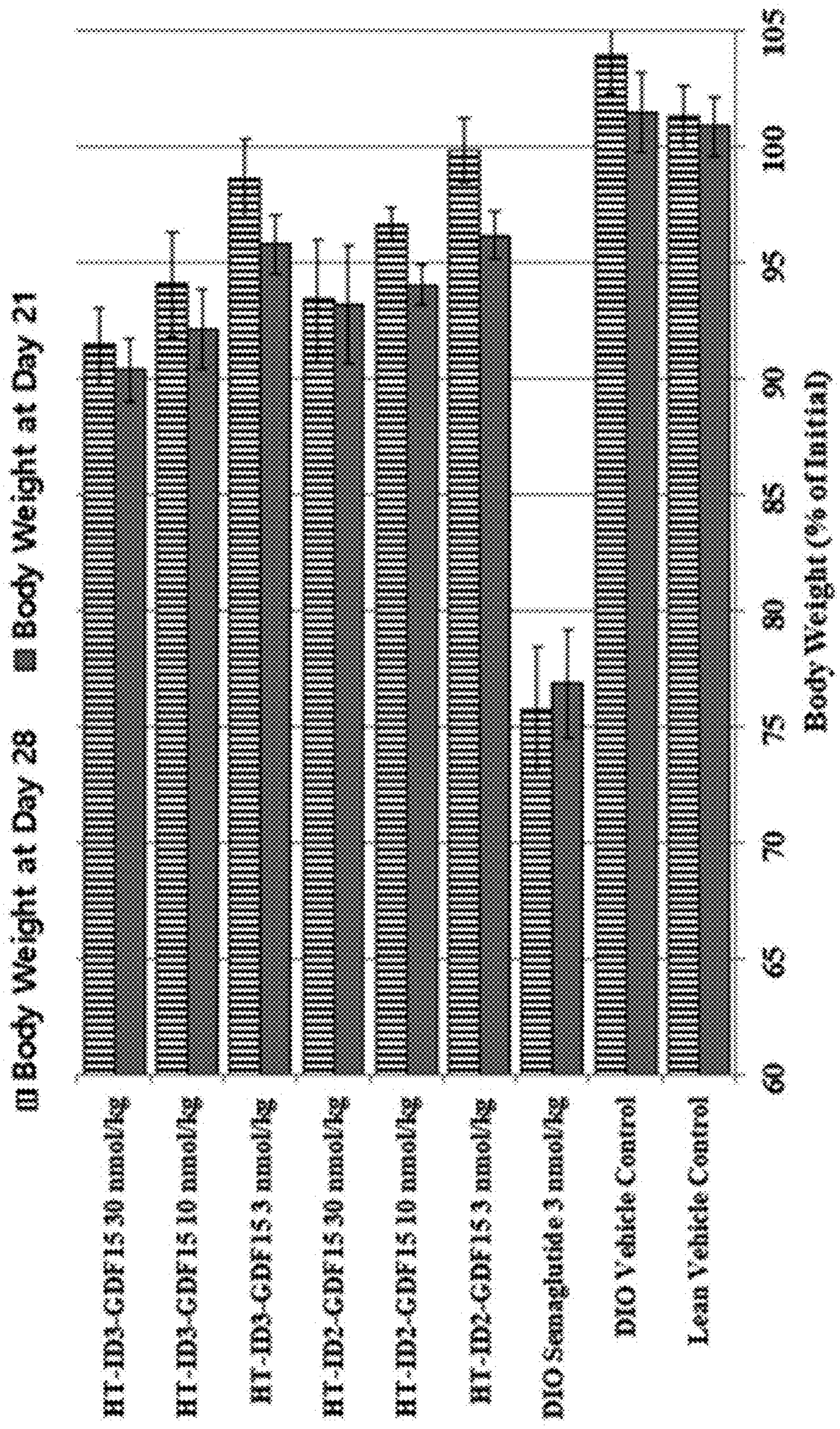

【FIG. 11】
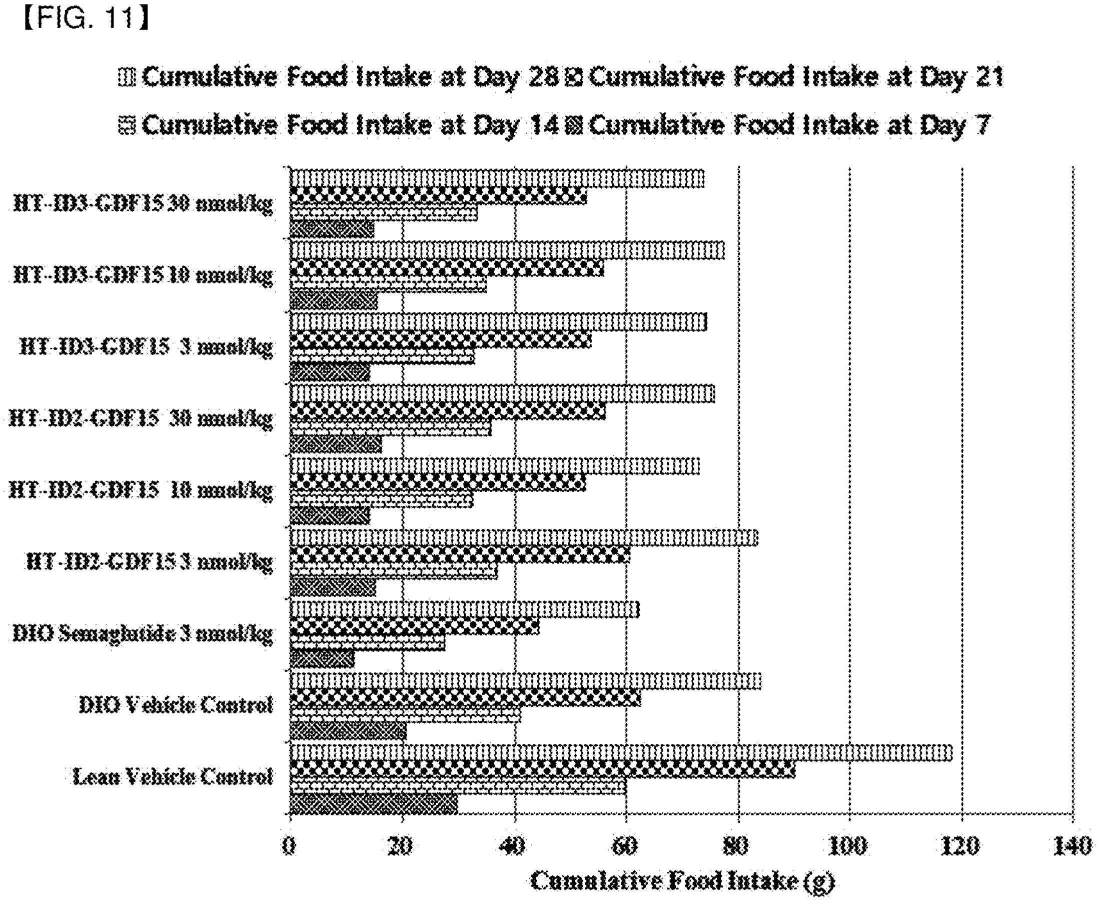

【FIG. 12】
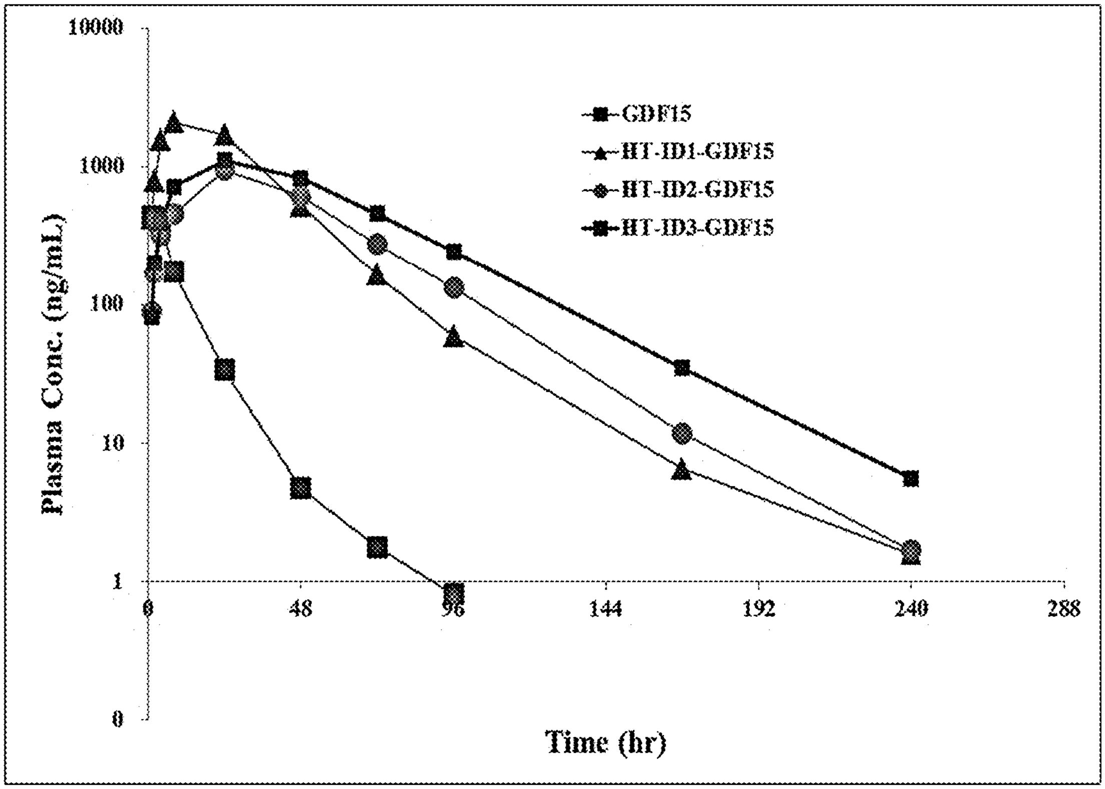

SEQUENCE LISTING

<160> NUMBER OF SEQ ID NOS: 113

<210> SEQ ID NO 1
<211> LENGTH: 34
<212> TYPE: PRT
<213> ORGANISM: Artificial Sequence
<220> FEATURE:
<223> OTHER INFORMATION: Synthetic_Human IgD hinge region (ID1)

<400> SEQUENCE: 1

```
Glu Ser Pro Lys Ala Gln Ala Ser Ser Val Pro Thr Ala Gln Pro Gln
1               5                   10                  15

Ala Glu Gly Ser Leu Ala Lys Ala Thr Thr Ala Pro Ala Thr Thr Arg
            20                  25                  30

Asn Thr
```

<210> SEQ ID NO 2
<211> LENGTH: 19
<212> TYPE: PRT
<213> ORGANISM: Artificial Sequence
<220> FEATURE:
<223> OTHER INFORMATION: Synthetic_Human IgA1 hinge region

<400> SEQUENCE: 2

```
Val Pro Ser Thr Pro Pro Thr Pro Ser Pro Ser Thr Pro Pro Thr Pro
1               5                   10                  15

Ser Pro Ser
```

<210> SEQ ID NO 3
<211> LENGTH: 112
<212> TYPE: PRT
<213> ORGANISM: Artificial Sequence
<220> FEATURE:
<223> OTHER INFORMATION: Synthetic_mature GDF15 (wild type)

<400> SEQUENCE: 3

```
Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 4
<211> LENGTH: 98
<212> TYPE: PRT
<213> ORGANISM: Artificial Sequence
<220> FEATURE:
<223> OTHER INFORMATION: Synthetic_GDF15 (mutant)

<400> SEQUENCE: 4

```
Cys Arg Leu His Thr Val Arg Ala Ser Leu Glu Asp Leu Gly Trp Ala
1               5                   10                  15
```

```
Asp Trp Val Leu Ser Pro Arg Glu Val Gln Val Thr Met Cys Ile Gly
            20                  25                  30

Ala Cys Pro Ser Gln Phe Arg Ala Ala Asn Met His Ala Gln Ile Lys
        35                  40                  45

Thr Ser Leu His Arg Leu Lys Pro Asp Thr Val Pro Ala Pro Cys Cys
    50                  55                  60

Val Pro Ala Ser Tyr Asn Pro Met Val Leu Ile Gln Lys Thr Asp Thr
65                  70                  75                  80

Gly Val Ser Leu Gln Thr Tyr Asp Asp Leu Leu Ala Lys Asp Cys His
                85                  90                  95

Cys Ile


<210> SEQ ID NO 5
<211> LENGTH: 339
<212> TYPE: DNA
<213> ORGANISM: Artificial Sequence
<220> FEATURE:
<223> OTHER INFORMATION: Synthetic_Polynucleotide encoding Mature GDF15

<400> SEQUENCE: 5

gcccggaacg gcgaccactg ccccctgggg cccggacggt gctgccggct gcacaccgtg     60

cgggcctccc tggaggacct gggctgggcc gactgggtgc tgtccccaag ggaggtgcaa    120

gtgaccatgt gcatcggcgc ctgcccatct cagttccggg ccgccaacat gcacgctcag    180

atcaagacca gcctgcaccg gctgaagccc gacaccgtgc ccgcccccctg ctgcgtgccc    240

gcctcctaca accccatggt gctgattcag aagaccgaca ccggcgtgag cctgcagacc    300

tacgacgacc tgctggccaa ggactgccac tgcatctaa                           339


<210> SEQ ID NO 6
<211> LENGTH: 306
<212> TYPE: DNA
<213> ORGANISM: Artificial Sequence
<220> FEATURE:
<223> OTHER INFORMATION: Synthetic_Polynucleotide encoding 3 human IgD
      Hinge regions (ID3)

<400> SEQUENCE: 6

gagagcccta aggctcaggc ctctagcgtg ccaacagctc agccacaagc tgaaggaagc     60

ctggccaagg ctacaaccgc ccctgccaca acacggaata cagagtcccc caaggcccag    120

gctagcagcg tgcctaccgc ccagcctcag gccgagggct ccctggctaa ggccacaacc    180

gctcccgcta caaccaggaa caccgagtct ccaaaggcac aggcctcctc cgtgcccact    240

gcacaacccc aagcagaggg cagcctcgcc aaggcaacca cagccccagc caccacccgg    300

aacaca                                                               306


<210> SEQ ID NO 7
<211> LENGTH: 384
<212> TYPE: PRT
<213> ORGANISM: Artificial Sequence
<220> FEATURE:
<223> OTHER INFORMATION: Synthetic_Human IgD heavy chain constant region
     (UniProtKB P01880)

<400> SEQUENCE: 7

Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
            20                  25                  30
```

Tyr His Pro Thr Ser Val Thr Val Thr Trp Tyr Met Gly Thr Gln Ser
35 40 45

Gln Pro Gln Arg Thr Phe Pro Glu Ile Gln Arg Arg Asp Ser Tyr Tyr
50 55 60

Met Thr Ser Ser Gln Leu Ser Thr Pro Leu Gln Gln Trp Arg Gln Gly
65 70 75 80

Glu Tyr Lys Cys Val Val Gln His Thr Ala Ser Lys Ser Lys Lys Glu
85 90 95

Ile Phe Arg Trp Pro Glu Ser Pro Lys Ala Gln Ala Ser Ser Val Pro
100 105 110

Thr Ala Gln Pro Gln Ala Glu Gly Ser Leu Ala Lys Ala Thr Thr Ala
115 120 125

Pro Ala Thr Thr Arg Asn Thr Gly Arg Gly Gly Glu Glu Lys Lys Lys
130 135 140

Glu Lys Glu Lys Glu Glu Gln Glu Glu Arg Glu Thr Lys Thr Pro Glu
145 150 155 160

Cys Pro Ser His Thr Gln Pro Leu Gly Val Tyr Leu Leu Thr Pro Ala
165 170 175

Val Gln Asp Leu Trp Leu Arg Asp Lys Ala Thr Phe Thr Cys Phe Val
180 185 190

Val Gly Ser Asp Leu Lys Asp Ala His Leu Thr Trp Glu Val Ala Gly
195 200 205

Lys Val Pro Thr Gly Gly Val Glu Glu Gly Leu Leu Glu Arg His Ser
210 215 220

Asn Gly Ser Gln Ser Gln His Ser Arg Leu Thr Leu Pro Arg Ser Leu
225 230 235 240

Trp Asn Ala Gly Thr Ser Val Thr Cys Thr Leu Asn His Pro Ser Leu
245 250 255

Pro Pro Gln Arg Leu Met Ala Leu Arg Glu Pro Ala Ala Gln Ala Pro
260 265 270

Val Lys Leu Ser Leu Asn Leu Leu Ala Ser Ser Asp Pro Pro Glu Ala
275 280 285

Ala Ser Trp Leu Leu Cys Glu Val Ser Gly Phe Ser Pro Pro Asn Ile
290 295 300

Leu Leu Met Trp Leu Glu Asp Gln Arg Glu Val Asn Thr Ser Gly Phe
305 310 315 320

Ala Pro Ala Arg Pro Pro Pro Gln Pro Arg Ser Thr Thr Phe Trp Ala
325 330 335

Trp Ser Val Leu Arg Val Pro Ala Pro Pro Ser Pro Gln Pro Ala Thr
340 345 350

Tyr Thr Cys Val Val Ser His Glu Asp Ser Arg Thr Leu Leu Asn Ala
355 360 365

Ser Arg Ser Leu Glu Val Ser Tyr Val Thr Asp His Gly Pro Met Lys
370 375 380

<210> SEQ ID NO 8
<211> LENGTH: 353
<212> TYPE: PRT
<213> ORGANISM: Artificial Sequence
<220> FEATURE:
<223> OTHER INFORMATION: Synthetic_Human IgA heavy chain constant region (UniProtKB P01876)

<400> SEQUENCE: 8

Ala Ser Pro Thr Ser Pro Lys Val Phe Pro Leu Ser Leu Cys Ser Thr
1 5 10 15

```
Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
    130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
        195                 200                 205

Pro Glu Ser Lys Thr Pro Leu Thr Ala Thr Leu Ser Lys Ser Gly Asn
    210                 215                 220

Thr Phe Arg Pro Glu Val His Leu Leu Pro Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
        275                 280                 285

Thr Thr Thr Phe Ala Val Thr Ser Ile Leu Arg Val Ala Ala Glu Asp
    290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
            340                 345                 350

Tyr
```

<210> SEQ ID NO 9
<211> LENGTH: 5
<212> TYPE: PRT
<213> ORGANISM: Artificial Sequence
<220> FEATURE:
<223> OTHER INFORMATION: Synthetic_a part of human IgD hinge region

<400> SEQUENCE: 9

```
Ser Ser Val Pro Thr
1               5
```

<210> SEQ ID NO 10
<211> LENGTH: 7
<212> TYPE: PRT
<213> ORGANISM: Artificial Sequence
<220> FEATURE:
<223> OTHER INFORMATION: Synthetic_a part of human IgD hinge region

<400> SEQUENCE: 10

Thr Thr Ala Pro Ala Thr Thr
1               5

<210> SEQ ID NO 11
<211> LENGTH: 58
<212> TYPE: PRT
<213> ORGANISM: Artificial Sequence
<220> FEATURE:
<223> OTHER INFORMATION: Synthetic_a extended part of human IgD hinge region

<400> SEQUENCE: 11

Glu Ser Pro Lys Ala Gln Ala Ser Ser Val Pro Thr Ala Gln Pro Gln
1               5                   10                  15

Ala Glu Gly Ser Leu Ala Lys Ala Thr Thr Ala Pro Ala Thr Thr Arg
            20                  25                  30

Asn Thr Gly Arg Gly Gly Glu Glu Lys Lys Lys Glu Lys Glu Lys Glu
        35                  40                  45

Glu Gln Glu Glu Arg Glu Thr Lys Thr Pro
    50                  55

<210> SEQ ID NO 12
<211> LENGTH: 8
<212> TYPE: PRT
<213> ORGANISM: Artificial Sequence
<220> FEATURE:
<223> OTHER INFORMATION: Synthetic_a part of human IgA1 hinge region

<400> SEQUENCE: 12

Ser Thr Pro Pro Thr Pro Ser Pro
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic_peptide linker

<400> SEQUENCE: 13

Gly Gly Gly Gly Ser
1               5

<210> SEQ ID NO 14
<211> LENGTH: 22
<212> TYPE: PRT
<213> ORGANISM: Artificial Sequence
<220> FEATURE:
<223> OTHER INFORMATION: Synthetic_Signal Peptide

<400> SEQUENCE: 14

Met His Arg Pro Glu Ala Met Leu Leu Leu Leu Thr Leu Ala Leu Leu
1               5                   10                  15

Gly Gly Pro Thr Trp Ala
            20

<210> SEQ ID NO 15
<211> LENGTH: 8
<212> TYPE: PRT
<213> ORGANISM: Artificial Sequence
<220> FEATURE:
<223> OTHER INFORMATION: Synthetic_His-Tag

<400> SEQUENCE: 15

His His His His His His His His
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic_TEV Cleavage Site

<400> SEQUENCE: 16

Glu Asn Leu Tyr Phe Gln Gly
1               5

<210> SEQ ID NO 17
<211> LENGTH: 20
<212> TYPE: PRT
<213> ORGANISM: Artificial Sequence
<220> FEATURE:
<223> OTHER INFORMATION: Synthetic_GS linker

<400> SEQUENCE: 17

Gly Gly Gly Gly Ser Gly Gly Gly Gly Ser Gly Gly Gly Gly Ser Gly
1               5                   10                  15

Gly Gly Gly Ser
            20

<210> SEQ ID NO 18
<211> LENGTH: 68
<212> TYPE: PRT
<213> ORGANISM: Artificial Sequence
<220> FEATURE:
<223> OTHER INFORMATION: Synthetic_2 human IgD hinge regions (ID2)

<400> SEQUENCE: 18

Glu Ser Pro Lys Ala Gln Ala Ser Ser Val Pro Thr Ala Gln Pro Gln
1               5                   10                  15

Ala Glu Gly Ser Leu Ala Lys Ala Thr Thr Ala Pro Ala Thr Thr Arg
            20                  25                  30

Asn Thr Glu Ser Pro Lys Ala Gln Ala Ser Ser Val Pro Thr Ala Gln
        35                  40                  45

Pro Gln Ala Glu Gly Ser Leu Ala Lys Ala Thr Thr Ala Pro Ala Thr
    50                  55                  60

Thr Arg Asn Thr
65

<210> SEQ ID NO 19
<211> LENGTH: 102
<212> TYPE: PRT
<213> ORGANISM: Artificial Sequence
<220> FEATURE:
<223> OTHER INFORMATION: Synthetic_3 human IgD hinge regions (ID3)

<400> SEQUENCE: 19

Glu Ser Pro Lys Ala Gln Ala Ser Ser Val Pro Thr Ala Gln Pro Gln
1               5                   10                  15

```
Ala Glu Gly Ser Leu Ala Lys Ala Thr Thr Ala Pro Ala Thr Thr Arg
            20                  25                  30

Asn Thr Glu Ser Pro Lys Ala Gln Ala Ser Ser Val Pro Thr Ala Gln
        35                  40                  45

Pro Gln Ala Glu Gly Ser Leu Ala Lys Ala Thr Thr Ala Pro Ala Thr
    50                  55                  60

Thr Arg Asn Thr Glu Ser Pro Lys Ala Gln Ala Ser Ser Val Pro Thr
65                  70                  75                  80

Ala Gln Pro Gln Ala Glu Gly Ser Leu Ala Lys Ala Thr Thr Ala Pro
                85                  90                  95

Ala Thr Thr Arg Asn Thr
            100


<210> SEQ ID NO 20
<211> LENGTH: 8
<212> TYPE: PRT
<213> ORGANISM: Artificial Sequence
<220> FEATURE:
<223> OTHER INFORMATION: Synthetic_a part of human IgA hinge region

<400> SEQUENCE: 20

Ser Thr Pro Pro Thr Pro Ser Pro
1               5


<210> SEQ ID NO 21
<211> LENGTH: 102
<212> TYPE: DNA
<213> ORGANISM: Artificial Sequence
<220> FEATURE:
<223> OTHER INFORMATION: Synthetic_Polynucleotide encoding human IgD
      hinge region (ID1)

<400> SEQUENCE: 21

gagagcccta aggctcaggc ctctagcgtg ccaacagctc agccacaagc tgaaggaagc      60

ctggccaagg ctacaaccgc ccctgccaca acacggaata ca                         102


<210> SEQ ID NO 22
<211> LENGTH: 204
<212> TYPE: DNA
<213> ORGANISM: Artificial Sequence
<220> FEATURE:
<223> OTHER INFORMATION: Synthetic_Polynucleotide encoding 2 human IgD
      hinge regions (ID2)

<400> SEQUENCE: 22

gagagcccta aggctcaggc ctctagcgtg ccaacagctc agccacaagc tgaaggaagc      60

ctggccaagg ctacaaccgc ccctgccaca acacggaata cagagtcccc caaggcccag     120

gctagcagcg tgcctaccgc ccagcctcag gccgagggct ccctggctaa ggccacaacc     180

gctcccgcta caaccaggaa cacc                                             204


<210> SEQ ID NO 23
<211> LENGTH: 90
<212> TYPE: PRT
<213> ORGANISM: Artificial Sequence
<220> FEATURE:
<223> OTHER INFORMATION: Synthetic_MUCL1_HUMAN

<400> SEQUENCE: 23

Met Lys Phe Leu Ala Val Leu Val Leu Leu Gly Val Ser Ile Phe Leu
1               5                   10                  15

Val Ser Ala Gln Asn Pro Thr Thr Ala Ala Pro Ala Asp Thr Tyr Pro
```

```
            20                  25                  30

Ala Thr Gly Pro Ala Asp Asp Glu Ala Pro Asp Ala Glu Thr Thr Ala
        35                  40                  45

Ala Ala Thr Thr Ala Thr Thr Ala Ala Pro Thr Thr Ala Thr Thr Ala
    50                  55                  60

Ala Ser Thr Thr Ala Arg Lys Asp Ile Pro Val Leu Pro Lys Trp Val
65                  70                  75                  80

Gly Asp Leu Pro Asn Gly Arg Val Cys Pro
                85                  90


<210> SEQ ID NO 24
<211> LENGTH: 97
<212> TYPE: PRT
<213> ORGANISM: Artificial Sequence
<220> FEATURE:
<223> OTHER INFORMATION: Synthetic_SMAGP_HUMAN

<400> SEQUENCE: 24

Met Thr Ser Leu Leu Thr Thr Pro Ser Pro Arg Glu Glu Leu Met Thr
1               5                   10                  15

Thr Pro Ile Leu Gln Pro Thr Glu Ala Leu Ser Pro Glu Asp Gly Ala
            20                  25                  30

Ser Thr Ala Leu Ile Ala Val Val Ile Thr Val Val Phe Leu Thr Leu
        35                  40                  45

Leu Ser Val Val Ile Leu Ile Phe Phe Tyr Leu Tyr Lys Asn Lys Gly
    50                  55                  60

Ser Tyr Val Thr Tyr Glu Pro Thr Glu Gly Glu Pro Ser Ala Ile Val
65                  70                  75                  80

Gln Met Glu Ser Asp Leu Ala Lys Gly Ser Glu Lys Glu Glu Tyr Phe
                85                  90                  95

Ile


<210> SEQ ID NO 25
<211> LENGTH: 128
<212> TYPE: PRT
<213> ORGANISM: Artificial Sequence
<220> FEATURE:
<223> OTHER INFORMATION: Synthetic_GLPC_HUMAN

<400> SEQUENCE: 25

Met Trp Ser Thr Arg Ser Pro Asn Ser Thr Ala Trp Pro Leu Ser Leu
1               5                   10                  15

Glu Pro Asp Pro Gly Met Ala Ser Ala Ser Thr Thr Met His Thr Thr
            20                  25                  30

Thr Ile Ala Glu Pro Asp Pro Gly Met Ser Gly Trp Pro Asp Gly Arg
        35                  40                  45

Met Glu Thr Ser Thr Pro Thr Ile Met Asp Ile Val Val Ile Ala Gly
    50                  55                  60

Val Ile Ala Ala Val Ala Ile Val Leu Val Ser Leu Leu Phe Val Met
65                  70                  75                  80

Leu Arg Tyr Met Tyr Arg His Lys Gly Thr Tyr His Thr Asn Glu Ala
                85                  90                  95

Lys Gly Thr Glu Phe Ala Glu Ser Ala Asp Ala Ala Leu Gln Gly Asp
            100                 105                 110

Pro Ala Leu Gln Asp Ala Gly Asp Ser Ser Arg Lys Glu Tyr Phe Ile
        115                 120                 125
```

<210> SEQ ID NO 26
<211> LENGTH: 134
<212> TYPE: PRT
<213> ORGANISM: Artificial Sequence
<220> FEATURE:
<223> OTHER INFORMATION: Synthetic_ANFB_HUMAN

<400> SEQUENCE: 26

```
Met Asp Pro Gln Thr Ala Pro Ser Arg Ala Leu Leu Leu Leu Leu Phe
1               5                   10                  15

Leu His Leu Ala Phe Leu Gly Gly Arg Ser His Pro Leu Gly Ser Pro
            20                  25                  30

Gly Ser Ala Ser Asp Leu Glu Thr Ser Gly Leu Gln Glu Gln Arg Asn
        35                  40                  45

His Leu Gln Gly Lys Leu Ser Glu Leu Gln Val Glu Gln Thr Ser Leu
    50                  55                  60

Glu Pro Leu Gln Glu Ser Pro Arg Pro Thr Gly Val Trp Lys Ser Arg
65                  70                  75                  80

Glu Val Ala Thr Glu Gly Ile Arg Gly His Arg Lys Met Val Leu Tyr
                85                  90                  95

Thr Leu Arg Ala Pro Arg Ser Pro Lys Met Val Gln Gly Ser Gly Cys
            100                 105                 110

Phe Gly Arg Lys Met Asp Arg Ile Ser Ser Ser Ser Gly Leu Gly Cys
        115                 120                 125

Lys Val Leu Arg Arg His
    130
```

<210> SEQ ID NO 27
<211> LENGTH: 144
<212> TYPE: PRT
<213> ORGANISM: Artificial Sequence
<220> FEATURE:
<223> OTHER INFORMATION: Synthetic_CSF2_HUMAN

<400> SEQUENCE: 27

```
Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140
```

<210> SEQ ID NO 28
<211> LENGTH: 150
<212> TYPE: PRT
<213> ORGANISM: Artificial Sequence
<220> FEATURE:

<223> OTHER INFORMATION: Synthetic_GLPA_HUMAN

<400> SEQUENCE: 28

Met Tyr Gly Lys Ile Ile Phe Val Leu Leu Leu Ser Glu Ile Val Ser
1 5 10 15

Ile Ser Ala Ser Ser Thr Thr Gly Val Ala Met His Thr Ser Thr Ser
20 25 30

Ser Ser Val Thr Lys Ser Tyr Ile Ser Ser Gln Thr Asn Asp Thr His
35 40 45

Lys Arg Asp Thr Tyr Ala Ala Thr Pro Arg Ala His Glu Val Ser Glu
50 55 60

Ile Ser Val Arg Thr Val Tyr Pro Pro Glu Glu Glu Thr Gly Glu Arg
65 70 75 80

Val Gln Leu Ala His His Phe Ser Glu Pro Glu Ile Thr Leu Ile Ile
85 90 95

Phe Gly Val Met Ala Gly Val Ile Gly Thr Ile Leu Leu Ile Ser Tyr
100 105 110

Gly Ile Arg Arg Leu Ile Lys Lys Ser Pro Ser Asp Val Lys Pro Leu
115 120 125

Pro Ser Pro Asp Thr Asp Val Pro Leu Ser Ser Val Glu Ile Glu Asn
130 135 140

Pro Glu Thr Ser Asp Gln
145 150

<210> SEQ ID NO 29
<211> LENGTH: 158
<212> TYPE: PRT
<213> ORGANISM: Artificial Sequence
<220> FEATURE:
<223> OTHER INFORMATION: Synthetic_SRGN_HUMAN

<400> SEQUENCE: 29

Met Met Gln Lys Leu Leu Lys Cys Ser Arg Leu Val Leu Ala Leu Ala
1 5 10 15

Leu Ile Leu Val Leu Glu Ser Ser Val Gln Gly Tyr Pro Thr Arg Arg
20 25 30

Ala Arg Tyr Gln Trp Val Arg Cys Asn Pro Asp Ser Asn Ser Ala Asn
35 40 45

Cys Leu Glu Glu Lys Gly Pro Met Phe Glu Leu Leu Pro Gly Glu Ser
50 55 60

Asn Lys Ile Pro Arg Leu Arg Thr Asp Leu Phe Pro Lys Thr Arg Ile
65 70 75 80

Gln Asp Leu Asn Arg Ile Phe Pro Leu Ser Glu Asp Tyr Ser Gly Ser
85 90 95

Gly Phe Gly Ser Gly Ser Gly Ser Gly Ser Gly Ser Gly Ser Gly Phe
100 105 110

Leu Thr Glu Met Glu Gln Asp Tyr Gln Leu Val Asp Glu Ser Asp Ala
115 120 125

Phe His Asp Asn Leu Arg Ser Leu Asp Arg Asn Leu Pro Ser Asp Ser
130 135 140

Gln Asp Leu Gly Gln His Gly Leu Glu Glu Asp Phe Met Leu
145 150 155

<210> SEQ ID NO 30
<211> LENGTH: 162
<212> TYPE: PRT
<213> ORGANISM: Artificial Sequence

```
<220> FEATURE:
<223> OTHER INFORMATION: Synthetic_PDPN_HUMAN

<400> SEQUENCE: 30

Met Trp Lys Val Ser Ala Leu Leu Phe Val Leu Gly Ser Ala Ser Leu
1               5                   10                  15

Trp Val Leu Ala Glu Gly Ala Ser Thr Gly Gln Pro Glu Asp Asp Thr
            20                  25                  30

Glu Thr Thr Gly Leu Glu Gly Gly Val Ala Met Pro Gly Ala Glu Asp
        35                  40                  45

Asp Val Val Thr Pro Gly Thr Ser Glu Asp Arg Tyr Lys Ser Gly Leu
    50                  55                  60

Thr Thr Leu Val Ala Thr Ser Val Asn Ser Val Thr Gly Ile Arg Ile
65                  70                  75                  80

Glu Asp Leu Pro Thr Ser Glu Ser Thr Val His Ala Gln Glu Gln Ser
                85                  90                  95

Pro Ser Ala Thr Ala Ser Asn Val Ala Thr Ser His Ser Thr Glu Lys
            100                 105                 110

Val Asp Gly Asp Thr Gln Thr Thr Val Glu Lys Asp Gly Leu Ser Thr
        115                 120                 125

Val Thr Leu Val Gly Ile Ile Val Gly Val Leu Leu Ala Ile Gly Phe
    130                 135                 140

Ile Gly Ala Ile Ile Val Val Val Met Arg Lys Met Ser Gly Arg Tyr
145                 150                 155                 160

Ser Pro


<210> SEQ ID NO 31
<211> LENGTH: 165
<212> TYPE: PRT
<213> ORGANISM: Artificial Sequence
<220> FEATURE:
<223> OTHER INFORMATION: Synthetic_CGB7_HUMAN

<400> SEQUENCE: 31

Met Glu Met Phe Gln Gly Leu Leu Leu Leu Leu Leu Leu Ser Met Gly
1               5                   10                  15

Gly Thr Trp Ala Ser Arg Glu Met Leu Arg Pro Arg Cys Arg Pro Ile
            20                  25                  30

Asn Ala Thr Leu Ala Val Glu Lys Glu Gly Cys Pro Val Cys Ile Thr
        35                  40                  45

Val Asn Thr Thr Ile Cys Ala Gly Tyr Cys Pro Thr Met Thr Arg Val
    50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
            100                 105                 110

Cys Arg Arg Ser Thr Thr Asp Cys Gly Gly Pro Lys Asp His Pro Leu
        115                 120                 125

Thr Cys Asp Asp Pro Arg Phe Gln Ala Ser Ser Ser Ser Lys Ala Pro
    130                 135                 140

Pro Pro Ser Leu Pro Ser Pro Ser Arg Leu Pro Gly Pro Ser Asp Thr
145                 150                 155                 160

Pro Ile Leu Pro Gln
                165
```

<210> SEQ ID NO 32
<211> LENGTH: 165
<212> TYPE: PRT
<213> ORGANISM: Artificial Sequence
<220> FEATURE:
<223> OTHER INFORMATION: Synthetic_CGB3_HUMAN

<400> SEQUENCE: 32

```
Met Glu Met Phe Gln Gly Leu Leu Leu Leu Leu Leu Leu Ser Met Gly
1               5                   10                  15

Gly Thr Trp Ala Ser Lys Glu Pro Leu Arg Pro Arg Cys Arg Pro Ile
            20                  25                  30

Asn Ala Thr Leu Ala Val Glu Lys Glu Gly Cys Pro Val Cys Ile Thr
        35                  40                  45

Val Asn Thr Thr Ile Cys Ala Gly Tyr Cys Pro Thr Met Thr Arg Val
    50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
            100                 105                 110

Cys Arg Arg Ser Thr Thr Asp Cys Gly Gly Pro Lys Asp His Pro Leu
        115                 120                 125

Thr Cys Asp Asp Pro Arg Phe Gln Asp Ser Ser Ser Ser Lys Ala Pro
    130                 135                 140

Pro Pro Ser Leu Pro Ser Pro Ser Arg Leu Pro Gly Pro Ser Asp Thr
145                 150                 155                 160

Pro Ile Leu Pro Gln
                165
```

<210> SEQ ID NO 33
<211> LENGTH: 180
<212> TYPE: PRT
<213> ORGANISM: Artificial Sequence
<220> FEATURE:
<223> OTHER INFORMATION: Synthetic_IGF2_HUMAN

<400> SEQUENCE: 33

```
Met Gly Ile Pro Met Gly Lys Ser Met Leu Val Leu Leu Thr Phe Leu
1               5                   10                  15

Ala Phe Ala Ser Cys Cys Ile Ala Ala Tyr Arg Pro Ser Glu Thr Leu
            20                  25                  30

Cys Gly Gly Glu Leu Val Asp Thr Leu Gln Phe Val Cys Gly Asp Arg
        35                  40                  45

Gly Phe Tyr Phe Ser Arg Pro Ala Ser Arg Val Ser Arg Arg Ser Arg
    50                  55                  60

Gly Ile Val Glu Glu Cys Cys Phe Arg Ser Cys Asp Leu Ala Leu Leu
65                  70                  75                  80

Glu Thr Tyr Cys Ala Thr Pro Ala Lys Ser Glu Arg Asp Val Ser Thr
                85                  90                  95

Pro Pro Thr Val Leu Pro Asp Asn Phe Pro Arg Tyr Pro Val Gly Lys
            100                 105                 110

Phe Phe Gln Tyr Asp Thr Trp Lys Gln Ser Thr Gln Arg Leu Arg Arg
        115                 120                 125

Gly Leu Pro Ala Leu Leu Arg Ala Arg Arg Gly His Val Leu Ala Lys
```

```
    130                 135                 140

Glu Leu Glu Ala Phe Arg Glu Ala Lys Arg His Arg Pro Leu Ile Ala
145                 150                 155                 160

Leu Pro Thr Gln Asp Pro Ala His Gly Gly Ala Pro Pro Glu Met Ala
                165                 170                 175

Ser Asn Arg Lys
            180


<210> SEQ ID NO 34
<211> LENGTH: 182
<212> TYPE: PRT
<213> ORGANISM: Artificial Sequence
<220> FEATURE:
<223> OTHER INFORMATION: Synthetic_CASK_HUMAN

<400> SEQUENCE: 34

Met Lys Ser Phe Leu Leu Val Val Asn Ala Leu Ala Leu Thr Leu Pro
1               5                   10                  15

Phe Leu Ala Val Glu Val Gln Asn Gln Lys Gln Pro Ala Cys His Glu
            20                  25                  30

Asn Asp Glu Arg Pro Phe Tyr Gln Lys Thr Ala Pro Tyr Val Pro Met
        35                  40                  45

Tyr Tyr Val Pro Asn Ser Tyr Pro Tyr Tyr Gly Thr Asn Leu Tyr Gln
    50                  55                  60

Arg Arg Pro Ala Ile Ala Ile Asn Asn Pro Tyr Val Pro Arg Thr Tyr
65                  70                  75                  80

Tyr Ala Asn Pro Ala Val Val Arg Pro His Ala Gln Ile Pro Gln Arg
                85                  90                  95

Gln Tyr Leu Pro Asn Ser His Pro Pro Thr Val Val Arg Arg Pro Asn
            100                 105                 110

Leu His Pro Ser Phe Ile Ala Ile Pro Pro Lys Lys Ile Gln Asp Lys
        115                 120                 125

Ile Ile Ile Pro Thr Ile Asn Thr Ile Ala Thr Val Glu Pro Thr Pro
    130                 135                 140

Ala Pro Ala Thr Glu Pro Thr Val Asp Ser Val Val Thr Pro Glu Ala
145                 150                 155                 160

Phe Ser Glu Ser Ile Ile Thr Ser Thr Pro Glu Thr Thr Thr Val Ala
                165                 170                 175

Val Thr Pro Pro Thr Ala
            180


<210> SEQ ID NO 35
<211> LENGTH: 198
<212> TYPE: PRT
<213> ORGANISM: Artificial Sequence
<220> FEATURE:
<223> OTHER INFORMATION: Synthetic_SDC4_HUMAN

<400> SEQUENCE: 35

Met Ala Pro Ala Arg Leu Phe Ala Leu Leu Leu Phe Phe Val Gly Gly
1               5                   10                  15

Val Ala Glu Ser Ile Arg Glu Thr Glu Val Ile Asp Pro Gln Asp Leu
            20                  25                  30

Leu Glu Gly Arg Tyr Phe Ser Gly Ala Leu Pro Asp Asp Glu Asp Val
        35                  40                  45

Val Gly Pro Gly Gln Glu Ser Asp Asp Phe Glu Leu Ser Gly Ser Gly
    50                  55                  60
```

Asp Leu Asp Asp Leu Glu Asp Ser Met Ile Gly Pro Glu Val Val His
65 70 75 80

Pro Leu Val Pro Leu Asp Asn His Ile Pro Glu Arg Ala Gly Ser Gly
85 90 95

Ser Gln Val Pro Thr Glu Pro Lys Lys Leu Glu Glu Asn Glu Val Ile
100 105 110

Pro Lys Arg Ile Ser Pro Val Glu Glu Ser Glu Asp Val Ser Asn Lys
115 120 125

Val Ser Met Ser Ser Thr Val Gln Gly Ser Asn Ile Phe Glu Arg Thr
130 135 140

Glu Val Leu Ala Ala Leu Ile Val Gly Gly Ile Val Gly Ile Leu Phe
145 150 155 160

Ala Val Phe Leu Ile Leu Leu Leu Met Tyr Arg Met Lys Lys Lys Asp
165 170 175

Glu Gly Ser Tyr Asp Leu Gly Lys Lys Pro Ile Tyr Lys Lys Ala Pro
180 185 190

Thr Asn Glu Phe Tyr Ala
195

<210> SEQ ID NO 36
<211> LENGTH: 201
<212> TYPE: PRT
<213> ORGANISM: Artificial Sequence
<220> FEATURE:
<223> OTHER INFORMATION: Synthetic_SDC2_HUMAN

<400> SEQUENCE: 36

Met Arg Arg Ala Trp Ile Leu Leu Thr Leu Gly Leu Val Ala Cys Val
1 5 10 15

Ser Ala Glu Ser Arg Ala Glu Leu Thr Ser Asp Lys Asp Met Tyr Leu
20 25 30

Asp Asn Ser Ser Ile Glu Glu Ala Ser Gly Val Tyr Pro Ile Asp Asp
35 40 45

Asp Asp Tyr Ala Ser Ala Ser Gly Ser Gly Ala Asp Glu Asp Val Glu
50 55 60

Ser Pro Glu Leu Thr Thr Ser Arg Pro Leu Pro Lys Ile Leu Leu Thr
65 70 75 80

Ser Ala Ala Pro Lys Val Glu Thr Thr Thr Leu Asn Ile Gln Asn Lys
85 90 95

Ile Pro Ala Gln Thr Lys Ser Pro Glu Glu Thr Asp Lys Glu Lys Val
100 105 110

His Leu Ser Asp Ser Glu Arg Lys Met Asp Pro Ala Glu Glu Asp Thr
115 120 125

Asn Val Tyr Thr Glu Lys His Ser Asp Ser Leu Phe Lys Arg Thr Glu
130 135 140

Val Leu Ala Ala Val Ile Ala Gly Gly Val Ile Gly Phe Leu Phe Ala
145 150 155 160

Ile Phe Leu Ile Leu Leu Leu Val Tyr Arg Met Arg Lys Lys Asp Glu
165 170 175

Gly Ser Tyr Asp Leu Gly Glu Arg Lys Pro Ser Ser Ala Ala Tyr Gln
180 185 190

Lys Ala Pro Thr Lys Glu Phe Tyr Ala
195 200

<210> SEQ ID NO 37
<211> LENGTH: 208

```
<212> TYPE: PRT
<213> ORGANISM: Artificial Sequence
<220> FEATURE:
<223> OTHER INFORMATION: Synthetic_HBEGF_HUMAN

<400> SEQUENCE: 37

Met Lys Leu Leu Pro Ser Val Val Leu Lys Leu Phe Leu Ala Ala Val
1               5                   10                  15

Leu Ser Ala Leu Val Thr Gly Glu Ser Leu Glu Arg Leu Arg Arg Gly
            20                  25                  30

Leu Ala Ala Gly Thr Ser Asn Pro Asp Pro Pro Thr Val Ser Thr Asp
        35                  40                  45

Gln Leu Leu Pro Leu Gly Gly Gly Arg Asp Arg Lys Val Arg Asp Leu
    50                  55                  60

Gln Glu Ala Asp Leu Asp Leu Leu Arg Val Thr Leu Ser Ser Lys Pro
65                  70                  75                  80

Gln Ala Leu Ala Thr Pro Asn Lys Glu Glu His Gly Lys Arg Lys Lys
                85                  90                  95

Lys Gly Lys Gly Leu Gly Lys Lys Arg Asp Pro Cys Leu Arg Lys Tyr
            100                 105                 110

Lys Asp Phe Cys Ile His Gly Glu Cys Lys Tyr Val Lys Glu Leu Arg
        115                 120                 125

Ala Pro Ser Cys Ile Cys His Pro Gly Tyr His Gly Glu Arg Cys His
    130                 135                 140

Gly Leu Ser Leu Pro Val Glu Asn Arg Leu Tyr Thr Tyr Asp His Thr
145                 150                 155                 160

Thr Ile Leu Ala Val Val Ala Val Val Leu Ser Ser Val Cys Leu Leu
                165                 170                 175

Val Ile Val Gly Leu Leu Met Phe Arg Tyr His Arg Arg Gly Gly Tyr
            180                 185                 190

Asp Val Glu Asn Glu Glu Lys Val Lys Leu Gly Met Thr Asn Ser His
        195                 200                 205


<210> SEQ ID NO 38
<211> LENGTH: 222
<212> TYPE: PRT
<213> ORGANISM: Artificial Sequence
<220> FEATURE:
<223> OTHER INFORMATION: Synthetic_PRG2_HUMAN

<400> SEQUENCE: 38

Met Lys Leu Pro Leu Leu Leu Ala Leu Leu Phe Gly Ala Val Ser Ala
1               5                   10                  15

Leu His Leu Arg Ser Glu Thr Ser Thr Phe Glu Thr Pro Leu Gly Ala
            20                  25                  30

Lys Thr Leu Pro Glu Asp Glu Glu Thr Pro Glu Gln Glu Met Glu Glu
        35                  40                  45

Thr Pro Cys Arg Glu Leu Glu Glu Glu Glu Glu Trp Gly Ser Gly Ser
    50                  55                  60

Glu Asp Ala Ser Lys Lys Asp Gly Ala Val Glu Ser Ile Ser Val Pro
65                  70                  75                  80

Asp Met Val Asp Lys Asn Leu Thr Cys Pro Glu Glu Glu Asp Thr Val
                85                  90                  95

Lys Val Val Gly Ile Pro Gly Cys Gln Thr Cys Arg Tyr Leu Leu Val
            100                 105                 110

Arg Ser Leu Gln Thr Phe Ser Gln Ala Trp Phe Thr Cys Arg Arg Cys
        115                 120                 125
```

Tyr Arg Gly Asn Leu Val Ser Ile His Asn Phe Asn Ile Asn Tyr Arg
130 135 140

Ile Gln Cys Ser Val Ser Ala Leu Asn Gln Gly Gln Val Trp Ile Gly
145 150 155 160

Gly Arg Ile Thr Gly Ser Gly Arg Cys Arg Arg Phe Gln Trp Val Asp
165 170 175

Gly Ser Arg Trp Asn Phe Ala Tyr Trp Ala Ala His Gln Pro Trp Ser
180 185 190

Arg Gly Gly His Cys Val Ala Leu Cys Thr Arg Gly Gly His Trp Arg
195 200 205

Arg Ala His Cys Leu Arg Arg Leu Pro Phe Ile Cys Ser Tyr
210 215 220

<210> SEQ ID NO 39
<211> LENGTH: 240
<212> TYPE: PRT
<213> ORGANISM: Artificial Sequence
<220> FEATURE:
<223> OTHER INFORMATION: Synthetic_IBP6_HUMAN

<400> SEQUENCE: 39

Met Thr Pro His Arg Leu Leu Pro Pro Leu Leu Leu Leu Leu Ala Leu
1 5 10 15

Leu Leu Ala Ala Ser Pro Gly Gly Ala Leu Ala Arg Cys Pro Gly Cys
20 25 30

Gly Gln Gly Val Gln Ala Gly Cys Pro Gly Gly Cys Val Glu Glu Glu
35 40 45

Asp Gly Gly Ser Pro Ala Glu Gly Cys Ala Glu Ala Glu Gly Cys Leu
50 55 60

Arg Arg Glu Gly Gln Glu Cys Gly Val Tyr Thr Pro Asn Cys Ala Pro
65 70 75 80

Gly Leu Gln Cys His Pro Pro Lys Asp Asp Glu Ala Pro Leu Arg Ala
85 90 95

Leu Leu Leu Gly Arg Gly Arg Cys Leu Pro Ala Arg Ala Pro Ala Val
100 105 110

Ala Glu Glu Asn Pro Lys Glu Ser Lys Pro Gln Ala Gly Thr Ala Arg
115 120 125

Pro Gln Asp Val Asn Arg Arg Asp Gln Gln Arg Asn Pro Gly Thr Ser
130 135 140

Thr Thr Pro Ser Gln Pro Asn Ser Ala Gly Val Gln Asp Thr Glu Met
145 150 155 160

Gly Pro Cys Arg Arg His Leu Asp Ser Val Leu Gln Gln Leu Gln Thr
165 170 175

Glu Val Tyr Arg Gly Ala Gln Thr Leu Tyr Val Pro Asn Cys Asp His
180 185 190

Arg Gly Phe Tyr Arg Lys Arg Gln Cys Arg Ser Ser Gln Gly Gln Arg
195 200 205

Arg Gly Pro Cys Trp Cys Val Asp Arg Met Gly Lys Ser Leu Pro Gly
210 215 220

Ser Pro Asp Gly Asn Gly Ser Ser Ser Cys Pro Thr Gly Ser Ser Gly
225 230 235 240

<210> SEQ ID NO 40
<211> LENGTH: 260
<212> TYPE: PRT
<213> ORGANISM: Artificial Sequence
<220> FEATURE:
<223> OTHER INFORMATION: Synthetic_PCSK1_HUMAN

<400> SEQUENCE: 40

Met Ala Gly Ser Pro Leu Leu Trp Gly Pro Arg Ala Gly Gly Val Gly
1 5 10 15

Leu Leu Val Leu Leu Leu Leu Gly Leu Phe Arg Pro Pro Pro Ala Leu
20 25 30

Cys Ala Arg Pro Val Lys Glu Pro Arg Gly Leu Ser Ala Ala Ser Pro
35 40 45

Pro Leu Ala Glu Thr Gly Ala Pro Arg Arg Phe Arg Arg Ser Val Pro
50 55 60

Arg Gly Glu Ala Ala Gly Ala Val Gln Glu Leu Ala Arg Ala Leu Ala
65 70 75 80

His Leu Leu Glu Ala Glu Arg Gln Glu Arg Ala Arg Ala Glu Ala Gln
85 90 95

Glu Ala Glu Asp Gln Gln Ala Arg Val Leu Ala Gln Leu Leu Arg Val
100 105 110

Trp Gly Ala Pro Arg Asn Ser Asp Pro Ala Leu Gly Leu Asp Asp Asp
115 120 125

Pro Asp Ala Pro Ala Ala Gln Leu Ala Arg Ala Leu Leu Arg Ala Arg
130 135 140

Leu Asp Pro Ala Ala Leu Ala Ala Gln Leu Val Pro Ala Pro Val Pro
145 150 155 160

Ala Ala Ala Leu Arg Pro Arg Pro Pro Val Tyr Asp Asp Gly Pro Ala
165 170 175

Gly Pro Asp Ala Glu Glu Ala Gly Asp Glu Thr Pro Asp Val Asp Pro
180 185 190

Glu Leu Leu Arg Tyr Leu Leu Gly Arg Ile Leu Ala Gly Ser Ala Asp
195 200 205

Ser Glu Gly Val Ala Ala Pro Arg Arg Leu Arg Arg Ala Ala Asp His
210 215 220

Asp Val Gly Ser Glu Leu Pro Pro Glu Gly Val Leu Gly Ala Leu Leu
225 230 235 240

Arg Val Lys Arg Leu Glu Thr Pro Ala Pro Gln Val Pro Ala Arg Arg
245 250 255

Leu Leu Pro Pro
260

<210> SEQ ID NO 41
<211> LENGTH: 272
<212> TYPE: PRT
<213> ORGANISM: Artificial Sequence
<220> FEATURE:
<223> OTHER INFORMATION: Synthetic_IL2RA_HUMAN

<400> SEQUENCE: 41

Met Asp Ser Tyr Leu Leu Met Trp Gly Leu Leu Thr Phe Ile Met Val
1 5 10 15

Pro Gly Cys Gln Ala Glu Leu Cys Asp Asp Asp Pro Pro Glu Ile Pro
20 25 30

His Ala Thr Phe Lys Ala Met Ala Tyr Lys Glu Gly Thr Met Leu Asn
35 40 45

Cys Glu Cys Lys Arg Gly Phe Arg Arg Ile Lys Ser Gly Ser Leu Tyr
50 55 60

Met Leu Cys Thr Gly Asn Ser Ser His Ser Ser Trp Asp Asn Gln Cys

```
65                  70                  75                  80

Gln Cys Thr Ser Ser Ala Thr Arg Asn Thr Thr Lys Gln Val Thr Pro
                85                  90                  95

Gln Pro Glu Glu Gln Lys Glu Arg Lys Thr Thr Glu Met Gln Ser Pro
            100                 105                 110

Met Gln Pro Val Asp Gln Ala Ser Leu Pro Gly His Cys Arg Glu Pro
        115                 120                 125

Pro Pro Trp Glu Asn Glu Ala Thr Glu Arg Ile Tyr His Phe Val Val
    130                 135                 140

Gly Gln Met Val Tyr Tyr Gln Cys Val Gln Gly Tyr Arg Ala Leu His
145                 150                 155                 160

Arg Gly Pro Ala Glu Ser Val Cys Lys Met Thr His Gly Lys Thr Arg
                165                 170                 175

Trp Thr Gln Pro Gln Leu Ile Cys Thr Gly Glu Met Glu Thr Ser Gln
            180                 185                 190

Phe Pro Gly Glu Glu Lys Pro Gln Ala Ser Pro Glu Gly Arg Pro Glu
        195                 200                 205

Ser Glu Thr Ser Cys Leu Val Thr Thr Thr Asp Phe Gln Ile Gln Thr
    210                 215                 220

Glu Met Ala Ala Thr Met Glu Thr Ser Ile Phe Thr Thr Glu Tyr Gln
225                 230                 235                 240

Val Ala Val Ala Gly Cys Val Phe Leu Leu Ile Ser Val Leu Leu Leu
                245                 250                 255

Ser Gly Leu Thr Trp Gln Arg Arg Gln Arg Lys Ser Arg Arg Thr Ile
            260                 265                 270


<210> SEQ ID NO 42
<211> LENGTH: 273
<212> TYPE: PRT
<213> ORGANISM: Artificial Sequence
<220> FEATURE:
<223> OTHER INFORMATION: Synthetic_SCF_HUMAN

<400> SEQUENCE: 42

Met Lys Lys Thr Gln Thr Trp Ile Leu Thr Cys Ile Tyr Leu Gln Leu
1               5                   10                  15

Leu Leu Phe Asn Pro Leu Val Lys Thr Glu Gly Ile Cys Arg Asn Arg
            20                  25                  30

Val Thr Asn Asn Val Lys Asp Val Thr Lys Leu Val Ala Asn Leu Pro
        35                  40                  45

Lys Asp Tyr Met Ile Thr Leu Lys Tyr Val Pro Gly Met Asp Val Leu
    50                  55                  60

Pro Ser His Cys Trp Ile Ser Glu Met Val Val Gln Leu Ser Asp Ser
65                  70                  75                  80

Leu Thr Asp Leu Leu Asp Lys Phe Ser Asn Ile Ser Glu Gly Leu Ser
                85                  90                  95

Asn Tyr Ser Ile Ile Asp Lys Leu Val Asn Ile Val Asp Asp Leu Val
            100                 105                 110

Glu Cys Val Lys Glu Asn Ser Ser Lys Asp Leu Lys Lys Ser Phe Lys
        115                 120                 125

Ser Pro Glu Pro Arg Leu Phe Thr Pro Glu Glu Phe Phe Arg Ile Phe
    130                 135                 140

Asn Arg Ser Ile Asp Ala Phe Lys Asp Phe Val Val Ala Ser Glu Thr
145                 150                 155                 160

Ser Asp Cys Val Val Ser Ser Thr Leu Ser Pro Glu Lys Asp Ser Arg
```

```
                165                 170                 175

Val Ser Val Thr Lys Pro Phe Met Leu Pro Pro Val Ala Ala Ser Ser
            180                 185                 190

Leu Arg Asn Asp Ser Ser Ser Ser Asn Arg Lys Ala Lys Asn Pro Pro
        195                 200                 205

Gly Asp Ser Ser Leu His Trp Ala Ala Met Ala Leu Pro Ala Leu Phe
    210                 215                 220

Ser Leu Ile Ile Gly Phe Ala Phe Gly Ala Leu Tyr Trp Lys Lys Arg
225                 230                 235                 240

Gln Pro Ser Leu Thr Arg Ala Val Glu Asn Ile Gln Ile Asn Glu Glu
                245                 250                 255

Asp Asn Glu Ile Ser Met Leu Gln Glu Lys Glu Arg Glu Phe Gln Glu
            260                 265                 270

Val


<210> SEQ ID NO 43
<211> LENGTH: 279
<212> TYPE: PRT
<213> ORGANISM: Artificial Sequence
<220> FEATURE:
<223> OTHER INFORMATION: Synthetic_ODAM_HUMAN

<400> SEQUENCE: 43

Met Lys Ile Ile Ile Leu Leu Gly Phe Leu Gly Ala Thr Leu Ser Ala
1               5                   10                  15

Pro Leu Ile Pro Gln Arg Leu Met Ser Ala Ser Asn Ser Asn Glu Leu
            20                  25                  30

Leu Leu Asn Leu Asn Asn Gly Gln Leu Leu Pro Leu Gln Leu Gln Gly
        35                  40                  45

Pro Leu Asn Ser Trp Ile Pro Pro Phe Ser Gly Ile Leu Gln Gln Gln
    50                  55                  60

Gln Gln Ala Gln Ile Pro Gly Leu Ser Gln Phe Ser Leu Ser Ala Leu
65                  70                  75                  80

Asp Gln Phe Ala Gly Leu Leu Pro Asn Gln Ile Pro Leu Thr Gly Glu
                85                  90                  95

Ala Ser Phe Ala Gln Gly Ala Gln Ala Gly Gln Val Asp Pro Leu Gln
            100                 105                 110

Leu Gln Thr Pro Pro Gln Thr Gln Pro Gly Pro Ser His Val Met Pro
        115                 120                 125

Tyr Val Phe Ser Phe Lys Met Pro Gln Glu Gln Gly Gln Met Phe Gln
    130                 135                 140

Tyr Tyr Pro Val Tyr Met Val Leu Pro Trp Glu Gln Pro Gln Gln Thr
145                 150                 155                 160

Val Pro Arg Ser Pro Gln Gln Thr Arg Gln Gln Gln Tyr Glu Glu Gln
                165                 170                 175

Ile Pro Phe Tyr Ala Gln Phe Gly Tyr Ile Pro Gln Leu Ala Glu Pro
            180                 185                 190

Ala Ile Ser Gly Gly Gln Gln Gln Leu Ala Phe Asp Pro Gln Leu Gly
        195                 200                 205

Thr Ala Pro Glu Ile Ala Val Met Ser Thr Gly Glu Glu Ile Pro Tyr
    210                 215                 220

Leu Gln Lys Glu Ala Ile Asn Phe Arg His Asp Ser Ala Gly Val Phe
225                 230                 235                 240

Met Pro Ser Thr Ser Pro Lys Pro Ser Thr Thr Asn Val Phe Thr Ser
                245                 250                 255
```

```
Ala Val Asp Gln Thr Ile Thr Pro Glu Leu Pro Glu Glu Lys Asp Lys
            260                 265                 270

Thr Asp Ser Leu Arg Glu Pro
        275


<210> SEQ ID NO 44
<211> LENGTH: 314
<212> TYPE: PRT
<213> ORGANISM: Artificial Sequence
<220> FEATURE:
<223> OTHER INFORMATION: Synthetic_OSTP_HUMAN

<400> SEQUENCE: 44

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Asn Ala Val Ser Ser Glu
    50                  55                  60

Glu Thr Asn Asp Phe Lys Gln Glu Thr Leu Pro Ser Lys Ser Asn Glu
65                  70                  75                  80

Ser His Asp His Met Asp Asp Met Asp Asp Glu Asp Asp Asp Asp His
                85                  90                  95

Val Asp Ser Gln Asp Ser Ile Asp Ser Asn Asp Ser Asp Asp Val Asp
            100                 105                 110

Asp Thr Asp Asp Ser His Gln Ser Asp Glu Ser His His Ser Asp Glu
        115                 120                 125

Ser Asp Glu Leu Val Thr Asp Phe Pro Thr Asp Leu Pro Ala Thr Glu
    130                 135                 140

Val Phe Thr Pro Val Val Pro Thr Val Asp Thr Tyr Asp Gly Arg Gly
145                 150                 155                 160

Asp Ser Val Val Tyr Gly Leu Arg Ser Lys Ser Lys Lys Phe Arg Arg
                165                 170                 175

Pro Asp Ile Gln Tyr Pro Asp Ala Thr Asp Glu Asp Ile Thr Ser His
            180                 185                 190

Met Glu Ser Glu Glu Leu Asn Gly Ala Tyr Lys Ala Ile Pro Val Ala
        195                 200                 205

Gln Asp Leu Asn Ala Pro Ser Asp Trp Asp Ser Arg Gly Lys Asp Ser
    210                 215                 220

Tyr Glu Thr Ser Gln Leu Asp Asp Gln Ser Ala Glu Thr His Ser His
225                 230                 235                 240

Lys Gln Ser Arg Leu Tyr Lys Arg Lys Ala Asn Asp Glu Ser Asn Glu
                245                 250                 255

His Ser Asp Val Ile Asp Ser Gln Glu Leu Ser Lys Val Ser Arg Glu
            260                 265                 270

Phe His Ser His Glu Phe His Ser His Glu Asp Met Leu Val Val Asp
        275                 280                 285

Pro Lys Ser Lys Glu Glu Asp Lys His Leu Lys Phe Arg Ile Ser His
    290                 295                 300

Glu Leu Asp Ser Ala Ser Ser Glu Val Asn
305                 310


<210> SEQ ID NO 45
```

<211> LENGTH: 317
<212> TYPE: PRT
<213> ORGANISM: Artificial Sequence
<220> FEATURE:
<223> OTHER INFORMATION: Synthetic_SIAL_HUMAN

<400> SEQUENCE: 45

Met Lys Thr Ala Leu Ile Leu Leu Ser Ile Leu Gly Met Ala Cys Ala
1 5 10 15

Phe Ser Met Lys Asn Leu His Arg Arg Val Lys Ile Glu Asp Ser Glu
20 25 30

Glu Asn Gly Val Phe Lys Tyr Arg Pro Arg Tyr Tyr Leu Tyr Lys His
35 40 45

Ala Tyr Phe Tyr Pro His Leu Lys Arg Phe Pro Val Gln Gly Ser Ser
50 55 60

Asp Ser Ser Glu Glu Asn Gly Asp Asp Ser Ser Glu Glu Glu Glu Glu
65 70 75 80

Glu Glu Glu Thr Ser Asn Glu Gly Glu Asn Asn Glu Glu Ser Asn Glu
85 90 95

Asp Glu Asp Ser Glu Ala Glu Asn Thr Thr Leu Ser Ala Thr Thr Leu
100 105 110

Gly Tyr Gly Glu Asp Ala Thr Pro Gly Thr Gly Tyr Thr Gly Leu Ala
115 120 125

Ala Ile Gln Leu Pro Lys Lys Ala Gly Asp Ile Thr Asn Lys Ala Thr
130 135 140

Lys Glu Lys Glu Ser Asp Glu Glu Glu Glu Glu Glu Glu Glu Gly Asn
145 150 155 160

Glu Asn Glu Glu Ser Glu Ala Glu Val Asp Glu Asn Glu Gln Gly Ile
165 170 175

Asn Gly Thr Ser Thr Asn Ser Thr Glu Ala Glu Asn Gly Asn Gly Ser
180 185 190

Ser Gly Gly Asp Asn Gly Glu Glu Gly Glu Glu Glu Ser Val Thr Gly
195 200 205

Ala Asn Ala Glu Asp Thr Thr Glu Thr Gly Arg Gln Gly Lys Gly Thr
210 215 220

Ser Lys Thr Thr Thr Ser Pro Asn Gly Gly Phe Glu Pro Thr Thr Pro
225 230 235 240

Pro Gln Val Tyr Arg Thr Thr Ser Pro Pro Phe Gly Lys Thr Thr Thr
245 250 255

Val Glu Tyr Glu Gly Glu Tyr Glu Tyr Thr Gly Ala Asn Glu Tyr Asp
260 265 270

Asn Gly Tyr Glu Ile Tyr Glu Ser Glu Asn Gly Glu Pro Arg Gly Asp
275 280 285

Asn Tyr Arg Ala Tyr Glu Asp Glu Tyr Ser Tyr Phe Lys Gly Gln Gly
290 295 300

Tyr Asp Gly Tyr Asp Gly Gln Asn Tyr Tyr His His Gln
305 310 315

<210> SEQ ID NO 46
<211> LENGTH: 317
<212> TYPE: PRT
<213> ORGANISM: Artificial Sequence
<220> FEATURE:
<223> OTHER INFORMATION: Synthetic_APOE_HUMAN

<400> SEQUENCE: 46

Met Lys Val Leu Trp Ala Ala Leu Leu Val Thr Phe Leu Ala Gly Cys

```
1               5                   10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
            100                 105                 110

Lys Glu Leu Gln Ala Ala Gln Ala Arg Leu Gly Ala Asp Met Glu Asp
        115                 120                 125

Val Cys Gly Arg Leu Val Gln Tyr Arg Gly Glu Val Gln Ala Met Leu
    130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
                165                 170                 175

Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
        195                 200                 205

Arg Ala Ala Thr Val Gly Ser Leu Ala Gly Gln Pro Leu Gln Glu Arg
    210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
            260                 265                 270

Glu Ala Phe Gln Ala Arg Leu Lys Ser Trp Phe Glu Pro Leu Val Glu
        275                 280                 285

Asp Met Gln Arg Gln Trp Ala Gly Leu Val Glu Lys Val Gln Ala Ala
    290                 295                 300

Val Gly Thr Ser Ala Ala Pro Val Pro Ser Asp Asn His
305                 310                 315


<210> SEQ ID NO 47
<211> LENGTH: 322
<212> TYPE: PRT
<213> ORGANISM: Artificial Sequence
<220> FEATURE:
<223> OTHER INFORMATION: Synthetic_EPYC_HUMAN

<400> SEQUENCE: 47

Met Lys Thr Leu Ala Gly Leu Val Leu Gly Leu Val Ile Phe Asp Ala
1               5                   10                  15

Ala Val Thr Ala Pro Thr Leu Glu Ser Ile Asn Tyr Asp Ser Glu Thr
            20                  25                  30

Tyr Asp Ala Thr Leu Glu Asp Leu Asp Asn Leu Tyr Asn Tyr Glu Asn
        35                  40                  45

Ile Pro Val Asp Lys Val Glu Ile Glu Ile Ala Thr Val Met Pro Ser
```

```
    50                  55                  60

Gly Asn Arg Glu Leu Leu Thr Pro Pro Pro Gln Pro Glu Lys Ala Gln
65                  70                  75                  80

Glu Glu Glu Glu Glu Glu Glu Ser Thr Pro Arg Leu Ile Asp Gly Ser
                85                  90                  95

Ser Pro Gln Glu Pro Glu Phe Thr Gly Val Leu Gly Pro His Thr Asn
            100                 105                 110

Glu Asp Phe Pro Thr Cys Leu Leu Cys Thr Cys Ile Ser Thr Thr Val
        115                 120                 125

Tyr Cys Asp Asp His Glu Leu Asp Ala Ile Pro Pro Leu Pro Lys Asn
    130                 135                 140

Thr Ala Tyr Phe Tyr Ser Arg Phe Asn Arg Ile Lys Lys Ile Asn Lys
145                 150                 155                 160

Asn Asp Phe Ala Ser Leu Ser Asp Leu Lys Arg Ile Asp Leu Thr Ser
                165                 170                 175

Asn Leu Ile Ser Glu Ile Asp Glu Asp Ala Phe Arg Lys Leu Pro Gln
            180                 185                 190

Leu Arg Glu Leu Val Leu Arg Asp Asn Lys Ile Arg Gln Leu Pro Glu
        195                 200                 205

Leu Pro Thr Thr Leu Thr Phe Ile Asp Ile Ser Asn Asn Arg Leu Gly
    210                 215                 220

Arg Lys Gly Ile Lys Gln Glu Ala Phe Lys Asp Met Tyr Asp Leu His
225                 230                 235                 240

His Leu Tyr Leu Thr Asp Asn Asn Leu Asp His Ile Pro Leu Pro Leu
                245                 250                 255

Pro Glu Asn Leu Arg Ala Leu His Leu Gln Asn Asn Asn Ile Leu Glu
            260                 265                 270

Met His Glu Asp Thr Phe Cys Asn Val Lys Asn Leu Thr Tyr Ile Arg
        275                 280                 285

Lys Ala Leu Glu Asp Ile Arg Leu Asp Gly Asn Pro Ile Asn Leu Ser
    290                 295                 300

Lys Thr Pro Gln Ala Tyr Met Cys Leu Pro Arg Leu Pro Val Gly Ser
305                 310                 315                 320

Leu Val


<210> SEQ ID NO 48
<211> LENGTH: 332
<212> TYPE: PRT
<213> ORGANISM: Artificial Sequence
<220> FEATURE:
<223> OTHER INFORMATION: Synthetic_CLM9_HUMAN

<400> SEQUENCE: 48

Met Arg Leu Leu Val Leu Leu Trp Gly Cys Leu Leu Leu Pro Gly Tyr
1               5                   10                  15

Glu Ala Leu Glu Gly Pro Glu Glu Ile Ser Gly Phe Glu Gly Asp Thr
            20                  25                  30

Val Ser Leu Gln Cys Thr Tyr Arg Glu Glu Leu Arg Asp His Arg Lys
        35                  40                  45

Tyr Trp Cys Arg Lys Gly Gly Ile Leu Phe Ser Arg Cys Ser Gly Thr
    50                  55                  60

Ile Tyr Ala Glu Glu Glu Gly Gln Glu Thr Met Lys Gly Arg Val Ser
65                  70                  75                  80

Ile Arg Asp Ser Arg Gln Glu Leu Ser Leu Ile Val Thr Leu Trp Asn
                85                  90                  95
```

```
Leu Thr Leu Gln Asp Ala Gly Glu Tyr Trp Cys Gly Val Glu Lys Arg
            100                 105                 110

Gly Pro Asp Glu Ser Leu Leu Ile Ser Leu Phe Val Phe Pro Gly Pro
        115                 120                 125

Cys Cys Pro Pro Ser Pro Ser Pro Thr Phe Gln Pro Leu Ala Thr Thr
    130                 135                 140

Arg Leu Gln Pro Lys Ala Lys Ala Gln Gln Thr Gln Pro Pro Gly Leu
145                 150                 155                 160

Thr Ser Pro Gly Leu Tyr Pro Ala Ala Thr Thr Ala Lys Gln Gly Lys
                165                 170                 175

Thr Gly Ala Glu Ala Pro Pro Leu Pro Gly Thr Ser Gln Tyr Gly His
            180                 185                 190

Glu Arg Thr Ser Gln Tyr Thr Gly Thr Ser Pro His Pro Ala Thr Ser
        195                 200                 205

Pro Pro Ala Gly Ser Ser Arg Pro Pro Met Gln Leu Asp Ser Thr Ser
    210                 215                 220

Ala Glu Asp Thr Ser Pro Ala Leu Ser Ser Gly Ser Ser Lys Pro Arg
225                 230                 235                 240

Val Ser Ile Pro Met Val Arg Ile Leu Ala Pro Val Leu Val Leu Leu
                245                 250                 255

Ser Leu Leu Ser Ala Ala Gly Leu Ile Ala Phe Cys Ser His Leu Leu
            260                 265                 270

Leu Trp Arg Lys Glu Ala Gln Gln Ala Thr Glu Thr Gln Arg Asn Glu
        275                 280                 285

Lys Phe Cys Leu Ser Arg Leu Thr Ala Glu Glu Lys Glu Ala Pro Ser
    290                 295                 300

Gln Ala Pro Glu Gly Asp Val Ile Ser Met Pro Pro Leu His Thr Ser
305                 310                 315                 320

Glu Glu Glu Leu Gly Phe Ser Lys Phe Val Ser Ala
                325                 330


<210> SEQ ID NO 49
<211> LENGTH: 350
<212> TYPE: PRT
<213> ORGANISM: Artificial Sequence
<220> FEATURE:
<223> OTHER INFORMATION: Synthetic_YIPF3_HUMAN

<400> SEQUENCE: 49

Met Ala Thr Thr Ala Ala Pro Ala Gly Gly Ala Arg Asn Gly Ala Gly
1               5                   10                  15

Pro Glu Trp Gly Gly Phe Glu Glu Asn Ile Gln Gly Gly Gly Ser Ala
            20                  25                  30

Val Ile Asp Met Glu Asn Met Asp Asp Thr Ser Gly Ser Ser Phe Glu
        35                  40                  45

Asp Met Gly Glu Leu His Gln Arg Leu Arg Glu Glu Glu Val Asp Ala
    50                  55                  60

Asp Ala Ala Asp Ala Ala Ala Ala Glu Glu Glu Asp Gly Glu Phe Leu
65                  70                  75                  80

Gly Met Lys Gly Phe Lys Gly Gln Leu Ser Arg Gln Val Ala Asp Gln
                85                  90                  95

Met Trp Gln Ala Gly Lys Arg Gln Ala Ser Arg Ala Phe Ser Leu Tyr
            100                 105                 110

Ala Asn Ile Asp Ile Leu Arg Pro Tyr Phe Asp Val Glu Pro Ala Gln
        115                 120                 125
```

```
Val Arg Ser Arg Leu Leu Glu Ser Met Ile Pro Ile Lys Met Val Asn
    130                 135                 140

Phe Pro Gln Lys Ile Ala Gly Glu Leu Tyr Gly Pro Leu Met Leu Val
145                 150                 155                 160

Phe Thr Leu Val Ala Ile Leu Leu His Gly Met Lys Thr Ser Asp Thr
                165                 170                 175

Ile Ile Arg Glu Gly Thr Leu Met Gly Thr Ala Ile Gly Thr Cys Phe
            180                 185                 190

Gly Tyr Trp Leu Gly Val Ser Ser Phe Ile Tyr Phe Leu Ala Tyr Leu
        195                 200                 205

Cys Asn Ala Gln Ile Thr Met Leu Gln Met Leu Ala Leu Leu Gly Tyr
    210                 215                 220

Gly Leu Phe Gly His Cys Ile Val Leu Phe Ile Thr Tyr Asn Ile His
225                 230                 235                 240

Leu His Ala Leu Phe Tyr Leu Phe Trp Leu Leu Val Gly Gly Leu Ser
                245                 250                 255

Thr Leu Arg Met Val Ala Val Leu Val Ser Arg Thr Val Gly Pro Thr
            260                 265                 270

Gln Arg Leu Leu Leu Cys Gly Thr Leu Ala Ala Leu His Met Leu Phe
        275                 280                 285

Leu Leu Tyr Leu His Phe Ala Tyr His Lys Val Val Glu Gly Ile Leu
    290                 295                 300

Asp Thr Leu Glu Gly Pro Asn Ile Pro Pro Ile Gln Arg Val Pro Arg
305                 310                 315                 320

Asp Ile Pro Ala Met Leu Pro Ala Ala Arg Leu Pro Thr Thr Val Leu
                325                 330                 335

Asn Ala Thr Ala Lys Ala Val Ala Val Thr Leu Gln Ser His
            340                 345                 350


<210> SEQ ID NO 50
<211> LENGTH: 352
<212> TYPE: PRT
<213> ORGANISM: Artificial Sequence
<220> FEATURE:
<223> OTHER INFORMATION: Synthetic_CCR5_HUMAN

<400> SEQUENCE: 50

Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
            20                  25                  30

Leu Pro Pro Leu Tyr Ser Leu Val Phe Ile Phe Gly Phe Val Gly Asn
        35                  40                  45

Met Leu Val Ile Leu Ile Leu Ile Asn Cys Lys Arg Leu Lys Ser Met
    50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
            100                 105                 110

Phe Ser Gly Ile Phe Phe Ile Ile Leu Leu Thr Ile Asp Arg Tyr Leu
        115                 120                 125

Ala Val Val His Ala Val Phe Ala Leu Lys Ala Arg Thr Val Thr Phe
    130                 135                 140
```

```
Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
                165                 170                 175

Thr Cys Ser Ser His Phe Pro Tyr Ser Gln Tyr Gln Phe Trp Lys Asn
            180                 185                 190

Phe Gln Thr Leu Lys Ile Val Ile Leu Gly Leu Val Leu Pro Leu Leu
        195                 200                 205

Val Met Val Ile Cys Tyr Ser Gly Ile Leu Lys Thr Leu Leu Arg Cys
    210                 215                 220

Arg Asn Glu Lys Lys Arg His Arg Ala Val Arg Leu Ile Phe Thr Ile
225                 230                 235                 240

Met Ile Val Tyr Phe Leu Phe Trp Ala Pro Tyr Asn Ile Val Leu Leu
                245                 250                 255

Leu Asn Thr Phe Gln Glu Phe Phe Gly Leu Asn Asn Cys Ser Ser Ser
            260                 265                 270

Asn Arg Leu Asp Gln Ala Met Gln Val Thr Glu Thr Leu Gly Met Thr
        275                 280                 285

His Cys Cys Ile Asn Pro Ile Ile Tyr Ala Phe Val Gly Glu Lys Phe
    290                 295                 300

Arg Asn Tyr Leu Leu Val Phe Phe Gln Lys His Ile Ala Lys Arg Phe
305                 310                 315                 320

Cys Lys Cys Cys Ser Ile Phe Gln Gln Glu Ala Pro Glu Arg Ala Ser
                325                 330                 335

Ser Val Tyr Thr Arg Ser Thr Gly Glu Gln Glu Ile Ser Val Gly Leu
            340                 345                 350


<210> SEQ ID NO 51
<211> LENGTH: 353
<212> TYPE: PRT
<213> ORGANISM: Artificial Sequence
<220> FEATURE:
<223> OTHER INFORMATION: Synthetic_TPO_HUMAN

<400> SEQUENCE: 51

Met Glu Leu Thr Glu Leu Leu Leu Val Val Met Leu Leu Leu Thr Ala
1               5                   10                  15

Arg Leu Thr Leu Ser Ser Pro Ala Pro Pro Ala Cys Asp Leu Arg Val
            20                  25                  30

Leu Ser Lys Leu Leu Arg Asp Ser His Val Leu His Ser Arg Leu Ser
        35                  40                  45

Gln Cys Pro Glu Val His Pro Leu Pro Thr Pro Val Leu Leu Pro Ala
    50                  55                  60

Val Asp Phe Ser Leu Gly Glu Trp Lys Thr Gln Met Glu Glu Thr Lys
65                  70                  75                  80

Ala Gln Asp Ile Leu Gly Ala Val Thr Leu Leu Leu Glu Gly Val Met
                85                  90                  95

Ala Ala Arg Gly Gln Leu Gly Pro Thr Cys Leu Ser Ser Leu Leu Gly
            100                 105                 110

Gln Leu Ser Gly Gln Val Arg Leu Leu Leu Gly Ala Leu Gln Ser Leu
        115                 120                 125

Leu Gly Thr Gln Leu Pro Pro Gln Gly Arg Thr Thr Ala His Lys Asp
    130                 135                 140

Pro Asn Ala Ile Phe Leu Ser Phe Gln His Leu Leu Arg Gly Lys Val
145                 150                 155                 160
```

Arg Phe Leu Met Leu Val Gly Gly Ser Thr Leu Cys Val Arg Arg Ala
165 170 175

Pro Pro Thr Thr Ala Val Pro Ser Arg Thr Ser Leu Val Leu Thr Leu
180 185 190

Asn Glu Leu Pro Asn Arg Thr Ser Gly Leu Leu Glu Thr Asn Phe Thr
195 200 205

Ala Ser Ala Arg Thr Thr Gly Ser Gly Leu Leu Lys Trp Gln Gln Gly
210 215 220

Phe Arg Ala Lys Ile Pro Gly Leu Leu Asn Gln Thr Ser Arg Ser Leu
225 230 235 240

Asp Gln Ile Pro Gly Tyr Leu Asn Arg Ile His Glu Leu Leu Asn Gly
245 250 255

Thr Arg Gly Leu Phe Pro Gly Pro Ser Arg Arg Thr Leu Gly Ala Pro
260 265 270

Asp Ile Ser Ser Gly Thr Ser Asp Thr Gly Ser Leu Pro Pro Asn Leu
275 280 285

Gln Pro Gly Tyr Ser Pro Ser Pro Thr His Pro Pro Thr Gly Gln Tyr
290 295 300

Thr Leu Phe Pro Leu Pro Pro Thr Leu Pro Thr Pro Val Val Gln Leu
305 310 315 320

His Pro Leu Leu Pro Asp Pro Ser Ala Pro Thr Pro Thr Pro Thr Ser
325 330 335

Pro Leu Leu Asn Thr Ser Tyr Thr His Ser Gln Asn Leu Ser Gln Glu
340 345 350

Gly

<210> SEQ ID NO 52
<211> LENGTH: 367
<212> TYPE: PRT
<213> ORGANISM: Artificial Sequence
<220> FEATURE:
<223> OTHER INFORMATION: Synthetic_FETUA_HUMAN

<400> SEQUENCE: 52

Met Lys Ser Leu Val Leu Leu Leu Cys Leu Ala Gln Leu Trp Gly Cys
1 5 10 15

His Ser Ala Pro His Gly Pro Gly Leu Ile Tyr Arg Gln Pro Asn Cys
20 25 30

Asp Asp Pro Glu Thr Glu Glu Ala Ala Leu Val Ala Ile Asp Tyr Ile
35 40 45

Asn Gln Asn Leu Pro Trp Gly Tyr Lys His Thr Leu Asn Gln Ile Asp
50 55 60

Glu Val Lys Val Trp Pro Gln Gln Pro Ser Gly Glu Leu Phe Glu Ile
65 70 75 80

Glu Ile Asp Thr Leu Glu Thr Thr Cys His Val Leu Asp Pro Thr Pro
85 90 95

Val Ala Arg Cys Ser Val Arg Gln Leu Lys Glu His Ala Val Glu Gly
100 105 110

Asp Cys Asp Phe Gln Leu Leu Lys Leu Asp Gly Lys Phe Ser Val Val
115 120 125

Tyr Ala Lys Cys Asp Ser Ser Pro Asp Ser Ala Glu Asp Val Arg Lys
130 135 140

Val Cys Gln Asp Cys Pro Leu Leu Ala Pro Leu Asn Asp Thr Arg Val
145 150 155 160

```
Val His Ala Ala Lys Ala Ala Leu Ala Ala Phe Asn Ala Gln Asn Asn
                165                 170                 175

Gly Ser Asn Phe Gln Leu Glu Glu Ile Ser Arg Ala Gln Leu Val Pro
            180                 185                 190

Leu Pro Pro Ser Thr Tyr Val Glu Phe Thr Val Ser Gly Thr Asp Cys
        195                 200                 205

Val Ala Lys Glu Ala Thr Glu Ala Ala Lys Cys Asn Leu Leu Ala Glu
    210                 215                 220

Lys Gln Tyr Gly Phe Cys Lys Ala Thr Leu Ser Glu Lys Leu Gly Gly
225                 230                 235                 240

Ala Glu Val Ala Val Thr Cys Met Val Phe Gln Thr Gln Pro Val Ser
                245                 250                 255

Ser Gln Pro Gln Pro Glu Gly Ala Asn Glu Ala Val Pro Thr Pro Val
            260                 265                 270

Val Asp Pro Asp Ala Pro Pro Ser Pro Pro Leu Gly Ala Pro Gly Leu
        275                 280                 285

Pro Pro Ala Gly Ser Pro Pro Asp Ser His Val Leu Leu Ala Ala Pro
    290                 295                 300

Pro Gly His Gln Leu His Arg Ala His Tyr Asp Leu Arg His Thr Phe
305                 310                 315                 320

Met Gly Val Val Ser Leu Gly Ser Pro Ser Gly Glu Val Ser His Pro
                325                 330                 335

Arg Lys Thr Arg Thr Val Val Gln Pro Ser Val Gly Ala Ala Ala Gly
            340                 345                 350

Pro Val Val Pro Pro Cys Pro Gly Arg Ile Arg His Phe Lys Val
        355                 360                 365
```

<210> SEQ ID NO 53
<211> LENGTH: 368
<212> TYPE: PRT
<213> ORGANISM: Artificial Sequence
<220> FEATURE:
<223> OTHER INFORMATION: Synthetic_PGS1_HUMAN

<400> SEQUENCE: 53

```
Met Trp Pro Leu Trp Arg Leu Val Ser Leu Leu Ala Leu Ser Gln Ala
1               5                   10                  15

Leu Pro Phe Glu Gln Arg Gly Phe Trp Asp Phe Thr Leu Asp Asp Gly
            20                  25                  30

Pro Phe Met Met Asn Asp Glu Glu Ala Ser Gly Ala Asp Thr Ser Gly
        35                  40                  45

Val Leu Asp Pro Asp Ser Val Thr Pro Thr Tyr Ser Ala Met Cys Pro
    50                  55                  60

Phe Gly Cys His Cys His Leu Arg Val Val Gln Cys Ser Asp Leu Gly
65                  70                  75                  80

Leu Lys Ser Val Pro Lys Glu Ile Ser Pro Asp Thr Thr Leu Leu Asp
                85                  90                  95

Leu Gln Asn Asn Asp Ile Ser Glu Leu Arg Lys Asp Asp Phe Lys Gly
            100                 105                 110

Leu Gln His Leu Tyr Ala Leu Val Leu Val Asn Asn Lys Ile Ser Lys
        115                 120                 125

Ile His Glu Lys Ala Phe Ser Pro Leu Arg Lys Leu Gln Lys Leu Tyr
    130                 135                 140

Ile Ser Lys Asn His Leu Val Glu Ile Pro Pro Asn Leu Pro Ser Ser
145                 150                 155                 160
```

```
Leu Val Glu Leu Arg Ile His Asp Asn Arg Ile Arg Lys Val Pro Lys
                165                 170                 175

Gly Val Phe Ser Gly Leu Arg Asn Met Asn Cys Ile Glu Met Gly Gly
            180                 185                 190

Asn Pro Leu Glu Asn Ser Gly Phe Glu Pro Gly Ala Phe Asp Gly Leu
        195                 200                 205

Lys Leu Asn Tyr Leu Arg Ile Ser Glu Ala Lys Leu Thr Gly Ile Pro
    210                 215                 220

Lys Asp Leu Pro Glu Thr Leu Asn Glu Leu His Leu Asp His Asn Lys
225                 230                 235                 240

Ile Gln Ala Ile Glu Leu Glu Asp Leu Leu Arg Tyr Ser Lys Leu Tyr
                245                 250                 255

Arg Leu Gly Leu Gly His Asn Gln Ile Arg Met Ile Glu Asn Gly Ser
            260                 265                 270

Leu Ser Phe Leu Pro Thr Leu Arg Glu Leu His Leu Asp Asn Asn Lys
        275                 280                 285

Leu Ala Arg Val Pro Ser Gly Leu Pro Asp Leu Lys Leu Leu Gln Val
    290                 295                 300

Val Tyr Leu His Ser Asn Asn Ile Thr Lys Val Gly Val Asn Asp Phe
305                 310                 315                 320

Cys Pro Met Gly Phe Gly Val Lys Arg Ala Tyr Tyr Asn Gly Ile Ser
                325                 330                 335

Leu Phe Asn Asn Pro Val Pro Tyr Trp Glu Val Gln Pro Ala Thr Phe
            340                 345                 350

Arg Cys Val Thr Asp Arg Leu Ala Ile Gln Phe Gly Asn Tyr Lys Lys
        355                 360                 365


<210> SEQ ID NO 54
<211> LENGTH: 377
<212> TYPE: PRT
<213> ORGANISM: Artificial Sequence
<220> FEATURE:
<223> OTHER INFORMATION: Synthetic_IGHG3_HUMAN

<400> SEQUENCE: 54

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160
```

```
Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375
```

```
<210> SEQ ID NO 55
<211> LENGTH: 383
<212> TYPE: PRT
<213> ORGANISM: Artificial Sequence
<220> FEATURE:
<223> OTHER INFORMATION: Synthetic_DLK1_HUMAN

<400> SEQUENCE: 55

Met Thr Ala Thr Glu Ala Leu Leu Arg Val Leu Leu Leu Leu Leu Ala
1               5                   10                  15

Phe Gly His Ser Thr Tyr Gly Ala Glu Cys Phe Pro Ala Cys Asn Pro
            20                  25                  30

Gln Asn Gly Phe Cys Glu Asp Asp Asn Val Cys Arg Cys Gln Pro Gly
        35                  40                  45

Trp Gln Gly Pro Leu Cys Asp Gln Cys Val Thr Ser Pro Gly Cys Leu
    50                  55                  60

His Gly Leu Cys Gly Glu Pro Gly Gln Cys Ile Cys Thr Asp Gly Trp
65                  70                  75                  80

Asp Gly Glu Leu Cys Asp Arg Asp Val Arg Ala Cys Ser Ser Ala Pro
                85                  90                  95

Cys Ala Asn Asn Arg Thr Cys Val Ser Leu Asp Asp Gly Leu Tyr Glu
            100                 105                 110

Cys Ser Cys Ala Pro Gly Tyr Ser Gly Lys Asp Cys Gln Lys Lys Asp
        115                 120                 125

Gly Pro Cys Val Ile Asn Gly Ser Pro Cys Gln His Gly Gly Thr Cys
    130                 135                 140
```

```
Val Asp Asp Glu Gly Arg Ala Ser His Ala Ser Cys Leu Cys Pro Pro
145                 150                 155                 160

Gly Phe Ser Gly Asn Phe Cys Glu Ile Val Ala Asn Ser Cys Thr Pro
                165                 170                 175

Asn Pro Cys Glu Asn Asp Gly Val Cys Thr Asp Ile Gly Gly Asp Phe
            180                 185                 190

Arg Cys Arg Cys Pro Ala Gly Phe Ile Asp Lys Thr Cys Ser Arg Pro
        195                 200                 205

Val Thr Asn Cys Ala Ser Ser Pro Cys Gln Asn Gly Gly Thr Cys Leu
    210                 215                 220

Gln His Thr Gln Val Ser Tyr Glu Cys Leu Cys Lys Pro Glu Phe Thr
225                 230                 235                 240

Gly Leu Thr Cys Val Lys Lys Arg Ala Leu Ser Pro Gln Gln Val Thr
                245                 250                 255

Arg Leu Pro Ser Gly Tyr Gly Leu Ala Tyr Arg Leu Thr Pro Gly Val
            260                 265                 270

His Glu Leu Pro Val Gln Gln Pro Glu His Arg Ile Leu Lys Val Ser
        275                 280                 285

Met Lys Glu Leu Asn Lys Lys Thr Pro Leu Leu Thr Glu Gly Gln Ala
    290                 295                 300

Ile Cys Phe Thr Ile Leu Gly Val Leu Thr Ser Leu Val Val Leu Gly
305                 310                 315                 320

Thr Val Gly Ile Val Phe Leu Asn Lys Cys Glu Thr Trp Val Ser Asn
                325                 330                 335

Leu Arg Tyr Asn His Met Leu Arg Lys Lys Lys Asn Leu Leu Leu Gln
            340                 345                 350

Tyr Asn Ser Gly Glu Asp Leu Ala Val Asn Ile Ile Phe Pro Glu Lys
        355                 360                 365

Ile Asp Met Thr Thr Phe Ser Lys Glu Ala Gly Asp Glu Glu Ile
    370                 375                 380
```

<210> SEQ ID NO 56
<211> LENGTH: 392
<212> TYPE: PRT
<213> ORGANISM: Artificial Sequence
<220> FEATURE:
<223> OTHER INFORMATION: Synthetic_MCP_HUMAN

<400> SEQUENCE: 56

```
Met Glu Pro Pro Gly Arg Arg Glu Cys Pro Phe Pro Ser Trp Arg Phe
1               5                   10                  15

Pro Gly Leu Leu Leu Ala Ala Met Val Leu Leu Leu Tyr Ser Phe Ser
            20                  25                  30

Asp Ala Cys Glu Glu Pro Pro Thr Phe Glu Ala Met Glu Leu Ile Gly
        35                  40                  45

Lys Pro Lys Pro Tyr Tyr Glu Ile Gly Glu Arg Val Asp Tyr Lys Cys
    50                  55                  60

Lys Lys Gly Tyr Phe Tyr Ile Pro Pro Leu Ala Thr His Thr Ile Cys
65                  70                  75                  80

Asp Arg Asn His Thr Trp Leu Pro Val Ser Asp Asp Ala Cys Tyr Arg
                85                  90                  95

Glu Thr Cys Pro Tyr Ile Arg Asp Pro Leu Asn Gly Gln Ala Val Pro
            100                 105                 110

Ala Asn Gly Thr Tyr Glu Phe Gly Tyr Gln Met His Phe Ile Cys Asn
        115                 120                 125
```

Glu Gly Tyr Tyr Leu Ile Gly Glu Glu Ile Leu Tyr Cys Glu Leu Lys
130 135 140

Gly Ser Val Ala Ile Trp Ser Gly Lys Pro Pro Ile Cys Glu Lys Val
145 150 155 160

Leu Cys Thr Pro Pro Pro Lys Ile Lys Asn Gly Lys His Thr Phe Ser
165 170 175

Glu Val Glu Val Phe Glu Tyr Leu Asp Ala Val Thr Tyr Ser Cys Asp
180 185 190

Pro Ala Pro Gly Pro Asp Pro Phe Ser Leu Ile Gly Glu Ser Thr Ile
195 200 205

Tyr Cys Gly Asp Asn Ser Val Trp Ser Arg Ala Ala Pro Glu Cys Lys
210 215 220

Val Val Lys Cys Arg Phe Pro Val Val Glu Asn Gly Lys Gln Ile Ser
225 230 235 240

Gly Phe Gly Lys Lys Phe Tyr Tyr Lys Ala Thr Val Met Phe Glu Cys
245 250 255

Asp Lys Gly Phe Tyr Leu Asp Gly Ser Asp Thr Ile Val Cys Asp Ser
260 265 270

Asn Ser Thr Trp Asp Pro Pro Val Pro Lys Cys Leu Lys Val Leu Pro
275 280 285

Pro Ser Ser Thr Lys Pro Pro Ala Leu Ser His Ser Val Ser Thr Ser
290 295 300

Ser Thr Thr Lys Ser Pro Ala Ser Ser Ala Ser Gly Pro Arg Pro Thr
305 310 315 320

Tyr Lys Pro Pro Val Ser Asn Tyr Pro Gly Tyr Pro Lys Pro Glu Glu
325 330 335

Gly Ile Leu Asp Ser Leu Asp Val Trp Val Ile Ala Val Ile Val Ile
340 345 350

Ala Ile Val Val Gly Val Ala Val Ile Cys Val Val Pro Tyr Arg Tyr
355 360 365

Leu Gln Arg Arg Lys Lys Lys Gly Thr Tyr Leu Thr Asp Glu Thr His
370 375 380

Arg Glu Val Lys Phe Thr Ser Leu
385 390

<210> SEQ ID NO 57
<211> LENGTH: 392
<212> TYPE: PRT
<213> ORGANISM: Artificial Sequence
<220> FEATURE:
<223> OTHER INFORMATION: Synthetic_PRP1_HUMAN

<400> SEQUENCE: 57

Met Leu Leu Ile Leu Leu Ser Val Ala Leu Leu Ala Leu Ser Ser Ala
1 5 10 15

Gln Asn Leu Asn Glu Asp Val Ser Gln Glu Glu Ser Pro Ser Leu Ile
20 25 30

Ala Gly Asn Pro Gln Gly Pro Ser Pro Gln Gly Gly Asn Lys Pro Gln
35 40 45

Gly Pro Pro Pro Pro Pro Gly Lys Pro Gln Gly Pro Pro Pro Gln Gly
50 55 60

Gly Asn Lys Pro Gln Gly Pro Pro Pro Pro Gly Lys Pro Gln Gly Pro
65 70 75 80

Pro Pro Gln Gly Asp Lys Ser Arg Ser Pro Arg Ser Pro Pro Gly Lys
85 90 95

```
Pro Gln Gly Pro Pro Pro Gln Gly Gly Asn Gln Pro Gln Gly Pro Pro
            100                 105                 110

Pro Pro Pro Gly Lys Pro Gln Gly Pro Pro Pro Gln Gly Gly Asn Lys
        115                 120                 125

Pro Gln Gly Pro Pro Pro Pro Gly Lys Pro Gln Gly Pro Pro Pro Gln
    130                 135                 140

Gly Asp Lys Ser Gln Ser Pro Arg Ser Pro Pro Gly Lys Pro Gln Gly
145                 150                 155                 160

Pro Pro Pro Gln Gly Gly Asn Gln Pro Gln Gly Pro Pro Pro Pro Pro
                165                 170                 175

Gly Lys Pro Gln Gly Pro Pro Pro Gln Gly Gly Asn Lys Pro Gln Gly
            180                 185                 190

Pro Pro Pro Pro Gly Lys Pro Gln Gly Pro Pro Pro Gln Gly Asp Lys
        195                 200                 205

Ser Gln Ser Pro Arg Ser Pro Pro Gly Lys Pro Gln Gly Pro Pro Pro
    210                 215                 220

Gln Gly Gly Asn Gln Pro Gln Gly Pro Pro Pro Pro Pro Gly Lys Pro
225                 230                 235                 240

Gln Gly Pro Pro Gln Gln Gly Gly Asn Arg Pro Gln Gly Pro Pro Pro
                245                 250                 255

Pro Gly Lys Pro Gln Gly Pro Pro Pro Gln Gly Asp Lys Ser Arg Ser
            260                 265                 270

Pro Gln Ser Pro Pro Gly Lys Pro Gln Gly Pro Pro Pro Gln Gly Gly
        275                 280                 285

Asn Gln Pro Gln Gly Pro Pro Pro Pro Pro Gly Lys Pro Gln Gly Pro
    290                 295                 300

Pro Pro Gln Gly Gly Asn Lys Pro Gln Gly Pro Pro Pro Pro Gly Lys
305                 310                 315                 320

Pro Gln Gly Pro Pro Ala Gln Gly Gly Ser Lys Ser Gln Ser Ala Arg
                325                 330                 335

Ser Pro Pro Gly Lys Pro Gln Gly Pro Pro Gln Gln Glu Gly Asn Asn
            340                 345                 350

Pro Gln Gly Pro Pro Pro Pro Ala Gly Gly Asn Pro Gln Gln Pro Gln
        355                 360                 365

Ala Pro Pro Ala Gly Gln Pro Gln Gly Pro Pro Arg Pro Pro Gln Gly
    370                 375                 380

Gly Arg Pro Ser Arg Pro Pro Gln
385                 390
```

<210> SEQ ID NO 58
<211> LENGTH: 397
<212> TYPE: PRT
<213> ORGANISM: Artificial Sequence
<220> FEATURE:
<223> OTHER INFORMATION: Synthetic_X3CL1_HUMAN

<400> SEQUENCE: 58

```
Met Ala Pro Ile Ser Leu Ser Trp Leu Leu Arg Leu Ala Thr Phe Cys
1               5                   10                  15

His Leu Thr Val Leu Leu Ala Gly Gln His His Gly Val Thr Lys Cys
            20                  25                  30

Asn Ile Thr Cys Ser Lys Met Thr Ser Lys Ile Pro Val Ala Leu Leu
        35                  40                  45

Ile His Tyr Gln Gln Asn Gln Ala Ser Cys Gly Lys Arg Ala Ile Ile
    50                  55                  60
```

```
Leu Glu Thr Arg Gln His Arg Leu Phe Cys Ala Asp Pro Lys Glu Gln
65                  70                  75                  80

Trp Val Lys Asp Ala Met Gln His Leu Asp Arg Gln Ala Ala Ala Leu
                85                  90                  95

Thr Arg Asn Gly Gly Thr Phe Glu Lys Gln Ile Gly Glu Val Lys Pro
            100                 105                 110

Arg Thr Thr Pro Ala Ala Gly Gly Met Asp Glu Ser Val Val Leu Glu
        115                 120                 125

Pro Glu Ala Thr Gly Glu Ser Ser Ser Leu Glu Pro Thr Pro Ser Ser
    130                 135                 140

Gln Glu Ala Gln Arg Ala Leu Gly Thr Ser Pro Glu Leu Pro Thr Gly
145                 150                 155                 160

Val Thr Gly Ser Ser Gly Thr Arg Leu Pro Pro Thr Pro Lys Ala Gln
                165                 170                 175

Asp Gly Gly Pro Val Gly Thr Glu Leu Phe Arg Val Pro Pro Val Ser
            180                 185                 190

Thr Ala Ala Thr Trp Gln Ser Ser Ala Pro His Gln Pro Gly Pro Ser
        195                 200                 205

Leu Trp Ala Glu Ala Lys Thr Ser Glu Ala Pro Ser Thr Gln Asp Pro
    210                 215                 220

Ser Thr Gln Ala Ser Thr Ala Ser Ser Pro Ala Pro Glu Glu Asn Ala
225                 230                 235                 240

Pro Ser Glu Gly Gln Arg Val Trp Gly Gln Gly Gln Ser Pro Arg Pro
                245                 250                 255

Glu Asn Ser Leu Glu Arg Glu Glu Met Gly Pro Val Pro Ala His Thr
            260                 265                 270

Asp Ala Phe Gln Asp Trp Gly Pro Gly Ser Met Ala His Val Ser Val
        275                 280                 285

Val Pro Val Ser Ser Glu Gly Thr Pro Ser Arg Glu Pro Val Ala Ser
    290                 295                 300

Gly Ser Trp Thr Pro Lys Ala Glu Glu Pro Ile His Ala Thr Met Asp
305                 310                 315                 320

Pro Gln Arg Leu Gly Val Leu Ile Thr Pro Val Pro Asp Ala Gln Ala
                325                 330                 335

Ala Thr Arg Arg Gln Ala Val Gly Leu Leu Ala Phe Leu Gly Leu Leu
            340                 345                 350

Phe Cys Leu Gly Val Ala Met Phe Thr Tyr Gln Ser Leu Gln Gly Cys
        355                 360                 365

Pro Arg Lys Met Ala Gly Glu Met Ala Glu Gly Leu Arg Tyr Ile Pro
    370                 375                 380

Arg Ser Cys Gly Ser Asn Ser Tyr Val Leu Val Pro Val
385                 390                 395
```

<210> SEQ ID NO 59
<211> LENGTH: 400
<212> TYPE: PRT
<213> ORGANISM: Artificial Sequence
<220> FEATURE:
<223> OTHER INFORMATION: Synthetic_LEUK_HUMAN

<400> SEQUENCE: 59

```
Met Ala Thr Leu Leu Leu Leu Leu Gly Val Leu Val Val Ser Pro Asp
1               5                   10                  15

Ala Leu Gly Ser Thr Thr Ala Val Gln Thr Pro Thr Ser Gly Glu Pro
            20                  25                  30
```

```
Leu Val Ser Thr Ser Glu Pro Leu Ser Ser Lys Met Tyr Thr Thr Ser
        35                  40                  45

Ile Thr Ser Asp Pro Lys Ala Asp Ser Thr Gly Asp Gln Thr Ser Ala
    50                  55                  60

Leu Pro Pro Ser Thr Ser Ile Asn Glu Gly Ser Pro Leu Trp Thr Ser
65                  70                  75                  80

Ile Gly Ala Ser Thr Gly Ser Pro Leu Pro Glu Pro Thr Thr Tyr Gln
                85                  90                  95

Glu Val Ser Ile Lys Met Ser Ser Val Pro Gln Glu Thr Pro His Ala
            100                 105                 110

Thr Ser His Pro Ala Val Pro Ile Thr Ala Asn Ser Leu Gly Ser His
        115                 120                 125

Thr Val Thr Gly Gly Thr Ile Thr Thr Asn Ser Pro Glu Thr Ser Ser
    130                 135                 140

Arg Thr Ser Gly Ala Pro Val Thr Thr Ala Ala Ser Ser Leu Glu Thr
145                 150                 155                 160

Ser Arg Gly Thr Ser Gly Pro Pro Leu Thr Met Ala Thr Val Ser Leu
                165                 170                 175

Glu Thr Ser Lys Gly Thr Ser Gly Pro Pro Val Thr Met Ala Thr Asp
            180                 185                 190

Ser Leu Glu Thr Ser Thr Gly Thr Thr Gly Pro Pro Val Thr Met Thr
        195                 200                 205

Thr Gly Ser Leu Glu Pro Ser Ser Gly Ala Ser Gly Pro Gln Val Ser
    210                 215                 220

Ser Val Lys Leu Ser Thr Met Met Ser Pro Thr Thr Ser Thr Asn Ala
225                 230                 235                 240

Ser Thr Val Pro Phe Arg Asn Pro Asp Glu Asn Ser Arg Gly Met Leu
                245                 250                 255

Pro Val Ala Val Leu Val Ala Leu Leu Ala Val Ile Val Leu Val Ala
            260                 265                 270

Leu Leu Leu Leu Trp Arg Arg Arg Gln Lys Arg Arg Thr Gly Ala Leu
        275                 280                 285

Val Leu Ser Arg Gly Gly Lys Arg Asn Gly Val Val Asp Ala Trp Ala
    290                 295                 300

Gly Pro Ala Gln Val Pro Glu Glu Gly Ala Val Thr Val Thr Val Gly
305                 310                 315                 320

Gly Ser Gly Gly Asp Lys Gly Ser Gly Phe Pro Asp Gly Glu Gly Ser
                325                 330                 335

Ser Arg Arg Pro Thr Leu Thr Thr Phe Phe Gly Arg Arg Lys Ser Arg
            340                 345                 350

Gln Gly Ser Leu Ala Met Glu Glu Leu Lys Ser Gly Ser Gly Pro Ser
        355                 360                 365

Leu Lys Gly Glu Glu Glu Pro Leu Val Ala Ser Glu Asp Gly Ala Val
    370                 375                 380

Asp Ala Pro Ala Pro Asp Glu Pro Glu Gly Gly Asp Gly Ala Ala Pro
385                 390                 395                 400
```

<210> SEQ ID NO 60
<211> LENGTH: 410
<212> TYPE: PRT
<213> ORGANISM: Artificial Sequence
<220> FEATURE:
<223> OTHER INFORMATION: Synthetic_LAMP2_HUMAN

<400> SEQUENCE: 60

-continued

```
Met Val Cys Phe Arg Leu Phe Pro Val Pro Gly Ser Gly Leu Val Leu
1               5                   10                  15

Val Cys Leu Val Leu Gly Ala Val Arg Ser Tyr Ala Leu Glu Leu Asn
            20                  25                  30

Leu Thr Asp Ser Glu Asn Ala Thr Cys Leu Tyr Ala Lys Trp Gln Met
        35                  40                  45

Asn Phe Thr Val Arg Tyr Glu Thr Thr Asn Lys Thr Tyr Lys Thr Val
    50                  55                  60

Thr Ile Ser Asp His Gly Thr Val Thr Tyr Asn Gly Ser Ile Cys Gly
65                  70                  75                  80

Asp Asp Gln Asn Gly Pro Lys Ile Ala Val Gln Phe Gly Pro Gly Phe
                85                  90                  95

Ser Trp Ile Ala Asn Phe Thr Lys Ala Ala Ser Thr Tyr Ser Ile Asp
            100                 105                 110

Ser Val Ser Phe Ser Tyr Asn Thr Gly Asp Asn Thr Thr Phe Pro Asp
        115                 120                 125

Ala Glu Asp Lys Gly Ile Leu Thr Val Asp Glu Leu Leu Ala Ile Arg
    130                 135                 140

Ile Pro Leu Asn Asp Leu Phe Arg Cys Asn Ser Leu Ser Thr Leu Glu
145                 150                 155                 160

Lys Asn Asp Val Val Gln His Tyr Trp Asp Val Leu Val Gln Ala Phe
                165                 170                 175

Val Gln Asn Gly Thr Val Ser Thr Asn Glu Phe Leu Cys Asp Lys Asp
            180                 185                 190

Lys Thr Ser Thr Val Ala Pro Thr Ile His Thr Thr Val Pro Ser Pro
        195                 200                 205

Thr Thr Thr Pro Thr Pro Lys Glu Lys Pro Glu Ala Gly Thr Tyr Ser
    210                 215                 220

Val Asn Asn Gly Asn Asp Thr Cys Leu Leu Ala Thr Met Gly Leu Gln
225                 230                 235                 240

Leu Asn Ile Thr Gln Asp Lys Val Ala Ser Val Ile Asn Ile Asn Pro
                245                 250                 255

Asn Thr Thr His Ser Thr Gly Ser Cys Arg Ser His Thr Ala Leu Leu
            260                 265                 270

Arg Leu Asn Ser Ser Thr Ile Lys Tyr Leu Asp Phe Val Phe Ala Val
        275                 280                 285

Lys Asn Glu Asn Arg Phe Tyr Leu Lys Glu Val Asn Ile Ser Met Tyr
    290                 295                 300

Leu Val Asn Gly Ser Val Phe Ser Ile Ala Asn Asn Asn Leu Ser Tyr
305                 310                 315                 320

Trp Asp Ala Pro Leu Gly Ser Ser Tyr Met Cys Asn Lys Glu Gln Thr
                325                 330                 335

Val Ser Val Ser Gly Ala Phe Gln Ile Asn Thr Phe Asp Leu Arg Val
            340                 345                 350

Gln Pro Phe Asn Val Thr Gln Gly Lys Tyr Ser Thr Ala Gln Asp Cys
        355                 360                 365

Ser Ala Asp Asp Asp Asn Phe Leu Val Pro Ile Ala Val Gly Ala Ala
    370                 375                 380

Leu Ala Gly Val Leu Ile Leu Val Leu Leu Ala Tyr Phe Ile Gly Leu
385                 390                 395                 400

Lys His His His Ala Gly Tyr Glu Gln Phe
                405                 410
```

<210> SEQ ID NO 61
<211> LENGTH: 417
<212> TYPE: PRT
<213> ORGANISM: Artificial Sequence
<220> FEATURE:
<223> OTHER INFORMATION: Synthetic_LAMP1_HUMAN

<400> SEQUENCE: 61

Met Ala Ala Pro Gly Ser Ala Arg Arg Pro Leu Leu Leu Leu Leu Leu
1 5 10 15

Leu Leu Leu Leu Gly Leu Met His Cys Ala Ser Ala Ala Met Phe Met
20 25 30

Val Lys Asn Gly Asn Gly Thr Ala Cys Ile Met Ala Asn Phe Ser Ala
35 40 45

Ala Phe Ser Val Asn Tyr Asp Thr Lys Ser Gly Pro Lys Asn Met Thr
50 55 60

Phe Asp Leu Pro Ser Asp Ala Thr Val Val Leu Asn Arg Ser Ser Cys
65 70 75 80

Gly Lys Glu Asn Thr Ser Asp Pro Ser Leu Val Ile Ala Phe Gly Arg
85 90 95

Gly His Thr Leu Thr Leu Asn Phe Thr Arg Asn Ala Thr Arg Tyr Ser
100 105 110

Val Gln Leu Met Ser Phe Val Tyr Asn Leu Ser Asp Thr His Leu Phe
115 120 125

Pro Asn Ala Ser Ser Lys Glu Ile Lys Thr Val Glu Ser Ile Thr Asp
130 135 140

Ile Arg Ala Asp Ile Asp Lys Lys Tyr Arg Cys Val Ser Gly Thr Gln
145 150 155 160

Val His Met Asn Asn Val Thr Val Thr Leu His Asp Ala Thr Ile Gln
165 170 175

Ala Tyr Leu Ser Asn Ser Ser Phe Ser Arg Gly Glu Thr Arg Cys Glu
180 185 190

Gln Asp Arg Pro Ser Pro Thr Thr Ala Pro Pro Ala Pro Pro Ser Pro
195 200 205

Ser Pro Ser Pro Val Pro Lys Ser Pro Ser Val Asp Lys Tyr Asn Val
210 215 220

Ser Gly Thr Asn Gly Thr Cys Leu Leu Ala Ser Met Gly Leu Gln Leu
225 230 235 240

Asn Leu Thr Tyr Glu Arg Lys Asp Asn Thr Thr Val Thr Arg Leu Leu
245 250 255

Asn Ile Asn Pro Asn Lys Thr Ser Ala Ser Gly Ser Cys Gly Ala His
260 265 270

Leu Val Thr Leu Glu Leu His Ser Glu Gly Thr Thr Val Leu Leu Phe
275 280 285

Gln Phe Gly Met Asn Ala Ser Ser Ser Arg Phe Phe Leu Gln Gly Ile
290 295 300

Gln Leu Asn Thr Ile Leu Pro Asp Ala Arg Asp Pro Ala Phe Lys Ala
305 310 315 320

Ala Asn Gly Ser Leu Arg Ala Leu Gln Ala Thr Val Gly Asn Ser Tyr
325 330 335

Lys Cys Asn Ala Glu Glu His Val Arg Val Thr Lys Ala Phe Ser Val
340 345 350

Asn Ile Phe Lys Val Trp Val Gln Ala Phe Lys Val Glu Gly Gly Gln
355 360 365

Phe Gly Ser Val Glu Glu Cys Leu Leu Asp Glu Asn Ser Met Leu Ile

```
    370                 375                 380

Pro Ile Ala Val Gly Gly Ala Leu Ala Gly Leu Val Leu Ile Val Leu
385                 390                 395                 400

Ile Ala Tyr Leu Val Gly Arg Lys Arg Ser His Ala Gly Tyr Gln Thr
                405                 410                 415

Ile


<210> SEQ ID NO 62
<211> LENGTH: 424
<212> TYPE: PRT
<213> ORGANISM: Artificial Sequence
<220> FEATURE:
<223> OTHER INFORMATION: Synthetic_ZP3_HUMAN

<400> SEQUENCE: 62

Met Glu Leu Ser Tyr Arg Leu Phe Ile Cys Leu Leu Leu Trp Gly Ser
1               5                   10                  15

Thr Glu Leu Cys Tyr Pro Gln Pro Leu Trp Leu Leu Gln Gly Gly Ala
            20                  25                  30

Ser His Pro Glu Thr Ser Val Gln Pro Val Leu Val Glu Cys Gln Glu
        35                  40                  45

Ala Thr Leu Met Val Met Val Ser Lys Asp Leu Phe Gly Thr Gly Lys
    50                  55                  60

Leu Ile Arg Ala Ala Asp Leu Thr Leu Gly Pro Glu Ala Cys Glu Pro
65                  70                  75                  80

Leu Val Ser Met Asp Thr Glu Asp Val Val Arg Phe Glu Val Gly Leu
                85                  90                  95

His Glu Cys Gly Asn Ser Met Gln Val Thr Asp Asp Ala Leu Val Tyr
            100                 105                 110

Ser Thr Phe Leu Leu His Asp Pro Arg Pro Val Gly Asn Leu Ser Ile
        115                 120                 125

Val Arg Thr Asn Arg Ala Glu Ile Pro Ile Glu Cys Arg Tyr Pro Arg
    130                 135                 140

Gln Gly Asn Val Ser Ser Gln Ala Ile Leu Pro Thr Trp Leu Pro Phe
145                 150                 155                 160

Arg Thr Thr Val Phe Ser Glu Glu Lys Leu Thr Phe Ser Leu Arg Leu
                165                 170                 175

Met Glu Glu Asn Trp Asn Ala Glu Lys Arg Ser Pro Thr Phe His Leu
            180                 185                 190

Gly Asp Ala Ala His Leu Gln Ala Glu Ile His Thr Gly Ser His Val
        195                 200                 205

Pro Leu Arg Leu Phe Val Asp His Cys Val Ala Thr Pro Thr Pro Asp
    210                 215                 220

Gln Asn Ala Ser Pro Tyr His Thr Ile Val Asp Phe His Gly Cys Leu
225                 230                 235                 240

Val Asp Gly Leu Thr Asp Ala Ser Ser Ala Phe Lys Val Pro Arg Pro
                245                 250                 255

Gly Pro Asp Thr Leu Gln Phe Thr Val Asp Val Phe His Phe Ala Asn
            260                 265                 270

Asp Ser Arg Asn Met Ile Tyr Ile Thr Cys His Leu Lys Val Thr Leu
        275                 280                 285

Ala Glu Gln Asp Pro Asp Glu Leu Asn Lys Ala Cys Ser Phe Ser Lys
    290                 295                 300

Pro Ser Asn Ser Trp Phe Pro Val Glu Gly Ser Ala Asp Ile Cys Gln
305                 310                 315                 320
```

Cys Cys Asn Lys Gly Asp Cys Gly Thr Pro Ser His Ser Arg Arg Gln
325 330 335

Pro His Val Met Ser Gln Trp Ser Arg Ser Ala Ser Arg Asn Arg Arg
340 345 350

His Val Thr Glu Glu Ala Asp Val Thr Val Gly Pro Leu Ile Phe Leu
355 360 365

Asp Arg Arg Gly Asp His Glu Val Glu Gln Trp Ala Leu Pro Ser Asp
370 375 380

Thr Ser Val Val Leu Leu Gly Val Gly Leu Ala Val Val Val Ser Leu
385 390 395 400

Thr Leu Thr Ala Val Ile Leu Val Leu Thr Arg Arg Cys Arg Thr Ala
405 410 415

Ser His Pro Val Ser Ala Ser Glu
420

<210> SEQ ID NO 63
<211> LENGTH: 430
<212> TYPE: PRT
<213> ORGANISM: Artificial Sequence
<220> FEATURE:
<223> OTHER INFORMATION: Synthetic_K1C18_HUMAN

<400> SEQUENCE: 63

Met Ser Phe Thr Thr Arg Ser Thr Phe Ser Thr Asn Tyr Arg Ser Leu
1 5 10 15

Gly Ser Val Gln Ala Pro Ser Tyr Gly Ala Arg Pro Val Ser Ser Ala
20 25 30

Ala Ser Val Tyr Ala Gly Ala Gly Gly Ser Gly Ser Arg Ile Ser Val
35 40 45

Ser Arg Ser Thr Ser Phe Arg Gly Gly Met Gly Ser Gly Gly Leu Ala
50 55 60

Thr Gly Ile Ala Gly Gly Leu Ala Gly Met Gly Gly Ile Gln Asn Glu
65 70 75 80

Lys Glu Thr Met Gln Ser Leu Asn Asp Arg Leu Ala Ser Tyr Leu Asp
85 90 95

Arg Val Arg Ser Leu Glu Thr Glu Asn Arg Arg Leu Glu Ser Lys Ile
100 105 110

Arg Glu His Leu Glu Lys Lys Gly Pro Gln Val Arg Asp Trp Ser His
115 120 125

Tyr Phe Lys Ile Ile Glu Asp Leu Arg Ala Gln Ile Phe Ala Asn Thr
130 135 140

Val Asp Asn Ala Arg Ile Val Leu Gln Ile Asp Asn Ala Arg Leu Ala
145 150 155 160

Ala Asp Asp Phe Arg Val Lys Tyr Glu Thr Glu Leu Ala Met Arg Gln
165 170 175

Ser Val Glu Asn Asp Ile His Gly Leu Arg Lys Val Ile Asp Asp Thr
180 185 190

Asn Ile Thr Arg Leu Gln Leu Glu Thr Glu Ile Glu Ala Leu Lys Glu
195 200 205

Glu Leu Leu Phe Met Lys Lys Asn His Glu Glu Glu Val Lys Gly Leu
210 215 220

Gln Ala Gln Ile Ala Ser Ser Gly Leu Thr Val Glu Val Asp Ala Pro
225 230 235 240

Lys Ser Gln Asp Leu Ala Lys Ile Met Ala Asp Ile Arg Ala Gln Tyr
245 250 255

Asp Glu Leu Ala Arg Lys Asn Arg Glu Glu Leu Asp Lys Tyr Trp Ser
260 265 270

Gln Gln Ile Glu Glu Ser Thr Thr Val Val Thr Thr Gln Ser Ala Glu
275 280 285

Val Gly Ala Ala Glu Thr Thr Leu Thr Glu Leu Arg Arg Thr Val Gln
290 295 300

Ser Leu Glu Ile Asp Leu Asp Ser Met Arg Asn Leu Lys Ala Ser Leu
305 310 315 320

Glu Asn Ser Leu Arg Glu Val Glu Ala Arg Tyr Ala Leu Gln Met Glu
325 330 335

Gln Leu Asn Gly Ile Leu Leu His Leu Glu Ser Glu Leu Ala Gln Thr
340 345 350

Arg Ala Glu Gly Gln Arg Gln Ala Gln Glu Tyr Glu Ala Leu Leu Asn
355 360 365

Ile Lys Val Lys Leu Glu Ala Glu Ile Ala Thr Tyr Arg Arg Leu Leu
370 375 380

Glu Asp Gly Glu Asp Phe Asn Leu Gly Asp Ala Leu Asp Ser Ser Asn
385 390 395 400

Ser Met Gln Thr Ile Gln Lys Thr Thr Thr Arg Arg Ile Val Asp Gly
405 410 415

Lys Val Val Ser Glu Thr Asn Asp Thr Lys Val Leu Arg His
420 425 430

<210> SEQ ID NO 64
<211> LENGTH: 439
<212> TYPE: PRT
<213> ORGANISM: Artificial Sequence
<220> FEATURE:
<223> OTHER INFORMATION: Synthetic_TICN1_HUMAN

<400> SEQUENCE: 64

Met Pro Ala Ile Ala Val Leu Ala Ala Ala Ala Ala Ala Trp Cys Phe
1 5 10 15

Leu Gln Val Glu Ser Arg His Leu Asp Ala Leu Ala Gly Gly Ala Gly
20 25 30

Pro Asn His Gly Asn Phe Leu Asp Asn Asp Gln Trp Leu Ser Thr Val
35 40 45

Ser Gln Tyr Asp Arg Asp Lys Tyr Trp Asn Arg Phe Arg Asp Asp Asp
50 55 60

Tyr Phe Arg Asn Trp Asn Pro Asn Lys Pro Phe Asp Gln Ala Leu Asp
65 70 75 80

Pro Ser Lys Asp Pro Cys Leu Lys Val Lys Cys Ser Pro His Lys Val
85 90 95

Cys Val Thr Gln Asp Tyr Gln Thr Ala Leu Cys Val Ser Arg Lys His
100 105 110

Leu Leu Pro Arg Gln Lys Lys Gly Asn Val Ala Gln Lys His Trp Val
115 120 125

Gly Pro Ser Asn Leu Val Lys Cys Lys Pro Cys Pro Val Ala Gln Ser
130 135 140

Ala Met Val Cys Gly Ser Asp Gly His Ser Tyr Thr Ser Lys Cys Lys
145 150 155 160

Leu Glu Phe His Ala Cys Ser Thr Gly Lys Ser Leu Ala Thr Leu Cys
165 170 175

Asp Gly Pro Cys Pro Cys Leu Pro Glu Pro Glu Pro Pro Lys His Lys
180 185 190

```
Ala Glu Arg Ser Ala Cys Thr Asp Lys Glu Leu Arg Asn Leu Ala Ser
        195                 200                 205

Arg Leu Lys Asp Trp Phe Gly Ala Leu His Glu Asp Ala Asn Arg Val
    210                 215                 220

Ile Lys Pro Thr Ser Ser Asn Thr Ala Gln Gly Arg Phe Asp Thr Ser
225                 230                 235                 240

Ile Leu Pro Ile Cys Lys Asp Ser Leu Gly Trp Met Phe Asn Lys Leu
                245                 250                 255

Asp Met Asn Tyr Asp Leu Leu Leu Asp Pro Ser Glu Ile Asn Ala Ile
            260                 265                 270

Tyr Leu Asp Lys Tyr Glu Pro Cys Ile Lys Pro Leu Phe Asn Ser Cys
        275                 280                 285

Asp Ser Phe Lys Asp Gly Lys Leu Ser Asn Asn Glu Trp Cys Tyr Cys
    290                 295                 300

Phe Gln Lys Pro Gly Gly Leu Pro Cys Gln Asn Glu Met Asn Arg Ile
305                 310                 315                 320

Gln Lys Leu Ser Lys Gly Lys Ser Leu Leu Gly Ala Phe Ile Pro Arg
                325                 330                 335

Cys Asn Glu Glu Gly Tyr Tyr Lys Ala Thr Gln Cys His Gly Ser Thr
            340                 345                 350

Gly Gln Cys Trp Cys Val Asp Lys Tyr Gly Asn Glu Leu Ala Gly Ser
        355                 360                 365

Arg Lys Gln Gly Ala Val Ser Cys Glu Glu Glu Gln Glu Thr Ser Gly
    370                 375                 380

Asp Phe Gly Ser Gly Gly Ser Val Val Leu Leu Asp Asp Leu Glu Tyr
385                 390                 395                 400

Glu Arg Glu Leu Gly Pro Lys Asp Lys Glu Gly Lys Leu Arg Val His
                405                 410                 415

Thr Arg Ala Val Thr Glu Asp Asp Glu Asp Glu Asp Asp Asp Lys Glu
            420                 425                 430

Asp Glu Val Gly Tyr Ile Trp
        435
```

<210> SEQ ID NO 65
<211> LENGTH: 442
<212> TYPE: PRT
<213> ORGANISM: Artificial Sequence
<220> FEATURE:
<223> OTHER INFORMATION: Synthetic_SDC3_HUMAN

<400> SEQUENCE: 65

```
Met Lys Pro Gly Pro Pro His Arg Ala Gly Ala Ala His Gly Ala Gly
1               5                   10                  15

Ala Gly Ala Gly Ala Ala Ala Gly Pro Gly Ala Arg Gly Leu Leu Leu
            20                  25                  30

Pro Pro Leu Leu Leu Leu Leu Leu Ala Gly Arg Ala Ala Gly Ala Gln
        35                  40                  45

Arg Trp Arg Ser Glu Asn Phe Glu Arg Pro Val Asp Leu Glu Gly Ser
    50                  55                  60

Gly Asp Asp Asp Ser Phe Pro Asp Asp Glu Leu Asp Asp Leu Tyr Ser
65                  70                  75                  80

Gly Ser Gly Ser Gly Tyr Phe Glu Gln Glu Ser Gly Ile Glu Thr Ala
                85                  90                  95

Met Arg Phe Ser Pro Asp Val Ala Leu Ala Val Ser Thr Thr Pro Ala
            100                 105                 110
```

Val Leu Pro Thr Thr Asn Ile Gln Pro Val Gly Thr Pro Phe Glu Glu
115 120 125

Leu Pro Ser Glu Arg Pro Thr Leu Glu Pro Ala Thr Ser Pro Leu Val
130 135 140

Val Thr Glu Val Pro Glu Glu Pro Ser Gln Arg Ala Thr Thr Val Ser
145 150 155 160

Thr Thr Met Ala Thr Thr Ala Ala Thr Ser Thr Gly Asp Pro Thr Val
165 170 175

Ala Thr Val Pro Ala Thr Val Ala Thr Ala Thr Pro Ser Thr Pro Ala
180 185 190

Ala Pro Pro Phe Thr Ala Thr Thr Ala Val Ile Arg Thr Thr Gly Val
195 200 205

Arg Arg Leu Leu Pro Leu Pro Leu Thr Thr Val Ala Thr Ala Arg Ala
210 215 220

Thr Thr Pro Glu Ala Pro Ser Pro Pro Thr Thr Ala Ala Val Leu Asp
225 230 235 240

Thr Glu Ala Pro Thr Pro Arg Leu Val Ser Thr Ala Thr Ser Arg Pro
245 250 255

Arg Ala Leu Pro Arg Pro Ala Thr Thr Gln Glu Pro Asp Ile Pro Glu
260 265 270

Arg Ser Thr Leu Pro Leu Gly Thr Thr Ala Pro Gly Pro Thr Glu Val
275 280 285

Ala Gln Thr Pro Thr Pro Glu Thr Phe Leu Thr Thr Ile Arg Asp Glu
290 295 300

Pro Glu Val Pro Val Ser Gly Gly Pro Ser Gly Asp Phe Glu Leu Pro
305 310 315 320

Glu Glu Glu Thr Thr Gln Pro Asp Thr Ala Asn Glu Val Val Ala Val
325 330 335

Gly Gly Ala Ala Ala Lys Ala Ser Ser Pro Pro Gly Thr Leu Pro Lys
340 345 350

Gly Ala Arg Pro Gly Pro Gly Leu Leu Asp Asn Ala Ile Asp Ser Gly
355 360 365

Ser Ser Ala Ala Gln Leu Pro Gln Lys Ser Ile Leu Glu Arg Lys Glu
370 375 380

Val Leu Val Ala Val Ile Val Gly Gly Val Val Gly Ala Leu Phe Ala
385 390 395 400

Ala Phe Leu Val Thr Leu Leu Ile Tyr Arg Met Lys Lys Lys Asp Glu
405 410 415

Gly Ser Tyr Thr Leu Glu Glu Pro Lys Gln Ala Ser Val Thr Tyr Gln
420 425 430

Lys Pro Asp Lys Gln Glu Glu Phe Tyr Ala
435 440

<210> SEQ ID NO 66
<211> LENGTH: 457
<212> TYPE: PRT
<213> ORGANISM: Artificial Sequence
<220> FEATURE:
<223> OTHER INFORMATION: Synthetic_CMGA_HUMAN

<400> SEQUENCE: 66

Met Arg Ser Ala Ala Val Leu Ala Leu Leu Leu Cys Ala Gly Gln Val
1 5 10 15

Thr Ala Leu Pro Val Asn Ser Pro Met Asn Lys Gly Asp Thr Glu Val
20 25 30

-continued

```
Met Lys Cys Ile Val Glu Val Ile Ser Asp Thr Leu Ser Lys Pro Ser
        35                  40                  45

Pro Met Pro Val Ser Gln Glu Cys Phe Glu Thr Leu Arg Gly Asp Glu
    50                  55                  60

Arg Ile Leu Ser Ile Leu Arg His Gln Asn Leu Leu Lys Glu Leu Gln
65                  70                  75                  80

Asp Leu Ala Leu Gln Gly Ala Lys Glu Arg Ala His Gln Gln Lys Lys
                85                  90                  95

His Ser Gly Phe Glu Asp Glu Leu Ser Glu Val Leu Glu Asn Gln Ser
            100                 105                 110

Ser Gln Ala Glu Leu Lys Glu Ala Val Glu Glu Pro Ser Ser Lys Asp
        115                 120                 125

Val Met Glu Lys Arg Glu Asp Ser Lys Glu Ala Glu Lys Ser Gly Glu
    130                 135                 140

Ala Thr Asp Gly Ala Arg Pro Gln Ala Leu Pro Glu Pro Met Gln Glu
145                 150                 155                 160

Ser Lys Ala Glu Gly Asn Asn Gln Ala Pro Gly Glu Glu Glu Glu Glu
                165                 170                 175

Glu Glu Glu Ala Thr Asn Thr His Pro Pro Ala Ser Leu Pro Ser Gln
            180                 185                 190

Lys Tyr Pro Gly Pro Gln Ala Glu Gly Asp Ser Glu Gly Leu Ser Gln
        195                 200                 205

Gly Leu Val Asp Arg Glu Lys Gly Leu Ser Ala Glu Pro Gly Trp Gln
    210                 215                 220

Ala Lys Arg Glu Glu Glu Glu Glu Glu Glu Glu Glu Ala Glu Ala Gly
225                 230                 235                 240

Glu Glu Ala Val Pro Glu Glu Glu Gly Pro Thr Val Val Leu Asn Pro
                245                 250                 255

His Pro Ser Leu Gly Tyr Lys Glu Ile Arg Lys Gly Glu Ser Arg Ser
            260                 265                 270

Glu Ala Leu Ala Val Asp Gly Ala Gly Lys Pro Gly Ala Glu Glu Ala
        275                 280                 285

Gln Asp Pro Glu Gly Lys Gly Glu Gln Glu His Ser Gln Gln Lys Glu
    290                 295                 300

Glu Glu Glu Glu Met Ala Val Val Pro Gln Gly Leu Phe Arg Gly Gly
305                 310                 315                 320

Lys Ser Gly Glu Leu Glu Gln Glu Glu Glu Arg Leu Ser Lys Glu Trp
                325                 330                 335

Glu Asp Ser Lys Arg Trp Ser Lys Met Asp Gln Leu Ala Lys Glu Leu
            340                 345                 350

Thr Ala Glu Lys Arg Leu Glu Gly Gln Glu Glu Glu Glu Asp Asn Arg
        355                 360                 365

Asp Ser Ser Met Lys Leu Ser Phe Arg Ala Arg Ala Tyr Gly Phe Arg
    370                 375                 380

Gly Pro Gly Pro Gln Leu Arg Arg Gly Trp Arg Pro Ser Ser Arg Glu
385                 390                 395                 400

Asp Ser Leu Glu Ala Gly Leu Pro Leu Gln Val Arg Gly Tyr Pro Glu
                405                 410                 415

Glu Lys Lys Glu Glu Glu Gly Ser Ala Asn Arg Arg Pro Glu Asp Gln
            420                 425                 430

Glu Leu Glu Ser Leu Ser Ala Ile Glu Ala Glu Leu Glu Lys Val Ala
        435                 440                 445
```

```
His Gln Leu Gln Ala Leu Arg Arg Gly
    450                 455


<210> SEQ ID NO 67
<211> LENGTH: 458
<212> TYPE: PRT
<213> ORGANISM: Artificial Sequence
<220> FEATURE:
<223> OTHER INFORMATION: Synthetic_CBPN_HUMAN

<400> SEQUENCE: 67

Met Ser Asp Leu Leu Ser Val Phe Leu His Leu Leu Leu Leu Phe Lys
1               5                   10                  15

Leu Val Ala Pro Val Thr Phe Arg His His Arg Tyr Asp Asp Leu Val
            20                  25                  30

Arg Thr Leu Tyr Lys Val Gln Asn Glu Cys Pro Gly Ile Thr Arg Val
        35                  40                  45

Tyr Ser Ile Gly Arg Ser Val Glu Gly Arg His Leu Tyr Val Leu Glu
    50                  55                  60

Phe Ser Asp His Pro Gly Ile His Glu Pro Leu Glu Pro Glu Val Lys
65                  70                  75                  80

Tyr Val Gly Asn Met His Gly Asn Glu Ala Leu Gly Arg Glu Leu Met
                85                  90                  95

Leu Gln Leu Ser Glu Phe Leu Cys Glu Glu Phe Arg Asn Arg Asn Gln
            100                 105                 110

Arg Ile Val Gln Leu Ile Gln Asp Thr Arg Ile His Ile Leu Pro Ser
        115                 120                 125

Met Asn Pro Asp Gly Tyr Glu Val Ala Ala Ala Gln Gly Pro Asn Lys
    130                 135                 140

Pro Gly Tyr Leu Val Gly Arg Asn Asn Ala Asn Gly Val Asp Leu Asn
145                 150                 155                 160

Arg Asn Phe Pro Asp Leu Asn Thr Tyr Ile Tyr Tyr Asn Glu Lys Tyr
                165                 170                 175

Gly Gly Pro Asn His His Leu Pro Leu Pro Asp Asn Trp Lys Ser Gln
            180                 185                 190

Val Glu Pro Glu Thr Arg Ala Val Ile Arg Trp Met His Ser Phe Asn
        195                 200                 205

Phe Val Leu Ser Ala Asn Leu His Gly Gly Ala Val Val Ala Asn Tyr
    210                 215                 220

Pro Tyr Asp Lys Ser Phe Glu His Arg Val Arg Gly Val Arg Arg Thr
225                 230                 235                 240

Ala Ser Thr Pro Thr Pro Asp Asp Lys Leu Phe Gln Lys Leu Ala Lys
                245                 250                 255

Val Tyr Ser Tyr Ala His Gly Trp Met Phe Gln Gly Trp Asn Cys Gly
            260                 265                 270

Asp Tyr Phe Pro Asp Gly Ile Thr Asn Gly Ala Ser Trp Tyr Ser Leu
        275                 280                 285

Ser Lys Gly Met Gln Asp Phe Asn Tyr Leu His Thr Asn Cys Phe Glu
    290                 295                 300

Ile Thr Leu Glu Leu Ser Cys Asp Lys Phe Pro Pro Glu Glu Glu Leu
305                 310                 315                 320

Gln Arg Glu Trp Leu Gly Asn Arg Glu Ala Leu Ile Gln Phe Leu Glu
                325                 330                 335

Gln Val His Gln Gly Ile Lys Gly Met Val Leu Asp Glu Asn Tyr Asn
            340                 345                 350
```

```
Asn Leu Ala Asn Ala Val Ile Ser Val Ser Gly Ile Asn His Asp Val
        355                 360                 365

Thr Ser Gly Asp His Gly Asp Tyr Phe Arg Leu Leu Leu Pro Gly Ile
    370                 375                 380

Tyr Thr Val Ser Ala Thr Ala Pro Gly Tyr Asp Pro Glu Thr Val Thr
385                 390                 395                 400

Val Thr Val Gly Pro Ala Glu Pro Thr Leu Val Asn Phe His Leu Lys
                405                 410                 415

Arg Ser Ile Pro Gln Val Ser Pro Val Arg Arg Ala Pro Ser Arg Arg
            420                 425                 430

His Gly Val Arg Ala Lys Val Gln Pro Gln Ala Arg Lys Lys Glu Met
        435                 440                 445

Glu Met Arg Gln Leu Gln Arg Gly Pro Ala
    450                 455


<210> SEQ ID NO 68
<211> LENGTH: 461
<212> TYPE: PRT
<213> ORGANISM: Artificial Sequence
<220> FEATURE:
<223> OTHER INFORMATION: Synthetic_FA9_HUMAN

<400> SEQUENCE: 68

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255
```

Val Asn Glu Lys Trp Ile Val Thr Ala Ala His Cys Val Glu Thr Gly
260 265 270

Val Lys Ile Thr Val Val Ala Gly Glu His Asn Ile Glu Glu Thr Glu
275 280 285

His Thr Glu Gln Lys Arg Asn Val Ile Arg Ile Ile Pro His His Asn
290 295 300

Tyr Asn Ala Ala Ile Asn Lys Tyr Asn His Asp Ile Ala Leu Leu Glu
305 310 315 320

Leu Asp Glu Pro Leu Val Leu Asn Ser Tyr Val Thr Pro Ile Cys Ile
325 330 335

Ala Asp Lys Glu Tyr Thr Asn Ile Phe Leu Lys Phe Gly Ser Gly Tyr
340 345 350

Val Ser Gly Trp Gly Arg Val Phe His Lys Gly Arg Ser Ala Leu Val
355 360 365

Leu Gln Tyr Leu Arg Val Pro Leu Val Asp Arg Ala Thr Cys Leu Arg
370 375 380

Ser Thr Lys Phe Thr Ile Tyr Asn Asn Met Phe Cys Ala Gly Phe His
385 390 395 400

Glu Gly Gly Arg Asp Ser Cys Gln Gly Asp Ser Gly Gly Pro His Val
405 410 415

Thr Glu Val Glu Gly Thr Ser Phe Leu Thr Gly Ile Ile Ser Trp Gly
420 425 430

Glu Glu Cys Ala Met Lys Gly Lys Tyr Gly Ile Tyr Thr Lys Val Ser
435 440 445

Arg Tyr Val Asn Trp Ile Lys Glu Lys Thr Lys Leu Thr
450 455 460

<210> SEQ ID NO 69
<211> LENGTH: 461
<212> TYPE: PRT
<213> ORGANISM: Artificial Sequence
<220> FEATURE:
<223> OTHER INFORMATION: Synthetic_TNR1B_HUMAN

<400> SEQUENCE: 69

Met Ala Pro Val Ala Val Trp Ala Ala Leu Ala Val Gly Leu Glu Leu
1 5 10 15

Trp Ala Ala Ala His Ala Leu Pro Ala Gln Val Ala Phe Thr Pro Tyr
20 25 30

Ala Pro Glu Pro Gly Ser Thr Cys Arg Leu Arg Glu Tyr Tyr Asp Gln
35 40 45

Thr Ala Gln Met Cys Cys Ser Lys Cys Ser Pro Gly Gln His Ala Lys
50 55 60

Val Phe Cys Thr Lys Thr Ser Asp Thr Val Cys Asp Ser Cys Glu Asp
65 70 75 80

Ser Thr Tyr Thr Gln Leu Trp Asn Trp Val Pro Glu Cys Leu Ser Cys
85 90 95

Gly Ser Arg Cys Ser Ser Asp Gln Val Glu Thr Gln Ala Cys Thr Arg
100 105 110

Glu Gln Asn Arg Ile Cys Thr Cys Arg Pro Gly Trp Tyr Cys Ala Leu
115 120 125

Ser Lys Gln Glu Gly Cys Arg Leu Cys Ala Pro Leu Arg Lys Cys Arg
130 135 140

Pro Gly Phe Gly Val Ala Arg Pro Gly Thr Glu Thr Ser Asp Val Val
145 150 155 160

Cys Lys Pro Cys Ala Pro Gly Thr Phe Ser Asn Thr Thr Ser Ser Thr
165 170 175

Asp Ile Cys Arg Pro His Gln Ile Cys Asn Val Val Ala Ile Pro Gly
180 185 190

Asn Ala Ser Met Asp Ala Val Cys Thr Ser Thr Ser Pro Thr Arg Ser
195 200 205

Met Ala Pro Gly Ala Val His Leu Pro Gln Pro Val Ser Thr Arg Ser
210 215 220

Gln His Thr Gln Pro Thr Pro Glu Pro Ser Thr Ala Pro Ser Thr Ser
225 230 235 240

Phe Leu Leu Pro Met Gly Pro Ser Pro Pro Ala Glu Gly Ser Thr Gly
245 250 255

Asp Phe Ala Leu Pro Val Gly Leu Ile Val Gly Val Thr Ala Leu Gly
260 265 270

Leu Leu Ile Ile Gly Val Val Asn Cys Val Ile Met Thr Gln Val Lys
275 280 285

Lys Lys Pro Leu Cys Leu Gln Arg Glu Ala Lys Val Pro His Leu Pro
290 295 300

Ala Asp Lys Ala Arg Gly Thr Gln Gly Pro Glu Gln Gln His Leu Leu
305 310 315 320

Ile Thr Ala Pro Ser Ser Ser Ser Ser Ser Leu Glu Ser Ser Ala Ser
325 330 335

Ala Leu Asp Arg Arg Ala Pro Thr Arg Asn Gln Pro Gln Ala Pro Gly
340 345 350

Val Glu Ala Ser Gly Ala Gly Glu Ala Arg Ala Ser Thr Gly Ser Ser
355 360 365

Asp Ser Ser Pro Gly Gly His Gly Thr Gln Val Asn Val Thr Cys Ile
370 375 380

Val Asn Val Cys Ser Ser Ser Asp His Ser Ser Gln Cys Ser Ser Gln
385 390 395 400

Ala Ser Ser Thr Met Gly Asp Thr Asp Ser Ser Pro Ser Glu Ser Pro
405 410 415

Lys Asp Glu Gln Val Pro Phe Ser Lys Glu Glu Cys Ala Phe Arg Ser
420 425 430

Gln Leu Glu Thr Pro Glu Thr Leu Leu Gly Ser Thr Glu Glu Lys Pro
435 440 445

Leu Pro Leu Gly Val Pro Asp Ala Gly Met Lys Pro Ser
450 455 460

<210> SEQ ID NO 70
<211> LENGTH: 466
<212> TYPE: PRT
<213> ORGANISM: Artificial Sequence
<220> FEATURE:
<223> OTHER INFORMATION: Synthetic_VIME_HUMAN

<400> SEQUENCE: 70

Met Ser Thr Arg Ser Val Ser Ser Ser Ser Tyr Arg Arg Met Phe Gly
1 5 10 15

Gly Pro Gly Thr Ala Ser Arg Pro Ser Ser Ser Arg Ser Tyr Val Thr
20 25 30

Thr Ser Thr Arg Thr Tyr Ser Leu Gly Ser Ala Leu Arg Pro Ser Thr
35 40 45

Ser Arg Ser Leu Tyr Ala Ser Ser Pro Gly Gly Val Tyr Ala Thr Arg
50 55 60

```
Ser Ser Ala Val Arg Leu Arg Ser Ser Val Pro Gly Val Arg Leu Leu
65                  70                  75                  80

Gln Asp Ser Val Asp Phe Ser Leu Ala Asp Ala Ile Asn Thr Glu Phe
                85                  90                  95

Lys Asn Thr Arg Thr Asn Glu Lys Val Glu Leu Gln Glu Leu Asn Asp
            100                 105                 110

Arg Phe Ala Asn Tyr Ile Asp Lys Val Arg Phe Leu Glu Gln Gln Asn
        115                 120                 125

Lys Ile Leu Leu Ala Glu Leu Glu Gln Leu Lys Gly Gln Gly Lys Ser
    130                 135                 140

Arg Leu Gly Asp Leu Tyr Glu Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
            180                 185                 190

Met Leu Gln Arg Glu Glu Ala Glu Asn Thr Leu Gln Ser Phe Arg Gln
        195                 200                 205

Asp Val Asp Asn Ala Ser Leu Ala Arg Leu Asp Leu Glu Arg Lys Val
    210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
            260                 265                 270

Arg Gln Gln Tyr Glu Ser Val Ala Ala Lys Asn Leu Gln Glu Ala Glu
        275                 280                 285

Glu Trp Tyr Lys Ser Lys Phe Ala Asp Leu Ser Glu Ala Ala Asn Arg
    290                 295                 300

Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
                325                 330                 335

Asn Glu Ser Leu Glu Arg Gln Met Arg Glu Met Glu Glu Asn Phe Ala
            340                 345                 350

Val Glu Ala Ala Asn Tyr Gln Asp Thr Ile Gly Arg Leu Gln Asp Glu
        355                 360                 365

Ile Gln Asn Met Lys Glu Glu Met Ala Arg His Leu Arg Glu Tyr Gln
    370                 375                 380

Asp Leu Leu Asn Val Lys Met Ala Leu Asp Ile Glu Ile Ala Thr Tyr
385                 390                 395                 400

Arg Lys Leu Leu Glu Gly Glu Glu Ser Arg Ile Ser Leu Pro Leu Pro
                405                 410                 415

Asn Phe Ser Ser Leu Asn Leu Arg Glu Thr Asn Leu Asp Ser Leu Pro
            420                 425                 430

Leu Val Asp Thr His Ser Lys Arg Thr Leu Leu Ile Lys Thr Val Glu
        435                 440                 445

Thr Arg Asp Gly Gln Val Ile Asn Glu Thr Ser Gln His His Asp Asp
    450                 455                 460

Leu Glu
465
```

<210> SEQ ID NO 71
<211> LENGTH: 468
<212> TYPE: PRT
<213> ORGANISM: Artificial Sequence
<220> FEATURE:
<223> OTHER INFORMATION: Synthetic_SCG3_HUMAN

<400> SEQUENCE: 71

```
Met Gly Phe Leu Gly Thr Gly Thr Trp Ile Leu Val Leu Val Leu Pro
1               5                   10                  15

Ile Gln Ala Phe Pro Lys Pro Gly Gly Ser Gln Asp Lys Ser Leu His
            20                  25                  30

Asn Arg Glu Leu Ser Ala Glu Arg Pro Leu Asn Glu Gln Ile Ala Glu
        35                  40                  45

Ala Glu Glu Asp Lys Ile Lys Lys Thr Tyr Pro Pro Glu Asn Lys Pro
    50                  55                  60

Gly Gln Ser Asn Tyr Ser Phe Val Asp Asn Leu Asn Leu Leu Lys Ala
65                  70                  75                  80

Ile Thr Glu Lys Glu Lys Ile Glu Lys Glu Arg Gln Ser Ile Arg Ser
                85                  90                  95

Ser Pro Leu Asp Asn Lys Leu Asn Val Glu Asp Val Asp Ser Thr Lys
            100                 105                 110

Asn Arg Lys Leu Ile Asp Asp Tyr Asp Ser Thr Lys Ser Gly Leu Asp
        115                 120                 125

His Lys Phe Gln Asp Asp Pro Asp Gly Leu His Gln Leu Asp Gly Thr
    130                 135                 140

Pro Leu Thr Ala Glu Asp Ile Val His Lys Ile Ala Ala Arg Ile Tyr
145                 150                 155                 160

Glu Glu Asn Asp Arg Ala Val Phe Asp Lys Ile Val Ser Lys Leu Leu
                165                 170                 175

Asn Leu Gly Leu Ile Thr Glu Ser Gln Ala His Thr Leu Glu Asp Glu
            180                 185                 190

Val Ala Glu Val Leu Gln Lys Leu Ile Ser Lys Glu Ala Asn Asn Tyr
        195                 200                 205

Glu Glu Asp Pro Asn Lys Pro Thr Ser Trp Thr Glu Asn Gln Ala Gly
    210                 215                 220

Lys Ile Pro Glu Lys Val Thr Pro Met Ala Ala Ile Gln Asp Gly Leu
225                 230                 235                 240

Ala Lys Gly Glu Asn Asp Glu Thr Val Ser Asn Thr Leu Thr Leu Thr
                245                 250                 255

Asn Gly Leu Glu Arg Arg Thr Lys Thr Tyr Ser Glu Asp Asn Phe Glu
            260                 265                 270

Glu Leu Gln Tyr Phe Pro Asn Phe Tyr Ala Leu Leu Lys Ser Ile Asp
        275                 280                 285

Ser Glu Lys Glu Ala Lys Glu Lys Glu Thr Leu Ile Thr Ile Met Lys
    290                 295                 300

Thr Leu Ile Asp Phe Val Lys Met Met Val Lys Tyr Gly Thr Ile Ser
305                 310                 315                 320

Pro Glu Glu Gly Val Ser Tyr Leu Glu Asn Leu Asp Glu Met Ile Ala
                325                 330                 335

Leu Gln Thr Lys Asn Lys Leu Glu Lys Asn Ala Thr Asp Asn Ile Ser
            340                 345                 350

Lys Leu Phe Pro Ala Pro Ser Glu Lys Ser His Glu Glu Thr Asp Ser
        355                 360                 365

Thr Lys Glu Glu Ala Ala Lys Met Glu Lys Glu Tyr Gly Ser Leu Lys
```

```
    370                 375                 380

Asp Ser Thr Lys Asp Asp Asn Ser Asn Pro Gly Gly Lys Thr Asp Glu
385                 390                 395                 400

Pro Lys Gly Lys Thr Glu Ala Tyr Leu Glu Ala Ile Arg Lys Asn Ile
                405                 410                 415

Glu Trp Leu Lys Lys His Asp Lys Lys Gly Asn Lys Glu Asp Tyr Asp
            420                 425                 430

Leu Ser Lys Met Arg Asp Phe Ile Asn Lys Gln Ala Asp Ala Tyr Val
        435                 440                 445

Glu Lys Gly Ile Leu Asp Lys Glu Glu Ala Glu Ala Ile Lys Arg Ile
    450                 455                 460

Tyr Ser Ser Leu
465


<210> SEQ ID NO 72
<211> LENGTH: 473
<212> TYPE: PRT
<213> ORGANISM: Artificial Sequence
<220> FEATURE:
<223> OTHER INFORMATION: Synthetic_KCC4_HUMAN

<400> SEQUENCE: 72

Met Leu Lys Val Thr Val Pro Ser Cys Ser Ala Ser Ser Cys Ser Ser
1               5                   10                  15

Val Thr Ala Ser Ala Ala Pro Gly Thr Ala Ser Leu Val Pro Asp Tyr
            20                  25                  30

Trp Ile Asp Gly Ser Asn Arg Asp Ala Leu Ser Asp Phe Phe Glu Val
        35                  40                  45

Glu Ser Glu Leu Gly Arg Gly Ala Thr Ser Ile Val Tyr Arg Cys Lys
    50                  55                  60

Gln Lys Gly Thr Gln Lys Pro Tyr Ala Leu Lys Val Leu Lys Lys Thr
65                  70                  75                  80

Val Asp Lys Lys Ile Val Arg Thr Glu Ile Gly Val Leu Leu Arg Leu
                85                  90                  95

Ser His Pro Asn Ile Ile Lys Leu Lys Glu Ile Phe Glu Thr Pro Thr
            100                 105                 110

Glu Ile Ser Leu Val Leu Glu Leu Val Thr Gly Gly Glu Leu Phe Asp
        115                 120                 125

Arg Ile Val Glu Lys Gly Tyr Tyr Ser Glu Arg Asp Ala Ala Asp Ala
    130                 135                 140

Val Lys Gln Ile Leu Glu Ala Val Ala Tyr Leu His Glu Asn Gly Ile
145                 150                 155                 160

Val His Arg Asp Leu Lys Pro Glu Asn Leu Leu Tyr Ala Thr Pro Ala
                165                 170                 175

Pro Asp Ala Pro Leu Lys Ile Ala Asp Phe Gly Leu Ser Lys Ile Val
            180                 185                 190

Glu His Gln Val Leu Met Lys Thr Val Cys Gly Thr Pro Gly Tyr Cys
        195                 200                 205

Ala Pro Glu Ile Leu Arg Gly Cys Ala Tyr Gly Pro Glu Val Asp Met
    210                 215                 220

Trp Ser Val Gly Ile Ile Thr Tyr Ile Leu Leu Cys Gly Phe Glu Pro
225                 230                 235                 240

Phe Tyr Asp Glu Arg Gly Asp Gln Phe Met Phe Arg Arg Ile Leu Asn
                245                 250                 255

Cys Glu Tyr Tyr Phe Ile Ser Pro Trp Trp Asp Glu Val Ser Leu Asn
```

```
            260                 265                 270

Ala Lys Asp Leu Val Arg Lys Leu Ile Val Leu Asp Pro Lys Lys Arg
        275                 280                 285

Leu Thr Thr Phe Gln Ala Leu Gln His Pro Trp Val Thr Gly Lys Ala
    290                 295                 300

Ala Asn Phe Val His Met Asp Thr Ala Gln Lys Lys Leu Gln Glu Phe
305                 310                 315                 320

Asn Ala Arg Arg Lys Leu Lys Ala Ala Val Lys Ala Val Val Ala Ser
                325                 330                 335

Ser Arg Leu Gly Ser Ala Ser Ser Ser His Gly Ser Ile Gln Glu Ser
            340                 345                 350

His Lys Ala Ser Arg Asp Pro Ser Pro Ile Gln Asp Gly Asn Glu Asp
        355                 360                 365

Met Lys Ala Ile Pro Glu Gly Glu Lys Ile Gln Gly Asp Gly Ala Gln
    370                 375                 380

Ala Ala Val Lys Gly Ala Gln Ala Glu Leu Met Lys Val Gln Ala Leu
385                 390                 395                 400

Glu Lys Val Lys Gly Ala Asp Ile Asn Ala Glu Glu Ala Pro Lys Met
                405                 410                 415

Val Pro Lys Ala Val Glu Asp Gly Ile Lys Val Ala Asp Leu Glu Leu
            420                 425                 430

Glu Glu Gly Leu Ala Glu Glu Lys Leu Lys Thr Val Glu Glu Ala Ala
        435                 440                 445

Ala Pro Arg Glu Gly Gln Gly Ser Ser Ala Val Gly Phe Glu Val Pro
    450                 455                 460

Gln Gln Asp Val Ile Leu Pro Glu Tyr
465                 470


<210> SEQ ID NO 73
<211> LENGTH: 480
<212> TYPE: PRT
<213> ORGANISM: Artificial Sequence
<220> FEATURE:
<223> OTHER INFORMATION: Synthetic_AKT1_HUMAN

<400> SEQUENCE: 73

Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
            20                  25                  30

Gly Thr Phe Ile Gly Tyr Lys Glu Arg Pro Gln Asp Val Asp Gln Arg
        35                  40                  45

Glu Ala Pro Leu Asn Asn Phe Ser Val Ala Gln Cys Gln Leu Met Lys
    50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
            100                 105                 110

Gln Glu Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
    130                 135                 140

Val Thr Met Asn Glu Phe Glu Tyr Leu Lys Leu Leu Gly Lys Gly Thr
```

```
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
    290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
        355                 360                 365

Pro Arg Thr Leu Gly Pro Glu Ala Lys Ser Leu Leu Ser Gly Leu Leu
    370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
            420                 425                 430

Thr Asp Thr Arg Tyr Phe Asp Glu Glu Phe Thr Ala Gln Met Ile Thr
        435                 440                 445

Ile Thr Pro Pro Asp Gln Asp Asp Ser Met Glu Cys Val Asp Ser Glu
    450                 455                 460

Arg Arg Pro His Phe Pro Gln Phe Ser Tyr Ser Ala Ser Gly Thr Ala
465                 470                 475                 480
```

<210> SEQ ID NO 74
<211> LENGTH: 481
<212> TYPE: PRT
<213> ORGANISM: Artificial Sequence
<220> FEATURE:
<223> OTHER INFORMATION: Synthetic_AKT2_HUMAN

<400> SEQUENCE: 74

```
Met Asn Glu Val Ser Val Ile Lys Glu Gly Trp Leu His Lys Arg Gly
1               5                   10                  15

Glu Tyr Ile Lys Thr Trp Arg Pro Arg Tyr Phe Leu Leu Lys Ser Asp
            20                  25                  30

Gly Ser Phe Ile Gly Tyr Lys Glu Arg Pro Glu Ala Pro Asp Gln Thr
```

```
        35                  40                  45

Leu Pro Pro Leu Asn Asn Phe Ser Val Ala Glu Cys Gln Leu Met Lys
    50                  55                  60

Thr Glu Arg Pro Arg Pro Asn Thr Phe Val Ile Arg Cys Leu Gln Trp
65                  70                  75                  80

Thr Thr Val Ile Glu Arg Thr Phe His Val Asp Ser Pro Asp Glu Arg
                85                  90                  95

Glu Glu Trp Met Arg Ala Ile Gln Met Val Ala Asn Ser Leu Lys Gln
            100                 105                 110

Arg Ala Pro Gly Glu Asp Pro Met Asp Tyr Lys Cys Gly Ser Pro Ser
        115                 120                 125

Asp Ser Ser Thr Thr Glu Glu Met Glu Val Ala Val Ser Lys Ala Arg
    130                 135                 140

Ala Lys Val Thr Met Asn Asp Phe Asp Tyr Leu Lys Leu Leu Gly Lys
145                 150                 155                 160

Gly Thr Phe Gly Lys Val Ile Leu Val Arg Glu Lys Ala Thr Gly Arg
                165                 170                 175

Tyr Tyr Ala Met Lys Ile Leu Arg Lys Glu Val Ile Ile Ala Lys Asp
            180                 185                 190

Glu Val Ala His Thr Val Thr Glu Ser Arg Val Leu Gln Asn Thr Arg
        195                 200                 205

His Pro Phe Leu Thr Ala Leu Lys Tyr Ala Phe Gln Thr His Asp Arg
    210                 215                 220

Leu Cys Phe Val Met Glu Tyr Ala Asn Gly Gly Glu Leu Phe Phe His
225                 230                 235                 240

Leu Ser Arg Glu Arg Val Phe Thr Glu Glu Arg Ala Arg Phe Tyr Gly
                245                 250                 255

Ala Glu Ile Val Ser Ala Leu Glu Tyr Leu His Ser Arg Asp Val Val
            260                 265                 270

Tyr Arg Asp Ile Lys Leu Glu Asn Leu Met Leu Asp Lys Asp Gly His
        275                 280                 285

Ile Lys Ile Thr Asp Phe Gly Leu Cys Lys Glu Gly Ile Ser Asp Gly
    290                 295                 300

Ala Thr Met Lys Thr Phe Cys Gly Thr Pro Glu Tyr Leu Ala Pro Glu
305                 310                 315                 320

Val Leu Glu Asp Asn Asp Tyr Gly Arg Ala Val Asp Trp Trp Gly Leu
                325                 330                 335

Gly Val Val Met Tyr Glu Met Met Cys Gly Arg Leu Pro Phe Tyr Asn
            340                 345                 350

Gln Asp His Glu Arg Leu Phe Glu Leu Ile Leu Met Glu Glu Ile Arg
        355                 360                 365

Phe Pro Arg Thr Leu Ser Pro Glu Ala Lys Ser Leu Leu Ala Gly Leu
    370                 375                 380

Leu Lys Lys Asp Pro Lys Gln Arg Leu Gly Gly Gly Pro Ser Asp Ala
385                 390                 395                 400

Lys Glu Val Met Glu His Arg Phe Phe Leu Ser Ile Asn Trp Gln Asp
                405                 410                 415

Val Val Gln Lys Lys Leu Leu Pro Pro Phe Lys Pro Gln Val Thr Ser
            420                 425                 430

Glu Val Asp Thr Arg Tyr Phe Asp Asp Glu Phe Thr Ala Gln Ser Ile
        435                 440                 445

Thr Ile Thr Pro Pro Asp Arg Tyr Asp Ser Leu Gly Leu Leu Glu Leu
    450                 455                 460
```

Asp Gln Arg Thr His Phe Pro Gln Phe Ser Tyr Ser Ala Ser Ile Arg
465 470 475 480

Glu

<210> SEQ ID NO 75
<211> LENGTH: 481
<212> TYPE: PRT
<213> ORGANISM: Artificial Sequence
<220> FEATURE:
<223> OTHER INFORMATION: Synthetic_G37L1_HUMAN

<400> SEQUENCE: 75

Met Arg Trp Leu Trp Pro Leu Ala Val Ser Leu Ala Val Ile Leu Ala
1 5 10 15

Val Gly Leu Ser Arg Val Ser Gly Gly Ala Pro Leu His Leu Gly Arg
20 25 30

His Arg Ala Glu Thr Gln Glu Gln Gln Ser Arg Ser Lys Arg Gly Thr
35 40 45

Glu Asp Glu Glu Ala Lys Gly Val Gln Gln Tyr Val Pro Glu Glu Trp
50 55 60

Ala Glu Tyr Pro Arg Pro Ile His Pro Ala Gly Leu Gln Pro Thr Lys
65 70 75 80

Pro Leu Val Ala Thr Ser Pro Asn Pro Gly Lys Asp Gly Gly Thr Pro
85 90 95

Asp Ser Gly Gln Glu Leu Arg Gly Asn Leu Thr Gly Ala Pro Gly Gln
100 105 110

Arg Leu Gln Ile Gln Asn Pro Leu Tyr Pro Val Thr Glu Ser Ser Tyr
115 120 125

Ser Ala Tyr Ala Ile Met Leu Leu Ala Leu Val Val Phe Ala Val Gly
130 135 140

Ile Val Gly Asn Leu Ser Val Met Cys Ile Val Trp His Ser Tyr Tyr
145 150 155 160

Leu Lys Ser Ala Trp Asn Ser Ile Leu Ala Ser Leu Ala Leu Trp Asp
165 170 175

Phe Leu Val Leu Phe Phe Cys Leu Pro Ile Val Ile Phe Asn Glu Ile
180 185 190

Thr Lys Gln Arg Leu Leu Gly Asp Val Ser Cys Arg Ala Val Pro Phe
195 200 205

Met Glu Val Ser Ser Leu Gly Val Thr Thr Phe Ser Leu Cys Ala Leu
210 215 220

Gly Ile Asp Arg Phe His Val Ala Thr Ser Thr Leu Pro Lys Val Arg
225 230 235 240

Pro Ile Glu Arg Cys Gln Ser Ile Leu Ala Lys Leu Ala Val Ile Trp
245 250 255

Val Gly Ser Met Thr Leu Ala Val Pro Glu Leu Leu Leu Trp Gln Leu
260 265 270

Ala Gln Glu Pro Ala Pro Thr Met Gly Thr Leu Asp Ser Cys Ile Met
275 280 285

Lys Pro Ser Ala Ser Leu Pro Glu Ser Leu Tyr Ser Leu Val Met Thr
290 295 300

Tyr Gln Asn Ala Arg Met Trp Trp Tyr Phe Gly Cys Tyr Phe Cys Leu
305 310 315 320

Pro Ile Leu Phe Thr Val Thr Cys Gln Leu Val Thr Trp Arg Val Arg
325 330 335

```
Gly Pro Pro Gly Arg Lys Ser Glu Cys Arg Ala Ser Lys His Glu Gln
            340                 345                 350

Cys Glu Ser Gln Leu Asn Ser Thr Val Val Gly Leu Thr Val Val Tyr
        355                 360                 365

Ala Phe Cys Thr Leu Pro Glu Asn Val Cys Asn Ile Val Val Ala Tyr
    370                 375                 380

Leu Ser Thr Glu Leu Thr Arg Gln Thr Leu Asp Leu Leu Gly Leu Ile
385                 390                 395                 400

Asn Gln Phe Ser Thr Phe Phe Lys Gly Ala Ile Thr Pro Val Leu Leu
                405                 410                 415

Leu Cys Ile Cys Arg Pro Leu Gly Gln Ala Phe Leu Asp Cys Cys Cys
            420                 425                 430

Cys Cys Cys Cys Glu Glu Cys Gly Gly Ala Ser Glu Ala Ser Ala Ala
        435                 440                 445

Asn Gly Ser Asp Asn Lys Leu Lys Thr Glu Val Ser Ser Ser Ile Tyr
    450                 455                 460

Phe His Lys Pro Arg Glu Ser Pro Pro Leu Leu Pro Leu Gly Thr Pro
465                 470                 475                 480

Cys


<210> SEQ ID NO 76
<211> LENGTH: 490
<212> TYPE: PRT
<213> ORGANISM: Artificial Sequence
<220> FEATURE:
<223> OTHER INFORMATION: Synthetic_TEKT3_HUMAN

<400> SEQUENCE: 76

Met Glu Arg Val Gly Cys Thr Leu Thr Thr Thr Tyr Ala His Pro Arg
1               5                   10                  15

Pro Thr Pro Thr Asn Phe Leu Pro Ala Ile Ser Thr Met Ala Ser Ser
            20                  25                  30

Tyr Arg Asp Arg Phe Pro His Ser Asn Leu Thr His Ser Leu Ser Leu
        35                  40                  45

Pro Trp Arg Pro Ser Thr Tyr Tyr Lys Val Ala Ser Asn Ser Pro Ser
    50                  55                  60

Val Ala Pro Tyr Cys Thr Arg Ser Gln Arg Val Ser Glu Asn Thr Met
65                  70                  75                  80

Leu Pro Phe Val Ser Asn Arg Thr Thr Phe Phe Thr Arg Tyr Thr Pro
                85                  90                  95

Asp Asp Trp Tyr Arg Ser Asn Leu Thr Asn Tyr Gln Glu Ser Asn Thr
            100                 105                 110

Ser Arg His Asn Ser Glu Lys Leu Arg Val Asp Thr Ser Arg Leu Ile
        115                 120                 125

Gln Asp Lys Tyr Gln Gln Thr Arg Lys Thr Gln Ala Asp Thr Thr Gln
    130                 135                 140

Asn Leu Gly Glu Arg Val Asn Asp Ile Gly Phe Trp Lys Ser Glu Ile
145                 150                 155                 160

Ile His Glu Leu Asp Glu Met Ile Gly Glu Thr Asn Ala Leu Thr Asp
                165                 170                 175

Val Lys Lys Arg Leu Glu Arg Ala Leu Met Glu Thr Glu Ala Pro Leu
            180                 185                 190

Gln Val Ala Arg Glu Cys Leu Phe His Arg Glu Lys Arg Met Gly Ile
        195                 200                 205

Asp Leu Val His Asp Glu Val Glu Ala Gln Leu Leu Thr Glu Val Asp
```

```
    210                 215                 220

Thr Ile Leu Cys Cys Gln Glu Arg Met Lys Leu His Leu Asp Lys Ala
225                 230                 235                 240

Ile Ala Gln Leu Ala Ala Asn Arg Ala Ser Gln His Glu Leu Glu Lys
                245                 250                 255

Asp Leu Ser Asp Lys Gln Thr Ala Tyr Arg Ile Asp Asp Lys Cys His
            260                 265                 270

His Leu Arg Asn Thr Ser Asp Gly Val Gly Tyr Phe Arg Gly Val Glu
        275                 280                 285

Arg Val Asp Ala Thr Val Ser Val Pro Glu Ser Trp Ala Lys Phe Thr
    290                 295                 300

Asp Asp Asn Ile Leu Arg Ser Gln Ser Glu Arg Ala Ala Ser Ala Lys
305                 310                 315                 320

Leu Arg Asp Asp Ile Glu Asn Leu Leu Val Val Thr Ala Asn Glu Met
                325                 330                 335

Trp Asn Gln Phe Asn Lys Val Asn Leu Ser Phe Thr Asn Arg Ile Ala
            340                 345                 350

Glu Thr Ala Asp Ala Lys Asn Lys Ile Gln Thr His Leu Ala Lys Thr
        355                 360                 365

Leu Gln Glu Ile Phe Gln Thr Glu Met Thr Ile Glu Ser Ile Lys Lys
    370                 375                 380

Ala Ile Lys Asp Lys Thr Ala Phe Leu Lys Val Ala Gln Thr Arg Leu
385                 390                 395                 400

Asp Glu Arg Thr Arg Arg Pro Asn Ile Glu Leu Cys Arg Asp Met Ala
                405                 410                 415

Gln Leu Arg Leu Val Asn Glu Val His Glu Val Asp Asp Thr Ile Gln
            420                 425                 430

Thr Leu Gln Gln Arg Leu Arg Asp Ala Glu Asp Thr Leu Gln Ser Leu
        435                 440                 445

Val His Ile Lys Ala Thr Leu Glu Tyr Asp Leu Ala Val Lys Ala Asn
    450                 455                 460

Ser Leu Tyr Ile Asp Gln Glu Lys Cys Met Ser Met Arg Lys Ser Tyr
465                 470                 475                 480

Pro Asn Thr Leu Arg Leu Val Gly Phe Cys
                485                 490
```

<210> SEQ ID NO 77
<211> LENGTH: 500
<212> TYPE: PRT
<213> ORGANISM: Artificial Sequence
<220> FEATURE:
<223> OTHER INFORMATION: Synthetic_IC1_HUMAN

<400> SEQUENCE: 77

```
Met Ala Ser Arg Leu Thr Leu Leu Thr Leu Leu Leu Leu Leu Leu Ala
1               5                   10                  15

Gly Asp Arg Ala Ser Ser Asn Pro Asn Ala Thr Ser Ser Ser Ser Gln
            20                  25                  30

Asp Pro Glu Ser Leu Gln Asp Arg Gly Glu Gly Lys Val Ala Thr Thr
        35                  40                  45

Val Ile Ser Lys Met Leu Phe Val Glu Pro Ile Leu Glu Val Ser Ser
    50                  55                  60

Leu Pro Thr Thr Asn Ser Thr Thr Asn Ser Ala Thr Lys Ile Thr Ala
65                  70                  75                  80

Asn Thr Thr Asp Glu Pro Thr Thr Gln Pro Thr Thr Glu Pro Thr Thr
```

-continued

```
                85                  90                  95

Gln Pro Thr Ile Gln Pro Thr Gln Pro Thr Thr Gln Leu Pro Thr Asp
            100                 105                 110

Ser Pro Thr Gln Pro Thr Thr Gly Ser Phe Cys Pro Gly Pro Val Thr
        115                 120                 125

Leu Cys Ser Asp Leu Glu Ser His Ser Thr Glu Ala Val Leu Gly Asp
    130                 135                 140

Ala Leu Val Asp Phe Ser Leu Lys Leu Tyr His Ala Phe Ser Ala Met
145                 150                 155                 160

Lys Lys Val Glu Thr Asn Met Ala Phe Ser Pro Phe Ser Ile Ala Ser
                165                 170                 175

Leu Leu Thr Gln Val Leu Leu Gly Ala Gly Glu Asn Thr Lys Thr Asn
            180                 185                 190

Leu Glu Ser Ile Leu Ser Tyr Pro Lys Asp Phe Thr Cys Val His Gln
        195                 200                 205

Ala Leu Lys Gly Phe Thr Thr Lys Gly Val Thr Ser Val Ser Gln Ile
    210                 215                 220

Phe His Ser Pro Asp Leu Ala Ile Arg Asp Thr Phe Val Asn Ala Ser
225                 230                 235                 240

Arg Thr Leu Tyr Ser Ser Ser Pro Arg Val Leu Ser Asn Asn Ser Asp
                245                 250                 255

Ala Asn Leu Glu Leu Ile Asn Thr Trp Val Ala Lys Asn Thr Asn Asn
            260                 265                 270

Lys Ile Ser Arg Leu Leu Asp Ser Leu Pro Ser Asp Thr Arg Leu Val
        275                 280                 285

Leu Leu Asn Ala Ile Tyr Leu Ser Ala Lys Trp Lys Thr Thr Phe Asp
    290                 295                 300

Pro Lys Lys Thr Arg Met Glu Pro Phe His Phe Lys Asn Ser Val Ile
305                 310                 315                 320

Lys Val Pro Met Met Asn Ser Lys Lys Tyr Pro Val Ala His Phe Ile
                325                 330                 335

Asp Gln Thr Leu Lys Ala Lys Val Gly Gln Leu Gln Leu Ser His Asn
            340                 345                 350

Leu Ser Leu Val Ile Leu Val Pro Gln Asn Leu Lys His Arg Leu Glu
        355                 360                 365

Asp Met Glu Gln Ala Leu Ser Pro Ser Val Phe Lys Ala Ile Met Glu
    370                 375                 380

Lys Leu Glu Met Ser Lys Phe Gln Pro Thr Leu Leu Thr Leu Pro Arg
385                 390                 395                 400

Ile Lys Val Thr Thr Ser Gln Asp Met Leu Ser Ile Met Glu Lys Leu
                405                 410                 415

Glu Phe Phe Asp Phe Ser Tyr Asp Leu Asn Leu Cys Gly Leu Thr Glu
            420                 425                 430

Asp Pro Asp Leu Gln Val Ser Ala Met Gln His Gln Thr Val Leu Glu
        435                 440                 445

Leu Thr Glu Thr Gly Val Glu Ala Ala Ala Ala Ser Ala Ile Ser Val
    450                 455                 460

Ala Arg Thr Leu Leu Val Phe Glu Val Gln Gln Pro Phe Leu Phe Val
465                 470                 475                 480

Leu Trp Asp Gln Gln His Lys Phe Pro Val Phe Met Gly Arg Val Tyr
                485                 490                 495

Asp Pro Arg Ala
            500
```

<210> SEQ ID NO 78
<211> LENGTH: 508
<212> TYPE: PRT
<213> ORGANISM: Artificial Sequence
<220> FEATURE:
<223> OTHER INFORMATION: Synthetic_SRF_HUMAN

<400> SEQUENCE: 78

```
Met Leu Pro Thr Gln Ala Gly Ala Ala Ala Ala Leu Gly Arg Gly Ser
1               5                   10                  15

Ala Leu Gly Gly Ser Leu Asn Arg Thr Pro Thr Gly Arg Pro Gly Gly
            20                  25                  30

Gly Gly Gly Thr Arg Gly Ala Asn Gly Gly Arg Val Pro Gly Asn Gly
        35                  40                  45

Ala Gly Leu Gly Pro Gly Arg Leu Glu Arg Glu Ala Ala Ala Ala Ala
    50                  55                  60

Ala Thr Thr Pro Ala Pro Thr Ala Gly Ala Leu Tyr Ser Gly Ser Glu
65                  70                  75                  80

Gly Asp Ser Glu Ser Gly Glu Glu Glu Glu Leu Gly Ala Glu Arg Arg
                85                  90                  95

Gly Leu Lys Arg Ser Leu Ser Glu Met Glu Ile Gly Met Val Val Gly
            100                 105                 110

Gly Pro Glu Ala Ser Ala Ala Ala Thr Gly Gly Tyr Gly Pro Val Ser
        115                 120                 125

Gly Ala Val Ser Gly Ala Lys Pro Gly Lys Lys Thr Arg Gly Arg Val
    130                 135                 140

Lys Ile Lys Met Glu Phe Ile Asp Asn Lys Leu Arg Arg Tyr Thr Thr
145                 150                 155                 160

Phe Ser Lys Arg Lys Thr Gly Ile Met Lys Lys Ala Tyr Glu Leu Ser
                165                 170                 175

Thr Leu Thr Gly Thr Gln Val Leu Leu Leu Val Ala Ser Glu Thr Gly
            180                 185                 190

His Val Tyr Thr Phe Ala Thr Arg Lys Leu Gln Pro Met Ile Thr Ser
        195                 200                 205

Glu Thr Gly Lys Ala Leu Ile Gln Thr Cys Leu Asn Ser Pro Asp Ser
    210                 215                 220

Pro Pro Arg Ser Asp Pro Thr Thr Asp Gln Arg Met Ser Ala Thr Gly
225                 230                 235                 240

Phe Glu Glu Thr Asp Leu Thr Tyr Gln Val Ser Glu Ser Asp Ser Ser
                245                 250                 255

Gly Glu Thr Lys Asp Thr Leu Lys Pro Ala Phe Thr Val Thr Asn Leu
            260                 265                 270

Pro Gly Thr Thr Ser Thr Ile Gln Thr Ala Pro Ser Thr Ser Thr Thr
        275                 280                 285

Met Gln Val Ser Ser Gly Pro Ser Phe Pro Ile Thr Asn Tyr Leu Ala
    290                 295                 300

Pro Val Ser Ala Ser Val Ser Pro Ser Ala Val Ser Ser Ala Asn Gly
305                 310                 315                 320

Thr Val Leu Lys Ser Thr Gly Ser Gly Pro Val Ser Ser Gly Gly Leu
                325                 330                 335

Met Gln Leu Pro Thr Ser Phe Thr Leu Met Pro Gly Gly Ala Val Ala
            340                 345                 350

Gln Gln Val Pro Val Gln Ala Ile Gln Val His Gln Ala Pro Gln Gln
        355                 360                 365
```

```
Ala Ser Pro Ser Arg Asp Ser Ser Thr Asp Leu Thr Gln Thr Ser Ser
    370                 375                 380

Ser Gly Thr Val Thr Leu Pro Ala Thr Ile Met Thr Ser Ser Val Pro
385                 390                 395                 400

Thr Thr Val Gly Gly His Met Met Tyr Pro Ser Pro His Ala Val Met
                405                 410                 415

Tyr Ala Pro Thr Ser Gly Leu Gly Asp Gly Ser Leu Thr Val Leu Asn
            420                 425                 430

Ala Phe Ser Gln Ala Pro Ser Thr Met Gln Val Ser His Ser Gln Val
        435                 440                 445

Gln Glu Pro Gly Gly Val Pro Gln Val Phe Leu Thr Ala Ser Ser Gly
    450                 455                 460

Thr Val Gln Ile Pro Val Ser Ala Val Gln Leu His Gln Met Ala Val
465                 470                 475                 480

Ile Gly Gln Gln Ala Gly Ser Ser Ser Asn Leu Thr Glu Leu Gln Val
                485                 490                 495

Val Asn Leu Asp Thr Ala His Ser Thr Lys Ser Glu
            500                 505


<210> SEQ ID NO 79
<211> LENGTH: 512
<212> TYPE: PRT
<213> ORGANISM: Artificial Sequence
<220> FEATURE:
<223> OTHER INFORMATION: Synthetic_IGD_HUMAN

<400> SEQUENCE: 79

Arg Leu Gln Leu Gln Glu Ser Gly Pro Gly Leu Val Lys Pro Ser Glu
1               5                   10                  15

Thr Leu Ser Leu Thr Cys Ile Val Ser Gly Gly Pro Ile Arg Arg Thr
            20                  25                  30

Gly Tyr Tyr Trp Gly Trp Ile Arg Gln Pro Pro Gly Lys Gly Leu Glu
        35                  40                  45

Trp Ile Gly Gly Val Tyr Tyr Thr Gly Ser Ile Tyr Tyr Asn Pro Ser
    50                  55                  60

Leu Arg Gly Arg Val Thr Ile Ser Val Asp Thr Ser Arg Asn Gln Phe
65                  70                  75                  80

Ser Leu Asn Leu Arg Ser Met Ser Ala Ala Asp Thr Ala Met Tyr Tyr
                85                  90                  95

Cys Ala Arg Gly Asn Pro Pro Pro Tyr Tyr Asp Ile Gly Thr Gly Ser
            100                 105                 110

Asp Asp Gly Ile Asp Val Trp Gly Gln Gly Thr Thr Val His Val Ser
        115                 120                 125

Ser Ala Pro Thr Lys Ala Pro Asp Val Phe Pro Ile Ile Ser Gly Cys
    130                 135                 140

Arg His Pro Lys Asp Asn Ser Pro Val Val Leu Ala Cys Leu Ile Thr
145                 150                 155                 160

Gly Tyr His Pro Thr Ser Val Thr Val Thr Trp Tyr Met Gly Thr Gln
                165                 170                 175

Ser Gln Pro Gln Arg Thr Phe Pro Glu Ile Gln Arg Arg Asp Ser Tyr
            180                 185                 190

Tyr Met Thr Ser Ser Gln Leu Ser Thr Pro Leu Gln Gln Trp Arg Gln
        195                 200                 205

Gly Glu Tyr Lys Cys Val Val Gln His Thr Ala Ser Lys Ser Lys Lys
    210                 215                 220
```

Glu Ile Phe Arg Trp Pro Glu Ser Pro Lys Ala Gln Ala Ser Ser Val
225 230 235 240

Pro Thr Ala Gln Pro Gln Ala Glu Gly Ser Leu Ala Lys Ala Thr Thr
245 250 255

Ala Pro Ala Thr Thr Arg Asn Thr Gly Arg Gly Gly Glu Glu Lys Lys
260 265 270

Lys Glu Lys Glu Lys Glu Glu Gln Glu Glu Arg Glu Thr Lys Thr Pro
275 280 285

Glu Cys Pro Ser His Thr Gln Pro Leu Gly Val Tyr Leu Leu Thr Pro
290 295 300

Ala Val Gln Asp Leu Trp Leu Arg Asp Lys Ala Thr Phe Thr Cys Phe
305 310 315 320

Val Val Gly Ser Asp Leu Lys Asp Ala His Leu Thr Trp Glu Val Ala
325 330 335

Gly Lys Val Pro Thr Gly Gly Val Glu Glu Gly Leu Leu Glu Arg His
340 345 350

Ser Asn Gly Ser Gln Ser Gln His Ser Arg Leu Thr Leu Pro Arg Ser
355 360 365

Leu Trp Asn Ala Gly Thr Ser Val Thr Cys Thr Leu Asn His Pro Ser
370 375 380

Leu Pro Pro Gln Arg Leu Met Ala Leu Arg Glu Pro Ala Ala Gln Ala
385 390 395 400

Pro Val Lys Leu Ser Leu Asn Leu Leu Ala Ser Ser Asp Pro Pro Glu
405 410 415

Ala Ala Ser Trp Leu Leu Cys Glu Val Ser Gly Phe Ser Pro Pro Asn
420 425 430

Ile Leu Leu Met Trp Leu Glu Asp Gln Arg Glu Val Asn Thr Ser Gly
435 440 445

Phe Ala Pro Ala Arg Pro Pro Pro Gln Pro Gly Ser Thr Thr Phe Trp
450 455 460

Ala Trp Ser Val Leu Arg Val Pro Ala Pro Pro Ser Pro Gln Pro Ala
465 470 475 480

Thr Tyr Thr Cys Val Val Ser His Glu Asp Ser Arg Thr Leu Leu Asn
485 490 495

Ala Ser Arg Ser Leu Glu Val Ser Tyr Val Thr Asp His Gly Pro Met
500 505 510

<210> SEQ ID NO 80
<211> LENGTH: 556
<212> TYPE: PRT
<213> ORGANISM: Artificial Sequence
<220> FEATURE:
<223> OTHER INFORMATION: Synthetic_GPC4_HUMAN

<400> SEQUENCE: 80

Met Ala Arg Phe Gly Leu Pro Ala Leu Leu Cys Thr Leu Ala Val Leu
1 5 10 15

Ser Ala Ala Leu Leu Ala Ala Glu Leu Lys Ser Lys Ser Cys Ser Glu
20 25 30

Val Arg Arg Leu Tyr Val Ser Lys Gly Phe Asn Lys Asn Asp Ala Pro
35 40 45

Leu His Glu Ile Asn Gly Asp His Leu Lys Ile Cys Pro Gln Gly Ser
50 55 60

Thr Cys Cys Ser Gln Glu Met Glu Glu Lys Tyr Ser Leu Gln Ser Lys
65 70 75 80

```
Asp Asp Phe Lys Ser Val Val Ser Glu Gln Cys Asn His Leu Gln Ala
                85                  90                  95

Val Phe Ala Ser Arg Tyr Lys Lys Phe Asp Glu Phe Phe Lys Glu Leu
            100                 105                 110

Leu Glu Asn Ala Glu Lys Ser Leu Asn Asp Met Phe Val Lys Thr Tyr
        115                 120                 125

Gly His Leu Tyr Met Gln Asn Ser Glu Leu Phe Lys Asp Leu Phe Val
    130                 135                 140

Glu Leu Lys Arg Tyr Tyr Val Val Gly Asn Val Asn Leu Glu Glu Met
145                 150                 155                 160

Leu Asn Asp Phe Trp Ala Arg Leu Leu Glu Arg Met Phe Arg Leu Val
                165                 170                 175

Asn Ser Gln Tyr His Phe Thr Asp Glu Tyr Leu Glu Cys Val Ser Lys
            180                 185                 190

Tyr Thr Glu Gln Leu Lys Pro Phe Gly Asp Val Pro Arg Lys Leu Lys
        195                 200                 205

Leu Gln Val Thr Arg Ala Phe Val Ala Ala Arg Thr Phe Ala Gln Gly
    210                 215                 220

Leu Ala Val Ala Gly Asp Val Val Ser Lys Val Ser Val Val Asn Pro
225                 230                 235                 240

Thr Ala Gln Cys Thr His Ala Leu Leu Lys Met Ile Tyr Cys Ser His
                245                 250                 255

Cys Arg Gly Leu Val Thr Val Lys Pro Cys Tyr Asn Tyr Cys Ser Asn
            260                 265                 270

Ile Met Arg Gly Cys Leu Ala Asn Gln Gly Asp Leu Asp Phe Glu Trp
        275                 280                 285

Asn Asn Phe Ile Asp Ala Met Leu Met Val Ala Glu Arg Leu Glu Gly
    290                 295                 300

Pro Phe Asn Ile Glu Ser Val Met Asp Pro Ile Asp Val Lys Ile Ser
305                 310                 315                 320

Asp Ala Ile Met Asn Met Gln Asp Asn Ser Val Gln Val Ser Gln Lys
                325                 330                 335

Val Phe Gln Gly Cys Gly Pro Pro Lys Pro Leu Pro Ala Gly Arg Ile
            340                 345                 350

Ser Arg Ser Ile Ser Glu Ser Ala Phe Ser Ala Arg Phe Arg Pro His
        355                 360                 365

His Pro Glu Glu Arg Pro Thr Thr Ala Ala Gly Thr Ser Leu Asp Arg
    370                 375                 380

Leu Val Thr Asp Val Lys Glu Lys Leu Lys Gln Ala Lys Lys Phe Trp
385                 390                 395                 400

Ser Ser Leu Pro Ser Asn Val Cys Asn Asp Glu Arg Met Ala Ala Gly
                405                 410                 415

Asn Gly Asn Glu Asp Asp Cys Trp Asn Gly Lys Gly Lys Ser Arg Tyr
            420                 425                 430

Leu Phe Ala Val Thr Gly Asn Gly Leu Ala Asn Gln Gly Asn Asn Pro
        435                 440                 445

Glu Val Gln Val Asp Thr Ser Lys Pro Asp Ile Leu Ile Leu Arg Gln
    450                 455                 460

Ile Met Ala Leu Arg Val Met Thr Ser Lys Met Lys Asn Ala Tyr Asn
465                 470                 475                 480

Gly Asn Asp Val Asp Phe Phe Asp Ile Ser Asp Glu Ser Ser Gly Glu
                485                 490                 495
```

Gly Ser Gly Ser Gly Cys Glu Tyr Gln Gln Cys Pro Ser Glu Phe Asp
500 505 510

Tyr Asn Ala Thr Asp His Ala Gly Lys Ser Ala Asn Glu Lys Ala Asp
515 520 525

Ser Ala Gly Val Arg Pro Gly Ala Gln Ala Tyr Leu Leu Thr Val Phe
530 535 540

Cys Ile Leu Phe Leu Val Met Gln Arg Glu Trp Arg
545 550 555

<210> SEQ ID NO 81
<211> LENGTH: 558
<212> TYPE: PRT
<213> ORGANISM: Artificial Sequence
<220> FEATURE:
<223> OTHER INFORMATION: Synthetic_GPC1_HUMAN

<400> SEQUENCE: 81

Met Glu Leu Arg Ala Arg Gly Trp Trp Leu Leu Cys Ala Ala Ala Ala
1 5 10 15

Leu Val Ala Cys Ala Arg Gly Asp Pro Ala Ser Lys Ser Arg Ser Cys
20 25 30

Gly Glu Val Arg Gln Ile Tyr Gly Ala Lys Gly Phe Ser Leu Ser Asp
35 40 45

Val Pro Gln Ala Glu Ile Ser Gly Glu His Leu Arg Ile Cys Pro Gln
50 55 60

Gly Tyr Thr Cys Cys Thr Ser Glu Met Glu Glu Asn Leu Ala Asn Arg
65 70 75 80

Ser His Ala Glu Leu Glu Thr Ala Leu Arg Asp Ser Ser Arg Val Leu
85 90 95

Gln Ala Met Leu Ala Thr Gln Leu Arg Ser Phe Asp Asp His Phe Gln
100 105 110

His Leu Leu Asn Asp Ser Glu Arg Thr Leu Gln Ala Thr Phe Pro Gly
115 120 125

Ala Phe Gly Glu Leu Tyr Thr Gln Asn Ala Arg Ala Phe Arg Asp Leu
130 135 140

Tyr Ser Glu Leu Arg Leu Tyr Tyr Arg Gly Ala Asn Leu His Leu Glu
145 150 155 160

Glu Thr Leu Ala Glu Phe Trp Ala Arg Leu Leu Glu Arg Leu Phe Lys
165 170 175

Gln Leu His Pro Gln Leu Leu Leu Pro Asp Asp Tyr Leu Asp Cys Leu
180 185 190

Gly Lys Gln Ala Glu Ala Leu Arg Pro Phe Gly Glu Ala Pro Arg Glu
195 200 205

Leu Arg Leu Arg Ala Thr Arg Ala Phe Val Ala Ala Arg Ser Phe Val
210 215 220

Gln Gly Leu Gly Val Ala Ser Asp Val Val Arg Lys Val Ala Gln Val
225 230 235 240

Pro Leu Gly Pro Glu Cys Ser Arg Ala Val Met Lys Leu Val Tyr Cys
245 250 255

Ala His Cys Leu Gly Val Pro Gly Ala Arg Pro Cys Pro Asp Tyr Cys
260 265 270

Arg Asn Val Leu Lys Gly Cys Leu Ala Asn Gln Ala Asp Leu Asp Ala
275 280 285

Glu Trp Arg Asn Leu Leu Asp Ser Met Val Leu Ile Thr Asp Lys Phe
290 295 300

Trp Gly Thr Ser Gly Val Glu Ser Val Ile Gly Ser Val His Thr Trp
305 310 315 320

Leu Ala Glu Ala Ile Asn Ala Leu Gln Asp Asn Arg Asp Thr Leu Thr
325 330 335

Ala Lys Val Ile Gln Gly Cys Gly Asn Pro Lys Val Asn Pro Gln Gly
340 345 350

Pro Gly Pro Glu Glu Lys Arg Arg Arg Gly Lys Leu Ala Pro Arg Glu
355 360 365

Arg Pro Pro Ser Gly Thr Leu Glu Lys Leu Val Ser Glu Ala Lys Ala
370 375 380

Gln Leu Arg Asp Val Gln Asp Phe Trp Ile Ser Leu Pro Gly Thr Leu
385 390 395 400

Cys Ser Glu Lys Met Ala Leu Ser Thr Ala Ser Asp Asp Arg Cys Trp
405 410 415

Asn Gly Met Ala Arg Gly Arg Tyr Leu Pro Glu Val Met Gly Asp Gly
420 425 430

Leu Ala Asn Gln Ile Asn Asn Pro Glu Val Glu Val Asp Ile Thr Lys
435 440 445

Pro Asp Met Thr Ile Arg Gln Gln Ile Met Gln Leu Lys Ile Met Thr
450 455 460

Asn Arg Leu Arg Ser Ala Tyr Asn Gly Asn Asp Val Asp Phe Gln Asp
465 470 475 480

Ala Ser Asp Asp Gly Ser Gly Ser Gly Ser Gly Asp Gly Cys Leu Asp
485 490 495

Asp Leu Cys Ser Arg Lys Val Ser Arg Lys Ser Ser Ser Ser Arg Thr
500 505 510

Pro Leu Thr His Ala Leu Pro Gly Leu Ser Glu Gln Glu Gly Gln Lys
515 520 525

Thr Ser Ala Ala Ser Cys Pro Gln Pro Pro Thr Phe Leu Leu Pro Leu
530 535 540

Leu Leu Phe Leu Ala Leu Thr Val Ala Arg Pro Arg Trp Arg
545 550 555

<210> SEQ ID NO 82
<211> LENGTH: 572
<212> TYPE: PRT
<213> ORGANISM: Artificial Sequence
<220> FEATURE:
<223> OTHER INFORMATION: Synthetic_GPC5_HUMAN

<400> SEQUENCE: 82

Met Asp Ala Gln Thr Trp Pro Val Gly Phe Arg Cys Leu Leu Leu Leu
1 5 10 15

Ala Leu Val Gly Ser Ala Arg Ser Glu Gly Val Gln Thr Cys Glu Glu
20 25 30

Val Arg Lys Leu Phe Gln Trp Arg Leu Leu Gly Ala Val Arg Gly Leu
35 40 45

Pro Asp Ser Pro Arg Ala Gly Pro Asp Leu Gln Val Cys Ile Ser Lys
50 55 60

Lys Pro Thr Cys Cys Thr Arg Lys Met Glu Glu Arg Tyr Gln Ile Ala
65 70 75 80

Ala Arg Gln Asp Met Gln Gln Phe Leu Gln Thr Ser Ser Ser Thr Leu
85 90 95

Lys Phe Leu Ile Ser Arg Asn Ala Ala Ala Phe Gln Glu Thr Leu Glu
100 105 110

```
Thr Leu Ile Lys Gln Ala Glu Asn Tyr Thr Ser Ile Leu Phe Cys Ser
        115                 120                 125

Thr Tyr Arg Asn Met Ala Leu Glu Ala Ala Ala Ser Val Gln Glu Phe
    130                 135                 140

Phe Thr Asp Val Gly Leu Tyr Leu Phe Gly Ala Asp Val Asn Pro Glu
145                 150                 155                 160

Glu Phe Val Asn Arg Phe Phe Asp Ser Leu Phe Pro Leu Val Tyr Asn
                165                 170                 175

His Leu Ile Asn Pro Gly Val Thr Asp Ser Ser Leu Glu Tyr Ser Glu
            180                 185                 190

Cys Ile Arg Met Ala Arg Arg Asp Val Ser Pro Phe Gly Asn Ile Pro
        195                 200                 205

Gln Arg Val Met Gly Gln Met Gly Arg Ser Leu Leu Pro Ser Arg Thr
    210                 215                 220

Phe Leu Gln Ala Leu Asn Leu Gly Ile Glu Val Ile Asn Thr Thr Asp
225                 230                 235                 240

Tyr Leu His Phe Ser Lys Glu Cys Ser Arg Ala Leu Leu Lys Met Gln
                245                 250                 255

Tyr Cys Pro His Cys Gln Gly Leu Ala Leu Thr Lys Pro Cys Met Gly
            260                 265                 270

Tyr Cys Leu Asn Val Met Arg Gly Cys Leu Ala His Met Ala Glu Leu
        275                 280                 285

Asn Pro His Trp His Ala Tyr Ile Arg Ser Leu Glu Glu Leu Ser Asp
    290                 295                 300

Ala Met His Gly Thr Tyr Asp Ile Gly His Val Leu Leu Asn Phe His
305                 310                 315                 320

Leu Leu Val Asn Asp Ala Val Leu Gln Ala His Leu Asn Gly Gln Lys
                325                 330                 335

Leu Leu Glu Gln Val Asn Arg Ile Cys Gly Arg Pro Val Arg Thr Pro
            340                 345                 350

Thr Gln Ser Pro Arg Cys Ser Phe Asp Gln Ser Lys Glu Lys His Gly
        355                 360                 365

Met Lys Thr Thr Thr Arg Asn Ser Glu Glu Thr Leu Ala Asn Arg Arg
    370                 375                 380

Lys Glu Phe Ile Asn Ser Leu Arg Leu Tyr Arg Ser Phe Tyr Gly Gly
385                 390                 395                 400

Leu Ala Asp Gln Leu Cys Ala Asn Glu Leu Ala Ala Ala Asp Gly Leu
                405                 410                 415

Pro Cys Trp Asn Gly Glu Asp Ile Val Lys Ser Tyr Thr Gln Arg Val
            420                 425                 430

Val Gly Asn Gly Ile Lys Ala Gln Ser Gly Asn Pro Glu Val Lys Val
        435                 440                 445

Lys Gly Ile Asp Pro Val Ile Asn Gln Ile Ile Asp Lys Leu Lys His
    450                 455                 460

Val Val Gln Leu Leu Gln Gly Arg Ser Pro Lys Pro Asp Lys Trp Glu
465                 470                 475                 480

Leu Leu Gln Leu Gly Ser Gly Gly Gly Met Val Glu Gln Val Ser Gly
                485                 490                 495

Asp Cys Asp Asp Glu Asp Gly Cys Gly Gly Ser Gly Ser Gly Glu Val
            500                 505                 510

Lys Arg Thr Leu Lys Ile Thr Asp Trp Met Pro Asp Asp Met Asn Phe
        515                 520                 525

Ser Asp Val Lys Gln Ile His Gln Thr Asp Thr Gly Ser Thr Leu Asp
```

530 535 540

Thr Thr Gly Ala Gly Cys Ala Val Ala Thr Glu Ser Met Thr Phe Thr
545 550 555 560

Leu Ile Ser Val Val Met Leu Leu Pro Gly Ile Trp
565 570

<210> SEQ ID NO 83
<211> LENGTH: 579
<212> TYPE: PRT
<213> ORGANISM: Artificial Sequence
<220> FEATURE:
<223> OTHER INFORMATION: Synthetic_GPC2_HUMAN

<400> SEQUENCE: 83

Met Ser Ala Leu Arg Pro Leu Leu Leu Leu Leu Leu Pro Leu Cys Pro
1 5 10 15

Gly Pro Gly Pro Gly Pro Gly Ser Glu Ala Lys Val Thr Arg Ser Cys
20 25 30

Ala Glu Thr Arg Gln Val Leu Gly Ala Arg Gly Tyr Ser Leu Asn Leu
35 40 45

Ile Pro Pro Ala Leu Ile Ser Gly Glu His Leu Arg Val Cys Pro Gln
50 55 60

Glu Tyr Thr Cys Cys Ser Ser Glu Thr Glu Gln Arg Leu Ile Arg Glu
65 70 75 80

Thr Glu Ala Thr Phe Arg Gly Leu Val Glu Asp Ser Gly Ser Phe Leu
85 90 95

Val His Thr Leu Ala Ala Arg His Arg Lys Phe Asp Glu Phe Phe Leu
100 105 110

Glu Met Leu Ser Val Ala Gln His Ser Leu Thr Gln Leu Phe Ser His
115 120 125

Ser Tyr Gly Arg Leu Tyr Ala Gln His Ala Leu Ile Phe Asn Gly Leu
130 135 140

Phe Ser Arg Leu Arg Asp Phe Tyr Gly Glu Ser Gly Glu Gly Leu Asp
145 150 155 160

Asp Thr Leu Ala Asp Phe Trp Ala Gln Leu Leu Glu Arg Val Phe Pro
165 170 175

Leu Leu His Pro Gln Tyr Ser Phe Pro Pro Asp Tyr Leu Leu Cys Leu
180 185 190

Ser Arg Leu Ala Ser Ser Thr Asp Gly Ser Leu Gln Pro Phe Gly Asp
195 200 205

Ser Pro Arg Arg Leu Arg Leu Gln Ile Thr Arg Thr Leu Val Ala Ala
210 215 220

Arg Ala Phe Val Gln Gly Leu Glu Thr Gly Arg Asn Val Val Ser Glu
225 230 235 240

Ala Leu Lys Val Pro Val Ser Glu Gly Cys Ser Gln Ala Leu Met Arg
245 250 255

Leu Ile Gly Cys Pro Leu Cys Arg Gly Val Pro Ser Leu Met Pro Cys
260 265 270

Gln Gly Phe Cys Leu Asn Val Val Arg Gly Cys Leu Ser Ser Arg Gly
275 280 285

Leu Glu Pro Asp Trp Gly Asn Tyr Leu Asp Gly Leu Leu Ile Leu Ala
290 295 300

Asp Lys Leu Gln Gly Pro Phe Ser Phe Glu Leu Thr Ala Glu Ser Ile
305 310 315 320

Gly Val Lys Ile Ser Glu Gly Leu Met Tyr Leu Gln Glu Asn Ser Ala

```
                325                 330                 335

Lys Val Ser Ala Gln Val Phe Gln Glu Cys Gly Pro Pro Asp Pro Val
            340                 345                 350

Pro Ala Arg Asn Arg Arg Ala Pro Pro Pro Arg Glu Glu Ala Gly Arg
        355                 360                 365

Leu Trp Ser Met Val Thr Glu Glu Glu Arg Pro Thr Thr Ala Ala Gly
    370                 375                 380

Thr Asn Leu His Arg Leu Val Trp Glu Leu Arg Glu Arg Leu Ala Arg
385                 390                 395                 400

Met Arg Gly Phe Trp Ala Arg Leu Ser Leu Thr Val Cys Gly Asp Ser
                405                 410                 415

Arg Met Ala Ala Asp Ala Ser Leu Glu Ala Ala Pro Cys Trp Thr Gly
            420                 425                 430

Ala Gly Arg Gly Arg Tyr Leu Pro Pro Val Val Gly Gly Ser Pro Ala
        435                 440                 445

Glu Gln Val Asn Asn Pro Glu Leu Lys Val Asp Ala Ser Gly Pro Asp
    450                 455                 460

Val Pro Thr Arg Arg Arg Arg Leu Gln Leu Arg Ala Ala Thr Ala Arg
465                 470                 475                 480

Met Lys Thr Ala Ala Leu Gly His Asp Leu Asp Gly Gln Asp Ala Asp
                485                 490                 495

Glu Asp Ala Ser Gly Ser Gly Gly Gly Gln Gln Tyr Ala Asp Asp Trp
            500                 505                 510

Met Ala Gly Ala Val Ala Pro Pro Ala Arg Pro Pro Arg Pro Pro Tyr
        515                 520                 525

Pro Pro Arg Arg Asp Gly Ser Gly Gly Lys Gly Gly Gly Gly Ser Ala
    530                 535                 540

Arg Tyr Asn Gln Gly Arg Ser Arg Ser Gly Gly Ala Ser Ile Gly Phe
545                 550                 555                 560

His Thr Gln Thr Ile Leu Ile Leu Ser Leu Ser Ala Leu Ala Leu Leu
                565                 570                 575

Gly Pro Arg


<210> SEQ ID NO 84
<211> LENGTH: 615
<212> TYPE: PRT
<213> ORGANISM: Artificial Sequence
<220> FEATURE:
<223> OTHER INFORMATION: Synthetic_FA12_HUMAN

<400> SEQUENCE: 84

Met Arg Ala Leu Leu Leu Leu Gly Phe Leu Leu Val Ser Leu Glu Ser
1               5                   10                  15

Thr Leu Ser Ile Pro Pro Trp Glu Ala Pro Lys Glu His Lys Tyr Lys
            20                  25                  30

Ala Glu Glu His Thr Val Val Leu Thr Val Thr Gly Glu Pro Cys His
        35                  40                  45

Phe Pro Phe Gln Tyr His Arg Gln Leu Tyr His Lys Cys Thr His Lys
    50                  55                  60

Gly Arg Pro Gly Pro Gln Pro Trp Cys Ala Thr Thr Pro Asn Phe Asp
65                  70                  75                  80

Gln Asp Gln Arg Trp Gly Tyr Cys Leu Glu Pro Lys Lys Val Lys Asp
                85                  90                  95

His Cys Ser Lys His Ser Pro Cys Gln Lys Gly Gly Thr Cys Val Asn
            100                 105                 110
```

```
Met Pro Ser Gly Pro His Cys Leu Cys Pro Gln His Leu Thr Gly Asn
        115                 120                 125

His Cys Gln Lys Glu Lys Cys Phe Glu Pro Gln Leu Leu Arg Phe Phe
    130                 135                 140

His Lys Asn Glu Ile Trp Tyr Arg Thr Glu Gln Ala Ala Val Ala Arg
145                 150                 155                 160

Cys Gln Cys Lys Gly Pro Asp Ala His Cys Gln Arg Leu Ala Ser Gln
                165                 170                 175

Ala Cys Arg Thr Asn Pro Cys Leu His Gly Gly Arg Cys Leu Glu Val
            180                 185                 190

Glu Gly His Arg Leu Cys His Cys Pro Val Gly Tyr Thr Gly Ala Phe
        195                 200                 205

Cys Asp Val Asp Thr Lys Ala Ser Cys Tyr Asp Gly Arg Gly Leu Ser
    210                 215                 220

Tyr Arg Gly Leu Ala Arg Thr Thr Leu Ser Gly Ala Pro Cys Gln Pro
225                 230                 235                 240

Trp Ala Ser Glu Ala Thr Tyr Arg Asn Val Thr Ala Glu Gln Ala Arg
                245                 250                 255

Asn Trp Gly Leu Gly Gly His Ala Phe Cys Arg Asn Pro Asp Asn Asp
            260                 265                 270

Ile Arg Pro Trp Cys Phe Val Leu Asn Arg Asp Arg Leu Ser Trp Glu
        275                 280                 285

Tyr Cys Asp Leu Ala Gln Cys Gln Thr Pro Thr Gln Ala Ala Pro Pro
    290                 295                 300

Thr Pro Val Ser Pro Arg Leu His Val Pro Leu Met Pro Ala Gln Pro
305                 310                 315                 320

Ala Pro Pro Lys Pro Gln Pro Thr Thr Arg Thr Pro Pro Gln Ser Gln
                325                 330                 335

Thr Pro Gly Ala Leu Pro Ala Lys Arg Glu Gln Pro Pro Ser Leu Thr
            340                 345                 350

Arg Asn Gly Pro Leu Ser Cys Gly Gln Arg Leu Arg Lys Ser Leu Ser
        355                 360                 365

Ser Met Thr Arg Val Val Gly Gly Leu Val Ala Leu Arg Gly Ala His
    370                 375                 380

Pro Tyr Ile Ala Ala Leu Tyr Trp Gly His Ser Phe Cys Ala Gly Ser
385                 390                 395                 400

Leu Ile Ala Pro Cys Trp Val Leu Thr Ala Ala His Cys Leu Gln Asp
                405                 410                 415

Arg Pro Ala Pro Glu Asp Leu Thr Val Val Leu Gly Gln Glu Arg Arg
            420                 425                 430

Asn His Ser Cys Glu Pro Cys Gln Thr Leu Ala Val Arg Ser Tyr Arg
        435                 440                 445

Leu His Glu Ala Phe Ser Pro Val Ser Tyr Gln His Asp Leu Ala Leu
    450                 455                 460

Leu Arg Leu Gln Glu Asp Ala Asp Gly Ser Cys Ala Leu Leu Ser Pro
465                 470                 475                 480

Tyr Val Gln Pro Val Cys Leu Pro Ser Gly Ala Ala Arg Pro Ser Glu
                485                 490                 495

Thr Thr Leu Cys Gln Val Ala Gly Trp Gly His Gln Phe Glu Gly Ala
            500                 505                 510

Glu Glu Tyr Ala Ser Phe Leu Gln Glu Ala Gln Val Pro Phe Leu Ser
        515                 520                 525
```

Leu Glu Arg Cys Ser Ala Pro Asp Val His Gly Ser Ser Ile Leu Pro
530 535 540

Gly Met Leu Cys Ala Gly Phe Leu Glu Gly Gly Thr Asp Ala Cys Gln
545 550 555 560

Gly Asp Ser Gly Gly Pro Leu Val Cys Glu Asp Gln Ala Ala Glu Arg
565 570 575

Arg Leu Thr Leu Gln Gly Ile Ile Ser Trp Gly Ser Gly Cys Gly Asp
580 585 590

Arg Asn Lys Pro Gly Val Tyr Thr Asp Val Ala Tyr Tyr Leu Ala Trp
595 600 605

Ile Arg Glu His Thr Val Ser
610 615

<210> SEQ ID NO 85
<211> LENGTH: 644
<212> TYPE: PRT
<213> ORGANISM: Artificial Sequence
<220> FEATURE:
<223> OTHER INFORMATION: Synthetic_KNG1_HUMAN

<400> SEQUENCE: 85

Met Lys Leu Ile Thr Ile Leu Phe Leu Cys Ser Arg Leu Leu Leu Ser
1 5 10 15

Leu Thr Gln Glu Ser Gln Ser Glu Glu Ile Asp Cys Asn Asp Lys Asp
20 25 30

Leu Phe Lys Ala Val Asp Ala Ala Leu Lys Lys Tyr Asn Ser Gln Asn
35 40 45

Gln Ser Asn Asn Gln Phe Val Leu Tyr Arg Ile Thr Glu Ala Thr Lys
50 55 60

Thr Val Gly Ser Asp Thr Phe Tyr Ser Phe Lys Tyr Glu Ile Lys Glu
65 70 75 80

Gly Asp Cys Pro Val Gln Ser Gly Lys Thr Trp Gln Asp Cys Glu Tyr
85 90 95

Lys Asp Ala Ala Lys Ala Ala Thr Gly Glu Cys Thr Ala Thr Val Gly
100 105 110

Lys Arg Ser Ser Thr Lys Phe Ser Val Ala Thr Gln Thr Cys Gln Ile
115 120 125

Thr Pro Ala Glu Gly Pro Val Val Thr Ala Gln Tyr Asp Cys Leu Gly
130 135 140

Cys Val His Pro Ile Ser Thr Gln Ser Pro Asp Leu Glu Pro Ile Leu
145 150 155 160

Arg His Gly Ile Gln Tyr Phe Asn Asn Asn Thr Gln His Ser Ser Leu
165 170 175

Phe Met Leu Asn Glu Val Lys Arg Ala Gln Arg Gln Val Val Ala Gly
180 185 190

Leu Asn Phe Arg Ile Thr Tyr Ser Ile Val Gln Thr Asn Cys Ser Lys
195 200 205

Glu Asn Phe Leu Phe Leu Thr Pro Asp Cys Lys Ser Leu Trp Asn Gly
210 215 220

Asp Thr Gly Glu Cys Thr Asp Asn Ala Tyr Ile Asp Ile Gln Leu Arg
225 230 235 240

Ile Ala Ser Phe Ser Gln Asn Cys Asp Ile Tyr Pro Gly Lys Asp Phe
245 250 255

Val Gln Pro Pro Thr Lys Ile Cys Val Gly Cys Pro Arg Asp Ile Pro
260 265 270

```
Thr Asn Ser Pro Glu Leu Glu Glu Thr Leu Thr His Thr Ile Thr Lys
        275                 280                 285

Leu Asn Ala Glu Asn Asn Ala Thr Phe Tyr Phe Lys Ile Asp Asn Val
    290                 295                 300

Lys Lys Ala Arg Val Gln Val Val Ala Gly Lys Lys Tyr Phe Ile Asp
305                 310                 315                 320

Phe Val Ala Arg Glu Thr Thr Cys Ser Lys Glu Ser Asn Glu Glu Leu
                325                 330                 335

Thr Glu Ser Cys Glu Thr Lys Lys Leu Gly Gln Ser Leu Asp Cys Asn
            340                 345                 350

Ala Glu Val Tyr Val Val Pro Trp Glu Lys Lys Ile Tyr Pro Thr Val
        355                 360                 365

Asn Cys Gln Pro Leu Gly Met Ile Ser Leu Met Lys Arg Pro Pro Gly
    370                 375                 380

Phe Ser Pro Phe Arg Ser Ser Arg Ile Gly Glu Ile Lys Glu Glu Thr
385                 390                 395                 400

Thr Val Ser Pro Pro His Thr Ser Met Ala Pro Ala Gln Asp Glu Glu
                405                 410                 415

Arg Asp Ser Gly Lys Glu Gln Gly His Thr Arg Arg His Asp Trp Gly
            420                 425                 430

His Glu Lys Gln Arg Lys His Asn Leu Gly His Gly His Lys His Glu
        435                 440                 445

Arg Asp Gln Gly His Gly His Gln Arg Gly His Gly Leu Gly His Gly
    450                 455                 460

His Glu Gln Gln His Gly Leu Gly His Gly His Lys Phe Lys Leu Asp
465                 470                 475                 480

Asp Asp Leu Glu His Gln Gly Gly His Val Leu Asp His Gly His Lys
                485                 490                 495

His Lys His Gly His Gly His Gly Lys His Lys Asn Lys Gly Lys Lys
            500                 505                 510

Asn Gly Lys His Asn Gly Trp Lys Thr Glu His Leu Ala Ser Ser Ser
        515                 520                 525

Glu Asp Ser Thr Thr Pro Ser Ala Gln Thr Gln Glu Lys Thr Glu Gly
    530                 535                 540

Pro Thr Pro Ile Pro Ser Leu Ala Lys Pro Gly Val Thr Val Thr Phe
545                 550                 555                 560

Ser Asp Phe Gln Asp Ser Asp Leu Ile Ala Thr Met Met Pro Pro Ile
                565                 570                 575

Ser Pro Ala Pro Ile Gln Ser Asp Asp Asp Trp Ile Pro Asp Ile Gln
            580                 585                 590

Ile Asp Pro Asn Gly Leu Ser Phe Asn Pro Ile Ser Asp Phe Pro Asp
        595                 600                 605

Thr Thr Ser Pro Lys Cys Pro Gly Arg Pro Trp Lys Ser Val Ser Glu
    610                 615                 620

Ile Asn Pro Thr Thr Gln Met Lys Glu Ser Tyr Tyr Phe Asp Leu Thr
625                 630                 635                 640

Asp Gly Leu Ser
```

<210> SEQ ID NO 86
<211> LENGTH: 650
<212> TYPE: PRT
<213> ORGANISM: Artificial Sequence
<220> FEATURE:
<223> OTHER INFORMATION: Synthetic_APLP1_HUMAN

<400> SEQUENCE: 86

```
Met Gly Pro Ala Ser Pro Ala Ala Arg Gly Leu Ser Arg Arg Pro Gly
1               5                   10                  15

Gln Pro Pro Leu Pro Leu Leu Leu Pro Leu Leu Leu Leu Leu Leu Arg
            20                  25                  30

Ala Gln Pro Ala Ile Gly Ser Leu Ala Gly Gly Ser Pro Gly Ala Ala
        35                  40                  45

Glu Ala Pro Gly Ser Ala Gln Val Ala Gly Leu Cys Gly Arg Leu Thr
    50                  55                  60

Leu His Arg Asp Leu Arg Thr Gly Arg Trp Glu Pro Asp Pro Gln Arg
65                  70                  75                  80

Ser Arg Arg Cys Leu Arg Asp Pro Gln Arg Val Leu Glu Tyr Cys Arg
                85                  90                  95

Gln Met Tyr Pro Glu Leu Gln Ile Ala Arg Val Glu Gln Ala Thr Gln
            100                 105                 110

Ala Ile Pro Met Glu Arg Trp Cys Gly Gly Ser Arg Ser Gly Ser Cys
        115                 120                 125

Ala His Pro His His Gln Val Val Pro Phe Arg Cys Leu Pro Gly Glu
    130                 135                 140

Phe Val Ser Glu Ala Leu Leu Val Pro Glu Gly Cys Arg Phe Leu His
145                 150                 155                 160

Gln Glu Arg Met Asp Gln Cys Glu Ser Ser Thr Arg Arg His Gln Glu
                165                 170                 175

Ala Gln Glu Ala Cys Ser Ser Gln Gly Leu Ile Leu His Gly Ser Gly
            180                 185                 190

Met Leu Leu Pro Cys Gly Ser Asp Arg Phe Arg Gly Val Glu Tyr Val
        195                 200                 205

Cys Cys Pro Pro Pro Gly Thr Pro Asp Pro Ser Gly Thr Ala Val Gly
    210                 215                 220

Asp Pro Ser Thr Arg Ser Trp Pro Pro Gly Ser Arg Val Glu Gly Ala
225                 230                 235                 240

Glu Asp Glu Glu Glu Glu Glu Ser Phe Pro Gln Pro Val Asp Asp Tyr
                245                 250                 255

Phe Val Glu Pro Pro Gln Ala Glu Glu Glu Glu Glu Thr Val Pro Pro
            260                 265                 270

Pro Ser Ser His Thr Leu Ala Val Val Gly Lys Val Thr Pro Thr Pro
        275                 280                 285

Arg Pro Thr Asp Gly Val Asp Ile Tyr Phe Gly Met Pro Gly Glu Ile
    290                 295                 300

Ser Glu His Glu Gly Phe Leu Arg Ala Lys Met Asp Leu Glu Glu Arg
305                 310                 315                 320

Arg Met Arg Gln Ile Asn Glu Val Met Arg Glu Trp Ala Met Ala Asp
                325                 330                 335

Asn Gln Ser Lys Asn Leu Pro Lys Ala Asp Arg Gln Ala Leu Asn Glu
            340                 345                 350

His Phe Gln Ser Ile Leu Gln Thr Leu Glu Glu Gln Val Ser Gly Glu
        355                 360                 365

Arg Gln Arg Leu Val Glu Thr His Ala Thr Arg Val Ile Ala Leu Ile
    370                 375                 380

Asn Asp Gln Arg Arg Ala Ala Leu Glu Gly Phe Leu Ala Ala Leu Gln
385                 390                 395                 400

Ala Asp Pro Pro Gln Ala Glu Arg Val Leu Leu Ala Leu Arg Arg Tyr
                405                 410                 415
```

Leu Arg Ala Glu Gln Lys Glu Gln Arg His Thr Leu Arg His Tyr Gln
        420                 425                 430

His Val Ala Ala Val Asp Pro Glu Lys Ala Gln Gln Met Arg Phe Gln
    435                 440                 445

Val His Thr His Leu Gln Val Ile Glu Glu Arg Val Asn Gln Ser Leu
    450                 455                 460

Gly Leu Leu Asp Gln Asn Pro His Leu Ala Gln Glu Leu Arg Pro Gln
465                 470                 475                 480

Ile Gln Glu Leu Leu His Ser Glu His Leu Gly Pro Ser Glu Leu Glu
                485                 490                 495

Ala Pro Ala Pro Gly Gly Ser Ser Glu Asp Lys Gly Gly Leu Gln Pro
            500                 505                 510

Pro Asp Ser Lys Asp Asp Thr Pro Met Thr Leu Pro Lys Gly Ser Thr
        515                 520                 525

Glu Gln Asp Ala Ala Ser Pro Glu Lys Glu Lys Met Asn Pro Leu Glu
    530                 535                 540

Gln Tyr Glu Arg Lys Val Asn Ala Ser Val Pro Arg Gly Phe Pro Phe
545                 550                 555                 560

His Ser Ser Glu Ile Gln Arg Asp Glu Leu Ala Pro Ala Gly Thr Gly
                565                 570                 575

Val Ser Arg Glu Ala Val Ser Gly Leu Leu Ile Met Gly Ala Gly Gly
            580                 585                 590

Gly Ser Leu Ile Val Leu Ser Met Leu Leu Leu Arg Arg Lys Lys Pro
        595                 600                 605

Tyr Gly Ala Ile Ser His Gly Val Val Glu Val Asp Pro Met Leu Thr
    610                 615                 620

Leu Glu Glu Gln Gln Leu Arg Glu Leu Gln Arg His Gly Tyr Glu Asn
625                 630                 635                 640

Pro Thr Tyr Arg Phe Leu Glu Glu Arg Pro
                645                 650

<210> SEQ ID NO 87
<211> LENGTH: 661
<212> TYPE: PRT
<213> ORGANISM: Artificial Sequence
<220> FEATURE:
<223> OTHER INFORMATION: Synthetic_CRAC1_HUMAN

<400> SEQUENCE: 87

Met Ala Pro Ser Ala Asp Pro Gly Met Ser Arg Met Leu Pro Phe Leu
1               5                   10                  15

Leu Leu Leu Trp Phe Leu Pro Ile Thr Glu Gly Ser Gln Arg Ala Glu
            20                  25                  30

Pro Met Phe Thr Ala Val Thr Asn Ser Val Leu Pro Pro Asp Tyr Asp
        35                  40                  45

Ser Asn Pro Thr Gln Leu Asn Tyr Gly Val Ala Val Thr Asp Val Asp
    50                  55                  60

His Asp Gly Asp Phe Glu Ile Val Val Ala Gly Tyr Asn Gly Pro Asn
65                  70                  75                  80

Leu Val Leu Lys Tyr Asp Arg Ala Gln Lys Arg Leu Val Asn Ile Ala
                85                  90                  95

Val Asp Glu Arg Ser Ser Pro Tyr Tyr Ala Leu Arg Asp Arg Gln Gly
            100                 105                 110

Asn Ala Ile Gly Val Thr Ala Cys Asp Ile Asp Gly Asp Gly Arg Glu
        115                 120                 125

-continued

```
Glu Ile Tyr Phe Leu Asn Thr Asn Asn Ala Phe Ser Gly Val Ala Thr
    130                 135                 140

Tyr Thr Asp Lys Leu Phe Lys Phe Arg Asn Asn Arg Trp Glu Asp Ile
145                 150                 155                 160

Leu Ser Asp Glu Val Asn Val Ala Arg Gly Val Ala Ser Leu Phe Ala
                165                 170                 175

Gly Arg Ser Val Ala Cys Val Asp Arg Lys Gly Ser Gly Arg Tyr Ser
            180                 185                 190

Ile Tyr Ile Ala Asn Tyr Ala Tyr Gly Asn Val Gly Pro Asp Ala Leu
        195                 200                 205

Ile Glu Met Asp Pro Glu Ala Ser Asp Leu Ser Arg Gly Ile Leu Ala
    210                 215                 220

Leu Arg Asp Val Ala Ala Glu Ala Gly Val Ser Lys Tyr Thr Gly Gly
225                 230                 235                 240

Arg Gly Val Ser Val Gly Pro Ile Leu Ser Ser Ser Ala Ser Asp Ile
                245                 250                 255

Phe Cys Asp Asn Glu Asn Gly Pro Asn Phe Leu Phe His Asn Arg Gly
            260                 265                 270

Asp Gly Thr Phe Val Asp Ala Ala Ala Ser Ala Gly Val Asp Asp Pro
        275                 280                 285

His Gln His Gly Arg Gly Val Ala Leu Ala Asp Phe Asn Arg Asp Gly
    290                 295                 300

Lys Val Asp Ile Val Tyr Gly Asn Trp Asn Gly Pro His Arg Leu Tyr
305                 310                 315                 320

Leu Gln Met Ser Thr His Gly Lys Val Arg Phe Arg Asp Ile Ala Ser
                325                 330                 335

Pro Lys Phe Ser Met Pro Ser Pro Val Arg Thr Val Ile Thr Ala Asp
            340                 345                 350

Phe Asp Asn Asp Gln Glu Leu Glu Ile Phe Phe Asn Asn Ile Ala Tyr
        355                 360                 365

Arg Ser Ser Ser Ala Asn Arg Leu Phe Arg Val Ile Arg Arg Glu His
    370                 375                 380

Gly Asp Pro Leu Ile Glu Glu Leu Asn Pro Gly Asp Ala Leu Glu Pro
385                 390                 395                 400

Glu Gly Arg Gly Thr Gly Gly Val Val Thr Asp Phe Asp Gly Asp Gly
                405                 410                 415

Met Leu Asp Leu Ile Leu Ser His Gly Glu Ser Met Ala Gln Pro Leu
            420                 425                 430

Ser Val Phe Arg Gly Asn Gln Gly Phe Asn Asn Asn Trp Leu Arg Val
        435                 440                 445

Val Pro Arg Thr Arg Phe Gly Ala Phe Ala Arg Gly Ala Lys Val Val
    450                 455                 460

Leu Tyr Thr Lys Lys Ser Gly Ala His Leu Arg Ile Ile Asp Gly Gly
465                 470                 475                 480

Ser Gly Tyr Leu Cys Glu Met Glu Pro Val Ala His Phe Gly Leu Gly
                485                 490                 495

Lys Asp Glu Ala Ser Ser Val Glu Val Thr Trp Pro Asp Gly Lys Met
            500                 505                 510

Val Ser Arg Asn Val Ala Ser Gly Glu Met Asn Ser Val Leu Glu Ile
        515                 520                 525

Leu Tyr Pro Arg Asp Glu Asp Thr Leu Gln Asp Pro Ala Pro Leu Glu
    530                 535                 540
```

```
Cys Gly Gln Gly Phe Ser Gln Gln Glu Asn Gly His Cys Met Asp Thr
545                 550                 555                 560

Asn Glu Cys Ile Gln Phe Pro Phe Val Cys Pro Arg Asp Lys Pro Val
                565                 570                 575

Cys Val Asn Thr Tyr Gly Ser Tyr Arg Cys Arg Thr Asn Lys Lys Cys
            580                 585                 590

Ser Arg Gly Tyr Glu Pro Asn Glu Asp Gly Thr Ala Cys Val Gly Thr
        595                 600                 605

Leu Gly Gln Ser Pro Gly Pro Arg Pro Thr Thr Pro Thr Ala Ala Ala
    610                 615                 620

Ala Thr Ala Ala Ala Ala Ala Ala Ala Gly Ala Ala Thr Ala Ala Pro
625                 630                 635                 640

Val Leu Val Asp Gly Asp Leu Asn Leu Gly Ser Val Val Lys Glu Ser
                645                 650                 655

Cys Glu Pro Ser Cys
            660


<210> SEQ ID NO 88
<211> LENGTH: 664
<212> TYPE: PRT
<213> ORGANISM: Artificial Sequence
<220> FEATURE:
<223> OTHER INFORMATION: Synthetic_SPRL1_HUMAN

<400> SEQUENCE: 88

Met Lys Thr Gly Leu Phe Phe Leu Cys Leu Leu Gly Thr Ala Ala Ala
1               5                   10                  15

Ile Pro Thr Asn Ala Arg Leu Leu Ser Asp His Ser Lys Pro Thr Ala
            20                  25                  30

Glu Thr Val Ala Pro Asp Asn Thr Ala Ile Pro Ser Leu Arg Ala Glu
        35                  40                  45

Ala Glu Glu Asn Glu Lys Glu Thr Ala Val Ser Thr Glu Asp Asp Ser
    50                  55                  60

His His Lys Ala Glu Lys Ser Ser Val Leu Lys Ser Lys Glu Glu Ser
65                  70                  75                  80

His Glu Gln Ser Ala Glu Gln Gly Lys Ser Ser Ser Gln Glu Leu Gly
                85                  90                  95

Leu Lys Asp Gln Glu Asp Ser Asp Gly His Leu Ser Val Asn Leu Glu
            100                 105                 110

Tyr Ala Pro Thr Glu Gly Thr Leu Asp Ile Lys Glu Asp Met Ser Glu
        115                 120                 125

Pro Gln Glu Lys Lys Leu Ser Glu Asn Thr Asp Phe Leu Ala Pro Gly
    130                 135                 140

Val Ser Ser Phe Thr Asp Ser Asn Gln Gln Glu Ser Ile Thr Lys Arg
145                 150                 155                 160

Glu Glu Asn Gln Glu Gln Pro Arg Asn Tyr Ser His His Gln Leu Asn
                165                 170                 175

Arg Ser Ser Lys His Ser Gln Gly Leu Arg Asp Gln Gly Asn Gln Glu
            180                 185                 190

Gln Asp Pro Asn Ile Ser Asn Gly Glu Glu Glu Glu Glu Lys Glu Pro
        195                 200                 205

Gly Glu Val Gly Thr His Asn Asp Asn Gln Glu Arg Lys Thr Glu Leu
    210                 215                 220

Pro Arg Glu His Ala Asn Ser Lys Gln Glu Glu Asp Asn Thr Gln Ser
225                 230                 235                 240
```

```
Asp Asp Ile Leu Glu Glu Ser Asp Gln Pro Thr Gln Val Ser Lys Met
                245                 250                 255

Gln Glu Asp Glu Phe Asp Gln Gly Asn Gln Glu Gln Glu Asp Asn Ser
            260                 265                 270

Asn Ala Glu Met Glu Glu Glu Asn Ala Ser Asn Val Asn Lys His Ile
        275                 280                 285

Gln Glu Thr Glu Trp Gln Ser Gln Glu Gly Lys Thr Gly Leu Glu Ala
    290                 295                 300

Ile Ser Asn His Lys Glu Thr Glu Glu Lys Thr Val Ser Glu Ala Leu
305                 310                 315                 320

Leu Met Glu Pro Thr Asp Asp Gly Asn Thr Thr Pro Arg Asn His Gly
                325                 330                 335

Val Asp Asp Asp Gly Asp Asp Asp Gly Asp Asp Gly Gly Thr Asp Gly
            340                 345                 350

Pro Arg His Ser Ala Ser Asp Asp Tyr Phe Ile Pro Ser Gln Ala Phe
        355                 360                 365

Leu Glu Ala Glu Arg Ala Gln Ser Ile Ala Tyr His Leu Lys Ile Glu
    370                 375                 380

Glu Gln Arg Glu Lys Val His Glu Asn Glu Asn Ile Gly Thr Thr Glu
385                 390                 395                 400

Pro Gly Glu His Gln Glu Ala Lys Lys Ala Glu Asn Ser Ser Asn Glu
                405                 410                 415

Glu Glu Thr Ser Ser Glu Gly Asn Met Arg Val His Ala Val Asp Ser
            420                 425                 430

Cys Met Ser Phe Gln Cys Lys Arg Gly His Ile Cys Lys Ala Asp Gln
        435                 440                 445

Gln Gly Lys Pro His Cys Val Cys Gln Asp Pro Val Thr Cys Pro Pro
    450                 455                 460

Thr Lys Pro Leu Asp Gln Val Cys Gly Thr Asp Asn Gln Thr Tyr Ala
465                 470                 475                 480

Ser Ser Cys His Leu Phe Ala Thr Lys Cys Arg Leu Glu Gly Thr Lys
                485                 490                 495

Lys Gly His Gln Leu Gln Leu Asp Tyr Phe Gly Ala Cys Lys Ser Ile
            500                 505                 510

Pro Thr Cys Thr Asp Phe Glu Val Ile Gln Phe Pro Leu Arg Met Arg
        515                 520                 525

Asp Trp Leu Lys Asn Ile Leu Met Gln Leu Tyr Glu Ala Asn Ser Glu
    530                 535                 540

His Ala Gly Tyr Leu Asn Glu Lys Gln Arg Asn Lys Val Lys Lys Ile
545                 550                 555                 560

Tyr Leu Asp Glu Lys Arg Leu Leu Ala Gly Asp His Pro Ile Asp Leu
                565                 570                 575

Leu Leu Arg Asp Phe Lys Lys Asn Tyr His Met Tyr Val Tyr Pro Val
            580                 585                 590

His Trp Gln Phe Ser Glu Leu Asp Gln His Pro Met Asp Arg Val Leu
        595                 600                 605

Thr His Ser Glu Leu Ala Pro Leu Arg Ala Ser Leu Val Pro Met Glu
    610                 615                 620

His Cys Ile Thr Arg Phe Phe Glu Glu Cys Asp Pro Asn Lys Asp Lys
625                 630                 635                 640

His Ile Thr Leu Lys Glu Trp Gly His Cys Phe Gly Ile Lys Glu Glu
                645                 650                 655

Asp Ile Asp Glu Asn Leu Leu Phe
```

660

<210> SEQ ID NO 89
<211> LENGTH: 701
<212> TYPE: PRT
<213> ORGANISM: Artificial Sequence
<220> FEATURE:
<223> OTHER INFORMATION: Synthetic_MEP1B_HUMAN

<400> SEQUENCE: 89

Met Asp Leu Trp Asn Leu Ser Trp Phe Leu Phe Leu Asp Ala Leu Leu
1 5 10 15

Val Ile Ser Gly Leu Ala Thr Pro Glu Asn Phe Asp Val Asp Gly Gly
20 25 30

Met Asp Gln Asp Ile Phe Asp Ile Asn Glu Gly Leu Gly Leu Asp Leu
35 40 45

Phe Glu Gly Asp Ile Arg Leu Asp Arg Ala Gln Ile Arg Asn Ser Ile
50 55 60

Ile Gly Glu Lys Tyr Arg Trp Pro His Thr Ile Pro Tyr Val Leu Glu
65 70 75 80

Asp Ser Leu Glu Met Asn Ala Lys Gly Val Ile Leu Asn Ala Phe Glu
85 90 95

Arg Tyr Arg Leu Lys Thr Cys Ile Asp Phe Lys Pro Trp Ala Gly Glu
100 105 110

Thr Asn Tyr Ile Ser Val Phe Lys Gly Ser Gly Cys Trp Ser Ser Val
115 120 125

Gly Asn Arg Arg Val Gly Lys Gln Glu Leu Ser Ile Gly Ala Asn Cys
130 135 140

Asp Arg Ile Ala Thr Val Gln His Glu Phe Leu His Ala Leu Gly Phe
145 150 155 160

Trp His Glu Gln Ser Arg Ser Asp Arg Asp Asp Tyr Val Arg Ile Met
165 170 175

Trp Asp Arg Ile Leu Ser Gly Arg Glu His Asn Phe Asn Thr Tyr Ser
180 185 190

Asp Asp Ile Ser Asp Ser Leu Asn Val Pro Tyr Asp Tyr Thr Ser Val
195 200 205

Met His Tyr Ser Lys Thr Ala Phe Gln Asn Gly Thr Glu Pro Thr Ile
210 215 220

Val Thr Arg Ile Ser Asp Phe Glu Asp Val Ile Gly Gln Arg Met Asp
225 230 235 240

Phe Ser Asp Ser Asp Leu Leu Lys Leu Asn Gln Leu Tyr Asn Cys Ser
245 250 255

Ser Ser Leu Ser Phe Met Asp Ser Cys Ser Phe Glu Leu Glu Asn Val
260 265 270

Cys Gly Met Ile Gln Ser Ser Gly Asp Asn Ala Asp Trp Gln Arg Val
275 280 285

Ser Gln Val Pro Arg Gly Pro Glu Ser Asp His Ser Asn Met Gly Gln
290 295 300

Cys Gln Gly Ser Gly Phe Phe Met His Phe Asp Ser Ser Ser Val Asn
305 310 315 320

Val Gly Ala Thr Ala Val Leu Glu Ser Arg Thr Leu Tyr Pro Lys Arg
325 330 335

Gly Phe Gln Cys Leu Gln Phe Tyr Leu Tyr Asn Ser Gly Ser Glu Ser
340 345 350

Asp Gln Leu Asn Ile Tyr Ile Arg Glu Tyr Ser Ala Asp Asn Val Asp

```
        355                 360                 365

Gly Asn Leu Thr Leu Val Glu Glu Ile Lys Glu Ile Pro Thr Gly Ser
    370                 375                 380

Trp Gln Leu Tyr His Val Thr Leu Lys Val Thr Lys Lys Phe Arg Val
385                 390                 395                 400

Val Phe Glu Gly Arg Lys Gly Ser Gly Ala Ser Leu Gly Gly Leu Ser
                405                 410                 415

Ile Asp Asp Ile Asn Leu Ser Glu Thr Arg Cys Pro His His Ile Trp
            420                 425                 430

His Ile Arg Asn Phe Thr Gln Phe Ile Gly Ser Pro Asn Gly Thr Leu
        435                 440                 445

Tyr Ser Pro Pro Phe Tyr Ser Ser Lys Gly Tyr Ala Phe Gln Ile Tyr
    450                 455                 460

Leu Asn Leu Ala His Val Thr Asn Ala Gly Ile Tyr Phe His Leu Ile
465                 470                 475                 480

Ser Gly Ala Asn Asp Asp Gln Leu Gln Trp Pro Cys Pro Trp Gln Gln
                485                 490                 495

Ala Thr Met Thr Leu Leu Asp Gln Asn Pro Asp Ile Arg Gln Arg Met
            500                 505                 510

Ser Asn Gln Arg Ser Ile Thr Thr Asp Pro Phe Met Thr Thr Asp Asn
        515                 520                 525

Gly Asn Tyr Phe Trp Asp Arg Pro Ser Lys Val Gly Thr Val Ala Leu
    530                 535                 540

Phe Ser Asn Gly Thr Gln Phe Arg Arg Gly Gly Gly Tyr Gly Thr Ser
545                 550                 555                 560

Ala Phe Ile Thr His Glu Arg Leu Lys Ser Arg Asp Phe Ile Lys Gly
                565                 570                 575

Asp Asp Val Tyr Ile Leu Leu Thr Val Glu Asp Ile Ser His Leu Asn
            580                 585                 590

Ser Thr Gln Ile Gln Leu Thr Pro Ala Pro Ser Val Gln Asp Leu Cys
        595                 600                 605

Ser Lys Thr Thr Cys Lys Asn Asp Gly Val Cys Thr Val Arg Asp Gly
    610                 615                 620

Lys Ala Glu Cys Arg Cys Gln Ser Gly Glu Asp Trp Trp Tyr Met Gly
625                 630                 635                 640

Glu Arg Cys Glu Lys Arg Gly Ser Thr Arg Asp Thr Ile Val Ile Ala
                645                 650                 655

Val Ser Ser Thr Val Ala Val Phe Ala Leu Met Leu Ile Ile Thr Leu
            660                 665                 670

Val Ser Val Tyr Cys Thr Arg Lys Lys Tyr Arg Glu Arg Met Ser Ser
        675                 680                 685

Asn Arg Pro Asn Leu Thr Pro Gln Asn Gln His Ala Phe
    690                 695                 700


<210> SEQ ID NO 90
<211> LENGTH: 705
<212> TYPE: PRT
<213> ORGANISM: Artificial Sequence
<220> FEATURE:
<223> OTHER INFORMATION: Synthetic_SYN1_HUMAN

<400> SEQUENCE: 90

Met Asn Tyr Leu Arg Arg Arg Leu Ser Asp Ser Asn Phe Met Ala Asn
1               5                   10                  15

Leu Pro Asn Gly Tyr Met Thr Asp Leu Gln Arg Pro Gln Pro Pro Pro
```

```
                20                  25                  30

Pro Pro Pro Gly Ala His Ser Pro Gly Ala Thr Pro Gly Pro Gly Thr
        35                  40                  45

Ala Thr Ala Glu Arg Ser Ser Gly Val Ala Pro Ala Ala Ser Pro Ala
    50                  55                  60

Ala Pro Ser Pro Gly Ser Ser Gly Gly Gly Gly Phe Phe Ser Ser Leu
65                  70                  75                  80

Ser Asn Ala Val Lys Gln Thr Thr Ala Ala Ala Ala Thr Phe Ser
                85                  90                  95

Glu Gln Val Gly Gly Gly Ser Gly Gly Ala Gly Arg Gly Gly Ala Ala
            100                 105                 110

Ser Arg Val Leu Leu Val Ile Asp Glu Pro His Thr Asp Trp Ala Lys
        115                 120                 125

Tyr Phe Lys Gly Lys Lys Ile His Gly Glu Ile Asp Ile Lys Val Glu
    130                 135                 140

Gln Ala Glu Phe Ser Asp Leu Asn Leu Val Ala His Ala Asn Gly Gly
145                 150                 155                 160

Phe Ser Val Asp Met Glu Val Leu Arg Asn Gly Val Lys Val Val Arg
                165                 170                 175

Ser Leu Lys Pro Asp Phe Val Leu Ile Arg Gln His Ala Phe Ser Met
            180                 185                 190

Ala Arg Asn Gly Asp Tyr Arg Ser Leu Val Ile Gly Leu Gln Tyr Ala
        195                 200                 205

Gly Ile Pro Ser Val Asn Ser Leu His Ser Val Tyr Asn Phe Cys Asp
    210                 215                 220

Lys Pro Trp Val Phe Ala Gln Met Val Arg Leu His Lys Lys Leu Gly
225                 230                 235                 240

Thr Glu Glu Phe Pro Leu Ile Asp Gln Thr Phe Tyr Pro Asn His Lys
                245                 250                 255

Glu Met Leu Ser Ser Thr Thr Tyr Pro Val Val Val Lys Met Gly His
            260                 265                 270

Ala His Ser Gly Met Gly Lys Val Lys Val Asp Asn Gln His Asp Phe
        275                 280                 285

Gln Asp Ile Ala Ser Val Val Ala Leu Thr Lys Thr Tyr Ala Thr Ala
    290                 295                 300

Glu Pro Phe Ile Asp Ala Lys Tyr Asp Val Arg Val Gln Lys Ile Gly
305                 310                 315                 320

Gln Asn Tyr Lys Ala Tyr Met Arg Thr Ser Val Ser Gly Asn Trp Lys
                325                 330                 335

Thr Asn Thr Gly Ser Ala Met Leu Glu Gln Ile Ala Met Ser Asp Arg
            340                 345                 350

Tyr Lys Leu Trp Val Asp Thr Cys Ser Glu Ile Phe Gly Gly Leu Asp
        355                 360                 365

Ile Cys Ala Val Glu Ala Leu His Gly Lys Asp Gly Arg Asp His Ile
    370                 375                 380

Ile Glu Val Val Gly Ser Ser Met Pro Leu Ile Gly Asp His Gln Asp
385                 390                 395                 400

Glu Asp Lys Gln Leu Ile Val Glu Leu Val Val Asn Lys Met Ala Gln
                405                 410                 415

Ala Leu Pro Arg Gln Arg Gln Arg Asp Ala Ser Pro Gly Arg Gly Ser
            420                 425                 430

His Gly Gln Thr Pro Ser Pro Gly Ala Leu Pro Leu Gly Arg Gln Thr
        435                 440                 445
```

Ser Gln Gln Pro Ala Gly Pro Pro Ala Gln Gln Arg Pro Pro Pro Gln
    450                 455                 460

Gly Gly Pro Pro Gln Pro Gly Pro Gly Pro Gln Arg Gln Gly Pro Pro
465                 470                 475                 480

Leu Gln Gln Arg Pro Pro Pro Gln Gly Gln Gln His Leu Ser Gly Leu
                485                 490                 495

Gly Pro Pro Ala Gly Ser Pro Leu Pro Gln Arg Leu Pro Ser Pro Thr
            500                 505                 510

Ser Ala Pro Gln Gln Pro Ala Ser Gln Ala Ala Pro Pro Thr Gln Gly
        515                 520                 525

Gln Gly Arg Gln Ser Arg Pro Val Ala Gly Gly Pro Gly Ala Pro Pro
    530                 535                 540

Ala Ala Arg Pro Pro Ala Ser Pro Ser Pro Gln Arg Gln Ala Gly Pro
545                 550                 555                 560

Pro Gln Ala Thr Arg Gln Thr Ser Val Ser Gly Pro Ala Pro Pro Lys
                565                 570                 575

Ala Ser Gly Ala Pro Pro Gly Gly Gln Gln Arg Gln Gly Pro Pro Gln
            580                 585                 590

Lys Pro Pro Gly Pro Ala Gly Pro Thr Arg Gln Ala Ser Gln Ala Gly
        595                 600                 605

Pro Val Pro Arg Thr Gly Pro Pro Thr Thr Gln Gln Pro Arg Pro Ser
    610                 615                 620

Gly Pro Gly Pro Ala Gly Arg Pro Lys Pro Gln Leu Ala Gln Lys Pro
625                 630                 635                 640

Ser Gln Asp Val Pro Pro Pro Ala Thr Ala Ala Ala Gly Gly Pro Pro
                645                 650                 655

His Pro Gln Leu Asn Lys Ser Gln Ser Leu Thr Asn Ala Phe Asn Leu
            660                 665                 670

Pro Glu Pro Ala Pro Pro Arg Pro Ser Leu Ser Gln Asp Glu Val Lys
        675                 680                 685

Ala Glu Thr Ile Arg Ser Leu Arg Lys Ser Phe Ala Ser Leu Phe Ser
    690                 695                 700

Asp
705

<210> SEQ ID NO 91
<211> LENGTH: 753
<212> TYPE: PRT
<213> ORGANISM: Artificial Sequence
<220> FEATURE:
<223> OTHER INFORMATION: Synthetic_CEL_HUMAN

<400> SEQUENCE: 91

Met Gly Arg Leu Gln Leu Val Val Leu Gly Leu Thr Cys Cys Trp Ala
1               5                   10                  15

Val Ala Ser Ala Ala Lys Leu Gly Ala Val Tyr Thr Glu Gly Gly Phe
            20                  25                  30

Val Glu Gly Val Asn Lys Lys Leu Gly Leu Leu Gly Asp Ser Val Asp
        35                  40                  45

Ile Phe Lys Gly Ile Pro Phe Ala Ala Pro Thr Lys Ala Leu Glu Asn
    50                  55                  60

Pro Gln Pro His Pro Gly Trp Gln Gly Thr Leu Lys Ala Lys Asn Phe
65                  70                  75                  80

Lys Lys Arg Cys Leu Gln Ala Thr Ile Thr Gln Asp Ser Thr Tyr Gly
                85                  90                  95

```
Asp Glu Asp Cys Leu Tyr Leu Asn Ile Trp Val Pro Gln Gly Arg Lys
            100                 105                 110

Gln Val Ser Arg Asp Leu Pro Val Met Ile Trp Ile Tyr Gly Gly Ala
        115                 120                 125

Phe Leu Met Gly Ser Gly His Gly Ala Asn Phe Leu Asn Asn Tyr Leu
    130                 135                 140

Tyr Asp Gly Glu Glu Ile Ala Thr Arg Gly Asn Val Ile Val Val Thr
145                 150                 155                 160

Phe Asn Tyr Arg Val Gly Pro Leu Gly Phe Leu Ser Thr Gly Asp Ala
                165                 170                 175

Asn Leu Pro Gly Asn Tyr Gly Leu Arg Asp Gln His Met Ala Ile Ala
            180                 185                 190

Trp Val Lys Arg Asn Ile Ala Ala Phe Gly Gly Asp Pro Asn Asn Ile
        195                 200                 205

Thr Leu Phe Gly Glu Ser Ala Gly Gly Ala Ser Val Ser Leu Gln Thr
    210                 215                 220

Leu Ser Pro Tyr Asn Lys Gly Leu Ile Arg Arg Ala Ile Ser Gln Ser
225                 230                 235                 240

Gly Val Ala Leu Ser Pro Trp Val Ile Gln Lys Asn Pro Leu Phe Trp
                245                 250                 255

Ala Lys Lys Val Ala Glu Lys Val Gly Cys Pro Val Gly Asp Ala Ala
            260                 265                 270

Arg Met Ala Gln Cys Leu Lys Val Thr Asp Pro Arg Ala Leu Thr Leu
        275                 280                 285

Ala Tyr Lys Val Pro Leu Ala Gly Leu Glu Tyr Pro Met Leu His Tyr
    290                 295                 300

Val Gly Phe Val Pro Val Ile Asp Gly Asp Phe Ile Pro Ala Asp Pro
305                 310                 315                 320

Ile Asn Leu Tyr Ala Asn Ala Ala Asp Ile Asp Tyr Ile Ala Gly Thr
                325                 330                 335

Asn Asn Met Asp Gly His Ile Phe Ala Ser Ile Asp Met Pro Ala Ile
            340                 345                 350

Asn Lys Gly Asn Lys Lys Val Thr Glu Glu Asp Phe Tyr Lys Leu Val
        355                 360                 365

Ser Glu Phe Thr Ile Thr Lys Gly Leu Arg Gly Ala Lys Thr Thr Phe
    370                 375                 380

Asp Val Tyr Thr Glu Ser Trp Ala Gln Asp Pro Ser Gln Glu Asn Lys
385                 390                 395                 400

Lys Lys Thr Val Val Asp Phe Glu Thr Asp Val Leu Phe Leu Val Pro
                405                 410                 415

Thr Glu Ile Ala Leu Ala Gln His Arg Ala Asn Ala Lys Ser Ala Lys
            420                 425                 430

Thr Tyr Ala Tyr Leu Phe Ser His Pro Ser Arg Met Pro Val Tyr Pro
        435                 440                 445

Lys Trp Val Gly Ala Asp His Ala Asp Asp Ile Gln Tyr Val Phe Gly
    450                 455                 460

Lys Pro Phe Ala Thr Pro Thr Gly Tyr Arg Pro Gln Asp Arg Thr Val
465                 470                 475                 480

Ser Lys Ala Met Ile Ala Tyr Trp Thr Asn Phe Ala Lys Thr Gly Asp
                485                 490                 495

Pro Asn Met Gly Asp Ser Ala Val Pro Thr His Trp Glu Pro Tyr Thr
            500                 505                 510
```

```
Thr Glu Asn Ser Gly Tyr Leu Glu Ile Thr Lys Lys Met Gly Ser Ser
        515                 520                 525

Ser Met Lys Arg Ser Leu Arg Thr Asn Phe Leu Arg Tyr Trp Thr Leu
    530                 535                 540

Thr Tyr Leu Ala Leu Pro Thr Val Thr Asp Gln Glu Ala Thr Pro Val
545                 550                 555                 560

Pro Pro Thr Gly Asp Ser Glu Ala Thr Pro Val Pro Pro Thr Gly Asp
                565                 570                 575

Ser Glu Thr Ala Pro Val Pro Pro Thr Gly Asp Ser Gly Ala Pro Pro
            580                 585                 590

Val Pro Pro Thr Gly Asp Ser Gly Ala Pro Pro Val Pro Pro Thr Gly
        595                 600                 605

Asp Ser Gly Ala Pro Pro Val Pro Pro Thr Gly Asp Ser Gly Ala Pro
    610                 615                 620

Pro Val Pro Pro Thr Gly Asp Ser Gly Ala Pro Pro Val Pro Pro Thr
625                 630                 635                 640

Gly Asp Ser Gly Ala Pro Pro Val Pro Pro Thr Gly Asp Ser Gly Ala
                645                 650                 655

Pro Pro Val Pro Pro Thr Gly Asp Ser Gly Ala Pro Pro Val Pro Pro
            660                 665                 670

Thr Gly Asp Ala Gly Pro Pro Pro Val Pro Pro Thr Gly Asp Ser Gly
        675                 680                 685

Ala Pro Pro Val Pro Pro Thr Gly Asp Ser Gly Ala Pro Pro Val Thr
    690                 695                 700

Pro Thr Gly Asp Ser Glu Thr Ala Pro Val Pro Pro Thr Gly Asp Ser
705                 710                 715                 720

Gly Ala Pro Pro Val Pro Pro Thr Gly Asp Ser Glu Ala Ala Pro Val
                725                 730                 735

Pro Pro Thr Asp Asp Ser Lys Glu Ala Gln Met Pro Ala Val Ile Arg
            740                 745                 750

Phe


<210> SEQ ID NO 92
<211> LENGTH: 757
<212> TYPE: PRT
<213> ORGANISM: Artificial Sequence
<220> FEATURE:
<223> OTHER INFORMATION: Synthetic_CD248_HUMAN

<400> SEQUENCE: 92

Met Leu Leu Arg Leu Leu Leu Ala Trp Ala Ala Ala Gly Pro Thr Leu
1               5                   10                  15

Gly Gln Asp Pro Trp Ala Ala Glu Pro Arg Ala Ala Cys Gly Pro Ser
            20                  25                  30

Ser Cys Tyr Ala Leu Phe Pro Arg Arg Arg Thr Phe Leu Glu Ala Trp
        35                  40                  45

Arg Ala Cys Arg Glu Leu Gly Gly Asp Leu Ala Thr Pro Arg Thr Pro
    50                  55                  60

Glu Glu Ala Gln Arg Val Asp Ser Leu Val Gly Ala Gly Pro Ala Ser
65                  70                  75                  80

Arg Leu Leu Trp Ile Gly Leu Gln Arg Gln Ala Arg Gln Cys Gln Leu
                85                  90                  95

Gln Arg Pro Leu Arg Gly Phe Thr Trp Thr Thr Gly Asp Gln Asp Thr
            100                 105                 110

Ala Phe Thr Asn Trp Ala Gln Pro Ala Ser Gly Gly Pro Cys Pro Ala
```

```
        115                 120                 125

Gln Arg Cys Val Ala Leu Glu Ala Ser Gly Glu His Arg Trp Leu Glu
    130                 135                 140

Gly Ser Cys Thr Leu Ala Val Asp Gly Tyr Leu Cys Gln Phe Gly Phe
145                 150                 155                 160

Glu Gly Ala Cys Pro Ala Leu Gln Asp Glu Ala Gly Gln Ala Gly Pro
                165                 170                 175

Ala Val Tyr Thr Thr Pro Phe His Leu Val Ser Thr Glu Phe Glu Trp
            180                 185                 190

Leu Pro Phe Gly Ser Val Ala Ala Val Gln Cys Gln Ala Gly Arg Gly
        195                 200                 205

Ala Ser Leu Leu Cys Val Lys Gln Pro Glu Gly Gly Val Gly Trp Ser
    210                 215                 220

Arg Ala Gly Pro Leu Cys Leu Gly Thr Gly Cys Ser Pro Asp Asn Gly
225                 230                 235                 240

Gly Cys Glu His Glu Cys Val Glu Glu Val Asp Gly His Val Ser Cys
                245                 250                 255

Arg Cys Thr Glu Gly Phe Arg Leu Ala Ala Asp Gly Arg Ser Cys Glu
            260                 265                 270

Asp Pro Cys Ala Gln Ala Pro Cys Glu Gln Gln Cys Glu Pro Gly Gly
        275                 280                 285

Pro Gln Gly Tyr Ser Cys His Cys Arg Leu Gly Phe Arg Pro Ala Glu
    290                 295                 300

Asp Asp Pro His Arg Cys Val Asp Thr Asp Glu Cys Gln Ile Ala Gly
305                 310                 315                 320

Val Cys Gln Gln Met Cys Val Asn Tyr Val Gly Gly Phe Glu Cys Tyr
                325                 330                 335

Cys Ser Glu Gly His Glu Leu Glu Ala Asp Gly Ile Ser Cys Ser Pro
            340                 345                 350

Ala Gly Ala Met Gly Ala Gln Ala Ser Gln Asp Leu Gly Asp Glu Leu
        355                 360                 365

Leu Asp Asp Gly Glu Asp Glu Glu Asp Glu Asp Glu Ala Trp Lys Ala
    370                 375                 380

Phe Asn Gly Gly Trp Thr Glu Met Pro Gly Ile Leu Trp Met Glu Pro
385                 390                 395                 400

Thr Gln Pro Pro Asp Phe Ala Leu Ala Tyr Arg Pro Ser Phe Pro Glu
                405                 410                 415

Asp Arg Glu Pro Gln Ile Pro Tyr Pro Glu Pro Thr Trp Pro Pro Pro
            420                 425                 430

Leu Ser Ala Pro Arg Val Pro Tyr His Ser Ser Val Leu Ser Val Thr
        435                 440                 445

Arg Pro Val Val Val Ser Ala Thr His Pro Thr Leu Pro Ser Ala His
    450                 455                 460

Gln Pro Pro Val Ile Pro Ala Thr His Pro Ala Leu Ser Arg Asp His
465                 470                 475                 480

Gln Ile Pro Val Ile Ala Ala Asn Tyr Pro Asp Leu Pro Ser Ala Tyr
                485                 490                 495

Gln Pro Gly Ile Leu Ser Val Ser His Ser Ala Gln Pro Pro Ala His
            500                 505                 510

Gln Pro Pro Met Ile Ser Thr Lys Tyr Pro Glu Leu Phe Pro Ala His
        515                 520                 525

Gln Ser Pro Met Phe Pro Asp Thr Arg Val Ala Gly Thr Gln Thr Thr
    530                 535                 540
```

Thr His Leu Pro Gly Ile Pro Pro Asn His Ala Pro Leu Val Thr Thr
545 550 555 560

Leu Gly Ala Gln Leu Pro Pro Gln Ala Pro Asp Ala Leu Val Leu Arg
565 570 575

Thr Gln Ala Thr Gln Leu Pro Ile Ile Pro Thr Ala Gln Pro Ser Leu
580 585 590

Thr Thr Thr Ser Arg Ser Pro Val Ser Pro Ala His Gln Ile Ser Val
595 600 605

Pro Ala Ala Thr Gln Pro Ala Ala Leu Pro Thr Leu Leu Pro Ser Gln
610 615 620

Ser Pro Thr Asn Gln Thr Ser Pro Ile Ser Pro Thr His Pro His Ser
625 630 635 640

Lys Ala Pro Gln Ile Pro Arg Glu Asp Gly Pro Ser Pro Lys Leu Ala
645 650 655

Leu Trp Leu Pro Ser Pro Ala Pro Thr Ala Ala Pro Thr Ala Leu Gly
660 665 670

Glu Ala Gly Leu Ala Glu His Ser Gln Arg Asp Asp Arg Trp Leu Leu
675 680 685

Val Ala Leu Leu Val Pro Thr Cys Val Phe Leu Val Val Leu Leu Ala
690 695 700

Leu Gly Ile Val Tyr Cys Thr Arg Cys Gly Pro His Ala Pro Asn Lys
705 710 715 720

Arg Ile Thr Asp Cys Tyr Arg Trp Val Ile His Ala Gly Ser Lys Ser
725 730 735

Pro Thr Glu Pro Met Pro Pro Arg Gly Ser Leu Thr Gly Val Gln Thr
740 745 750

Cys Arg Thr Ser Val
755

<210> SEQ ID NO 93
<211> LENGTH: 770
<212> TYPE: PRT
<213> ORGANISM: Artificial Sequence
<220> FEATURE:
<223> OTHER INFORMATION: Synthetic_A4_HUMAN

<400> SEQUENCE: 93

Met Leu Pro Gly Leu Ala Leu Leu Leu Leu Ala Ala Trp Thr Ala Arg
1 5 10 15

Ala Leu Glu Val Pro Thr Asp Gly Asn Ala Gly Leu Leu Ala Glu Pro
20 25 30

Gln Ile Ala Met Phe Cys Gly Arg Leu Asn Met His Met Asn Val Gln
35 40 45

Asn Gly Lys Trp Asp Ser Asp Pro Ser Gly Thr Lys Thr Cys Ile Asp
50 55 60

Thr Lys Glu Gly Ile Leu Gln Tyr Cys Gln Glu Val Tyr Pro Glu Leu
65 70 75 80

Gln Ile Thr Asn Val Val Glu Ala Asn Gln Pro Val Thr Ile Gln Asn
85 90 95

Trp Cys Lys Arg Gly Arg Lys Gln Cys Lys Thr His Pro His Phe Val
100 105 110

Ile Pro Tyr Arg Cys Leu Val Gly Glu Phe Val Ser Asp Ala Leu Leu
115 120 125

Val Pro Asp Lys Cys Lys Phe Leu His Gln Glu Arg Met Asp Val Cys
130 135 140

```
Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Glu Val Cys Ser Glu Gln Ala Glu Thr Gly Pro Cys Arg Ala Met Ile
    290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Met Ser Gln Ser Leu Leu Lys Thr
            340                 345                 350

Thr Gln Glu Pro Leu Ala Arg Asp Pro Val Lys Leu Pro Thr Thr Ala
        355                 360                 365

Ala Ser Thr Pro Asp Ala Val Asp Lys Tyr Leu Glu Thr Pro Gly Asp
    370                 375                 380

Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Glu Ala
                405                 410                 415

Glu Arg Gln Ala Lys Asn Leu Pro Lys Ala Asp Lys Lys Ala Val Ile
            420                 425                 430

Gln His Phe Gln Glu Lys Val Glu Ser Leu Glu Gln Glu Ala Ala Asn
        435                 440                 445

Glu Arg Gln Gln Leu Val Glu Thr His Met Ala Arg Val Glu Ala Met
    450                 455                 460

Leu Asn Asp Arg Arg Arg Leu Ala Leu Glu Asn Tyr Ile Thr Ala Leu
465                 470                 475                 480

Gln Ala Val Pro Pro Arg Pro Arg His Val Phe Asn Met Leu Lys Lys
                485                 490                 495

Tyr Val Arg Ala Glu Gln Lys Asp Arg Gln His Thr Leu Lys His Phe
            500                 505                 510

Glu His Val Arg Met Val Asp Pro Lys Lys Ala Ala Gln Ile Arg Ser
        515                 520                 525

Gln Val Met Thr His Leu Arg Val Ile Tyr Glu Arg Met Asn Gln Ser
    530                 535                 540

Leu Ser Leu Leu Tyr Asn Val Pro Ala Val Ala Glu Glu Ile Gln Asp
545                 550                 555                 560
```

```
Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
            580                 585                 590

Leu Met Pro Ser Leu Thr Glu Thr Lys Thr Thr Val Glu Leu Leu Pro
        595                 600                 605

Val Asn Gly Glu Phe Ser Leu Asp Asp Leu Gln Pro Trp His Ser Phe
    610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
            660                 665                 670

Ala Glu Phe Arg His Asp Ser Gly Tyr Glu Val His His Gln Lys Leu
        675                 680                 685

Val Phe Phe Ala Glu Asp Val Gly Ser Asn Lys Gly Ala Ile Ile Gly
    690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
            740                 745                 750

Gln Gln Asn Gly Tyr Glu Asn Pro Thr Tyr Lys Phe Phe Glu Gln Met
        755                 760                 765

Gln Asn
    770


<210> SEQ ID NO 94
<211> LENGTH: 780
<212> TYPE: PRT
<213> ORGANISM: Artificial Sequence
<220> FEATURE:
<223> OTHER INFORMATION: Synthetic_ASAH2_HUMAN

<400> SEQUENCE: 94

Met Ala Lys Arg Thr Phe Ser Asn Leu Glu Thr Phe Leu Ile Phe Leu
1               5                   10                  15

Leu Val Met Met Ser Ala Ile Thr Val Ala Leu Leu Ser Leu Leu Phe
            20                  25                  30

Ile Thr Ser Gly Thr Ile Glu Asn His Lys Asp Leu Gly Gly His Phe
        35                  40                  45

Phe Ser Thr Thr Gln Ser Pro Pro Ala Thr Gln Gly Ser Thr Ala Ala
    50                  55                  60

Gln Arg Ser Thr Ala Thr Gln His Ser Thr Ala Thr Gln Ser Ser Thr
65                  70                  75                  80

Ala Thr Gln Thr Ser Pro Val Pro Leu Thr Pro Glu Ser Pro Leu Phe
                85                  90                  95

Gln Asn Phe Ser Gly Tyr His Ile Gly Val Gly Arg Ala Asp Cys Thr
            100                 105                 110

Gly Gln Val Ala Asp Ile Asn Leu Met Gly Tyr Gly Lys Ser Gly Gln
        115                 120                 125

Asn Ala Gln Gly Ile Leu Thr Arg Leu Tyr Ser Arg Ala Phe Ile Met
    130                 135                 140
```

```
Ala Glu Pro Asp Gly Ser Asn Arg Thr Val Phe Val Ser Ile Asp Ile
145                 150                 155                 160

Gly Met Val Ser Gln Arg Leu Arg Leu Glu Val Leu Asn Arg Leu Gln
                165                 170                 175

Ser Lys Tyr Gly Ser Leu Tyr Arg Arg Asp Asn Val Ile Leu Ser Gly
            180                 185                 190

Thr His Thr His Ser Gly Pro Ala Gly Tyr Phe Gln Tyr Thr Val Phe
        195                 200                 205

Val Ile Ala Ser Glu Gly Phe Ser Asn Gln Thr Phe Gln His Met Val
    210                 215                 220

Thr Gly Ile Leu Lys Ser Ile Asp Ile Ala His Thr Asn Met Lys Pro
225                 230                 235                 240

Gly Lys Ile Phe Ile Asn Lys Gly Asn Val Asp Gly Val Gln Ile Asn
                245                 250                 255

Arg Ser Pro Tyr Ser Tyr Leu Gln Asn Pro Gln Ser Glu Arg Ala Arg
            260                 265                 270

Tyr Ser Ser Asn Thr Asp Lys Glu Met Ile Val Leu Lys Met Val Asp
        275                 280                 285

Leu Asn Gly Asp Asp Leu Gly Leu Ile Ser Trp Phe Ala Ile His Pro
    290                 295                 300

Val Ser Met Asn Asn Ser Asn His Leu Val Asn Ser Asp Asn Val Gly
305                 310                 315                 320

Tyr Ala Ser Tyr Leu Leu Glu Gln Glu Lys Asn Lys Gly Tyr Leu Pro
                325                 330                 335

Gly Gln Gly Pro Phe Val Ala Ala Phe Ala Ser Ser Asn Leu Gly Asp
            340                 345                 350

Val Ser Pro Asn Ile Leu Gly Pro Arg Cys Ile Asn Thr Gly Glu Ser
        355                 360                 365

Cys Asp Asn Ala Asn Ser Thr Cys Pro Ile Gly Gly Pro Ser Met Cys
    370                 375                 380

Ile Ala Lys Gly Pro Gly Gln Asp Met Phe Asp Ser Thr Gln Ile Ile
385                 390                 395                 400

Gly Arg Ala Met Tyr Gln Arg Ala Lys Glu Leu Tyr Ala Ser Ala Ser
                405                 410                 415

Gln Glu Val Thr Gly Pro Leu Ala Ser Ala His Gln Trp Val Asp Met
            420                 425                 430

Thr Asp Val Thr Val Trp Leu Asn Ser Thr His Ala Ser Lys Thr Cys
        435                 440                 445

Lys Pro Ala Leu Gly Tyr Ser Phe Ala Ala Gly Thr Ile Asp Gly Val
    450                 455                 460

Gly Gly Leu Asn Phe Thr Gln Gly Lys Thr Glu Gly Asp Pro Phe Trp
465                 470                 475                 480

Asp Thr Ile Arg Asp Gln Ile Leu Gly Lys Pro Ser Glu Glu Ile Lys
                485                 490                 495

Glu Cys His Lys Pro Lys Pro Ile Leu Leu His Thr Gly Glu Leu Ser
            500                 505                 510

Lys Pro His Pro Trp His Pro Asp Ile Val Asp Val Gln Ile Ile Thr
        515                 520                 525

Leu Gly Ser Leu Ala Ile Thr Ala Ile Pro Gly Glu Phe Thr Thr Met
    530                 535                 540

Ser Gly Arg Arg Leu Arg Glu Ala Val Gln Ala Glu Phe Ala Ser His
545                 550                 555                 560

Gly Met Gln Asn Met Thr Val Val Ile Ser Gly Leu Cys Asn Val Tyr
```

```
                565                 570                 575

Thr His Tyr Ile Thr Thr Tyr Glu Glu Tyr Gln Ala Gln Arg Tyr Glu
            580                 585                 590

Ala Ala Ser Thr Ile Tyr Gly Pro His Thr Leu Ser Ala Tyr Ile Gln
        595                 600                 605

Leu Phe Arg Asn Leu Ala Lys Ala Ile Ala Thr Asp Thr Val Ala Asn
    610                 615                 620

Leu Ser Arg Gly Pro Glu Pro Pro Phe Phe Lys Gln Leu Ile Val Pro
625                 630                 635                 640

Leu Ile Pro Ser Ile Val Asp Arg Ala Pro Lys Gly Arg Thr Phe Gly
                645                 650                 655

Asp Val Leu Gln Pro Ala Lys Pro Glu Tyr Arg Val Gly Glu Val Ala
            660                 665                 670

Glu Val Ile Phe Val Gly Ala Asn Pro Lys Asn Ser Val Gln Asn Gln
        675                 680                 685

Thr His Gln Thr Phe Leu Thr Val Glu Lys Tyr Glu Ala Thr Ser Thr
    690                 695                 700

Ser Trp Gln Ile Val Cys Asn Asp Ala Ser Trp Glu Thr Arg Phe Tyr
705                 710                 715                 720

Trp His Lys Gly Leu Leu Gly Leu Ser Asn Ala Thr Val Glu Trp His
                725                 730                 735

Ile Pro Asp Thr Ala Gln Pro Gly Ile Tyr Arg Ile Arg Tyr Phe Gly
            740                 745                 750

His Asn Arg Lys Gln Asp Ile Leu Lys Pro Ala Val Ile Leu Ser Phe
        755                 760                 765

Glu Gly Thr Ser Pro Ala Phe Glu Val Val Thr Ile
    770                 775                 780


<210> SEQ ID NO 95
<211> LENGTH: 785
<212> TYPE: PRT
<213> ORGANISM: Artificial Sequence
<220> FEATURE:
<223> OTHER INFORMATION: Synthetic_SP1_HUMAN

<400> SEQUENCE: 95

Met Ser Asp Gln Asp His Ser Met Asp Glu Met Thr Ala Val Val Lys
1               5                   10                  15

Ile Glu Lys Gly Val Gly Gly Asn Asn Gly Gly Asn Gly Asn Gly Gly
            20                  25                  30

Gly Ala Phe Ser Gln Ala Arg Ser Ser Ser Thr Gly Ser Ser Ser Ser
        35                  40                  45

Thr Gly Gly Gly Gly Gln Glu Ser Gln Pro Ser Pro Leu Ala Leu Leu
    50                  55                  60

Ala Ala Thr Cys Ser Arg Ile Glu Ser Pro Asn Glu Asn Ser Asn Asn
65                  70                  75                  80

Ser Gln Gly Pro Ser Gln Ser Gly Gly Thr Gly Glu Leu Asp Leu Thr
                85                  90                  95

Ala Thr Gln Leu Ser Gln Gly Ala Asn Gly Trp Gln Ile Ile Ser Ser
            100                 105                 110

Ser Ser Gly Ala Thr Pro Thr Ser Lys Glu Gln Ser Gly Ser Ser Thr
        115                 120                 125

Asn Gly Ser Asn Gly Ser Glu Ser Ser Lys Asn Arg Thr Val Ser Gly
    130                 135                 140

Gly Gln Tyr Val Val Ala Ala Ala Pro Asn Leu Gln Asn Gln Gln Val
```

```
145                 150                 155                 160

Leu Thr Gly Leu Pro Gly Val Met Pro Asn Ile Gln Tyr Gln Val Ile
                165                 170                 175

Pro Gln Phe Gln Thr Val Asp Gly Gln Gln Leu Gln Phe Ala Ala Thr
            180                 185                 190

Gly Ala Gln Val Gln Gln Asp Gly Ser Gly Gln Ile Gln Ile Ile Pro
        195                 200                 205

Gly Ala Asn Gln Gln Ile Ile Thr Asn Arg Gly Ser Gly Gly Asn Ile
    210                 215                 220

Ile Ala Ala Met Pro Asn Leu Leu Gln Gln Ala Val Pro Leu Gln Gly
225                 230                 235                 240

Leu Ala Asn Asn Val Leu Ser Gly Gln Thr Gln Tyr Val Thr Asn Val
                245                 250                 255

Pro Val Ala Leu Asn Gly Asn Ile Thr Leu Leu Pro Val Asn Ser Val
            260                 265                 270

Ser Ala Ala Thr Leu Thr Pro Ser Ser Gln Ala Val Thr Ile Ser Ser
        275                 280                 285

Ser Gly Ser Gln Glu Ser Gly Ser Gln Pro Val Thr Ser Gly Thr Thr
    290                 295                 300

Ile Ser Ser Ala Ser Leu Val Ser Ser Gln Ala Ser Ser Ser Ser Phe
305                 310                 315                 320

Phe Thr Asn Ala Asn Ser Tyr Ser Thr Thr Thr Thr Thr Ser Asn Met
                325                 330                 335

Gly Ile Met Asn Phe Thr Thr Ser Gly Ser Ser Gly Thr Asn Ser Gln
            340                 345                 350

Gly Gln Thr Pro Gln Arg Val Ser Gly Leu Gln Gly Ser Asp Ala Leu
        355                 360                 365

Asn Ile Gln Gln Asn Gln Thr Ser Gly Gly Ser Leu Gln Ala Gly Gln
    370                 375                 380

Gln Lys Glu Gly Glu Gln Asn Gln Gln Thr Gln Gln Gln Gln Ile Leu
385                 390                 395                 400

Ile Gln Pro Gln Leu Val Gln Gly Gly Gln Ala Leu Gln Ala Leu Gln
                405                 410                 415

Ala Ala Pro Leu Ser Gly Gln Thr Phe Thr Thr Gln Ala Ile Ser Gln
            420                 425                 430

Glu Thr Leu Gln Asn Leu Gln Leu Gln Ala Val Pro Asn Ser Gly Pro
        435                 440                 445

Ile Ile Ile Arg Thr Pro Thr Val Gly Pro Asn Gly Gln Val Ser Trp
    450                 455                 460

Gln Thr Leu Gln Leu Gln Asn Leu Gln Val Gln Asn Pro Gln Ala Gln
465                 470                 475                 480

Thr Ile Thr Leu Ala Pro Met Gln Gly Val Ser Leu Gly Gln Thr Ser
                485                 490                 495

Ser Ser Asn Thr Thr Leu Thr Pro Ile Ala Ser Ala Ala Ser Ile Pro
            500                 505                 510

Ala Gly Thr Val Thr Val Asn Ala Ala Gln Leu Ser Ser Met Pro Gly
        515                 520                 525

Leu Gln Thr Ile Asn Leu Ser Ala Leu Gly Thr Ser Gly Ile Gln Val
    530                 535                 540

His Pro Ile Gln Gly Leu Pro Leu Ala Ile Ala Asn Ala Pro Gly Asp
545                 550                 555                 560

His Gly Ala Gln Leu Gly Leu His Gly Ala Gly Gly Asp Gly Ile His
                565                 570                 575
```

Asp Asp Thr Ala Gly Gly Glu Glu Gly Glu Asn Ser Pro Asp Ala Gln
580 585 590

Pro Gln Ala Gly Arg Arg Thr Arg Arg Glu Ala Cys Thr Cys Pro Tyr
595 600 605

Cys Lys Asp Ser Glu Gly Arg Gly Ser Gly Asp Pro Gly Lys Lys Lys
610 615 620

Gln His Ile Cys His Ile Gln Gly Cys Gly Lys Val Tyr Gly Lys Thr
625 630 635 640

Ser His Leu Arg Ala His Leu Arg Trp His Thr Gly Glu Arg Pro Phe
645 650 655

Met Cys Thr Trp Ser Tyr Cys Gly Lys Arg Phe Thr Arg Ser Asp Glu
660 665 670

Leu Gln Arg His Lys Arg Thr His Thr Gly Glu Lys Lys Phe Ala Cys
675 680 685

Pro Glu Cys Pro Lys Arg Phe Met Arg Ser Asp His Leu Ser Lys His
690 695 700

Ile Lys Thr His Gln Asn Lys Lys Gly Gly Pro Gly Val Ala Leu Ser
705 710 715 720

Val Gly Thr Leu Pro Leu Asp Ser Gly Ala Gly Ser Glu Gly Ser Gly
725 730 735

Thr Ala Thr Pro Ser Ala Leu Ile Thr Thr Asn Met Val Ala Met Glu
740 745 750

Ala Ile Cys Pro Glu Gly Ile Ala Arg Leu Ala Asn Ser Gly Ile Asn
755 760 765

Val Met Gln Val Ala Asp Leu Gln Ser Ile Asn Ile Ser Gly Asn Gly
770 775 780

Phe
785

<210> SEQ ID NO 96
<211> LENGTH: 797
<212> TYPE: PRT
<213> ORGANISM: Artificial Sequence
<220> FEATURE:
<223> OTHER INFORMATION: Synthetic_IMPG1_HUMAN

<400> SEQUENCE: 96

Met Tyr Leu Glu Thr Arg Arg Ala Ile Phe Val Phe Trp Ile Phe Leu
1 5 10 15

Gln Val Gln Gly Thr Lys Asp Ile Ser Ile Asn Ile Tyr His Ser Glu
20 25 30

Thr Lys Asp Ile Asp Asn Pro Pro Arg Asn Glu Thr Thr Glu Ser Thr
35 40 45

Glu Lys Met Tyr Lys Met Ser Thr Met Arg Arg Ile Phe Asp Leu Ala
50 55 60

Lys His Arg Thr Lys Arg Ser Ala Phe Phe Pro Thr Gly Val Lys Val
65 70 75 80

Cys Pro Gln Glu Ser Met Lys Gln Ile Leu Asp Ser Leu Gln Ala Tyr
85 90 95

Tyr Arg Leu Arg Val Cys Gln Glu Ala Val Trp Glu Ala Tyr Arg Ile
100 105 110

Phe Leu Asp Arg Ile Pro Asp Thr Gly Glu Tyr Gln Asp Trp Val Ser
115 120 125

Ile Cys Gln Gln Glu Thr Phe Cys Leu Phe Asp Ile Gly Lys Asn Phe
130 135 140

-continued

Ser Asn Ser Gln Glu His Leu Asp Leu Leu Gln Gln Arg Ile Lys Gln
145 150 155 160

Arg Ser Phe Pro Asp Arg Lys Asp Glu Ile Ser Ala Glu Lys Thr Leu
165 170 175

Gly Glu Pro Gly Glu Thr Ile Val Ile Ser Thr Asp Val Ala Asn Val
180 185 190

Ser Leu Gly Pro Phe Pro Leu Thr Pro Asp Asp Thr Leu Leu Asn Glu
195 200 205

Ile Leu Asp Asn Thr Leu Asn Asp Thr Lys Met Pro Thr Thr Glu Arg
210 215 220

Glu Thr Glu Phe Ala Val Leu Glu Glu Gln Arg Val Glu Leu Ser Val
225 230 235 240

Ser Leu Val Asn Gln Lys Phe Lys Ala Glu Leu Ala Asp Ser Gln Ser
245 250 255

Pro Tyr Tyr Gln Glu Leu Ala Gly Lys Ser Gln Leu Gln Met Gln Lys
260 265 270

Ile Phe Lys Lys Leu Pro Gly Phe Lys Lys Ile His Val Leu Gly Phe
275 280 285

Arg Pro Lys Lys Glu Lys Asp Gly Ser Ser Ser Thr Glu Met Gln Leu
290 295 300

Thr Ala Ile Phe Lys Arg His Ser Ala Glu Ala Lys Ser Pro Ala Ser
305 310 315 320

Asp Leu Leu Ser Phe Asp Ser Asn Lys Ile Glu Ser Glu Glu Val Tyr
325 330 335

His Gly Thr Met Glu Glu Asp Lys Gln Pro Glu Ile Tyr Leu Thr Ala
340 345 350

Thr Asp Leu Lys Arg Leu Ile Ser Lys Ala Leu Glu Glu Glu Gln Ser
355 360 365

Leu Asp Val Gly Thr Ile Gln Phe Thr Asp Glu Ile Ala Gly Ser Leu
370 375 380

Pro Ala Phe Gly Pro Asp Thr Gln Ser Glu Leu Pro Thr Ser Phe Ala
385 390 395 400

Val Ile Thr Glu Asp Ala Thr Leu Ser Pro Glu Leu Pro Pro Val Glu
405 410 415

Pro Gln Leu Glu Thr Val Asp Gly Ala Glu His Gly Leu Pro Asp Thr
420 425 430

Ser Trp Ser Pro Pro Ala Met Ala Ser Thr Ser Leu Ser Glu Ala Pro
435 440 445

Pro Phe Phe Met Ala Ser Ser Ile Phe Ser Leu Thr Asp Gln Gly Thr
450 455 460

Thr Asp Thr Met Ala Thr Asp Gln Thr Met Leu Val Pro Gly Leu Thr
465 470 475 480

Ile Pro Thr Ser Asp Tyr Ser Ala Ile Ser Gln Leu Ala Leu Gly Ile
485 490 495

Ser His Pro Pro Ala Ser Ser Asp Asp Ser Arg Ser Ser Ala Gly Gly
500 505 510

Glu Asp Met Val Arg His Leu Asp Glu Met Asp Leu Ser Asp Thr Pro
515 520 525

Ala Pro Ser Glu Val Pro Glu Leu Ser Glu Tyr Val Ser Val Pro Asp
530 535 540

His Phe Leu Glu Asp Thr Thr Pro Val Ser Ala Leu Gln Tyr Ile Thr
545 550 555 560

Thr Ser Ser Met Thr Ile Ala Pro Lys Gly Arg Glu Leu Val Val Phe
565 570 575

Phe Ser Leu Arg Val Ala Asn Met Ala Phe Ser Asn Asp Leu Phe Asn
580 585 590

Lys Ser Ser Leu Glu Tyr Arg Ala Leu Glu Gln Gln Phe Thr Gln Leu
595 600 605

Leu Val Pro Tyr Leu Arg Ser Asn Leu Thr Gly Phe Lys Gln Leu Glu
610 615 620

Ile Leu Asn Phe Arg Asn Gly Ser Val Ile Val Asn Ser Lys Met Lys
625 630 635 640

Phe Ala Lys Ser Val Pro Tyr Asn Leu Thr Lys Ala Val His Gly Val
645 650 655

Leu Glu Asp Phe Arg Ser Ala Ala Ala Gln Gln Leu His Leu Glu Ile
660 665 670

Asp Ser Tyr Ser Leu Asn Ile Glu Pro Ala Asp Gln Ala Asp Pro Cys
675 680 685

Lys Phe Leu Ala Cys Gly Glu Phe Ala Gln Cys Val Lys Asn Glu Arg
690 695 700

Thr Glu Glu Ala Glu Cys Arg Cys Lys Pro Gly Tyr Asp Ser Gln Gly
705 710 715 720

Ser Leu Asp Gly Leu Glu Pro Gly Leu Cys Gly Pro Gly Thr Lys Glu
725 730 735

Cys Glu Val Leu Gln Gly Lys Gly Ala Pro Cys Arg Leu Pro Asp His
740 745 750

Ser Glu Asn Gln Ala Tyr Lys Thr Ser Val Lys Lys Phe Gln Asn Gln
755 760 765

Gln Asn Asn Lys Val Ile Ser Lys Arg Asn Ser Glu Leu Leu Thr Val
770 775 780

Glu Tyr Glu Glu Phe Asn His Gln Asp Trp Glu Gly Asn
785 790 795

<210> SEQ ID NO 97
<211> LENGTH: 815
<212> TYPE: PRT
<213> ORGANISM: Artificial Sequence
<220> FEATURE:
<223> OTHER INFORMATION: Synthetic_SL9A1_HUMAN

<400> SEQUENCE: 97

Met Val Leu Arg Ser Gly Ile Cys Gly Leu Ser Pro His Arg Ile Phe
1 5 10 15

Pro Ser Leu Leu Val Val Val Ala Leu Val Gly Leu Leu Pro Val Leu
20 25 30

Arg Ser His Gly Leu Gln Leu Ser Pro Thr Ala Ser Thr Ile Arg Ser
35 40 45

Ser Glu Pro Pro Arg Glu Arg Ser Ile Gly Asp Val Thr Thr Ala Pro
50 55 60

Pro Glu Val Thr Pro Glu Ser Arg Pro Val Asn His Ser Val Thr Asp
65 70 75 80

His Gly Met Lys Pro Arg Lys Ala Phe Pro Val Leu Gly Ile Asp Tyr
85 90 95

Thr His Val Arg Thr Pro Phe Glu Ile Ser Leu Trp Ile Leu Leu Ala
100 105 110

Cys Leu Met Lys Ile Gly Phe His Val Ile Pro Thr Ile Ser Ser Ile
115 120 125

```
Val Pro Glu Ser Cys Leu Leu Ile Val Val Gly Leu Leu Val Gly Gly
    130                 135                 140

Leu Ile Lys Gly Val Gly Glu Thr Pro Pro Phe Leu Gln Ser Asp Val
145                 150                 155                 160

Phe Phe Leu Phe Leu Leu Pro Pro Ile Ile Leu Asp Ala Gly Tyr Phe
                165                 170                 175

Leu Pro Leu Arg Gln Phe Thr Glu Asn Leu Gly Thr Ile Leu Ile Phe
            180                 185                 190

Ala Val Val Gly Thr Leu Trp Asn Ala Phe Phe Leu Gly Gly Leu Met
        195                 200                 205

Tyr Ala Val Cys Leu Val Gly Gly Glu Gln Ile Asn Asn Ile Gly Leu
    210                 215                 220

Leu Asp Asn Leu Leu Phe Gly Ser Ile Ile Ser Ala Val Asp Pro Val
225                 230                 235                 240

Ala Val Leu Ala Val Phe Glu Glu Ile His Ile Asn Glu Leu Leu His
                245                 250                 255

Ile Leu Val Phe Gly Glu Ser Leu Leu Asn Asp Ala Val Thr Val Val
            260                 265                 270

Leu Tyr His Leu Phe Glu Glu Phe Ala Asn Tyr Glu His Val Gly Ile
        275                 280                 285

Val Asp Ile Phe Leu Gly Phe Leu Ser Phe Phe Val Val Ala Leu Gly
    290                 295                 300

Gly Val Leu Val Gly Val Val Tyr Gly Val Ile Ala Ala Phe Thr Ser
305                 310                 315                 320

Arg Phe Thr Ser His Ile Arg Val Ile Glu Pro Leu Phe Val Phe Leu
                325                 330                 335

Tyr Ser Tyr Met Ala Tyr Leu Ser Ala Glu Leu Phe His Leu Ser Gly
            340                 345                 350

Ile Met Ala Leu Ile Ala Ser Gly Val Val Met Arg Pro Tyr Val Glu
        355                 360                 365

Ala Asn Ile Ser His Lys Ser His Thr Thr Ile Lys Tyr Phe Leu Lys
    370                 375                 380

Met Trp Ser Ser Val Ser Glu Thr Leu Ile Phe Ile Phe Leu Gly Val
385                 390                 395                 400

Ser Thr Val Ala Gly Ser His His Trp Asn Trp Thr Phe Val Ile Ser
                405                 410                 415

Thr Leu Leu Phe Cys Leu Ile Ala Arg Val Leu Gly Val Leu Gly Leu
            420                 425                 430

Thr Trp Phe Ile Asn Lys Phe Arg Ile Val Lys Leu Thr Pro Lys Asp
        435                 440                 445

Gln Phe Ile Ile Ala Tyr Gly Gly Leu Arg Gly Ala Ile Ala Phe Ser
    450                 455                 460

Leu Gly Tyr Leu Leu Asp Lys Lys His Phe Pro Met Cys Asp Leu Phe
465                 470                 475                 480

Leu Thr Ala Ile Ile Thr Val Ile Phe Phe Thr Val Phe Val Gln Gly
                485                 490                 495

Met Thr Ile Arg Pro Leu Val Asp Leu Leu Ala Val Lys Lys Lys Gln
            500                 505                 510

Glu Thr Lys Arg Ser Ile Asn Glu Glu Ile His Thr Gln Phe Leu Asp
        515                 520                 525

His Leu Leu Thr Gly Ile Glu Asp Ile Cys Gly His Tyr Gly His His
    530                 535                 540

His Trp Lys Asp Lys Leu Asn Arg Phe Asn Lys Lys Tyr Val Lys Lys
```

545 550 555 560

Cys Leu Ile Ala Gly Glu Arg Ser Lys Glu Pro Gln Leu Ile Ala Phe
565 570 575

Tyr His Lys Met Glu Met Lys Gln Ala Ile Glu Leu Val Glu Ser Gly
580 585 590

Gly Met Gly Lys Ile Pro Ser Ala Val Ser Thr Val Ser Met Gln Asn
595 600 605

Ile His Pro Lys Ser Leu Pro Ser Glu Arg Ile Leu Pro Ala Leu Ser
610 615 620

Lys Asp Lys Glu Glu Glu Ile Arg Lys Ile Leu Arg Asn Asn Leu Gln
625 630 635 640

Lys Thr Arg Gln Arg Leu Arg Ser Tyr Asn Arg His Thr Leu Val Ala
645 650 655

Asp Pro Tyr Glu Glu Ala Trp Asn Gln Met Leu Leu Arg Arg Gln Lys
660 665 670

Ala Arg Gln Leu Glu Gln Lys Ile Asn Asn Tyr Leu Thr Val Pro Ala
675 680 685

His Lys Leu Asp Ser Pro Thr Met Ser Arg Ala Arg Ile Gly Ser Asp
690 695 700

Pro Leu Ala Tyr Glu Pro Lys Glu Asp Leu Pro Val Ile Thr Ile Asp
705 710 715 720

Pro Ala Ser Pro Gln Ser Pro Glu Ser Val Asp Leu Val Asn Glu Glu
725 730 735

Leu Lys Gly Lys Val Leu Gly Leu Ser Arg Asp Pro Ala Lys Val Ala
740 745 750

Glu Glu Asp Glu Asp Asp Asp Gly Gly Ile Met Met Arg Ser Lys Glu
755 760 765

Thr Ser Ser Pro Gly Thr Asp Asp Val Phe Thr Pro Ala Pro Ser Asp
770 775 780

Ser Pro Ser Ser Gln Arg Ile Gln Arg Cys Leu Ser Asp Pro Gly Pro
785 790 795 800

His Pro Glu Pro Gly Glu Gly Glu Pro Phe Phe Pro Lys Gly Gln
805 810 815

<210> SEQ ID NO 98
<211> LENGTH: 882
<212> TYPE: PRT
<213> ORGANISM: Artificial Sequence
<220> FEATURE:
<223> OTHER INFORMATION: Synthetic_CADH1_HUMAN

<400> SEQUENCE: 98

Met Gly Pro Trp Ser Arg Ser Leu Ser Ala Leu Leu Leu Leu Leu Gln
1 5 10 15

Val Ser Ser Trp Leu Cys Gln Glu Pro Glu Pro Cys His Pro Gly Phe
20 25 30

Asp Ala Glu Ser Tyr Thr Phe Thr Val Pro Arg Arg His Leu Glu Arg
35 40 45

Gly Arg Val Leu Gly Arg Val Asn Phe Glu Asp Cys Thr Gly Arg Gln
50 55 60

Arg Thr Ala Tyr Phe Ser Leu Asp Thr Arg Phe Lys Val Gly Thr Asp
65 70 75 80

Gly Val Ile Thr Val Lys Arg Pro Leu Arg Phe His Asn Pro Gln Ile
85 90 95

His Phe Leu Val Tyr Ala Trp Asp Ser Thr Tyr Arg Lys Phe Ser Thr

```
            100                 105                 110

Lys Val Thr Leu Asn Thr Val Gly His His His Arg Pro Pro Pro His
        115                 120                 125

Gln Ala Ser Val Ser Gly Ile Gln Ala Glu Leu Leu Thr Phe Pro Asn
    130                 135                 140

Ser Ser Pro Gly Leu Arg Arg Gln Lys Arg Asp Trp Val Ile Pro Pro
145                 150                 155                 160

Ile Ser Cys Pro Glu Asn Glu Lys Gly Pro Phe Pro Lys Asn Leu Val
                165                 170                 175

Gln Ile Lys Ser Asn Lys Asp Lys Glu Gly Lys Val Phe Tyr Ser Ile
            180                 185                 190

Thr Gly Gln Gly Ala Asp Thr Pro Pro Val Gly Val Phe Ile Ile Glu
        195                 200                 205

Arg Glu Thr Gly Trp Leu Lys Val Thr Glu Pro Leu Asp Arg Glu Arg
    210                 215                 220

Ile Ala Thr Tyr Thr Leu Phe Ser His Ala Val Ser Ser Asn Gly Asn
225                 230                 235                 240

Ala Val Glu Asp Pro Met Glu Ile Leu Ile Thr Val Thr Asp Gln Asn
                245                 250                 255

Asp Asn Lys Pro Glu Phe Thr Gln Glu Val Phe Lys Gly Ser Val Met
            260                 265                 270

Glu Gly Ala Leu Pro Gly Thr Ser Val Met Glu Val Thr Ala Thr Asp
        275                 280                 285

Ala Asp Asp Asp Val Asn Thr Tyr Asn Ala Ala Ile Ala Tyr Thr Ile
    290                 295                 300

Leu Ser Gln Asp Pro Glu Leu Pro Asp Lys Asn Met Phe Thr Ile Asn
305                 310                 315                 320

Arg Asn Thr Gly Val Ile Ser Val Val Thr Thr Gly Leu Asp Arg Glu
                325                 330                 335

Ser Phe Pro Thr Tyr Thr Leu Val Val Gln Ala Ala Asp Leu Gln Gly
            340                 345                 350

Glu Gly Leu Ser Thr Thr Ala Thr Ala Val Ile Thr Val Thr Asp Thr
        355                 360                 365

Asn Asp Asn Pro Pro Ile Phe Asn Pro Thr Thr Tyr Lys Gly Gln Val
    370                 375                 380

Pro Glu Asn Glu Ala Asn Val Val Ile Thr Thr Leu Lys Val Thr Asp
385                 390                 395                 400

Ala Asp Ala Pro Asn Thr Pro Ala Trp Glu Ala Val Tyr Thr Ile Leu
                405                 410                 415

Asn Asp Asp Gly Gly Gln Phe Val Val Thr Thr Asn Pro Val Asn Asn
            420                 425                 430

Asp Gly Ile Leu Lys Thr Ala Lys Gly Leu Asp Phe Glu Ala Lys Gln
        435                 440                 445

Gln Tyr Ile Leu His Val Ala Val Thr Asn Val Val Pro Phe Glu Val
    450                 455                 460

Ser Leu Thr Thr Ser Thr Ala Thr Val Thr Val Asp Val Leu Asp Val
465                 470                 475                 480

Asn Glu Ala Pro Ile Phe Val Pro Pro Glu Lys Arg Val Glu Val Ser
                485                 490                 495

Glu Asp Phe Gly Val Gly Gln Glu Ile Thr Ser Tyr Thr Ala Gln Glu
            500                 505                 510

Pro Asp Thr Phe Met Glu Gln Lys Ile Thr Tyr Arg Ile Trp Arg Asp
        515                 520                 525
```

```
Thr Ala Asn Trp Leu Glu Ile Asn Pro Asp Thr Gly Ala Ile Ser Thr
    530                 535                 540

Arg Ala Glu Leu Asp Arg Glu Asp Phe Glu His Val Lys Asn Ser Thr
545                 550                 555                 560

Tyr Thr Ala Leu Ile Ile Ala Thr Asp Asn Gly Ser Pro Val Ala Thr
                565                 570                 575

Gly Thr Gly Thr Leu Leu Leu Ile Leu Ser Asp Val Asn Asp Asn Ala
            580                 585                 590

Pro Ile Pro Glu Pro Arg Thr Ile Phe Phe Cys Glu Arg Asn Pro Lys
        595                 600                 605

Pro Gln Val Ile Asn Ile Ile Asp Ala Asp Leu Pro Pro Asn Thr Ser
    610                 615                 620

Pro Phe Thr Ala Glu Leu Thr His Gly Ala Ser Ala Asn Trp Thr Ile
625                 630                 635                 640

Gln Tyr Asn Asp Pro Thr Gln Glu Ser Ile Ile Leu Lys Pro Lys Met
                645                 650                 655

Ala Leu Glu Val Gly Asp Tyr Lys Ile Asn Leu Lys Leu Met Asp Asn
            660                 665                 670

Gln Asn Lys Asp Gln Val Thr Thr Leu Glu Val Ser Val Cys Asp Cys
        675                 680                 685

Glu Gly Ala Ala Gly Val Cys Arg Lys Ala Gln Pro Val Glu Ala Gly
    690                 695                 700

Leu Gln Ile Pro Ala Ile Leu Gly Ile Leu Gly Gly Ile Leu Ala Leu
705                 710                 715                 720

Leu Ile Leu Ile Leu Leu Leu Leu Leu Phe Leu Arg Arg Arg Ala Val
                725                 730                 735

Val Lys Glu Pro Leu Leu Pro Pro Glu Asp Asp Thr Arg Asp Asn Val
            740                 745                 750

Tyr Tyr Tyr Asp Glu Glu Gly Gly Gly Glu Glu Asp Gln Asp Phe Asp
        755                 760                 765

Leu Ser Gln Leu His Arg Gly Leu Asp Ala Arg Pro Glu Val Thr Arg
    770                 775                 780

Asn Asp Val Ala Pro Thr Leu Met Ser Val Pro Arg Tyr Leu Pro Arg
785                 790                 795                 800

Pro Ala Asn Pro Asp Glu Ile Gly Asn Phe Ile Asp Glu Asn Leu Lys
                805                 810                 815

Ala Ala Asp Thr Asp Pro Thr Ala Pro Pro Tyr Asp Ser Leu Leu Val
            820                 825                 830

Phe Asp Tyr Glu Gly Ser Gly Ser Glu Ala Ala Ser Leu Ser Ser Leu
        835                 840                 845

Asn Ser Ser Glu Ser Asp Lys Asp Gln Asp Tyr Asp Tyr Leu Asn Glu
    850                 855                 860

Trp Gly Asn Arg Phe Lys Lys Leu Ala Asp Met Tyr Gly Gly Gly Glu
865                 870                 875                 880

Asp Asp
```

<210> SEQ ID NO 99
<211> LENGTH: 895
<212> TYPE: PRT
<213> ORGANISM: Artificial Sequence
<220> FEATURE:
<223> OTHER INFORMATION: Synthetic_DAG1_HUMAN

<400> SEQUENCE: 99

-continued

```
Met Arg Met Ser Val Gly Leu Ser Leu Leu Leu Pro Leu Ser Gly Arg
1               5                   10                  15

Thr Phe Leu Leu Leu Leu Ser Val Val Met Ala Gln Ser His Trp Pro
            20                  25                  30

Ser Glu Pro Ser Glu Ala Val Arg Asp Trp Glu Asn Gln Leu Glu Ala
        35                  40                  45

Ser Met His Ser Val Leu Ser Asp Leu His Glu Ala Val Pro Thr Val
    50                  55                  60

Val Gly Ile Pro Asp Gly Thr Ala Val Val Gly Arg Ser Phe Arg Val
65                  70                  75                  80

Thr Ile Pro Thr Asp Leu Ile Ala Ser Ser Gly Asp Ile Ile Lys Val
                85                  90                  95

Ser Ala Ala Gly Lys Glu Ala Leu Pro Ser Trp Leu His Trp Asp Ser
            100                 105                 110

Gln Ser His Thr Leu Glu Gly Leu Pro Leu Asp Thr Asp Lys Gly Val
        115                 120                 125

His Tyr Ile Ser Val Ser Ala Thr Arg Leu Gly Ala Asn Gly Ser His
    130                 135                 140

Ile Pro Gln Thr Ser Ser Val Phe Ser Ile Glu Val Tyr Pro Glu Asp
145                 150                 155                 160

His Ser Glu Leu Gln Ser Val Arg Thr Ala Ser Pro Asp Pro Gly Glu
                165                 170                 175

Val Val Ser Ser Ala Cys Ala Ala Asp Glu Pro Val Thr Val Leu Thr
            180                 185                 190

Val Ile Leu Asp Ala Asp Leu Thr Lys Met Thr Pro Lys Gln Arg Ile
        195                 200                 205

Asp Leu Leu His Arg Met Arg Ser Phe Ser Glu Val Glu Leu His Asn
    210                 215                 220

Met Lys Leu Val Pro Val Val Asn Asn Arg Leu Phe Asp Met Ser Ala
225                 230                 235                 240

Phe Met Ala Gly Pro Gly Asn Ala Lys Lys Val Val Glu Asn Gly Ala
                245                 250                 255

Leu Leu Ser Trp Lys Leu Gly Cys Ser Leu Asn Gln Asn Ser Val Pro
            260                 265                 270

Asp Ile His Gly Val Glu Ala Pro Ala Arg Glu Gly Ala Met Ser Ala
        275                 280                 285

Gln Leu Gly Tyr Pro Val Val Gly Trp His Ile Ala Asn Lys Lys Pro
    290                 295                 300

Pro Leu Pro Lys Arg Val Arg Arg Gln Ile His Ala Thr Pro Thr Pro
305                 310                 315                 320

Val Thr Ala Ile Gly Pro Pro Thr Thr Ala Ile Gln Glu Pro Pro Ser
                325                 330                 335

Arg Ile Val Pro Thr Pro Thr Ser Pro Ala Ile Ala Pro Pro Thr Glu
            340                 345                 350

Thr Met Ala Pro Pro Val Arg Asp Pro Val Pro Gly Lys Pro Thr Val
        355                 360                 365

Thr Ile Arg Thr Arg Gly Ala Ile Ile Gln Thr Pro Thr Leu Gly Pro
    370                 375                 380

Ile Gln Pro Thr Arg Val Ser Glu Ala Gly Thr Thr Val Pro Gly Gln
385                 390                 395                 400

Ile Arg Pro Thr Met Thr Ile Pro Gly Tyr Val Glu Pro Thr Ala Val
                405                 410                 415

Ala Thr Pro Pro Thr Thr Thr Thr Lys Lys Pro Arg Val Ser Thr Pro
```

```
            420                 425                 430

Lys Pro Ala Thr Pro Ser Thr Asp Ser Thr Thr Thr Thr Thr Arg Arg
        435                 440                 445

Pro Thr Lys Lys Pro Arg Thr Pro Arg Pro Val Pro Arg Val Thr Thr
    450                 455                 460

Lys Val Ser Ile Thr Arg Leu Glu Thr Ala Ser Pro Pro Thr Arg Ile
465                 470                 475                 480

Arg Thr Thr Thr Ser Gly Val Pro Arg Gly Gly Glu Pro Asn Gln Arg
                485                 490                 495

Pro Glu Leu Lys Asn His Ile Asp Arg Val Asp Ala Trp Val Gly Thr
            500                 505                 510

Tyr Phe Glu Val Lys Ile Pro Ser Asp Thr Phe Tyr Asp His Glu Asp
        515                 520                 525

Thr Thr Thr Asp Lys Leu Lys Leu Thr Leu Lys Leu Arg Glu Gln Gln
    530                 535                 540

Leu Val Gly Glu Lys Ser Trp Val Gln Phe Asn Ser Asn Ser Gln Leu
545                 550                 555                 560

Met Tyr Gly Leu Pro Asp Ser Ser His Val Gly Lys His Glu Tyr Phe
                565                 570                 575

Met His Ala Thr Asp Lys Gly Gly Leu Ser Ala Val Asp Ala Phe Glu
            580                 585                 590

Ile His Val His Arg Arg Pro Gln Gly Asp Arg Ala Pro Ala Arg Phe
        595                 600                 605

Lys Ala Lys Phe Val Gly Asp Pro Ala Leu Val Leu Asn Asp Ile His
    610                 615                 620

Lys Lys Ile Ala Leu Val Lys Lys Leu Ala Phe Ala Phe Gly Asp Arg
625                 630                 635                 640

Asn Cys Ser Thr Ile Thr Leu Gln Asn Ile Thr Arg Gly Ser Ile Val
                645                 650                 655

Val Glu Trp Thr Asn Asn Thr Leu Pro Leu Glu Pro Cys Pro Lys Glu
            660                 665                 670

Gln Ile Ala Gly Leu Ser Arg Arg Ile Ala Glu Asp Asp Gly Lys Pro
        675                 680                 685

Arg Pro Ala Phe Ser Asn Ala Leu Glu Pro Asp Phe Lys Ala Thr Ser
    690                 695                 700

Ile Thr Val Thr Gly Ser Gly Ser Cys Arg His Leu Gln Phe Ile Pro
705                 710                 715                 720

Val Val Pro Pro Arg Arg Val Pro Ser Glu Ala Pro Pro Thr Glu Val
                725                 730                 735

Pro Asp Arg Asp Pro Glu Lys Ser Ser Glu Asp Asp Val Tyr Leu His
            740                 745                 750

Thr Val Ile Pro Ala Val Val Val Ala Ala Ile Leu Leu Ile Ala Gly
        755                 760                 765

Ile Ile Ala Met Ile Cys Tyr Arg Lys Lys Arg Lys Gly Lys Leu Thr
    770                 775                 780

Leu Glu Asp Gln Ala Thr Phe Ile Lys Lys Gly Val Pro Ile Ile Phe
785                 790                 795                 800

Ala Asp Glu Leu Asp Asp Ser Lys Pro Pro Pro Ser Ser Ser Met Pro
                805                 810                 815

Leu Ile Leu Gln Glu Glu Lys Ala Pro Leu Pro Pro Pro Glu Tyr Pro
            820                 825                 830

Asn Gln Ser Val Pro Glu Thr Thr Pro Leu Asn Gln Asp Thr Met Gly
        835                 840                 845
```

```
Glu Tyr Thr Pro Leu Arg Asp Glu Asp Pro Asn Ala Pro Pro Tyr Gln
    850                 855                 860

Pro Pro Pro Pro Phe Thr Ala Pro Met Glu Gly Lys Gly Ser Arg Pro
865                 870                 875                 880

Lys Asn Met Thr Pro Tyr Arg Ser Pro Pro Pro Tyr Val Pro Pro
                885                 890                 895


<210> SEQ ID NO 100
<211> LENGTH: 930
<212> TYPE: PRT
<213> ORGANISM: Artificial Sequence
<220> FEATURE:
<223> OTHER INFORMATION: Synthetic_ITIH4_HUMAN

<400> SEQUENCE: 100

Met Lys Pro Pro Arg Pro Val Arg Thr Cys Ser Lys Val Leu Val Leu
1               5                   10                  15

Leu Ser Leu Leu Ala Ile His Gln Thr Thr Thr Ala Glu Lys Asn Gly
            20                  25                  30

Ile Asp Ile Tyr Ser Leu Thr Val Asp Ser Arg Val Ser Ser Arg Phe
        35                  40                  45

Ala His Thr Val Val Thr Ser Arg Val Val Asn Arg Ala Asn Thr Val
    50                  55                  60

Gln Glu Ala Thr Phe Gln Met Glu Leu Pro Lys Lys Ala Phe Ile Thr
65                  70                  75                  80

Asn Phe Ser Met Ile Ile Asp Gly Met Thr Tyr Pro Gly Ile Ile Lys
                85                  90                  95

Glu Lys Ala Glu Ala Gln Ala Gln Tyr Ser Ala Ala Val Ala Lys Gly
            100                 105                 110

Lys Ser Ala Gly Leu Val Lys Ala Thr Gly Arg Asn Met Glu Gln Phe
        115                 120                 125

Gln Val Ser Val Ser Val Ala Pro Asn Ala Lys Ile Thr Phe Glu Leu
    130                 135                 140

Val Tyr Glu Glu Leu Leu Lys Arg Arg Leu Gly Val Tyr Glu Leu Leu
145                 150                 155                 160

Leu Lys Val Arg Pro Gln Gln Leu Val Lys His Leu Gln Met Asp Ile
                165                 170                 175

His Ile Phe Glu Pro Gln Gly Ile Ser Phe Leu Glu Thr Glu Ser Thr
            180                 185                 190

Phe Met Thr Asn Gln Leu Val Asp Ala Leu Thr Thr Trp Gln Asn Lys
        195                 200                 205

Thr Lys Ala His Ile Arg Phe Lys Pro Thr Leu Ser Gln Gln Gln Lys
    210                 215                 220

Ser Pro Glu Gln Gln Glu Thr Val Leu Asp Gly Asn Leu Ile Ile Arg
225                 230                 235                 240

Tyr Asp Val Asp Arg Ala Ile Ser Gly Gly Ser Ile Gln Ile Glu Asn
                245                 250                 255

Gly Tyr Phe Val His Tyr Phe Ala Pro Glu Gly Leu Thr Thr Met Pro
            260                 265                 270

Lys Asn Val Val Phe Val Ile Asp Lys Ser Gly Ser Met Ser Gly Arg
        275                 280                 285

Lys Ile Gln Gln Thr Arg Glu Ala Leu Ile Lys Ile Leu Asp Asp Leu
    290                 295                 300

Ser Pro Arg Asp Gln Phe Asn Leu Ile Val Phe Ser Thr Glu Ala Thr
305                 310                 315                 320
```

-continued

```
Gln Trp Arg Pro Ser Leu Val Pro Ala Ser Ala Glu Asn Val Asn Lys
                325                 330                 335

Ala Arg Ser Phe Ala Ala Gly Ile Gln Ala Leu Gly Gly Thr Asn Ile
            340                 345                 350

Asn Asp Ala Met Leu Met Ala Val Gln Leu Leu Asp Ser Ser Asn Gln
        355                 360                 365

Glu Glu Arg Leu Pro Glu Gly Ser Val Ser Leu Ile Ile Leu Leu Thr
    370                 375                 380

Asp Gly Asp Pro Thr Val Gly Glu Thr Asn Pro Arg Ser Ile Gln Asn
385                 390                 395                 400

Asn Val Arg Glu Ala Val Ser Gly Arg Tyr Ser Leu Phe Cys Leu Gly
                405                 410                 415

Phe Gly Phe Asp Val Ser Tyr Ala Phe Leu Glu Lys Leu Ala Leu Asp
            420                 425                 430

Asn Gly Gly Leu Ala Arg Arg Ile His Glu Asp Ser Asp Ser Ala Leu
        435                 440                 445

Gln Leu Gln Asp Phe Tyr Gln Glu Val Ala Asn Pro Leu Leu Thr Ala
    450                 455                 460

Val Thr Phe Glu Tyr Pro Ser Asn Ala Val Glu Glu Val Thr Gln Asn
465                 470                 475                 480

Asn Phe Arg Leu Leu Phe Lys Gly Ser Glu Met Val Val Ala Gly Lys
                485                 490                 495

Leu Gln Asp Arg Gly Pro Asp Val Leu Thr Ala Thr Val Ser Gly Lys
            500                 505                 510

Leu Pro Thr Gln Asn Ile Thr Phe Gln Thr Glu Ser Ser Val Ala Glu
        515                 520                 525

Gln Glu Ala Glu Phe Gln Ser Pro Lys Tyr Ile Phe His Asn Phe Met
    530                 535                 540

Glu Arg Leu Trp Ala Tyr Leu Thr Ile Gln Gln Leu Leu Glu Gln Thr
545                 550                 555                 560

Val Ser Ala Ser Asp Ala Asp Gln Gln Ala Leu Arg Asn Gln Ala Leu
                565                 570                 575

Asn Leu Ser Leu Ala Tyr Ser Phe Val Thr Pro Leu Thr Ser Met Val
            580                 585                 590

Val Thr Lys Pro Asp Asp Gln Glu Gln Ser Gln Val Ala Glu Lys Pro
        595                 600                 605

Met Glu Gly Glu Ser Arg Asn Arg Asn Val His Ser Gly Ser Thr Phe
    610                 615                 620

Phe Lys Tyr Tyr Leu Gln Gly Ala Lys Ile Pro Lys Pro Glu Ala Ser
625                 630                 635                 640

Phe Ser Pro Arg Arg Gly Trp Asn Arg Gln Ala Gly Ala Ala Gly Ser
                645                 650                 655

Arg Met Asn Phe Arg Pro Gly Val Leu Ser Ser Arg Gln Leu Gly Leu
            660                 665                 670

Pro Gly Pro Pro Asp Val Pro Asp His Ala Ala Tyr His Pro Phe Arg
        675                 680                 685

Arg Leu Ala Ile Leu Pro Ala Ser Ala Pro Pro Ala Thr Ser Asn Pro
    690                 695                 700

Asp Pro Ala Val Ser Arg Val Met Asn Met Lys Ile Glu Glu Thr Thr
705                 710                 715                 720

Met Thr Thr Gln Thr Pro Ala Pro Ile Gln Ala Pro Ser Ala Ile Leu
                725                 730                 735
```

Pro Leu Pro Gly Gln Ser Val Glu Arg Leu Cys Val Asp Pro Arg His
            740                 745                 750

Arg Gln Gly Pro Val Asn Leu Leu Ser Asp Pro Glu Gln Gly Val Glu
        755                 760                 765

Val Thr Gly Gln Tyr Glu Arg Glu Lys Ala Gly Phe Ser Trp Ile Glu
    770                 775                 780

Val Thr Phe Lys Asn Pro Leu Val Trp Val His Ala Ser Pro Glu His
785                 790                 795                 800

Val Val Val Thr Arg Asn Arg Arg Ser Ser Ala Tyr Lys Trp Lys Glu
                805                 810                 815

Thr Leu Phe Ser Val Met Pro Gly Leu Lys Met Thr Met Asp Lys Thr
            820                 825                 830

Gly Leu Leu Leu Leu Ser Asp Pro Asp Lys Val Thr Ile Gly Leu Leu
        835                 840                 845

Phe Trp Asp Gly Arg Gly Glu Gly Leu Arg Leu Leu Leu Arg Asp Thr
    850                 855                 860

Asp Arg Phe Ser Ser His Val Gly Gly Thr Leu Gly Gln Phe Tyr Gln
865                 870                 875                 880

Glu Val Leu Trp Gly Ser Pro Ala Ala Ser Asp Asp Gly Arg Arg Thr
                885                 890                 895

Leu Arg Val Gln Gly Asn Asp His Ser Ala Thr Arg Glu Arg Arg Leu
            900                 905                 910

Asp Tyr Gln Glu Gly Pro Pro Gly Val Glu Ile Ser Cys Trp Ser Val
        915                 920                 925

Glu Leu
    930

<210> SEQ ID NO 101
<211> LENGTH: 946
<212> TYPE: PRT
<213> ORGANISM: Artificial Sequence
<220> FEATURE:
<223> OTHER INFORMATION: Synthetic_ITIH2_HUMAN

<400> SEQUENCE: 101

Met Lys Arg Leu Thr Cys Phe Phe Ile Cys Phe Phe Leu Ser Glu Val
1               5                   10                  15

Ser Gly Phe Glu Ile Pro Ile Asn Gly Leu Ser Glu Phe Val Asp Tyr
            20                  25                  30

Glu Asp Leu Val Glu Leu Ala Pro Gly Lys Phe Gln Leu Val Ala Glu
        35                  40                  45

Asn Arg Arg Tyr Gln Arg Ser Leu Pro Gly Glu Ser Glu Glu Met Met
    50                  55                  60

Glu Glu Val Asp Gln Val Thr Leu Tyr Ser Tyr Lys Val Gln Ser Thr
65                  70                  75                  80

Ile Thr Ser Arg Met Ala Thr Thr Met Ile Gln Ser Lys Val Val Asn
                85                  90                  95

Asn Ser Pro Gln Pro Gln Asn Val Val Phe Asp Val Gln Ile Pro Lys
            100                 105                 110

Gly Ala Phe Ile Ser Asn Phe Ser Met Thr Val Asp Gly Lys Thr Phe
        115                 120                 125

Arg Ser Ser Ile Lys Glu Lys Thr Val Gly Arg Ala Leu Tyr Ala Gln
    130                 135                 140

Ala Arg Ala Lys Gly Lys Thr Ala Gly Leu Val Arg Ser Ser Ala Leu
145                 150                 155                 160

```
Asp Met Glu Asn Phe Arg Thr Glu Val Asn Val Leu Pro Gly Ala Lys
                165                 170                 175

Val Gln Phe Glu Leu His Tyr Gln Glu Val Lys Trp Arg Lys Leu Gly
            180                 185                 190

Ser Tyr Glu His Arg Ile Tyr Leu Gln Pro Gly Arg Leu Ala Lys His
        195                 200                 205

Leu Glu Val Asp Val Trp Val Ile Glu Pro Gln Gly Leu Arg Phe Leu
    210                 215                 220

His Val Pro Asp Thr Phe Glu Gly His Phe Asp Gly Val Pro Val Ile
225                 230                 235                 240

Ser Lys Gly Gln Gln Lys Ala His Val Ser Phe Lys Pro Thr Val Ala
                245                 250                 255

Gln Gln Arg Ile Cys Pro Asn Cys Arg Glu Thr Ala Val Asp Gly Glu
            260                 265                 270

Leu Val Val Leu Tyr Asp Val Lys Arg Glu Glu Lys Ala Gly Glu Leu
        275                 280                 285

Glu Val Phe Asn Gly Tyr Phe Val His Phe Phe Ala Pro Asp Asn Leu
    290                 295                 300

Asp Pro Ile Pro Lys Asn Ile Leu Phe Val Ile Asp Val Ser Gly Ser
305                 310                 315                 320

Met Trp Gly Val Lys Met Lys Gln Thr Val Glu Ala Met Lys Thr Ile
                325                 330                 335

Leu Asp Asp Leu Arg Ala Glu Asp His Phe Ser Val Ile Asp Phe Asn
            340                 345                 350

Gln Asn Ile Arg Thr Trp Arg Asn Asp Leu Ile Ser Ala Thr Lys Thr
        355                 360                 365

Gln Val Ala Asp Ala Lys Arg Tyr Ile Glu Lys Ile Gln Pro Ser Gly
    370                 375                 380

Gly Thr Asn Ile Asn Glu Ala Leu Leu Arg Ala Ile Phe Ile Leu Asn
385                 390                 395                 400

Glu Ala Asn Asn Leu Gly Leu Leu Asp Pro Asn Ser Val Ser Leu Ile
                405                 410                 415

Ile Leu Val Ser Asp Gly Asp Pro Thr Val Gly Glu Leu Lys Leu Ser
            420                 425                 430

Lys Ile Gln Lys Asn Val Lys Glu Asn Ile Gln Asp Asn Ile Ser Leu
        435                 440                 445

Phe Ser Leu Gly Met Gly Phe Asp Val Asp Tyr Asp Phe Leu Lys Arg
    450                 455                 460

Leu Ser Asn Glu Asn His Gly Ile Ala Gln Arg Ile Tyr Gly Asn Gln
465                 470                 475                 480

Asp Thr Ser Ser Gln Leu Lys Lys Phe Tyr Asn Gln Val Ser Thr Pro
                485                 490                 495

Leu Leu Arg Asn Val Gln Phe Asn Tyr Pro His Thr Ser Val Thr Asp
            500                 505                 510

Val Thr Gln Asn Asn Phe His Asn Tyr Phe Gly Gly Ser Glu Ile Val
        515                 520                 525

Val Ala Gly Lys Phe Asp Pro Ala Lys Leu Asp Gln Ile Glu Ser Val
    530                 535                 540

Ile Thr Ala Thr Ser Ala Asn Thr Gln Leu Val Leu Glu Thr Leu Ala
545                 550                 555                 560

Gln Met Asp Asp Leu Gln Asp Phe Leu Ser Lys Asp Lys His Ala Asp
                565                 570                 575

Pro Asp Phe Thr Arg Lys Leu Trp Ala Tyr Leu Thr Ile Asn Gln Leu
```

```
            580                 585                 590

Leu Ala Glu Arg Ser Leu Ala Pro Thr Ala Ala Ala Lys Arg Arg Ile
        595                 600                 605

Thr Arg Ser Ile Leu Gln Met Ser Leu Asp His His Ile Val Thr Pro
    610                 615                 620

Leu Thr Ser Leu Val Ile Glu Asn Glu Ala Gly Asp Glu Arg Met Leu
625                 630                 635                 640

Ala Asp Ala Pro Pro Gln Asp Pro Ser Cys Cys Ser Gly Ala Leu Tyr
                645                 650                 655

Tyr Gly Ser Lys Val Val Pro Asp Ser Thr Pro Ser Trp Ala Asn Pro
            660                 665                 670

Ser Pro Thr Pro Val Ile Ser Met Leu Ala Gln Gly Ser Gln Val Leu
        675                 680                 685

Glu Ser Thr Pro Pro Pro His Val Met Arg Val Glu Asn Asp Pro His
    690                 695                 700

Phe Ile Ile Tyr Leu Pro Lys Ser Gln Lys Asn Ile Cys Phe Asn Ile
705                 710                 715                 720

Asp Ser Glu Pro Gly Lys Ile Leu Asn Leu Val Ser Asp Pro Glu Ser
                725                 730                 735

Gly Ile Val Val Asn Gly Gln Leu Val Gly Ala Lys Lys Pro Asn Asn
            740                 745                 750

Gly Lys Leu Ser Thr Tyr Phe Gly Lys Leu Gly Phe Tyr Phe Gln Ser
        755                 760                 765

Glu Asp Ile Lys Ile Glu Ile Ser Thr Glu Thr Ile Thr Leu Ser His
    770                 775                 780

Gly Ser Ser Thr Phe Ser Leu Ser Trp Ser Asp Thr Ala Gln Val Thr
785                 790                 795                 800

Asn Gln Arg Val Gln Ile Ser Val Lys Lys Glu Lys Val Val Thr Ile
                805                 810                 815

Thr Leu Asp Lys Glu Met Ser Phe Ser Val Leu Leu His Arg Val Trp
            820                 825                 830

Lys Lys His Pro Val Asn Val Asp Phe Leu Gly Ile Tyr Ile Pro Pro
        835                 840                 845

Thr Asn Lys Phe Ser Pro Lys Ala His Gly Leu Ile Gly Gln Phe Met
    850                 855                 860

Gln Glu Pro Lys Ile His Ile Phe Asn Glu Arg Pro Gly Lys Asp Pro
865                 870                 875                 880

Glu Lys Pro Glu Ala Ser Met Glu Val Lys Gly Gln Lys Leu Ile Ile
                885                 890                 895

Thr Arg Gly Leu Gln Lys Asp Tyr Arg Thr Asp Leu Val Phe Gly Thr
            900                 905                 910

Asp Val Thr Cys Trp Phe Val His Asn Ser Gly Lys Gly Phe Ile Asp
        915                 920                 925

Gly His Tyr Lys Asp Tyr Phe Val Pro Gln Leu Tyr Ser Phe Leu Lys
    930                 935                 940

Arg Pro
945
```

<210> SEQ ID NO 102
<211> LENGTH: 953
<212> TYPE: PRT
<213> ORGANISM: Artificial Sequence
<220> FEATURE:
<223> OTHER INFORMATION: Synthetic_TRAK1_HUMAN

<400> SEQUENCE: 102

```
Met Ala Leu Val Phe Gln Phe Gly Gln Pro Val Arg Ala Gln Pro Leu
1               5                   10                  15

Pro Gly Leu Cys His Gly Lys Leu Ile Arg Thr Asn Ala Cys Asp Val
            20                  25                  30

Cys Asn Ser Thr Asp Leu Pro Glu Val Glu Ile Ile Ser Leu Leu Glu
        35                  40                  45

Glu Gln Leu Pro His Tyr Lys Leu Arg Ala Asp Thr Ile Tyr Gly Tyr
    50                  55                  60

Asp His Asp Asp Trp Leu His Thr Pro Leu Ile Ser Pro Asp Ala Asn
65                  70                  75                  80

Ile Asp Leu Thr Thr Glu Gln Ile Glu Glu Thr Leu Lys Tyr Phe Leu
                85                  90                  95

Leu Cys Ala Glu Arg Val Gly Gln Met Thr Lys Thr Tyr Asn Asp Ile
            100                 105                 110

Asp Ala Val Thr Arg Leu Leu Glu Glu Lys Glu Arg Asp Leu Glu Leu
        115                 120                 125

Ala Ala Arg Ile Gly Gln Ser Leu Leu Lys Lys Asn Lys Thr Leu Thr
    130                 135                 140

Glu Arg Asn Glu Leu Leu Glu Glu Gln Val Glu His Ile Arg Glu Glu
145                 150                 155                 160

Val Ser Gln Leu Arg His Glu Leu Ser Met Lys Asp Glu Leu Leu Gln
                165                 170                 175

Phe Tyr Thr Ser Ala Ala Glu Glu Ser Glu Pro Glu Ser Val Cys Ser
            180                 185                 190

Thr Pro Leu Lys Arg Asn Glu Ser Ser Ser Ser Val Gln Asn Tyr Phe
        195                 200                 205

His Leu Asp Ser Leu Gln Lys Lys Leu Lys Asp Leu Glu Glu Glu Asn
    210                 215                 220

Val Val Leu Arg Ser Glu Ala Ser Gln Leu Lys Thr Glu Thr Ile Thr
225                 230                 235                 240

Tyr Glu Glu Lys Glu Gln Gln Leu Val Asn Asp Cys Val Lys Glu Leu
                245                 250                 255

Arg Asp Ala Asn Val Gln Ile Ala Ser Ile Ser Glu Glu Leu Ala Lys
            260                 265                 270

Lys Thr Glu Asp Ala Ala Arg Gln Gln Glu Glu Ile Thr His Leu Leu
        275                 280                 285

Ser Gln Ile Val Asp Leu Gln Lys Lys Ala Lys Ala Cys Ala Val Glu
    290                 295                 300

Asn Glu Glu Leu Val Gln His Leu Gly Ala Ala Lys Asp Ala Gln Arg
305                 310                 315                 320

Gln Leu Thr Ala Glu Leu Arg Glu Leu Glu Asp Lys Tyr Ala Glu Cys
                325                 330                 335

Met Glu Met Leu His Glu Ala Gln Glu Glu Leu Lys Asn Leu Arg Asn
            340                 345                 350

Lys Thr Met Pro Asn Thr Thr Ser Arg Arg Tyr His Ser Leu Gly Leu
        355                 360                 365

Phe Pro Met Asp Ser Leu Ala Ala Glu Ile Glu Gly Thr Met Arg Lys
    370                 375                 380

Glu Leu Gln Leu Glu Glu Ala Glu Ser Pro Asp Ile Thr His Gln Lys
385                 390                 395                 400

Arg Val Phe Glu Thr Val Arg Asn Ile Asn Gln Val Val Lys Gln Arg
                405                 410                 415
```

```
Ser Leu Thr Pro Ser Pro Met Asn Ile Pro Gly Ser Asn Gln Ser Ser
            420                 425                 430

Ala Met Asn Ser Leu Leu Ser Ser Cys Val Ser Thr Pro Arg Ser Ser
        435                 440                 445

Phe Tyr Gly Ser Asp Ile Gly Asn Val Val Leu Asp Asn Lys Thr Asn
    450                 455                 460

Ser Ile Ile Leu Glu Thr Glu Ala Ala Asp Leu Gly Asn Asp Glu Arg
465                 470                 475                 480

Ser Lys Lys Pro Gly Thr Pro Gly Thr Pro Gly Ser His Asp Leu Glu
                485                 490                 495

Thr Ala Leu Arg Arg Leu Ser Leu Arg Arg Glu Asn Tyr Leu Ser Glu
            500                 505                 510

Arg Arg Phe Phe Glu Glu Glu Gln Glu Arg Lys Leu Gln Glu Leu Ala
        515                 520                 525

Glu Lys Gly Glu Leu Arg Ser Gly Ser Leu Thr Pro Thr Glu Ser Ile
    530                 535                 540

Met Ser Leu Gly Thr His Ser Arg Phe Ser Glu Phe Thr Gly Phe Ser
545                 550                 555                 560

Gly Met Ser Phe Ser Ser Arg Ser Tyr Leu Pro Glu Lys Leu Gln Ile
                565                 570                 575

Val Lys Pro Leu Glu Gly Ser Ala Thr Leu His His Trp Gln Gln Leu
            580                 585                 590

Ala Gln Pro His Leu Gly Gly Ile Leu Asp Pro Arg Pro Gly Val Val
        595                 600                 605

Thr Lys Gly Phe Arg Thr Leu Asp Val Asp Leu Asp Glu Val Tyr Cys
    610                 615                 620

Leu Asn Asp Phe Glu Glu Asp Asp Thr Gly Asp His Ile Ser Leu Pro
625                 630                 635                 640

Arg Leu Ala Thr Ser Thr Pro Val Gln His Pro Glu Thr Ser Ala His
                645                 650                 655

His Pro Gly Lys Cys Met Ser Gln Thr Asn Ser Thr Phe Thr Phe Thr
            660                 665                 670

Thr Cys Arg Ile Leu His Pro Ser Asp Glu Leu Thr Arg Val Thr Pro
        675                 680                 685

Ser Leu Asn Ser Ala Pro Thr Pro Ala Cys Gly Ser Thr Ser His Leu
    690                 695                 700

Lys Ser Thr Pro Val Ala Thr Pro Cys Thr Pro Arg Arg Leu Ser Leu
705                 710                 715                 720

Ala Glu Ser Phe Thr Asn Thr Arg Glu Ser Thr Thr Thr Met Ser Thr
                725                 730                 735

Ser Leu Gly Leu Val Trp Leu Leu Lys Glu Arg Gly Ile Ser Ala Ala
            740                 745                 750

Val Tyr Asp Pro Gln Ser Trp Asp Arg Ala Gly Arg Gly Ser Leu Leu
        755                 760                 765

His Ser Tyr Thr Pro Lys Met Ala Val Ile Pro Ser Thr Pro Pro Asn
    770                 775                 780

Ser Pro Met Gln Thr Pro Thr Ser Ser Pro Pro Ser Phe Glu Phe Lys
785                 790                 795                 800

Cys Thr Ser Pro Pro Tyr Asp Asn Phe Leu Ala Ser Lys Pro Ala Ser
                805                 810                 815

Ser Ile Leu Arg Glu Val Arg Glu Lys Asn Val Arg Ser Ser Glu Ser
            820                 825                 830
```

```
Gln Thr Asp Val Ser Val Ser Asn Leu Asn Leu Val Asp Lys Val Arg
        835                 840                 845

Arg Phe Gly Val Ala Lys Val Val Asn Ser Gly Arg Ala His Val Pro
    850                 855                 860

Thr Leu Thr Glu Glu Gln Gly Pro Leu Leu Cys Gly Pro Pro Gly Pro
865                 870                 875                 880

Ala Pro Ala Leu Val Pro Arg Gly Leu Val Pro Glu Gly Leu Pro Leu
                885                 890                 895

Arg Cys Pro Thr Val Thr Ser Ala Ile Gly Gly Leu Gln Leu Asn Ser
            900                 905                 910

Gly Ile Arg Arg Asn Arg Ser Phe Pro Thr Met Val Gly Ser Ser Met
        915                 920                 925

Gln Met Lys Ala Pro Val Thr Leu Thr Ser Gly Ile Leu Met Gly Ala
    930                 935                 940

Lys Leu Ser Lys Gln Thr Ser Leu Arg
945                 950


<210> SEQ ID NO 103
<211> LENGTH: 1255
<212> TYPE: PRT
<213> ORGANISM: Artificial Sequence
<220> FEATURE:
<223> OTHER INFORMATION: Synthetic_MUC1_HUMAN

<400> SEQUENCE: 103

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Ala Pro Asp Thr
    130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
        195                 200                 205

Gly Ser Thr Ala Pro Pro Ala His Gly Val Thr Ser Ala Pro Asp Thr
    210                 215                 220

Arg Pro Ala Pro Gly Ser Thr Ala Pro Pro Ala His Gly Val Thr Ser
225                 230                 235                 240
```

```
Ala Pro Asp Thr Arg Pro Ala Pro Gly Ser Thr Ala Pro Pro Ala His
                245                 250                 255

Gly Val Thr Ser Ala Pro Asp Thr Arg Pro Ala Pro Gly Ser Thr Ala
            260                 265                 270

Pro Pro Ala His Gly Val Thr Ser Ala Pro Asp Thr Arg Pro Ala Pro
        275                 280                 285

Gly Ser Thr Ala Pro Pro Ala His Gly Val Thr Ser Ala Pro Asp Thr
    290                 295                 300

Arg Pro Ala Pro Gly Ser Thr Ala Pro Pro Ala His Gly Val Thr Ser
305                 310                 315                 320

Ala Pro Asp Thr Arg Pro Ala Pro Gly Ser Thr Ala Pro Pro Ala His
                325                 330                 335

Gly Val Thr Ser Ala Pro Asp Thr Arg Pro Ala Pro Gly Ser Thr Ala
            340                 345                 350

Pro Pro Ala His Gly Val Thr Ser Ala Pro Asp Thr Arg Pro Ala Pro
        355                 360                 365

Gly Ser Thr Ala Pro Pro Ala His Gly Val Thr Ser Ala Pro Asp Thr
    370                 375                 380

Arg Pro Ala Pro Gly Ser Thr Ala Pro Pro Ala His Gly Val Thr Ser
385                 390                 395                 400

Ala Pro Asp Thr Arg Pro Ala Pro Gly Ser Thr Ala Pro Pro Ala His
                405                 410                 415

Gly Val Thr Ser Ala Pro Asp Thr Arg Pro Ala Pro Gly Ser Thr Ala
            420                 425                 430

Pro Pro Ala His Gly Val Thr Ser Ala Pro Asp Thr Arg Pro Ala Pro
        435                 440                 445

Gly Ser Thr Ala Pro Pro Ala His Gly Val Thr Ser Ala Pro Asp Thr
    450                 455                 460

Arg Pro Ala Pro Gly Ser Thr Ala Pro Pro Ala His Gly Val Thr Ser
465                 470                 475                 480

Ala Pro Asp Thr Arg Pro Ala Pro Gly Ser Thr Ala Pro Pro Ala His
                485                 490                 495

Gly Val Thr Ser Ala Pro Asp Thr Arg Pro Ala Pro Gly Ser Thr Ala
            500                 505                 510

Pro Pro Ala His Gly Val Thr Ser Ala Pro Asp Thr Arg Pro Ala Pro
        515                 520                 525

Gly Ser Thr Ala Pro Pro Ala His Gly Val Thr Ser Ala Pro Asp Thr
    530                 535                 540

Arg Pro Ala Pro Gly Ser Thr Ala Pro Pro Ala His Gly Val Thr Ser
545                 550                 555                 560

Ala Pro Asp Thr Arg Pro Ala Pro Gly Ser Thr Ala Pro Pro Ala His
                565                 570                 575

Gly Val Thr Ser Ala Pro Asp Thr Arg Pro Ala Pro Gly Ser Thr Ala
            580                 585                 590

Pro Pro Ala His Gly Val Thr Ser Ala Pro Asp Thr Arg Pro Ala Pro
        595                 600                 605

Gly Ser Thr Ala Pro Pro Ala His Gly Val Thr Ser Ala Pro Asp Thr
    610                 615                 620

Arg Pro Ala Pro Gly Ser Thr Ala Pro Pro Ala His Gly Val Thr Ser
625                 630                 635                 640

Ala Pro Asp Thr Arg Pro Ala Pro Gly Ser Thr Ala Pro Pro Ala His
                645                 650                 655

Gly Val Thr Ser Ala Pro Asp Thr Arg Pro Ala Pro Gly Ser Thr Ala
```

```
            660                 665                 670

Pro Pro Ala His Gly Val Thr Ser Ala Pro Asp Thr Arg Pro Ala Pro
        675                 680                 685

Gly Ser Thr Ala Pro Pro Ala His Gly Val Thr Ser Ala Pro Asp Thr
    690                 695                 700

Arg Pro Ala Pro Gly Ser Thr Ala Pro Pro Ala His Gly Val Thr Ser
705                 710                 715                 720

Ala Pro Asp Thr Arg Pro Ala Pro Gly Ser Thr Ala Pro Pro Ala His
                725                 730                 735

Gly Val Thr Ser Ala Pro Asp Thr Arg Pro Ala Pro Gly Ser Thr Ala
            740                 745                 750

Pro Pro Ala His Gly Val Thr Ser Ala Pro Asp Thr Arg Pro Ala Pro
        755                 760                 765

Gly Ser Thr Ala Pro Pro Ala His Gly Val Thr Ser Ala Pro Asp Thr
    770                 775                 780

Arg Pro Ala Pro Gly Ser Thr Ala Pro Pro Ala His Gly Val Thr Ser
785                 790                 795                 800

Ala Pro Asp Thr Arg Pro Ala Pro Gly Ser Thr Ala Pro Pro Ala His
                805                 810                 815

Gly Val Thr Ser Ala Pro Asp Thr Arg Pro Ala Pro Gly Ser Thr Ala
            820                 825                 830

Pro Pro Ala His Gly Val Thr Ser Ala Pro Asp Thr Arg Pro Ala Pro
        835                 840                 845

Gly Ser Thr Ala Pro Pro Ala His Gly Val Thr Ser Ala Pro Asp Thr
    850                 855                 860

Arg Pro Ala Pro Gly Ser Thr Ala Pro Pro Ala His Gly Val Thr Ser
865                 870                 875                 880

Ala Pro Asp Thr Arg Pro Ala Pro Gly Ser Thr Ala Pro Pro Ala His
                885                 890                 895

Gly Val Thr Ser Ala Pro Asp Thr Arg Pro Ala Pro Gly Ser Thr Ala
            900                 905                 910

Pro Pro Ala His Gly Val Thr Ser Ala Pro Asp Thr Arg Pro Ala Pro
        915                 920                 925

Gly Ser Thr Ala Pro Pro Ala His Gly Val Thr Ser Ala Pro Asp Asn
    930                 935                 940

Arg Pro Ala Leu Gly Ser Thr Ala Pro Pro Val His Asn Val Thr Ser
945                 950                 955                 960

Ala Ser Gly Ser Ala Ser Gly Ser Ala Ser Thr Leu Val His Asn Gly
                965                 970                 975

Thr Ser Ala Arg Ala Thr Thr Thr Pro Ala Ser Lys Ser Thr Pro Phe
            980                 985                 990

Ser Ile Pro Ser His His Ser Asp  Thr Pro Thr Thr Leu  Ala Ser His
        995                 1000                 1005

Ser Thr  Lys Thr Asp Ala Ser  Ser Thr His His Ser  Ser Val Pro
    1010                 1015                 1020

Pro Leu  Thr Ser Ser Asn His  Ser Thr Ser Pro Gln  Leu Ser Thr
    1025                 1030                 1035

Gly Val  Ser Phe Phe Phe Leu  Ser Phe His Ile Ser  Asn Leu Gln
    1040                 1045                 1050

Phe Asn  Ser Ser Leu Glu Asp  Pro Ser Thr Asp Tyr  Tyr Gln Glu
    1055                 1060                 1065

Leu Gln  Arg Asp Ile Ser Glu  Met Phe Leu Gln Ile  Tyr Lys Gln
    1070                 1075                 1080
```

Gly Gly Phe Leu Gly Leu Ser Asn Ile Lys Phe Arg Pro Gly Ser
1085 1090 1095

Val Val Val Gln Leu Thr Leu Ala Phe Arg Glu Gly Thr Ile Asn
1100 1105 1110

Val His Asp Val Glu Thr Gln Phe Asn Gln Tyr Lys Thr Glu Ala
1115 1120 1125

Ala Ser Arg Tyr Asn Leu Thr Ile Ser Asp Val Ser Val Ser Asp
1130 1135 1140

Val Pro Phe Pro Phe Ser Ala Gln Ser Gly Ala Gly Val Pro Gly
1145 1150 1155

Trp Gly Ile Ala Leu Leu Val Leu Val Cys Val Leu Val Ala Leu
1160 1165 1170

Ala Ile Val Tyr Leu Ile Ala Leu Ala Val Cys Gln Cys Arg Arg
1175 1180 1185

Lys Asn Tyr Gly Gln Leu Asp Ile Phe Pro Ala Arg Asp Thr Tyr
1190 1195 1200

His Pro Met Ser Glu Tyr Pro Thr Tyr His Thr His Gly Arg Tyr
1205 1210 1215

Val Pro Pro Ser Ser Thr Asp Arg Ser Pro Tyr Glu Lys Val Ser
1220 1225 1230

Ala Gly Asn Gly Gly Ser Ser Leu Ser Tyr Thr Asn Pro Ala Val
1235 1240 1245

Ala Ala Thr Ser Ala Asn Leu
1250 1255

<210> SEQ ID NO 104
<211> LENGTH: 1322
<212> TYPE: PRT
<213> ORGANISM: Artificial Sequence
<220> FEATURE:
<223> OTHER INFORMATION: Synthetic_EMSY_HUMAN

<400> SEQUENCE: 104

Met Pro Val Val Trp Pro Thr Leu Leu Asp Leu Ser Arg Asp Glu Cys
1 5 10 15

Lys Arg Ile Leu Arg Lys Leu Glu Leu Glu Ala Tyr Ala Gly Val Ile
20 25 30

Ser Ala Leu Arg Ala Gln Gly Asp Leu Thr Lys Glu Lys Lys Asp Leu
35 40 45

Leu Gly Glu Leu Ser Lys Val Leu Ser Ile Ser Thr Glu Arg His Arg
50 55 60

Ala Glu Val Arg Arg Ala Val Asn Asp Glu Arg Leu Thr Thr Ile Ala
65 70 75 80

His Asn Met Ser Gly Pro Asn Ser Ser Ser Glu Trp Ser Ile Glu Gly
85 90 95

Arg Arg Leu Val Pro Leu Met Pro Arg Leu Val Pro Gln Thr Ala Phe
100 105 110

Thr Val Thr Ala Asn Ala Val Ala Asn Ala Ala Ile Gln His Asn Ala
115 120 125

Ser Leu Pro Val Pro Ala Glu Thr Gly Ser Lys Glu Val Val Cys Tyr
130 135 140

Ser Tyr Thr Ser Thr Thr Ser Thr Pro Thr Ser Thr Pro Val Pro Ser
145 150 155 160

Gly Ser Ile Ala Thr Val Lys Ser Pro Arg Pro Ala Ser Pro Ala Ser
165 170 175

Asn Val Val Val Leu Pro Ser Gly Ser Thr Val Tyr Val Lys Ser Val
180 185 190

Ser Cys Ser Asp Glu Asp Glu Lys Pro Arg Lys Arg Arg Arg Thr Asn
195 200 205

Ser Ser Ser Ser Ser Pro Val Val Leu Lys Glu Val Pro Lys Ala Val
210 215 220

Val Pro Val Ser Lys Thr Ile Thr Val Pro Val Ser Gly Ser Pro Lys
225 230 235 240

Met Ser Asn Ile Met Gln Ser Ile Ala Asn Ser Leu Pro Pro His Met
245 250 255

Ser Pro Val Lys Ile Thr Phe Thr Lys Pro Ser Thr Gln Thr Thr Asn
260 265 270

Thr Thr Thr Gln Lys Val Ile Ile Val Thr Thr Ser Pro Ser Ser Thr
275 280 285

Phe Val Pro Asn Ile Leu Ser Lys Ser His Asn Tyr Ala Ala Val Thr
290 295 300

Lys Leu Val Pro Thr Ser Val Ile Ala Ser Thr Thr Gln Lys Pro Pro
305 310 315 320

Val Val Ile Thr Ala Ser Gln Ser Ser Leu Val Ser Asn Ser Ser Ser
325 330 335

Gly Ser Ser Ser Ser Thr Pro Ser Pro Ile Pro Asn Thr Val Ala Val
340 345 350

Thr Ala Val Val Ser Ser Thr Pro Ser Val Val Met Ser Thr Val Ala
355 360 365

Gln Gly Val Ser Thr Ser Ala Ile Lys Met Ala Ser Thr Arg Leu Pro
370 375 380

Ser Pro Lys Ser Leu Val Ser Ala Pro Thr Gln Ile Leu Ala Gln Phe
385 390 395 400

Pro Lys Gln His Gln Gln Ser Pro Lys Gln Gln Leu Tyr Gln Val Gln
405 410 415

Gln Gln Thr Gln Gln Gln Val Ala Gln Pro Ser Pro Val Ser His Gln
420 425 430

Gln Gln Pro Gln Gln Ser Pro Leu Pro Pro Gly Ile Lys Pro Thr Ile
435 440 445

Gln Ile Lys Gln Glu Ser Gly Val Lys Ile Ile Thr Gln Gln Val Gln
450 455 460

Pro Ser Lys Ile Leu Pro Lys Pro Val Thr Ala Thr Leu Pro Thr Ser
465 470 475 480

Ser Asn Ser Pro Ile Met Val Val Ser Ser Asn Gly Ala Ile Met Thr
485 490 495

Thr Lys Leu Val Thr Thr Pro Thr Gly Thr Gln Ala Thr Tyr Thr Arg
500 505 510

Pro Thr Val Ser Pro Ser Ile Gly Arg Met Ala Ala Thr Pro Gly Ala
515 520 525

Ala Thr Tyr Val Lys Thr Thr Ser Gly Ser Ile Ile Thr Val Val Pro
530 535 540

Lys Ser Leu Ala Thr Leu Gly Gly Lys Ile Ile Ser Ser Asn Ile Val
545 550 555 560

Ser Gly Thr Thr Thr Lys Ile Thr Thr Ile Pro Met Thr Ser Lys Pro
565 570 575

Asn Val Ile Val Val Gln Lys Thr Thr Gly Lys Gly Thr Thr Ile Gln
580 585 590

```
Gly Leu Pro Gly Lys Asn Val Val Thr Thr Leu Leu Asn Ala Gly Gly
        595                 600                 605

Glu Lys Thr Ile Gln Thr Val Pro Thr Gly Ala Lys Pro Ala Ile Leu
    610                 615                 620

Thr Ala Thr Arg Pro Ile Thr Lys Met Ile Val Thr Gln Pro Lys Gly
625                 630                 635                 640

Ile Gly Ser Thr Val Gln Pro Ala Ala Lys Ile Ile Pro Thr Lys Ile
                645                 650                 655

Val Tyr Gly Gln Gln Gly Lys Thr Gln Val Leu Ile Lys Pro Lys Pro
            660                 665                 670

Val Thr Phe Gln Ala Thr Val Val Ser Glu Gln Thr Arg Gln Leu Val
        675                 680                 685

Thr Glu Thr Leu Gln Gln Ala Ser Arg Val Ala Glu Ala Gly Asn Ser
    690                 695                 700

Ser Ile Gln Glu Gly Lys Glu Glu Pro Gln Asn Tyr Thr Asp Ser Ser
705                 710                 715                 720

Ser Ser Ser Thr Glu Ser Ser Gln Ser Ser Gln Asp Ser Gln Pro Val
                725                 730                 735

Val His Val Ile Ala Ser Arg Arg Gln Asp Trp Ser Glu His Glu Ile
            740                 745                 750

Ala Met Glu Thr Ser Pro Thr Ile Ile Tyr Gln Asp Val Ser Ser Glu
        755                 760                 765

Ser Gln Ser Ala Thr Ser Thr Ile Lys Ala Leu Leu Glu Leu Gln Gln
    770                 775                 780

Thr Thr Val Lys Glu Lys Leu Glu Ser Lys Pro Arg Gln Pro Thr Ile
785                 790                 795                 800

Asp Leu Ser Gln Met Ala Val Pro Ile Gln Met Thr Gln Glu Lys Arg
                805                 810                 815

His Ser Pro Glu Ser Pro Ser Ile Ala Val Val Glu Ser Glu Leu Val
            820                 825                 830

Ala Glu Tyr Ile Thr Thr Glu Arg Thr Asp Glu Gly Thr Glu Val Ala
        835                 840                 845

Phe Pro Leu Leu Val Ser His Arg Ser Gln Pro Gln Gln Pro Ser Gln
    850                 855                 860

Pro Gln Arg Thr Leu Leu Gln His Val Ala Gln Ser Gln Thr Ala Thr
865                 870                 875                 880

Gln Thr Ser Val Val Val Lys Ser Ile Pro Ala Ser Ser Pro Gly Ala
                885                 890                 895

Ile Thr His Ile Met Gln Gln Ala Leu Ser Ser His Thr Ala Phe Thr
            900                 905                 910

Lys His Ser Glu Glu Leu Gly Thr Glu Glu Gly Glu Val Glu Glu Met
        915                 920                 925

Asp Thr Leu Asp Pro Gln Thr Gly Leu Phe Tyr Arg Ser Ala Leu Thr
    930                 935                 940

Gln Ser Gln Ser Ala Lys Gln Gln Lys Leu Ser Gln Pro Pro Leu Glu
945                 950                 955                 960

Gln Thr Gln Leu Gln Val Lys Thr Leu Gln Cys Phe Gln Thr Lys Gln
                965                 970                 975

Lys Gln Thr Ile His Leu Gln Ala Asp Gln Leu Gln His Lys Leu Pro
            980                 985                 990

Gln Met Pro Gln Leu Ser Ile Arg  His Gln Lys Leu Thr  Pro Leu Gln
        995                 1000                1005

Gln Glu  Gln Ala Gln Pro Lys  Pro Asp Val Gln His  Thr Gln His
```

```
    1010                1015                1020

Pro Met  Val Ala Lys Asp Arg  Gln Leu Pro Thr Leu  Met Ala Gln
    1025                1030                1035

Pro Pro  Gln Thr Val Val Gln  Val Leu Ala Val Lys  Thr Thr Gln
    1040                1045                1050

Gln Leu  Pro Lys Leu Gln Gln  Ala Pro Asn Gln Pro  Lys Ile Tyr
    1055                1060                1065

Val Gln  Pro Gln Thr Pro Gln  Ser Gln Met Ser Leu  Pro Ala Ser
    1070                1075                1080

Ser Glu  Lys Gln Thr Ala Ser  Gln Val Glu Gln Pro  Ile Ile Thr
    1085                1090                1095

Gln Gly  Ser Ser Val Thr Lys  Ile Thr Phe Glu Gly  Arg Gln Pro
    1100                1105                1110

Pro Thr  Val Thr Lys Ile Thr  Gly Gly Ser Ser Val  Pro Lys Leu
    1115                1120                1125

Thr Ser  Pro Val Thr Ser Ile  Ser Pro Ile Gln Ala  Ser Glu Lys
    1130                1135                1140

Thr Ala  Val Ser Asp Ile Leu  Lys Met Ser Leu Met  Glu Ala Gln
    1145                1150                1155

Ile Asp  Thr Asn Val Glu His  Met Ile Val Asp Pro  Pro Lys Lys
    1160                1165                1170

Ala Leu  Ala Thr Ser Met Leu  Thr Gly Glu Ala Gly  Ser Leu Pro
    1175                1180                1185

Ser Thr  His Met Val Val Ala  Gly Met Ala Asn Ser  Thr Pro Gln
    1190                1195                1200

Gln Gln  Lys Cys Arg Glu Ser  Cys Ser Ser Pro Ser  Thr Val Gly
    1205                1210                1215

Ser Ser  Leu Thr Thr Arg Lys  Ile Asp Pro Pro Ala  Val Pro Ala
    1220                1225                1230

Thr Gly  Gln Phe Met Arg Ile  Gln Asn Val Gly Gln  Lys Lys Ala
    1235                1240                1245

Glu Glu  Ser Pro Ala Glu Ile  Ile Ile Gln Ala Ile  Pro Gln Tyr
    1250                1255                1260

Ala Ile  Pro Cys His Ser Ser  Ser Asn Val Val Val  Glu Pro Ser
    1265                1270                1275

Gly Leu  Leu Glu Leu Asn Asn  Phe Thr Ser Gln Gln  Leu Asp Asp
    1280                1285                1290

Glu Glu  Thr Ala Met Glu Gln  Asp Ile Asp Ser Ser  Thr Glu Asp
    1295                1300                1305

Gly Thr  Glu Pro Ser Pro Ser  Gln Ser Ser Ala Glu  Arg Ser
    1310                1315                1320


<210> SEQ ID NO 105
<211> LENGTH: 1404
<212> TYPE: PRT
<213> ORGANISM: Artificial Sequence
<220> FEATURE:
<223> OTHER INFORMATION: Synthetic_PRG4_HUMAN

<400> SEQUENCE: 105

Met Ala Trp Lys Thr Leu Pro Ile Tyr Leu Leu Leu Leu Leu Ser Val
1               5                   10                  15

Phe Val Ile Gln Gln Val Ser Ser Gln Asp Leu Ser Ser Cys Ala Gly
            20                  25                  30

Arg Cys Gly Glu Gly Tyr Ser Arg Asp Ala Thr Cys Asn Cys Asp Tyr
```

```
        35                  40                  45

Asn Cys Gln His Tyr Met Glu Cys Cys Pro Asp Phe Lys Arg Val Cys
    50                  55                  60

Thr Ala Glu Leu Ser Cys Lys Gly Arg Cys Phe Glu Ser Phe Glu Arg
65                  70                  75                  80

Gly Arg Glu Cys Asp Cys Asp Ala Gln Cys Lys Lys Tyr Asp Lys Cys
                85                  90                  95

Cys Pro Asp Tyr Glu Ser Phe Cys Ala Glu Val His Asn Pro Thr Ser
            100                 105                 110

Pro Pro Ser Ser Lys Lys Ala Pro Pro Pro Ser Gly Ala Ser Gln Thr
        115                 120                 125

Ile Lys Ser Thr Thr Lys Arg Ser Pro Lys Pro Pro Asn Lys Lys Lys
    130                 135                 140

Thr Lys Lys Val Ile Glu Ser Glu Glu Ile Thr Glu Glu His Ser Val
145                 150                 155                 160

Ser Glu Asn Gln Glu Ser Ser Ser Ser Ser Ser Ser Ser Ser Ser Ser
                165                 170                 175

Ser Thr Ile Arg Lys Ile Lys Ser Ser Lys Asn Ser Ala Ala Asn Arg
            180                 185                 190

Glu Leu Gln Lys Lys Leu Lys Val Lys Asp Asn Lys Lys Asn Arg Thr
        195                 200                 205

Lys Lys Lys Pro Thr Pro Lys Pro Pro Val Val Asp Glu Ala Gly Ser
    210                 215                 220

Gly Leu Asp Asn Gly Asp Phe Lys Val Thr Thr Pro Asp Thr Ser Thr
225                 230                 235                 240

Thr Gln His Asn Lys Val Ser Thr Ser Pro Lys Ile Thr Thr Ala Lys
                245                 250                 255

Pro Ile Asn Pro Arg Pro Ser Leu Pro Pro Asn Ser Asp Thr Ser Lys
            260                 265                 270

Glu Thr Ser Leu Thr Val Asn Lys Glu Thr Thr Val Glu Thr Lys Glu
        275                 280                 285

Thr Thr Thr Thr Asn Lys Gln Thr Ser Thr Asp Gly Lys Glu Lys Thr
    290                 295                 300

Thr Ser Ala Lys Glu Thr Gln Ser Ile Glu Lys Thr Ser Ala Lys Asp
305                 310                 315                 320

Leu Ala Pro Thr Ser Lys Val Leu Ala Lys Pro Thr Pro Lys Ala Glu
                325                 330                 335

Thr Thr Thr Lys Gly Pro Ala Leu Thr Thr Pro Lys Glu Pro Thr Pro
            340                 345                 350

Thr Thr Pro Lys Glu Pro Ala Ser Thr Thr Pro Lys Glu Pro Thr Pro
        355                 360                 365

Thr Thr Ile Lys Ser Ala Pro Thr Thr Pro Lys Glu Pro Ala Pro Thr
    370                 375                 380

Thr Thr Lys Ser Ala Pro Thr Thr Pro Lys Glu Pro Ala Pro Thr Thr
385                 390                 395                 400

Thr Lys Glu Pro Ala Pro Thr Thr Pro Lys Glu Pro Ala Pro Thr Thr
                405                 410                 415

Thr Lys Glu Pro Ala Pro Thr Thr Thr Lys Ser Ala Pro Thr Thr Pro
            420                 425                 430

Lys Glu Pro Ala Pro Thr Thr Pro Lys Lys Pro Ala Pro Thr Thr Pro
        435                 440                 445

Lys Glu Pro Ala Pro Thr Thr Pro Lys Glu Pro Thr Pro Thr Thr Pro
    450                 455                 460
```

Lys Glu Pro Ala Pro Thr Thr Lys Glu Pro Ala Pro Thr Thr Pro Lys
465 470 475 480

Glu Pro Ala Pro Thr Ala Pro Lys Lys Pro Ala Pro Thr Thr Pro Lys
485 490 495

Glu Pro Ala Pro Thr Thr Pro Lys Glu Pro Ala Pro Thr Thr Thr Lys
500 505 510

Glu Pro Ser Pro Thr Thr Pro Lys Glu Pro Ala Pro Thr Thr Thr Lys
515 520 525

Ser Ala Pro Thr Thr Thr Lys Glu Pro Ala Pro Thr Thr Thr Lys Ser
530 535 540

Ala Pro Thr Thr Pro Lys Glu Pro Ser Pro Thr Thr Thr Lys Glu Pro
545 550 555 560

Ala Pro Thr Thr Pro Lys Glu Pro Ala Pro Thr Thr Pro Lys Lys Pro
565 570 575

Ala Pro Thr Thr Pro Lys Glu Pro Ala Pro Thr Thr Pro Lys Glu Pro
580 585 590

Ala Pro Thr Thr Thr Lys Lys Pro Ala Pro Thr Thr Pro Lys Glu Pro
595 600 605

Ala Pro Thr Thr Pro Lys Glu Thr Ala Pro Thr Thr Pro Lys Lys Leu
610 615 620

Thr Pro Thr Thr Pro Glu Lys Leu Ala Pro Thr Thr Pro Glu Lys Pro
625 630 635 640

Ala Pro Thr Thr Pro Glu Glu Leu Ala Pro Thr Thr Pro Glu Glu Pro
645 650 655

Thr Pro Thr Thr Pro Glu Glu Pro Ala Pro Thr Thr Pro Lys Ala Ala
660 665 670

Ala Pro Asn Thr Pro Lys Glu Pro Ala Pro Thr Thr Pro Lys Glu Pro
675 680 685

Ala Pro Thr Thr Pro Lys Glu Pro Ala Pro Thr Thr Pro Lys Glu Thr
690 695 700

Ala Pro Thr Thr Pro Lys Gly Thr Ala Pro Thr Thr Leu Lys Glu Pro
705 710 715 720

Ala Pro Thr Thr Pro Lys Lys Pro Ala Pro Lys Glu Leu Ala Pro Thr
725 730 735

Thr Thr Lys Glu Pro Thr Ser Thr Thr Ser Asp Lys Pro Ala Pro Thr
740 745 750

Thr Pro Lys Gly Thr Ala Pro Thr Thr Pro Lys Glu Pro Ala Pro Thr
755 760 765

Thr Pro Lys Glu Pro Ala Pro Thr Thr Pro Lys Gly Thr Ala Pro Thr
770 775 780

Thr Leu Lys Glu Pro Ala Pro Thr Thr Pro Lys Lys Pro Ala Pro Lys
785 790 795 800

Glu Leu Ala Pro Thr Thr Thr Lys Gly Pro Thr Ser Thr Thr Ser Asp
805 810 815

Lys Pro Ala Pro Thr Thr Pro Lys Glu Thr Ala Pro Thr Thr Pro Lys
820 825 830

Glu Pro Ala Pro Thr Thr Pro Lys Lys Pro Ala Pro Thr Thr Pro Glu
835 840 845

Thr Pro Pro Pro Thr Thr Ser Glu Val Ser Thr Pro Thr Thr Thr Lys
850 855 860

Glu Pro Thr Thr Ile His Lys Ser Pro Asp Glu Ser Thr Pro Glu Leu
865 870 875 880

```
Ser Ala Glu Pro Thr Pro Lys Ala Leu Glu Asn Ser Pro Lys Glu Pro
            885                 890                 895

Gly Val Pro Thr Thr Lys Thr Pro Ala Ala Thr Lys Pro Glu Met Thr
        900                 905                 910

Thr Thr Ala Lys Asp Lys Thr Thr Glu Arg Asp Leu Arg Thr Thr Pro
    915                 920                 925

Glu Thr Thr Thr Ala Ala Pro Lys Met Thr Lys Glu Thr Ala Thr Thr
    930                 935                 940

Thr Glu Lys Thr Thr Glu Ser Lys Ile Thr Ala Thr Thr Thr Gln Val
945                 950                 955                 960

Thr Ser Thr Thr Thr Gln Asp Thr Thr Pro Phe Lys Ile Thr Thr Leu
            965                 970                 975

Lys Thr Thr Thr Leu Ala Pro Lys Val Thr Thr Thr Lys Lys Thr Ile
        980                 985                 990

Thr Thr Thr Glu Ile Met Asn Lys  Pro Glu Glu Thr Ala  Lys Pro Lys
    995                 1000                1005

Asp Arg  Ala Thr Asn Ser Lys  Ala Thr Thr Pro Lys  Pro Gln Lys
    1010                1015                1020

Pro Thr  Lys Ala Pro Lys Lys  Pro Thr Ser Thr Lys  Lys Pro Lys
    1025                1030                1035

Thr Met  Pro Arg Val Arg Lys  Pro Lys Thr Thr Pro  Thr Pro Arg
    1040                1045                1050

Lys Met  Thr Ser Thr Met Pro  Glu Leu Asn Pro Thr  Ser Arg Ile
    1055                1060                1065

Ala Glu  Ala Met Leu Gln Thr  Thr Thr Arg Pro Asn  Gln Thr Pro
    1070                1075                1080

Asn Ser  Lys Leu Val Glu Val  Asn Pro Lys Ser Glu  Asp Ala Gly
    1085                1090                1095

Gly Ala  Glu Gly Glu Thr Pro  His Met Leu Leu Arg  Pro His Val
    1100                1105                1110

Phe Met  Pro Glu Val Thr Pro  Asp Met Asp Tyr Leu  Pro Arg Val
    1115                1120                1125

Pro Asn  Gln Gly Ile Ile Ile  Asn Pro Met Leu Ser  Asp Glu Thr
    1130                1135                1140

Asn Ile  Cys Asn Gly Lys Pro  Val Asp Gly Leu Thr  Thr Leu Arg
    1145                1150                1155

Asn Gly  Thr Leu Val Ala Phe  Arg Gly His Tyr Phe  Trp Met Leu
    1160                1165                1170

Ser Pro  Phe Ser Pro Pro Ser  Pro Ala Arg Arg Ile  Thr Glu Val
    1175                1180                1185

Trp Gly  Ile Pro Ser Pro Ile  Asp Thr Val Phe Thr  Arg Cys Asn
    1190                1195                1200

Cys Glu  Gly Lys Thr Phe Phe  Phe Lys Asp Ser Gln  Tyr Trp Arg
    1205                1210                1215

Phe Thr  Asn Asp Ile Lys Asp  Ala Gly Tyr Pro Lys  Pro Ile Phe
    1220                1225                1230

Lys Gly  Phe Gly Gly Leu Thr  Gly Gln Ile Val Ala  Ala Leu Ser
    1235                1240                1245

Thr Ala  Lys Tyr Lys Asn Trp  Pro Glu Ser Val Tyr  Phe Phe Lys
    1250                1255                1260

Arg Gly  Gly Ser Ile Gln Gln  Tyr Ile Tyr Lys Gln  Glu Pro Val
    1265                1270                1275

Gln Lys  Cys Pro Gly Arg Arg  Pro Ala Leu Asn Tyr  Pro Val Tyr
```

1280 1285 1290

Gly Glu Thr Thr Gln Val Arg Arg Arg Arg Phe Glu Arg Ala Ile
1295 1300 1305

Gly Pro Ser Gln Thr His Thr Ile Arg Ile Gln Tyr Ser Pro Ala
1310 1315 1320

Arg Leu Ala Tyr Gln Asp Lys Gly Val Leu His Asn Glu Val Lys
1325 1330 1335

Val Ser Ile Leu Trp Arg Gly Leu Pro Asn Val Val Thr Ser Ala
1340 1345 1350

Ile Ser Leu Pro Asn Ile Arg Lys Pro Asp Gly Tyr Asp Tyr Tyr
1355 1360 1365

Ala Phe Ser Lys Asp Gln Tyr Tyr Asn Ile Asp Val Pro Ser Arg
1370 1375 1380

Thr Ala Arg Ala Ile Thr Thr Arg Ser Gly Gln Thr Leu Ser Lys
1385 1390 1395

Val Trp Tyr Asn Cys Pro
1400

<210> SEQ ID NO 106
<211> LENGTH: 1427
<212> TYPE: PRT
<213> ORGANISM: Artificial Sequence
<220> FEATURE:
<223> OTHER INFORMATION: Synthetic_ATS13_HUMAN

<400> SEQUENCE: 106

Met His Gln Arg His Pro Arg Ala Arg Cys Pro Pro Leu Cys Val Ala
1 5 10 15

Gly Ile Leu Ala Cys Gly Phe Leu Leu Gly Cys Trp Gly Pro Ser His
20 25 30

Phe Gln Gln Ser Cys Leu Gln Ala Leu Glu Pro Gln Ala Val Ser Ser
35 40 45

Tyr Leu Ser Pro Gly Ala Pro Leu Lys Gly Arg Pro Pro Ser Pro Gly
50 55 60

Phe Gln Arg Gln Arg Gln Arg Gln Arg Arg Ala Ala Gly Gly Ile Leu
65 70 75 80

His Leu Glu Leu Leu Val Ala Val Gly Pro Asp Val Phe Gln Ala His
85 90 95

Gln Glu Asp Thr Glu Arg Tyr Val Leu Thr Asn Leu Asn Ile Gly Ala
100 105 110

Glu Leu Leu Arg Asp Pro Ser Leu Gly Ala Gln Phe Arg Val His Leu
115 120 125

Val Lys Met Val Ile Leu Thr Glu Pro Glu Gly Ala Pro Asn Ile Thr
130 135 140

Ala Asn Leu Thr Ser Ser Leu Leu Ser Val Cys Gly Trp Ser Gln Thr
145 150 155 160

Ile Asn Pro Glu Asp Asp Thr Asp Pro Gly His Ala Asp Leu Val Leu
165 170 175

Tyr Ile Thr Arg Phe Asp Leu Glu Leu Pro Asp Gly Asn Arg Gln Val
180 185 190

Arg Gly Val Thr Gln Leu Gly Gly Ala Cys Ser Pro Thr Trp Ser Cys
195 200 205

Leu Ile Thr Glu Asp Thr Gly Phe Asp Leu Gly Val Thr Ile Ala His
210 215 220

Glu Ile Gly His Ser Phe Gly Leu Glu His Asp Gly Ala Pro Gly Ser

```
225                 230                 235                 240

Gly Cys Gly Pro Ser Gly His Val Met Ala Ser Asp Gly Ala Ala Pro
                245                 250                 255

Arg Ala Gly Leu Ala Trp Ser Pro Cys Ser Arg Arg Gln Leu Leu Ser
            260                 265                 270

Leu Leu Ser Ala Gly Arg Ala Arg Cys Val Trp Asp Pro Pro Arg Pro
        275                 280                 285

Gln Pro Gly Ser Ala Gly His Pro Pro Asp Ala Gln Pro Gly Leu Tyr
    290                 295                 300

Tyr Ser Ala Asn Glu Gln Cys Arg Val Ala Phe Gly Pro Lys Ala Val
305                 310                 315                 320

Ala Cys Thr Phe Ala Arg Glu His Leu Asp Met Cys Gln Ala Leu Ser
                325                 330                 335

Cys His Thr Asp Pro Leu Asp Gln Ser Ser Cys Ser Arg Leu Leu Val
            340                 345                 350

Pro Leu Leu Asp Gly Thr Glu Cys Gly Val Glu Lys Trp Cys Ser Lys
        355                 360                 365

Gly Arg Cys Arg Ser Leu Val Glu Leu Thr Pro Ile Ala Ala Val His
    370                 375                 380

Gly Arg Trp Ser Ser Trp Gly Pro Arg Ser Pro Cys Ser Arg Ser Cys
385                 390                 395                 400

Gly Gly Gly Val Val Thr Arg Arg Arg Gln Cys Asn Asn Pro Arg Pro
                405                 410                 415

Ala Phe Gly Gly Arg Ala Cys Val Gly Ala Asp Leu Gln Ala Glu Met
            420                 425                 430

Cys Asn Thr Gln Ala Cys Glu Lys Thr Gln Leu Glu Phe Met Ser Gln
        435                 440                 445

Gln Cys Ala Arg Thr Asp Gly Gln Pro Leu Arg Ser Ser Pro Gly Gly
    450                 455                 460

Ala Ser Phe Tyr His Trp Gly Ala Ala Val Pro His Ser Gln Gly Asp
465                 470                 475                 480

Ala Leu Cys Arg His Met Cys Arg Ala Ile Gly Glu Ser Phe Ile Met
                485                 490                 495

Lys Arg Gly Asp Ser Phe Leu Asp Gly Thr Arg Cys Met Pro Ser Gly
            500                 505                 510

Pro Arg Glu Asp Gly Thr Leu Ser Leu Cys Val Ser Gly Ser Cys Arg
        515                 520                 525

Thr Phe Gly Cys Asp Gly Arg Met Asp Ser Gln Gln Val Trp Asp Arg
    530                 535                 540

Cys Gln Val Cys Gly Gly Asp Asn Ser Thr Cys Ser Pro Arg Lys Gly
545                 550                 555                 560

Ser Phe Thr Ala Gly Arg Ala Arg Glu Tyr Val Thr Phe Leu Thr Val
                565                 570                 575

Thr Pro Asn Leu Thr Ser Val Tyr Ile Ala Asn His Arg Pro Leu Phe
            580                 585                 590

Thr His Leu Ala Val Arg Ile Gly Gly Arg Tyr Val Val Ala Gly Lys
        595                 600                 605

Met Ser Ile Ser Pro Asn Thr Thr Tyr Pro Ser Leu Leu Glu Asp Gly
    610                 615                 620

Arg Val Glu Tyr Arg Val Ala Leu Thr Glu Asp Arg Leu Pro Arg Leu
625                 630                 635                 640

Glu Glu Ile Arg Ile Trp Gly Pro Leu Gln Glu Asp Ala Asp Ile Gln
                645                 650                 655
```

```
Val Tyr Arg Arg Tyr Gly Glu Glu Tyr Gly Asn Leu Thr Arg Pro Asp
            660                 665                 670

Ile Thr Phe Thr Tyr Phe Gln Pro Lys Pro Arg Gln Ala Trp Val Trp
        675                 680                 685

Ala Ala Val Arg Gly Pro Cys Ser Val Ser Cys Gly Ala Gly Leu Arg
    690                 695                 700

Trp Val Asn Tyr Ser Cys Leu Asp Gln Ala Arg Lys Glu Leu Val Glu
705                 710                 715                 720

Thr Val Gln Cys Gln Gly Ser Gln Gln Pro Pro Ala Trp Pro Glu Ala
                725                 730                 735

Cys Val Leu Glu Pro Cys Pro Pro Tyr Trp Ala Val Gly Asp Phe Gly
            740                 745                 750

Pro Cys Ser Ala Ser Cys Gly Gly Gly Leu Arg Glu Arg Pro Val Arg
        755                 760                 765

Cys Val Glu Ala Gln Gly Ser Leu Leu Lys Thr Leu Pro Pro Ala Arg
    770                 775                 780

Cys Arg Ala Gly Ala Gln Gln Pro Ala Val Ala Leu Glu Thr Cys Asn
785                 790                 795                 800

Pro Gln Pro Cys Pro Ala Arg Trp Glu Val Ser Glu Pro Ser Ser Cys
                805                 810                 815

Thr Ser Ala Gly Gly Ala Gly Leu Ala Leu Glu Asn Glu Thr Cys Val
            820                 825                 830

Pro Gly Ala Asp Gly Leu Glu Ala Pro Val Thr Glu Gly Pro Gly Ser
        835                 840                 845

Val Asp Glu Lys Leu Pro Ala Pro Glu Pro Cys Val Gly Met Ser Cys
    850                 855                 860

Pro Pro Gly Trp Gly His Leu Asp Ala Thr Ser Ala Gly Glu Lys Ala
865                 870                 875                 880

Pro Ser Pro Trp Gly Ser Ile Arg Thr Gly Ala Gln Ala Ala His Val
                885                 890                 895

Trp Thr Pro Ala Ala Gly Ser Cys Ser Val Ser Cys Gly Arg Gly Leu
            900                 905                 910

Met Glu Leu Arg Phe Leu Cys Met Asp Ser Ala Leu Arg Val Pro Val
        915                 920                 925

Gln Glu Glu Leu Cys Gly Leu Ala Ser Lys Pro Gly Ser Arg Arg Glu
    930                 935                 940

Val Cys Gln Ala Val Pro Cys Pro Ala Arg Trp Gln Tyr Lys Leu Ala
945                 950                 955                 960

Ala Cys Ser Val Ser Cys Gly Arg Gly Val Val Arg Arg Ile Leu Tyr
                965                 970                 975

Cys Ala Arg Ala His Gly Glu Asp Asp Gly Glu Glu Ile Leu Leu Asp
            980                 985                 990

Thr Gln Cys Gln Gly Leu Pro Arg  Pro Glu Pro Gln Glu  Ala Cys Ser
        995                 1000                 1005

Leu Glu  Pro Cys Pro Pro Arg  Trp Lys Val Met Ser  Leu Gly Pro
    1010                 1015                 1020

Cys Ser  Ala Ser Cys Gly Leu  Gly Thr Ala Arg Arg  Ser Val Ala
    1025                 1030                 1035

Cys Val  Gln Leu Asp Gln Gly  Gln Asp Val Glu Val  Asp Glu Ala
    1040                 1045                 1050

Ala Cys  Ala Ala Leu Val Arg  Pro Glu Ala Ser Val  Pro Cys Leu
    1055                 1060                 1065
```

```
Ile Ala Asp Cys Thr Tyr Arg Trp His Val Gly Thr Trp Met Glu
    1070                1075                1080

Cys Ser Val Ser Cys Gly Asp Gly Ile Gln Arg Arg Arg Asp Thr
    1085                1090                1095

Cys Leu Gly Pro Gln Ala Gln Ala Pro Val Pro Ala Asp Phe Cys
    1100                1105                1110

Gln His Leu Pro Lys Pro Val Thr Val Arg Gly Cys Trp Ala Gly
    1115                1120                1125

Pro Cys Val Gly Gln Gly Thr Pro Ser Leu Val Pro His Glu Glu
    1130                1135                1140

Ala Ala Ala Pro Gly Arg Thr Thr Ala Thr Pro Ala Gly Ala Ser
    1145                1150                1155

Leu Glu Trp Ser Gln Ala Arg Gly Leu Leu Phe Ser Pro Ala Pro
    1160                1165                1170

Gln Pro Arg Arg Leu Leu Pro Gly Pro Gln Glu Asn Ser Val Gln
    1175                1180                1185

Ser Ser Ala Cys Gly Arg Gln His Leu Glu Pro Thr Gly Thr Ile
    1190                1195                1200

Asp Met Arg Gly Pro Gly Gln Ala Asp Cys Ala Val Ala Ile Gly
    1205                1210                1215

Arg Pro Leu Gly Glu Val Val Thr Leu Arg Val Leu Glu Ser Ser
    1220                1225                1230

Leu Asn Cys Ser Ala Gly Asp Met Leu Leu Leu Trp Gly Arg Leu
    1235                1240                1245

Thr Trp Arg Lys Met Cys Arg Lys Leu Leu Asp Met Thr Phe Ser
    1250                1255                1260

Ser Lys Thr Asn Thr Leu Val Val Arg Gln Arg Cys Gly Arg Pro
    1265                1270                1275

Gly Gly Gly Val Leu Leu Arg Tyr Gly Ser Gln Leu Ala Pro Glu
    1280                1285                1290

Thr Phe Tyr Arg Glu Cys Asp Met Gln Leu Phe Gly Pro Trp Gly
    1295                1300                1305

Glu Ile Val Ser Pro Ser Leu Ser Pro Ala Thr Ser Asn Ala Gly
    1310                1315                1320

Gly Cys Arg Leu Phe Ile Asn Val Ala Pro His Ala Arg Ile Ala
    1325                1330                1335

Ile His Ala Leu Ala Thr Asn Met Gly Ala Gly Thr Glu Gly Ala
    1340                1345                1350

Asn Ala Ser Tyr Ile Leu Ile Arg Asp Thr His Ser Leu Arg Thr
    1355                1360                1365

Thr Ala Phe His Gly Gln Gln Val Leu Tyr Trp Glu Ser Glu Ser
    1370                1375                1380

Ser Gln Ala Glu Met Glu Phe Ser Glu Gly Phe Leu Lys Ala Gln
    1385                1390                1395

Ala Ser Leu Arg Gly Gln Tyr Trp Thr Leu Gln Ser Trp Val Pro
    1400                1405                1410

Glu Met Gln Asp Pro Gln Ser Trp Lys Gly Lys Glu Gly Thr
    1415                1420                1425
```

<210> SEQ ID NO 107
<211> LENGTH: 1475
<212> TYPE: PRT
<213> ORGANISM: Artificial Sequence
<220> FEATURE:
<223> OTHER INFORMATION: Synthetic_NU153_HUMAN

<400> SEQUENCE: 107

Met Ala Ser Gly Ala Gly Gly Val Gly Gly Gly Gly Gly Gly Lys Ile
1               5                   10                  15

Arg Thr Arg Arg Cys His Gln Gly Pro Ile Lys Pro Tyr Gln Gln Gly
            20                  25                  30

Arg Gln Gln His Gln Gly Ile Leu Ser Arg Val Thr Glu Ser Val Lys
        35                  40                  45

Asn Ile Val Pro Gly Trp Leu Gln Arg Tyr Phe Asn Lys Asn Glu Asp
    50                  55                  60

Val Cys Ser Cys Ser Thr Asp Thr Ser Glu Val Pro Arg Trp Pro Glu
65                  70                  75                  80

Asn Lys Glu Asp His Leu Val Tyr Ala Asp Glu Glu Ser Ser Asn Ile
                85                  90                  95

Thr Asp Gly Arg Ile Thr Pro Glu Pro Ala Val Ser Asn Thr Glu Glu
            100                 105                 110

Pro Ser Thr Thr Ser Thr Ala Ser Asn Tyr Pro Asp Val Leu Thr Arg
        115                 120                 125

Pro Ser Leu His Arg Ser His Leu Asn Phe Ser Met Leu Glu Ser Pro
    130                 135                 140

Ala Leu His Cys Gln Pro Ser Thr Ser Ser Ala Phe Pro Ile Gly Ser
145                 150                 155                 160

Ser Gly Phe Ser Leu Val Lys Glu Ile Lys Asp Ser Thr Ser Gln His
                165                 170                 175

Asp Asp Asp Asn Ile Ser Thr Thr Ser Gly Phe Ser Ser Arg Ala Ser
            180                 185                 190

Asp Lys Asp Ile Thr Val Ser Lys Asn Thr Ser Leu Pro Pro Leu Trp
        195                 200                 205

Ser Pro Glu Ala Glu Arg Ser His Ser Leu Ser Gln His Thr Ala Thr
    210                 215                 220

Ser Ser Lys Lys Pro Ala Phe Asn Leu Ser Ala Phe Gly Thr Leu Ser
225                 230                 235                 240

Pro Ser Leu Gly Asn Ser Ser Ile Leu Lys Thr Ser Gln Leu Gly Asp
                245                 250                 255

Ser Pro Phe Tyr Pro Gly Lys Thr Thr Tyr Gly Gly Ala Ala Ala Ala
            260                 265                 270

Val Arg Gln Ser Lys Leu Arg Asn Thr Pro Tyr Gln Ala Pro Val Arg
        275                 280                 285

Arg Gln Met Lys Ala Lys Gln Leu Ser Ala Gln Ser Tyr Gly Val Thr
    290                 295                 300

Ser Ser Thr Ala Arg Arg Ile Leu Gln Ser Leu Glu Lys Met Ser Ser
305                 310                 315                 320

Pro Leu Ala Asp Ala Lys Arg Ile Pro Ser Ile Val Ser Ser Pro Leu
                325                 330                 335

Asn Ser Pro Leu Asp Arg Ser Gly Ile Asp Ile Thr Asp Phe Gln Ala
            340                 345                 350

Lys Arg Glu Lys Val Asp Ser Gln Tyr Pro Pro Val Gln Arg Leu Met
        355                 360                 365

Thr Pro Lys Pro Val Ser Ile Ala Thr Asn Arg Ser Val Tyr Phe Lys
    370                 375                 380

Pro Ser Leu Thr Pro Ser Gly Glu Phe Arg Lys Thr Asn Gln Arg Ile
385                 390                 395                 400

Asp Asn Lys Cys Ser Thr Gly Tyr Glu Lys Asn Met Thr Pro Gly Gln

-continued

```
                405                 410                 415

Asn Arg Glu Gln Arg Glu Ser Gly Phe Ser Tyr Pro Asn Phe Ser Leu
            420                 425                 430

Pro Ala Ala Asn Gly Leu Ser Ser Gly Val Gly Gly Gly Gly Gly Lys
        435                 440                 445

Met Arg Arg Glu Arg Thr Arg Phe Val Ala Ser Lys Pro Leu Glu Glu
    450                 455                 460

Glu Glu Met Glu Val Pro Val Leu Pro Lys Ile Ser Leu Pro Ile Thr
465                 470                 475                 480

Ser Ser Ser Leu Pro Thr Phe Asn Phe Ser Ser Pro Glu Ile Thr Thr
                485                 490                 495

Ser Ser Pro Ser Pro Ile Asn Ser Ser Gln Ala Leu Thr Asn Lys Val
            500                 505                 510

Gln Met Thr Ser Pro Ser Ser Thr Gly Ser Pro Met Phe Lys Phe Ser
        515                 520                 525

Ser Pro Ile Val Lys Ser Thr Glu Ala Asn Val Leu Pro Pro Ser Ser
    530                 535                 540

Ile Gly Phe Thr Phe Ser Val Pro Val Ala Lys Thr Ala Glu Leu Ser
545                 550                 555                 560

Gly Ser Ser Ser Thr Leu Glu Pro Ile Ile Ser Ser Ser Ala His His
                565                 570                 575

Val Thr Thr Val Asn Ser Thr Asn Cys Lys Lys Thr Pro Pro Glu Asp
            580                 585                 590

Cys Glu Gly Pro Phe Arg Pro Ala Glu Ile Leu Lys Glu Gly Ser Val
        595                 600                 605

Leu Asp Ile Leu Lys Ser Pro Gly Phe Ala Ser Pro Lys Ile Asp Ser
    610                 615                 620

Val Ala Ala Gln Pro Thr Ala Thr Ser Pro Val Val Tyr Thr Arg Pro
625                 630                 635                 640

Ala Ile Ser Ser Phe Ser Ser Ser Gly Ile Gly Phe Gly Glu Ser Leu
                645                 650                 655

Lys Ala Gly Ser Ser Trp Gln Cys Asp Thr Cys Leu Leu Gln Asn Lys
            660                 665                 670

Val Thr Asp Asn Lys Cys Ile Ala Cys Gln Ala Ala Lys Leu Ser Pro
        675                 680                 685

Arg Asp Thr Ala Lys Gln Thr Gly Ile Glu Thr Pro Asn Lys Ser Gly
    690                 695                 700

Lys Thr Thr Leu Ser Ala Ser Gly Thr Gly Phe Gly Asp Lys Phe Lys
705                 710                 715                 720

Pro Val Ile Gly Thr Trp Asp Cys Asp Thr Cys Leu Val Gln Asn Lys
                725                 730                 735

Pro Glu Ala Ile Lys Cys Val Ala Cys Glu Thr Pro Lys Pro Gly Thr
            740                 745                 750

Cys Val Lys Arg Ala Leu Thr Leu Thr Val Val Ser Glu Ser Ala Glu
        755                 760                 765

Thr Met Thr Ala Ser Ser Ser Ser Cys Thr Val Thr Thr Gly Thr Leu
    770                 775                 780

Gly Phe Gly Asp Lys Phe Lys Arg Pro Ile Gly Ser Trp Glu Cys Ser
785                 790                 795                 800

Val Cys Cys Val Ser Asn Asn Ala Glu Asp Asn Lys Cys Val Ser Cys
                805                 810                 815

Met Ser Glu Lys Pro Gly Ser Ser Val Pro Ala Ser Ser Ser Ser Thr
            820                 825                 830
```

```
Val Pro Val Ser Leu Pro Ser Gly Gly Ser Leu Gly Leu Glu Lys Phe
        835                 840                 845

Lys Lys Pro Glu Gly Ser Trp Asp Cys Glu Leu Cys Leu Val Gln Asn
    850                 855                 860

Lys Ala Asp Ser Thr Lys Cys Leu Ala Cys Glu Ser Ala Lys Pro Gly
865                 870                 875                 880

Thr Lys Ser Gly Phe Lys Gly Phe Asp Thr Ser Ser Ser Ser Ser Asn
                885                 890                 895

Ser Ala Ala Ser Ser Ser Phe Lys Phe Gly Val Ser Ser Ser Ser Ser
            900                 905                 910

Gly Pro Ser Gln Thr Leu Thr Ser Thr Gly Asn Phe Lys Phe Gly Asp
        915                 920                 925

Gln Gly Gly Phe Lys Ile Gly Val Ser Ser Asp Ser Gly Ser Ile Asn
    930                 935                 940

Pro Met Ser Glu Gly Phe Lys Phe Ser Lys Pro Ile Gly Asp Phe Lys
945                 950                 955                 960

Phe Gly Val Ser Ser Glu Ser Lys Pro Glu Glu Val Lys Lys Asp Ser
                965                 970                 975

Lys Asn Asp Asn Phe Lys Phe Gly Leu Ser Ser Gly Leu Ser Asn Pro
            980                 985                 990

Val Ser Leu Thr Pro Phe Gln Phe  Gly Val Ser Asn Leu  Gly Gln Glu
        995                 1000                 1005

Glu Lys  Lys Glu Glu Leu Pro  Lys Ser Ser Ser Ala  Gly Phe Ser
    1010                 1015                 1020

Phe Gly  Thr Gly Val Ile Asn  Ser Thr Pro Ala Pro  Ala Asn Thr
    1025                 1030                 1035

Ile Val  Thr Ser Glu Asn Lys  Ser Ser Phe Asn Leu  Gly Thr Ile
    1040                 1045                 1050

Glu Thr  Lys Ser Ala Ser Val  Ala Pro Phe Thr Cys  Lys Thr Ser
    1055                 1060                 1065

Glu Ala  Lys Lys Glu Glu Met  Pro Ala Thr Lys Gly  Gly Phe Ser
    1070                 1075                 1080

Phe Gly  Asn Val Glu Pro Ala  Ser Leu Pro Ser Ala  Ser Val Phe
    1085                 1090                 1095

Val Leu  Gly Arg Thr Glu Glu  Lys Gln Gln Glu Pro  Val Thr Ser
    1100                 1105                 1110

Thr Ser  Leu Val Phe Gly Lys  Lys Ala Asp Asn Glu  Glu Pro Lys
    1115                 1120                 1125

Cys Gln  Pro Val Phe Ser Phe  Gly Asn Ser Glu Gln  Thr Lys Asp
    1130                 1135                 1140

Glu Asn  Ser Ser Lys Ser Thr  Phe Ser Phe Ser Met  Thr Lys Pro
    1145                 1150                 1155

Ser Glu  Lys Glu Ser Glu Gln  Pro Ala Lys Ala Thr  Phe Ala Phe
    1160                 1165                 1170

Gly Ala  Gln Thr Ser Thr Thr  Ala Asp Gln Gly Ala  Ala Lys Pro
    1175                 1180                 1185

Val Phe  Ser Phe Leu Asn Asn  Ser Ser Ser Ser Ser  Ser Thr Pro
    1190                 1195                 1200

Ala Thr  Ser Ala Gly Gly Gly  Ile Phe Gly Ser Ser  Thr Ser Ser
    1205                 1210                 1215

Ser Asn  Pro Pro Val Ala Thr  Phe Val Phe Gly Gln  Ser Ser Asn
    1220                 1225                 1230
```

```
Pro Val  Ser Ser Ser Ala Phe  Gly Asn Thr Ala Glu  Ser Ser Thr
    1235                 1240                 1245

Ser Gln  Ser Leu Leu Phe Ser  Gln Asp Ser Lys Leu  Ala Thr Thr
    1250                 1255                 1260

Ser Ser  Thr Gly Thr Ala Val  Thr Pro Phe Val Phe  Gly Pro Gly
    1265                 1270                 1275

Ala Ser  Ser Asn Asn Thr Thr  Thr Ser Gly Phe Gly  Phe Gly Ala
    1280                 1285                 1290

Thr Thr  Thr Ser Ser Ser Ala  Gly Ser Ser Phe Val  Phe Gly Thr
    1295                 1300                 1305

Gly Pro  Ser Ala Pro Ser Ala  Ser Pro Ala Phe Gly  Ala Asn Gln
    1310                 1315                 1320

Thr Pro  Thr Phe Gly Gln Ser  Gln Gly Ala Ser Gln  Pro Asn Pro
    1325                 1330                 1335

Pro Gly  Phe Gly Ser Ile Ser  Ser Ser Thr Ala Leu  Phe Pro Thr
    1340                 1345                 1350

Gly Ser  Gln Pro Ala Pro Pro  Thr Phe Gly Thr Val  Ser Ser Ser
    1355                 1360                 1365

Ser Gln  Pro Pro Val Phe Gly  Gln Gln Pro Ser Gln  Ser Ala Phe
    1370                 1375                 1380

Gly Ser  Gly Thr Thr Pro Asn  Ser Ser Ser Ala Phe  Gln Phe Gly
    1385                 1390                 1395

Ser Ser  Thr Thr Asn Phe Asn  Phe Thr Asn Asn Ser  Pro Ser Gly
    1400                 1405                 1410

Val Phe  Thr Phe Gly Ala Asn  Ser Ser Thr Pro Ala  Ala Ser Ala
    1415                 1420                 1425

Gln Pro  Ser Gly Ser Gly Gly  Phe Pro Phe Asn Gln  Ser Pro Ala
    1430                 1435                 1440

Ala Phe  Thr Val Gly Ser Asn  Gly Lys Asn Val Phe  Ser Ser Ser
    1445                 1450                 1455

Gly Thr  Ser Phe Ser Gly Arg  Lys Ile Lys Thr Ala  Val Arg Arg
    1460                 1465                 1470

Arg Lys
    1475
```

<210> SEQ ID NO 108
<211> LENGTH: 1500
<212> TYPE: PRT
<213> ORGANISM: Artificial Sequence
<220> FEATURE:
<223> OTHER INFORMATION: Synthetic_CPSM_HUMAN

<400> SEQUENCE: 108

```
Met Thr Arg Ile Leu Thr Ala Phe Lys Val Val Arg Thr Leu Lys Thr
1               5                   10                  15

Gly Phe Gly Phe Thr Asn Val Thr Ala His Gln Lys Trp Lys Phe Ser
            20                  25                  30

Arg Pro Gly Ile Arg Leu Leu Ser Val Lys Ala Gln Thr Ala His Ile
        35                  40                  45

Val Leu Glu Asp Gly Thr Lys Met Lys Gly Tyr Ser Phe Gly His Pro
    50                  55                  60

Ser Ser Val Ala Gly Glu Val Val Phe Asn Thr Gly Leu Gly Gly Tyr
65                  70                  75                  80

Pro Glu Ala Ile Thr Asp Pro Ala Tyr Lys Gly Gln Ile Leu Thr Met
                85                  90                  95
```

```
Ala Asn Pro Ile Ile Gly Asn Gly Gly Ala Pro Asp Thr Thr Ala Leu
            100                 105                 110

Asp Glu Leu Gly Leu Ser Lys Tyr Leu Glu Ser Asn Gly Ile Lys Val
        115                 120                 125

Ser Gly Leu Leu Val Leu Asp Tyr Ser Lys Asp Tyr Asn His Trp Leu
    130                 135                 140

Ala Thr Lys Ser Leu Gly Gln Trp Leu Gln Glu Glu Lys Val Pro Ala
145                 150                 155                 160

Ile Tyr Gly Val Asp Thr Arg Met Leu Thr Lys Ile Ile Arg Asp Lys
                165                 170                 175

Gly Thr Met Leu Gly Lys Ile Glu Phe Glu Gly Gln Pro Val Asp Phe
            180                 185                 190

Val Asp Pro Asn Lys Gln Asn Leu Ile Ala Glu Val Ser Thr Lys Asp
        195                 200                 205

Val Lys Val Tyr Gly Lys Gly Asn Pro Thr Lys Val Val Ala Val Asp
    210                 215                 220

Cys Gly Ile Lys Asn Asn Val Ile Arg Leu Leu Val Lys Arg Gly Ala
225                 230                 235                 240

Glu Val His Leu Val Pro Trp Asn His Asp Phe Thr Lys Met Glu Tyr
                245                 250                 255

Asp Gly Ile Leu Ile Ala Gly Gly Pro Gly Asn Pro Ala Leu Ala Glu
            260                 265                 270

Pro Leu Ile Gln Asn Val Arg Lys Ile Leu Glu Ser Asp Arg Lys Glu
        275                 280                 285

Pro Leu Phe Gly Ile Ser Thr Gly Asn Leu Ile Thr Gly Leu Ala Ala
    290                 295                 300

Gly Ala Lys Thr Tyr Lys Met Ser Met Ala Asn Arg Gly Gln Asn Gln
305                 310                 315                 320

Pro Val Leu Asn Ile Thr Asn Lys Gln Ala Phe Ile Thr Ala Gln Asn
                325                 330                 335

His Gly Tyr Ala Leu Asp Asn Thr Leu Pro Ala Gly Trp Lys Pro Leu
            340                 345                 350

Phe Val Asn Val Asn Asp Gln Thr Asn Glu Gly Ile Met His Glu Ser
        355                 360                 365

Lys Pro Phe Phe Ala Val Gln Phe His Pro Glu Val Thr Pro Gly Pro
    370                 375                 380

Ile Asp Thr Glu Tyr Leu Phe Asp Ser Phe Phe Ser Leu Ile Lys Lys
385                 390                 395                 400

Gly Lys Ala Thr Thr Ile Thr Ser Val Leu Pro Lys Pro Ala Leu Val
                405                 410                 415

Ala Ser Arg Val Glu Val Ser Lys Val Leu Ile Leu Gly Ser Gly Gly
            420                 425                 430

Leu Ser Ile Gly Gln Ala Gly Glu Phe Asp Tyr Ser Gly Ser Gln Ala
        435                 440                 445

Val Lys Ala Met Lys Glu Glu Asn Val Lys Thr Val Leu Met Asn Pro
    450                 455                 460

Asn Ile Ala Ser Val Gln Thr Asn Glu Val Gly Leu Lys Gln Ala Asp
465                 470                 475                 480

Thr Val Tyr Phe Leu Pro Ile Thr Pro Gln Phe Val Thr Glu Val Ile
                485                 490                 495

Lys Ala Glu Gln Pro Asp Gly Leu Ile Leu Gly Met Gly Gly Gln Thr
            500                 505                 510

Ala Leu Asn Cys Gly Val Glu Leu Phe Lys Arg Gly Val Leu Lys Glu
```

```
        515                 520                 525

Tyr Gly Val Lys Val Leu Gly Thr Ser Val Glu Ser Ile Met Ala Thr
    530                 535                 540

Glu Asp Arg Gln Leu Phe Ser Asp Lys Leu Asn Glu Ile Asn Glu Lys
545                 550                 555                 560

Ile Ala Pro Ser Phe Ala Val Glu Ser Ile Glu Asp Ala Leu Lys Ala
                565                 570                 575

Ala Asp Thr Ile Gly Tyr Pro Val Met Ile Arg Ser Ala Tyr Ala Leu
            580                 585                 590

Gly Gly Leu Gly Ser Gly Ile Cys Pro Asn Arg Glu Thr Leu Met Asp
        595                 600                 605

Leu Ser Thr Lys Ala Phe Ala Met Thr Asn Gln Ile Leu Val Glu Lys
    610                 615                 620

Ser Val Thr Gly Trp Lys Glu Ile Glu Tyr Glu Val Val Arg Asp Ala
625                 630                 635                 640

Asp Asp Asn Cys Val Thr Val Cys Asn Met Glu Asn Val Asp Ala Met
                645                 650                 655

Gly Val His Thr Gly Asp Ser Val Val Val Ala Pro Ala Gln Thr Leu
            660                 665                 670

Ser Asn Ala Glu Phe Gln Met Leu Arg Arg Thr Ser Ile Asn Val Val
        675                 680                 685

Arg His Leu Gly Ile Val Gly Glu Cys Asn Ile Gln Phe Ala Leu His
    690                 695                 700

Pro Thr Ser Met Glu Tyr Cys Ile Ile Glu Val Asn Ala Arg Leu Ser
705                 710                 715                 720

Arg Ser Ser Ala Leu Ala Ser Lys Ala Thr Gly Tyr Pro Leu Ala Phe
                725                 730                 735

Ile Ala Ala Lys Ile Ala Leu Gly Ile Pro Leu Pro Glu Ile Lys Asn
            740                 745                 750

Val Val Ser Gly Lys Thr Ser Ala Cys Phe Glu Pro Ser Leu Asp Tyr
        755                 760                 765

Met Val Thr Lys Ile Pro Arg Trp Asp Leu Asp Arg Phe His Gly Thr
    770                 775                 780

Ser Ser Arg Ile Gly Ser Ser Met Lys Ser Val Gly Glu Val Met Ala
785                 790                 795                 800

Ile Gly Arg Thr Phe Glu Glu Ser Phe Gln Lys Ala Leu Arg Met Cys
                805                 810                 815

His Pro Ser Ile Glu Gly Phe Thr Pro Arg Leu Pro Met Asn Lys Glu
            820                 825                 830

Trp Pro Ser Asn Leu Asp Leu Arg Lys Glu Leu Ser Glu Pro Ser Ser
        835                 840                 845

Thr Arg Ile Tyr Ala Ile Ala Lys Ala Ile Asp Asp Asn Met Ser Leu
    850                 855                 860

Asp Glu Ile Glu Lys Leu Thr Tyr Ile Asp Lys Trp Phe Leu Tyr Lys
865                 870                 875                 880

Met Arg Asp Ile Leu Asn Met Glu Lys Thr Leu Lys Gly Leu Asn Ser
                885                 890                 895

Glu Ser Met Thr Glu Glu Thr Leu Lys Arg Ala Lys Glu Ile Gly Phe
            900                 905                 910

Ser Asp Lys Gln Ile Ser Lys Cys Leu Gly Leu Thr Glu Ala Gln Thr
        915                 920                 925

Arg Glu Leu Arg Leu Lys Lys Asn Ile His Pro Trp Val Lys Gln Ile
    930                 935                 940
```

```
Asp Thr Leu Ala Ala Glu Tyr Pro Ser Val Thr Asn Tyr Leu Tyr Val
945                 950                 955                 960

Thr Tyr Asn Gly Gln Glu His Asp Val Asn Phe Asp Asp His Gly Met
                965                 970                 975

Met Val Leu Gly Cys Gly Pro Tyr His Ile Gly Ser Ser Val Glu Phe
            980                 985                 990

Asp Trp Cys Ala Val Ser Ser Ile  Arg Thr Leu Arg Gln  Leu Gly Lys
        995                 1000                1005

Lys Thr  Val Val Val Asn Cys  Asn Pro Glu Thr Val  Ser Thr Asp
    1010                1015                1020

Phe Asp  Glu Cys Asp Lys Leu  Tyr Phe Glu Glu Leu  Ser Leu Glu
    1025                1030                1035

Arg Ile  Leu Asp Ile Tyr His  Gln Glu Ala Cys Gly  Gly Cys Ile
    1040                1045                1050

Ile Ser  Val Gly Gly Gln Ile  Pro Asn Asn Leu Ala  Val Pro Leu
    1055                1060                1065

Tyr Lys  Asn Gly Val Lys Ile  Met Gly Thr Ser Pro  Leu Gln Ile
    1070                1075                1080

Asp Arg  Ala Glu Asp Arg Ser  Ile Phe Ser Ala Val  Leu Asp Glu
    1085                1090                1095

Leu Lys  Val Ala Gln Ala Pro  Trp Lys Ala Val Asn  Thr Leu Asn
    1100                1105                1110

Glu Ala  Leu Glu Phe Ala Lys  Ser Val Asp Tyr Pro  Cys Leu Leu
    1115                1120                1125

Arg Pro  Ser Tyr Val Leu Ser  Gly Ser Ala Met Asn  Val Val Phe
    1130                1135                1140

Ser Glu  Asp Glu Met Lys Lys  Phe Leu Glu Glu Ala  Thr Arg Val
    1145                1150                1155

Ser Gln  Glu His Pro Val Val  Leu Thr Lys Phe Val  Glu Gly Ala
    1160                1165                1170

Arg Glu  Val Glu Met Asp Ala  Val Gly Lys Asp Gly  Arg Val Ile
    1175                1180                1185

Ser His  Ala Ile Ser Glu His  Val Glu Asp Ala Gly  Val His Ser
    1190                1195                1200

Gly Asp  Ala Thr Leu Met Leu  Pro Thr Gln Thr Ile  Ser Gln Gly
    1205                1210                1215

Ala Ile  Glu Lys Val Lys Asp  Ala Thr Arg Lys Ile  Ala Lys Ala
    1220                1225                1230

Phe Ala  Ile Ser Gly Pro Phe  Asn Val Gln Phe Leu  Val Lys Gly
    1235                1240                1245

Asn Asp  Val Leu Val Ile Glu  Cys Asn Leu Arg Ala  Ser Arg Ser
    1250                1255                1260

Phe Pro  Phe Val Ser Lys Thr  Leu Gly Val Asp Phe  Ile Asp Val
    1265                1270                1275

Ala Thr  Lys Val Met Ile Gly  Glu Asn Val Asp Glu  Lys His Leu
    1280                1285                1290

Pro Thr  Leu Asp His Pro Ile  Ile Pro Ala Asp Tyr  Val Ala Ile
    1295                1300                1305

Lys Ala  Pro Met Phe Ser Trp  Pro Arg Leu Arg Asp  Ala Asp Pro
    1310                1315                1320

Ile Leu  Arg Cys Glu Met Ala  Ser Thr Gly Glu Val  Ala Cys Phe
    1325                1330                1335
```

Gly Glu Gly Ile His Thr Ala Phe Leu Lys Ala Met Leu Ser Thr
1340 1345 1350

Gly Phe Lys Ile Pro Gln Lys Gly Ile Leu Ile Gly Ile Gln Gln
1355 1360 1365

Ser Phe Arg Pro Arg Phe Leu Gly Val Ala Glu Gln Leu His Asn
1370 1375 1380

Glu Gly Phe Lys Leu Phe Ala Thr Glu Ala Thr Ser Asp Trp Leu
1385 1390 1395

Asn Ala Asn Asn Val Pro Ala Thr Pro Val Ala Trp Pro Ser Gln
1400 1405 1410

Glu Gly Gln Asn Pro Ser Leu Ser Ser Ile Arg Lys Leu Ile Arg
1415 1420 1425

Asp Gly Ser Ile Asp Leu Val Ile Asn Leu Pro Asn Asn Asn Thr
1430 1435 1440

Lys Phe Val His Asp Asn Tyr Val Ile Arg Arg Thr Ala Val Asp
1445 1450 1455

Ser Gly Ile Pro Leu Leu Thr Asn Phe Gln Val Thr Lys Leu Phe
1460 1465 1470

Ala Glu Ala Val Gln Lys Ser Arg Lys Val Asp Ser Lys Ser Leu
1475 1480 1485

Phe His Tyr Arg Gln Tyr Ser Ala Gly Lys Ala Ala
1490 1495 1500

<210> SEQ ID NO 109
<211> LENGTH: 1762
<212> TYPE: PRT
<213> ORGANISM: Artificial Sequence
<220> FEATURE:
<223> OTHER INFORMATION: Synthetic_ATL1_HUMAN

<400> SEQUENCE: 109

Met Glu Cys Cys Arg Arg Ala Thr Pro Gly Thr Leu Leu Leu Phe Leu
1 5 10 15

Ala Phe Leu Leu Leu Ser Ser Arg Thr Ala Arg Ser Glu Glu Asp Arg
20 25 30

Asp Gly Leu Trp Asp Ala Trp Gly Pro Trp Ser Glu Cys Ser Arg Thr
35 40 45

Cys Gly Gly Gly Ala Ser Tyr Ser Leu Arg Arg Cys Leu Ser Ser Lys
50 55 60

Ser Cys Glu Gly Arg Asn Ile Arg Tyr Arg Thr Cys Ser Asn Val Asp
65 70 75 80

Cys Pro Pro Glu Ala Gly Asp Phe Arg Ala Gln Gln Cys Ser Ala His
85 90 95

Asn Asp Val Lys His His Gly Gln Phe Tyr Glu Trp Leu Pro Val Ser
100 105 110

Asn Asp Pro Asp Asn Pro Cys Ser Leu Lys Cys Gln Ala Lys Gly Thr
115 120 125

Thr Leu Val Val Glu Leu Ala Pro Lys Val Leu Asp Gly Thr Arg Cys
130 135 140

Tyr Thr Glu Ser Leu Asp Met Cys Ile Ser Gly Leu Cys Gln Ile Val
145 150 155 160

Gly Cys Asp His Gln Leu Gly Ser Thr Val Lys Glu Asp Asn Cys Gly
165 170 175

Val Cys Asn Gly Asp Gly Ser Thr Cys Arg Leu Val Arg Gly Gln Tyr
180 185 190

```
Lys Ser Gln Leu Ser Ala Thr Lys Ser Asp Asp Thr Val Val Ala Ile
        195                 200                 205

Pro Tyr Gly Ser Arg His Ile Arg Leu Val Leu Lys Gly Pro Asp His
    210                 215                 220

Leu Tyr Leu Glu Thr Lys Thr Leu Gln Gly Thr Lys Gly Glu Asn Ser
225                 230                 235                 240

Leu Ser Ser Thr Gly Thr Phe Leu Val Asp Asn Ser Ser Val Asp Phe
                245                 250                 255

Gln Lys Phe Pro Asp Lys Glu Ile Leu Arg Met Ala Gly Pro Leu Thr
            260                 265                 270

Ala Asp Phe Ile Val Lys Ile Arg Asn Ser Gly Ser Ala Asp Ser Thr
        275                 280                 285

Val Gln Phe Ile Phe Tyr Gln Pro Ile Ile His Arg Trp Arg Glu Thr
    290                 295                 300

Asp Phe Phe Pro Cys Ser Ala Thr Cys Gly Gly Gly Tyr Gln Leu Thr
305                 310                 315                 320

Ser Ala Glu Cys Tyr Asp Leu Arg Ser Asn Arg Val Val Ala Asp Gln
                325                 330                 335

Tyr Cys His Tyr Tyr Pro Glu Asn Ile Lys Pro Lys Pro Lys Leu Gln
            340                 345                 350

Glu Cys Asn Leu Asp Pro Cys Pro Ala Ser Asp Gly Tyr Lys Gln Ile
        355                 360                 365

Met Pro Tyr Asp Leu Tyr His Pro Leu Pro Arg Trp Glu Ala Thr Pro
    370                 375                 380

Trp Thr Ala Cys Ser Ser Ser Cys Gly Gly Gly Ile Gln Ser Arg Ala
385                 390                 395                 400

Val Ser Cys Val Glu Glu Asp Ile Gln Gly His Val Thr Ser Val Glu
                405                 410                 415

Glu Trp Lys Cys Met Tyr Thr Pro Lys Met Pro Ile Ala Gln Pro Cys
            420                 425                 430

Asn Ile Phe Asp Cys Pro Lys Trp Leu Ala Gln Glu Trp Ser Pro Cys
        435                 440                 445

Thr Val Thr Cys Gly Gln Gly Leu Arg Tyr Arg Val Val Leu Cys Ile
    450                 455                 460

Asp His Arg Gly Met His Thr Gly Gly Cys Ser Pro Lys Thr Lys Pro
465                 470                 475                 480

His Ile Lys Glu Glu Cys Ile Val Pro Thr Pro Cys Tyr Lys Pro Lys
                485                 490                 495

Glu Lys Leu Pro Val Glu Ala Lys Leu Pro Trp Phe Lys Gln Ala Gln
            500                 505                 510

Glu Leu Glu Glu Gly Ala Ala Val Ser Glu Glu Pro Ser Phe Ile Pro
        515                 520                 525

Glu Ala Trp Ser Ala Cys Thr Val Thr Cys Gly Val Gly Thr Gln Val
    530                 535                 540

Arg Ile Val Arg Cys Gln Val Leu Leu Ser Phe Ser Gln Ser Val Ala
545                 550                 555                 560

Asp Leu Pro Ile Asp Glu Cys Glu Gly Pro Lys Pro Ala Ser Gln Arg
                565                 570                 575

Ala Cys Tyr Ala Gly Pro Cys Ser Gly Glu Ile Pro Glu Phe Asn Pro
            580                 585                 590

Asp Glu Thr Asp Gly Leu Phe Gly Gly Leu Gln Asp Phe Asp Glu Leu
        595                 600                 605

Tyr Asp Trp Glu Tyr Glu Gly Phe Thr Lys Cys Ser Glu Ser Cys Gly
```

```
    610                 615                 620

Gly Gly Val Gln Glu Ala Val Val Ser Cys Leu Asn Lys Gln Thr Arg
625                 630                 635                 640

Glu Pro Ala Glu Glu Asn Leu Cys Val Thr Ser Arg Arg Pro Pro Gln
                645                 650                 655

Leu Leu Lys Ser Cys Asn Leu Asp Pro Cys Pro Ala Arg Trp Glu Ile
            660                 665                 670

Gly Lys Trp Ser Pro Cys Ser Leu Thr Cys Gly Val Gly Leu Gln Thr
        675                 680                 685

Arg Asp Val Phe Cys Ser His Leu Leu Ser Arg Glu Met Asn Glu Thr
    690                 695                 700

Val Ile Leu Ala Asp Glu Leu Cys Arg Gln Pro Lys Pro Ser Thr Val
705                 710                 715                 720

Gln Ala Cys Asn Arg Phe Asn Cys Pro Pro Ala Trp Tyr Pro Ala Gln
                725                 730                 735

Trp Gln Pro Cys Ser Arg Thr Cys Gly Gly Gly Val Gln Lys Arg Glu
            740                 745                 750

Val Leu Cys Lys Gln Arg Met Ala Asp Gly Ser Phe Leu Glu Leu Pro
        755                 760                 765

Glu Thr Phe Cys Ser Ala Ser Lys Pro Ala Cys Gln Gln Ala Cys Lys
    770                 775                 780

Lys Asp Asp Cys Pro Ser Glu Trp Leu Leu Ser Asp Trp Thr Glu Cys
785                 790                 795                 800

Ser Thr Ser Cys Gly Glu Gly Thr Gln Thr Arg Ser Ala Ile Cys Arg
                805                 810                 815

Lys Met Leu Lys Thr Gly Leu Ser Thr Val Val Asn Ser Thr Leu Cys
            820                 825                 830

Pro Pro Leu Pro Phe Ser Ser Ser Ile Arg Pro Cys Met Leu Ala Thr
        835                 840                 845

Cys Ala Arg Pro Gly Arg Pro Ser Thr Lys His Ser Pro His Ile Ala
    850                 855                 860

Ala Ala Arg Lys Val Tyr Ile Gln Thr Arg Arg Gln Arg Lys Leu His
865                 870                 875                 880

Phe Val Val Gly Gly Phe Ala Tyr Leu Leu Pro Lys Thr Ala Val Val
                885                 890                 895

Leu Arg Cys Pro Ala Arg Arg Val Arg Lys Pro Leu Ile Thr Trp Glu
            900                 905                 910

Lys Asp Gly Gln His Leu Ile Ser Ser Thr His Val Thr Val Ala Pro
        915                 920                 925

Phe Gly Tyr Leu Lys Ile His Arg Leu Lys Pro Ser Asp Ala Gly Val
    930                 935                 940

Tyr Thr Cys Ser Ala Gly Pro Ala Arg Glu His Phe Val Ile Lys Leu
945                 950                 955                 960

Ile Gly Gly Asn Arg Lys Leu Val Ala Arg Pro Leu Ser Pro Arg Ser
                965                 970                 975

Glu Glu Glu Val Leu Ala Gly Arg Lys Gly Gly Pro Lys Glu Ala Leu
            980                 985                 990

Gln Thr His Lys His Gln Asn Gly  Ile Phe Ser Asn Gly  Ser Lys Ala
        995                 1000                1005

Glu Lys  Arg Gly Leu Ala Ala  Asn Pro Gly Ser Arg  Tyr Asp Asp
    1010                1015                1020

Leu Val  Ser Arg Leu Leu Glu  Gln Gly Gly Trp Pro  Gly Glu Leu
    1025                1030                1035
```

```
Leu Ala  Ser Trp Glu Ala Gln  Asp Ser Ala Glu Arg  Asn Thr Thr
    1040                 1045                 1050

Ser Glu  Glu Asp Pro Gly Ala  Glu Gln Val Leu Leu  His Leu Pro
    1055                 1060                 1065

Phe Thr  Met Val Thr Glu Gln  Arg Arg Leu Asp Asp  Ile Leu Gly
    1070                 1075                 1080

Asn Leu  Ser Gln Gln Pro Glu  Glu Leu Arg Asp Leu  Tyr Ser Lys
    1085                 1090                 1095

His Leu  Val Ala Gln Leu Ala  Gln Glu Ile Phe Arg  Ser His Leu
    1100                 1105                 1110

Glu His  Gln Asp Thr Leu Leu  Lys Pro Ser Glu Arg  Arg Thr Ser
    1115                 1120                 1125

Pro Val  Thr Leu Ser Pro His  Lys His Val Ser Gly  Phe Ser Ser
    1130                 1135                 1140

Ser Leu  Arg Thr Ser Ser Thr  Gly Asp Ala Gly Gly  Gly Ser Arg
    1145                 1150                 1155

Arg Pro  His Arg Lys Pro Thr  Ile Leu Arg Lys Ile  Ser Ala Ala
    1160                 1165                 1170

Gln Gln  Leu Ser Ala Ser Glu  Val Val Thr His Leu  Gly Gln Thr
    1175                 1180                 1185

Val Ala  Leu Ala Ser Gly Thr  Leu Ser Val Leu Leu  His Cys Glu
    1190                 1195                 1200

Ala Ile  Gly His Pro Arg Pro  Thr Ile Ser Trp Ala  Arg Asn Gly
    1205                 1210                 1215

Glu Glu  Val Gln Phe Ser Asp  Arg Ile Leu Leu Gln  Pro Asp Asp
    1220                 1225                 1230

Ser Leu  Gln Ile Leu Ala Pro  Val Glu Ala Asp Val  Gly Phe Tyr
    1235                 1240                 1245

Thr Cys  Asn Ala Thr Asn Ala  Leu Gly Tyr Asp Ser  Val Ser Ile
    1250                 1255                 1260

Ala Val  Thr Leu Ala Gly Lys  Pro Leu Val Lys Thr  Ser Arg Met
    1265                 1270                 1275

Thr Val  Ile Asn Thr Glu Lys  Pro Ala Val Thr Val  Asp Ile Gly
    1280                 1285                 1290

Ser Thr  Ile Lys Thr Val Gln  Gly Val Asn Val Thr  Ile Asn Cys
    1295                 1300                 1305

Gln Val  Ala Gly Val Pro Glu  Ala Glu Val Thr Trp  Phe Arg Asn
    1310                 1315                 1320

Lys Ser  Lys Leu Gly Ser Pro  His His Leu His Glu  Gly Ser Leu
    1325                 1330                 1335

Leu Leu  Thr Asn Val Ser Ser  Ser Asp Gln Gly Leu  Tyr Ser Cys
    1340                 1345                 1350

Arg Ala  Ala Asn Leu His Gly  Glu Leu Thr Glu Ser  Thr Gln Leu
    1355                 1360                 1365

Leu Ile  Leu Asp Pro Pro Gln  Val Pro Thr Gln Leu  Glu Asp Ile
    1370                 1375                 1380

Arg Ala  Leu Leu Ala Ala Thr  Gly Pro Asn Leu Pro  Ser Val Leu
    1385                 1390                 1395

Thr Ser  Pro Leu Gly Thr Gln  Leu Val Leu Asp Pro  Gly Asn Ser
    1400                 1405                 1410

Ala Leu  Leu Gly Cys Pro Ile  Lys Gly His Pro Val  Pro Asn Ile
    1415                 1420                 1425
```

Thr Trp Phe His Gly Gly Gln Pro Ile Val Thr Ala Thr Gly Leu
1430 1435 1440

Thr His His Ile Leu Ala Ala Gly Gln Ile Leu Gln Val Ala Asn
1445 1450 1455

Leu Ser Gly Gly Ser Gln Gly Glu Phe Ser Cys Leu Ala Gln Asn
1460 1465 1470

Glu Ala Gly Val Leu Met Gln Lys Ala Ser Leu Val Ile Gln Asp
1475 1480 1485

Tyr Trp Trp Ser Val Asp Arg Leu Ala Thr Cys Ser Ala Ser Cys
1490 1495 1500

Gly Asn Arg Gly Val Gln Gln Pro Arg Leu Arg Cys Leu Leu Asn
1505 1510 1515

Ser Thr Glu Val Asn Pro Ala His Cys Ala Gly Lys Val Arg Pro
1520 1525 1530

Ala Val Gln Pro Ile Ala Cys Asn Arg Arg Asp Cys Pro Ser Arg
1535 1540 1545

Trp Met Val Thr Ser Trp Ser Ala Cys Thr Arg Ser Cys Gly Gly
1550 1555 1560

Gly Val Gln Thr Arg Arg Val Thr Cys Gln Lys Leu Lys Ala Ser
1565 1570 1575

Gly Ile Ser Thr Pro Val Ser Asn Asp Met Cys Thr Gln Val Ala
1580 1585 1590

Lys Arg Pro Val Asp Thr Gln Ala Cys Asn Gln Gln Leu Cys Val
1595 1600 1605

Glu Trp Ala Phe Ser Ser Trp Gly Gln Cys Asn Gly Pro Cys Ile
1610 1615 1620

Gly Pro His Leu Ala Val Gln His Arg Gln Val Phe Cys Gln Thr
1625 1630 1635

Arg Asp Gly Ile Thr Leu Pro Ser Glu Gln Cys Ser Ala Leu Pro
1640 1645 1650

Arg Pro Val Ser Thr Gln Asn Cys Trp Ser Glu Ala Cys Ser Val
1655 1660 1665

His Trp Arg Val Ser Leu Trp Thr Leu Cys Thr Ala Thr Cys Gly
1670 1675 1680

Asn Tyr Gly Phe Gln Ser Arg Arg Val Glu Cys Val His Ala Arg
1685 1690 1695

Thr Asn Lys Ala Val Pro Glu His Leu Cys Ser Trp Gly Pro Arg
1700 1705 1710

Pro Ala Asn Trp Gln Arg Cys Asn Ile Thr Pro Cys Glu Asn Met
1715 1720 1725

Glu Cys Arg Asp Thr Thr Arg Tyr Cys Glu Lys Val Lys Gln Leu
1730 1735 1740

Lys Leu Cys Gln Leu Ser Gln Phe Lys Ser Arg Cys Cys Gly Thr
1745 1750 1755

Cys Gly Lys Ala
1760

<210> SEQ ID NO 110
<211> LENGTH: 2555
<212> TYPE: PRT
<213> ORGANISM: Artificial Sequence
<220> FEATURE:
<223> OTHER INFORMATION: Synthetic_NOTC1_HUMAN

<400> SEQUENCE: 110

-continued

```
Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
            20                  25                  30

Asn Gly Gly Lys Cys Glu Ala Ala Asn Gly Thr Glu Ala Cys Val Cys
        35                  40                  45

Gly Gly Ala Phe Val Gly Pro Arg Cys Gln Asp Pro Asn Pro Cys Leu
    50                  55                  60

Ser Thr Pro Cys Lys Asn Ala Gly Thr Cys His Val Val Asp Arg Arg
65                  70                  75                  80

Gly Val Ala Asp Tyr Ala Cys Ser Cys Ala Leu Gly Phe Ser Gly Pro
                85                  90                  95

Leu Cys Leu Thr Pro Leu Asp Asn Ala Cys Leu Thr Asn Pro Cys Arg
            100                 105                 110

Asn Gly Gly Thr Cys Asp Leu Leu Thr Leu Thr Glu Tyr Lys Cys Arg
        115                 120                 125

Cys Pro Pro Gly Trp Ser Gly Lys Ser Cys Gln Gln Ala Asp Pro Cys
    130                 135                 140

Ala Ser Asn Pro Cys Ala Asn Gly Gly Gln Cys Leu Pro Phe Glu Ala
145                 150                 155                 160

Ser Tyr Ile Cys His Cys Pro Pro Ser Phe His Gly Pro Thr Cys Arg
                165                 170                 175

Gln Asp Val Asn Glu Cys Gly Gln Lys Pro Gly Leu Cys Arg His Gly
            180                 185                 190

Gly Thr Cys His Asn Glu Val Gly Ser Tyr Arg Cys Val Cys Arg Ala
        195                 200                 205

Thr His Thr Gly Pro Asn Cys Glu Arg Pro Tyr Val Pro Cys Ser Pro
    210                 215                 220

Ser Pro Cys Gln Asn Gly Gly Thr Cys Arg Pro Thr Gly Asp Val Thr
225                 230                 235                 240

His Glu Cys Ala Cys Leu Pro Gly Phe Thr Gly Gln Asn Cys Glu Glu
                245                 250                 255

Asn Ile Asp Asp Cys Pro Gly Asn Asn Cys Lys Asn Gly Gly Ala Cys
            260                 265                 270

Val Asp Gly Val Asn Thr Tyr Asn Cys Arg Cys Pro Pro Glu Trp Thr
        275                 280                 285

Gly Gln Tyr Cys Thr Glu Asp Val Asp Glu Cys Gln Leu Met Pro Asn
    290                 295                 300

Ala Cys Gln Asn Gly Gly Thr Cys His Asn Thr His Gly Gly Tyr Asn
305                 310                 315                 320

Cys Val Cys Val Asn Gly Trp Thr Gly Glu Asp Cys Ser Glu Asn Ile
                325                 330                 335

Asp Asp Cys Ala Ser Ala Ala Cys Phe His Gly Ala Thr Cys His Asp
            340                 345                 350

Arg Val Ala Ser Phe Tyr Cys Glu Cys Pro His Gly Arg Thr Gly Leu
        355                 360                 365

Leu Cys His Leu Asn Asp Ala Cys Ile Ser Asn Pro Cys Asn Glu Gly
    370                 375                 380

Ser Asn Cys Asp Thr Asn Pro Val Asn Gly Lys Ala Ile Cys Thr Cys
385                 390                 395                 400

Pro Ser Gly Tyr Thr Gly Pro Ala Cys Ser Gln Asp Val Asp Glu Cys
                405                 410                 415

Ser Leu Gly Ala Asn Pro Cys Glu His Ala Gly Lys Cys Ile Asn Thr
```

```
            420                 425                 430

Leu Gly Ser Phe Glu Cys Gln Cys Leu Gln Gly Tyr Thr Gly Pro Arg
        435                 440                 445

Cys Glu Ile Asp Val Asn Glu Cys Val Ser Asn Pro Cys Gln Asn Asp
    450                 455                 460

Ala Thr Cys Leu Asp Gln Ile Gly Glu Phe Gln Cys Ile Cys Met Pro
465                 470                 475                 480

Gly Tyr Glu Gly Val His Cys Glu Val Asn Thr Asp Glu Cys Ala Ser
                485                 490                 495

Ser Pro Cys Leu His Asn Gly Arg Cys Leu Asp Lys Ile Asn Glu Phe
            500                 505                 510

Gln Cys Glu Cys Pro Thr Gly Phe Thr Gly His Leu Cys Gln Tyr Asp
        515                 520                 525

Val Asp Glu Cys Ala Ser Thr Pro Cys Lys Asn Gly Ala Lys Cys Leu
    530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
                565                 570                 575

Tyr Gly Ser Cys Lys Asp Gly Val Ala Thr Phe Thr Cys Leu Cys Arg
            580                 585                 590

Pro Gly Tyr Thr Gly His His Cys Glu Thr Asn Ile Asn Glu Cys Ser
        595                 600                 605

Ser Gln Pro Cys Arg His Gly Gly Thr Cys Gln Asp Arg Asp Asn Ala
    610                 615                 620

Tyr Leu Cys Phe Cys Leu Lys Gly Thr Thr Gly Pro Asn Cys Glu Ile
625                 630                 635                 640

Asn Leu Asp Asp Cys Ala Ser Ser Pro Cys Asp Ser Gly Thr Cys Leu
                645                 650                 655

Asp Lys Ile Asp Gly Tyr Glu Cys Ala Cys Glu Pro Gly Tyr Thr Gly
            660                 665                 670

Ser Met Cys Asn Ile Asn Ile Asp Glu Cys Ala Gly Asn Pro Cys His
        675                 680                 685

Asn Gly Gly Thr Cys Glu Asp Gly Ile Asn Gly Phe Thr Cys Arg Cys
    690                 695                 700

Pro Glu Gly Tyr His Asp Pro Thr Cys Leu Ser Glu Val Asn Glu Cys
705                 710                 715                 720

Asn Ser Asn Pro Cys Val His Gly Ala Cys Arg Asp Ser Leu Asn Gly
                725                 730                 735

Tyr Lys Cys Asp Cys Asp Pro Gly Trp Ser Gly Thr Asn Cys Asp Ile
            740                 745                 750

Asn Asn Asn Glu Cys Glu Ser Asn Pro Cys Val Asn Gly Gly Thr Cys
        755                 760                 765

Lys Asp Met Thr Ser Gly Tyr Val Cys Thr Cys Arg Glu Gly Phe Ser
    770                 775                 780

Gly Pro Asn Cys Gln Thr Asn Ile Asn Glu Cys Ala Ser Asn Pro Cys
785                 790                 795                 800

Leu Asn Gln Gly Thr Cys Ile Asp Asp Val Ala Gly Tyr Lys Cys Asn
                805                 810                 815

Cys Leu Leu Pro Tyr Thr Gly Ala Thr Cys Glu Val Val Leu Ala Pro
            820                 825                 830

Cys Ala Pro Ser Pro Cys Arg Asn Gly Gly Glu Cys Arg Gln Ser Glu
        835                 840                 845
```

```
Asp Tyr Glu Ser Phe Ser Cys Val Cys Pro Thr Gly Trp Gln Gly Gln
    850                 855                 860

Thr Cys Glu Val Asp Ile Asn Glu Cys Val Leu Ser Pro Cys Arg His
865                 870                 875                 880

Gly Ala Ser Cys Gln Asn Thr His Gly Gly Tyr Arg Cys His Cys Gln
                885                 890                 895

Ala Gly Tyr Ser Gly Arg Asn Cys Glu Thr Asp Ile Asp Asp Cys Arg
            900                 905                 910

Pro Asn Pro Cys His Asn Gly Gly Ser Cys Thr Asp Gly Ile Asn Thr
        915                 920                 925

Ala Phe Cys Asp Cys Leu Pro Gly Phe Arg Gly Thr Phe Cys Glu Glu
    930                 935                 940

Asp Ile Asn Glu Cys Ala Ser Asp Pro Cys Arg Asn Gly Ala Asn Cys
945                 950                 955                 960

Thr Asp Cys Val Asp Ser Tyr Thr Cys Thr Cys Pro Ala Gly Phe Ser
                965                 970                 975

Gly Ile His Cys Glu Asn Asn Thr Pro Asp Cys Thr Glu Ser Ser Cys
            980                 985                 990

Phe Asn Gly Gly Thr Cys Val Asp  Gly Ile Asn Ser Phe  Thr Cys Leu
        995                 1000                1005

Cys Pro  Pro Gly Phe Thr Gly  Ser Tyr Cys Gln His  Asp Val Asn
    1010                1015                1020

Glu Cys  Asp Ser Gln Pro Cys  Leu His Gly Gly Thr  Cys Gln Asp
    1025                1030                1035

Gly Cys  Gly Ser Tyr Arg Cys  Thr Cys Pro Gln Gly  Tyr Thr Gly
    1040                1045                1050

Pro Asn  Cys Gln Asn Leu Val  His Trp Cys Asp Ser  Ser Pro Cys
    1055                1060                1065

Lys Asn  Gly Gly Lys Cys Trp  Gln Thr His Thr Gln  Tyr Arg Cys
    1070                1075                1080

Glu Cys  Pro Ser Gly Trp Thr  Gly Leu Tyr Cys Asp  Val Pro Ser
    1085                1090                1095

Val Ser  Cys Glu Val Ala Ala  Gln Arg Gln Gly Val  Asp Val Ala
    1100                1105                1110

Arg Leu  Cys Gln His Gly Gly  Leu Cys Val Asp Ala  Gly Asn Thr
    1115                1120                1125

His His  Cys Arg Cys Gln Ala  Gly Tyr Thr Gly Ser  Tyr Cys Glu
    1130                1135                1140

Asp Leu  Val Asp Glu Cys Ser  Pro Ser Pro Cys Gln  Asn Gly Ala
    1145                1150                1155

Thr Cys  Thr Asp Tyr Leu Gly  Gly Tyr Ser Cys Lys  Cys Val Ala
    1160                1165                1170

Gly Tyr  His Gly Val Asn Cys  Ser Glu Glu Ile Asp  Glu Cys Leu
    1175                1180                1185

Ser His  Pro Cys Gln Asn Gly  Gly Thr Cys Leu Asp  Leu Pro Asn
    1190                1195                1200

Thr Tyr  Lys Cys Ser Cys Pro  Arg Gly Thr Gln Gly  Val His Cys
    1205                1210                1215

Glu Ile  Asn Val Asp Asp Cys  Asn Pro Pro Val Asp  Pro Val Ser
    1220                1225                1230

Arg Ser  Pro Lys Cys Phe Asn  Asn Gly Thr Cys Val  Asp Gln Val
    1235                1240                1245
```

```
Gly Gly  Tyr Ser Cys Thr Cys  Pro Pro Gly Phe Val  Gly Glu Arg
    1250                 1255                 1260

Cys Glu  Gly Asp Val Asn Glu  Cys Leu Ser Asn Pro  Cys Asp Ala
    1265                 1270                 1275

Arg Gly  Thr Gln Asn Cys Val  Gln Arg Val Asn Asp  Phe His Cys
    1280                 1285                 1290

Glu Cys  Arg Ala Gly His Thr  Gly Arg Arg Cys Glu  Ser Val Ile
    1295                 1300                 1305

Asn Gly  Cys Lys Gly Lys Pro  Cys Lys Asn Gly Gly  Thr Cys Ala
    1310                 1315                 1320

Val Ala  Ser Asn Thr Ala Arg  Gly Phe Ile Cys Lys  Cys Pro Ala
    1325                 1330                 1335

Gly Phe  Glu Gly Ala Thr Cys  Glu Asn Asp Ala Arg  Thr Cys Gly
    1340                 1345                 1350

Ser Leu  Arg Cys Leu Asn Gly  Gly Thr Cys Ile Ser  Gly Pro Arg
    1355                 1360                 1365

Ser Pro  Thr Cys Leu Cys Leu  Gly Pro Phe Thr Gly  Pro Glu Cys
    1370                 1375                 1380

Gln Phe  Pro Ala Ser Ser Pro  Cys Leu Gly Gly Asn  Pro Cys Tyr
    1385                 1390                 1395

Asn Gln  Gly Thr Cys Glu Pro  Thr Ser Glu Ser Pro  Phe Tyr Arg
    1400                 1405                 1410

Cys Leu  Cys Pro Ala Lys Phe  Asn Gly Leu Leu Cys  His Ile Leu
    1415                 1420                 1425

Asp Tyr  Ser Phe Gly Gly Gly  Ala Gly Arg Asp Ile  Pro Pro Pro
    1430                 1435                 1440

Leu Ile  Glu Glu Ala Cys Glu  Leu Pro Glu Cys Gln  Glu Asp Ala
    1445                 1450                 1455

Gly Asn  Lys Val Cys Ser Leu  Gln Cys Asn Asn His  Ala Cys Gly
    1460                 1465                 1470

Trp Asp  Gly Gly Asp Cys Ser  Leu Asn Phe Asn Asp  Pro Trp Lys
    1475                 1480                 1485

Asn Cys  Thr Gln Ser Leu Gln  Cys Trp Lys Tyr Phe  Ser Asp Gly
    1490                 1495                 1500

His Cys  Asp Ser Gln Cys Asn  Ser Ala Gly Cys Leu  Phe Asp Gly
    1505                 1510                 1515

Phe Asp  Cys Gln Arg Ala Glu  Gly Gln Cys Asn Pro  Leu Tyr Asp
    1520                 1525                 1530

Gln Tyr  Cys Lys Asp His Phe  Ser Asp Gly His Cys  Asp Gln Gly
    1535                 1540                 1545

Cys Asn  Ser Ala Glu Cys Glu  Trp Asp Gly Leu Asp  Cys Ala Glu
    1550                 1555                 1560

His Val  Pro Glu Arg Leu Ala  Ala Gly Thr Leu Val  Val Val Val
    1565                 1570                 1575

Leu Met  Pro Pro Glu Gln Leu  Arg Asn Ser Ser Phe  His Phe Leu
    1580                 1585                 1590

Arg Glu  Leu Ser Arg Val Leu  His Thr Asn Val Val  Phe Lys Arg
    1595                 1600                 1605

Asp Ala  His Gly Gln Gln Met  Ile Phe Pro Tyr Tyr  Gly Arg Glu
    1610                 1615                 1620

Glu Glu  Leu Arg Lys His Pro  Ile Lys Arg Ala Ala  Glu Gly Trp
    1625                 1630                 1635

Ala Ala  Pro Asp Ala Leu Leu  Gly Gln Val Lys Ala  Ser Leu Leu
```

```
    1640                1645                1650

Pro Gly  Gly Ser Glu Gly Gly  Arg Arg Arg Arg Glu  Leu Asp Pro
    1655                1660                1665

Met Asp  Val Arg Gly Ser Ile  Val Tyr Leu Glu Ile  Asp Asn Arg
    1670                1675                1680

Gln Cys  Val Gln Ala Ser Ser  Gln Cys Phe Gln Ser  Ala Thr Asp
    1685                1690                1695

Val Ala  Ala Phe Leu Gly Ala  Leu Ala Ser Leu Gly  Ser Leu Asn
    1700                1705                1710

Ile Pro  Tyr Lys Ile Glu Ala  Val Gln Ser Glu Thr  Val Glu Pro
    1715                1720                1725

Pro Pro  Pro Ala Gln Leu His  Phe Met Tyr Val Ala  Ala Ala Ala
    1730                1735                1740

Phe Val  Leu Leu Phe Phe Val  Gly Cys Gly Val Leu  Leu Ser Arg
    1745                1750                1755

Lys Arg  Arg Arg Gln His Gly  Gln Leu Trp Phe Pro  Glu Gly Phe
    1760                1765                1770

Lys Val  Ser Glu Ala Ser Lys  Lys Lys Arg Arg Glu  Pro Leu Gly
    1775                1780                1785

Glu Asp  Ser Val Gly Leu Lys  Pro Leu Lys Asn Ala  Ser Asp Gly
    1790                1795                1800

Ala Leu  Met Asp Asp Asn Gln  Asn Glu Trp Gly Asp  Glu Asp Leu
    1805                1810                1815

Glu Thr  Lys Lys Phe Arg Phe  Glu Glu Pro Val Val  Leu Pro Asp
    1820                1825                1830

Leu Asp  Asp Gln Thr Asp His  Arg Gln Trp Thr Gln  Gln His Leu
    1835                1840                1845

Asp Ala  Ala Asp Leu Arg Met  Ser Ala Met Ala Pro  Thr Pro Pro
    1850                1855                1860

Gln Gly  Glu Val Asp Ala Asp  Cys Met Asp Val Asn  Val Arg Gly
    1865                1870                1875

Pro Asp  Gly Phe Thr Pro Leu  Met Ile Ala Ser Cys  Ser Gly Gly
    1880                1885                1890

Gly Leu  Glu Thr Gly Asn Ser  Glu Glu Glu Glu Asp  Ala Pro Ala
    1895                1900                1905

Val Ile  Ser Asp Phe Ile Tyr  Gln Gly Ala Ser Leu  His Asn Gln
    1910                1915                1920

Thr Asp  Arg Thr Gly Glu Thr  Ala Leu His Leu Ala  Ala Arg Tyr
    1925                1930                1935

Ser Arg  Ser Asp Ala Ala Lys  Arg Leu Leu Glu Ala  Ser Ala Asp
    1940                1945                1950

Ala Asn  Ile Gln Asp Asn Met  Gly Arg Thr Pro Leu  His Ala Ala
    1955                1960                1965

Val Ser  Ala Asp Ala Gln Gly  Val Phe Gln Ile Leu  Ile Arg Asn
    1970                1975                1980

Arg Ala  Thr Asp Leu Asp Ala  Arg Met His Asp Gly  Thr Thr Pro
    1985                1990                1995

Leu Ile  Leu Ala Ala Arg Leu  Ala Val Glu Gly Met  Leu Glu Asp
    2000                2005                2010

Leu Ile  Asn Ser His Ala Asp  Val Asn Ala Val Asp  Asp Leu Gly
    2015                2020                2025

Lys Ser  Ala Leu His Trp Ala  Ala Ala Val Asn Asn  Val Asp Ala
    2030                2035                2040
```

```
Ala Val  Val Leu Leu Lys Asn  Gly Ala Asn Lys Asp  Met Gln Asn
    2045                 2050                 2055

Asn Arg  Glu Glu Thr Pro Leu  Phe Leu Ala Ala Arg  Glu Gly Ser
    2060                 2065                 2070

Tyr Glu  Thr Ala Lys Val Leu  Leu Asp His Phe Ala  Asn Arg Asp
    2075                 2080                 2085

Ile Thr  Asp His Met Asp Arg  Leu Pro Arg Asp Ile  Ala Gln Glu
    2090                 2095                 2100

Arg Met  His His Asp Ile Val  Arg Leu Leu Asp Glu  Tyr Asn Leu
    2105                 2110                 2115

Val Arg  Ser Pro Gln Leu His  Gly Ala Pro Leu Gly  Gly Thr Pro
    2120                 2125                 2130

Thr Leu  Ser Pro Pro Leu Cys  Ser Pro Asn Gly Tyr  Leu Gly Ser
    2135                 2140                 2145

Leu Lys  Pro Gly Val Gln Gly  Lys Lys Val Arg Lys  Pro Ser Ser
    2150                 2155                 2160

Lys Gly  Leu Ala Cys Gly Ser  Lys Glu Ala Lys Asp  Leu Lys Ala
    2165                 2170                 2175

Arg Arg  Lys Lys Ser Gln Asp  Gly Lys Gly Cys Leu  Leu Asp Ser
    2180                 2185                 2190

Ser Gly  Met Leu Ser Pro Val  Asp Ser Leu Glu Ser  Pro His Gly
    2195                 2200                 2205

Tyr Leu  Ser Asp Val Ala Ser  Pro Pro Leu Leu Pro  Ser Pro Phe
    2210                 2215                 2220

Gln Gln  Ser Pro Ser Val Pro  Leu Asn His Leu Pro  Gly Met Pro
    2225                 2230                 2235

Asp Thr  His Leu Gly Ile Gly  His Leu Asn Val Ala  Ala Lys Pro
    2240                 2245                 2250

Glu Met  Ala Ala Leu Gly Gly  Gly Gly Arg Leu Ala  Phe Glu Thr
    2255                 2260                 2265

Gly Pro  Pro Arg Leu Ser His  Leu Pro Val Ala Ser  Gly Thr Ser
    2270                 2275                 2280

Thr Val  Leu Gly Ser Ser Ser  Gly Gly Ala Leu Asn  Phe Thr Val
    2285                 2290                 2295

Gly Gly  Ser Thr Ser Leu Asn  Gly Gln Cys Glu Trp  Leu Ser Arg
    2300                 2305                 2310

Leu Gln  Ser Gly Met Val Pro  Asn Gln Tyr Asn Pro  Leu Arg Gly
    2315                 2320                 2325

Ser Val  Ala Pro Gly Pro Leu  Ser Thr Gln Ala Pro  Ser Leu Gln
    2330                 2335                 2340

His Gly  Met Val Gly Pro Leu  His Ser Ser Leu Ala  Ala Ser Ala
    2345                 2350                 2355

Leu Ser  Gln Met Met Ser Tyr  Gln Gly Leu Pro Ser  Thr Arg Leu
    2360                 2365                 2370

Ala Thr  Gln Pro His Leu Val  Gln Thr Gln Gln Val  Gln Pro Gln
    2375                 2380                 2385

Asn Leu  Gln Met Gln Gln Gln  Asn Leu Gln Pro Ala  Asn Ile Gln
    2390                 2395                 2400

Gln Gln  Gln Ser Leu Gln Pro  Pro Pro Pro Pro Pro  Gln Pro His
    2405                 2410                 2415

Leu Gly  Val Ser Ser Ala Ala  Ser Gly His Leu Gly  Arg Ser Phe
    2420                 2425                 2430
```

```
Leu Ser  Gly Glu Pro Ser Gln  Ala Asp Val Gln Pro  Leu Gly Pro
    2435                 2440                 2445

Ser Ser  Leu Ala Val His Thr  Ile Leu Pro Gln Glu  Ser Pro Ala
    2450                 2455                 2460

Leu Pro  Thr Ser Leu Pro Ser  Ser Leu Val Pro Pro  Val Thr Ala
    2465                 2470                 2475

Ala Gln  Phe Leu Thr Pro Pro  Ser Gln His Ser Tyr  Ser Ser Pro
    2480                 2485                 2490

Val Asp  Asn Thr Pro Ser His  Gln Leu Gln Val Pro  Glu His Pro
    2495                 2500                 2505

Phe Leu  Thr Pro Ser Pro Glu  Ser Pro Asp Gln Trp  Ser Ser Ser
    2510                 2515                 2520

Ser Pro  His Ser Asn Val Ser  Asp Trp Ser Glu Gly  Val Ser Ser
    2525                 2530                 2535

Pro Pro  Thr Ser Met Gln Ser  Gln Ile Ala Arg Ile  Pro Glu Ala
    2540                 2545                 2550

Phe Lys
    2555


<210> SEQ ID NO 111
<211> LENGTH: 2813
<212> TYPE: PRT
<213> ORGANISM: Artificial Sequence
<220> FEATURE:
<223> OTHER INFORMATION: Synthetic_VWF_HUMAN

<400> SEQUENCE: 111

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220
```

```
Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
        355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
        435                 440                 445

Pro Gly Leu His Asn Ser Leu Val Lys Leu Lys His Gly Ala Gly Val
    450                 455                 460

Ala Met Asp Gly Gln Asp Val Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
        515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
        595                 600                 605

Arg Tyr Asp Val Cys Ser Cys Ser Asp Gly Arg Glu Cys Leu Cys Gly
    610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
```

```
                645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
        675                 680                 685

Cys Pro Pro Gly Leu Tyr Met Asp Glu Arg Gly Asp Cys Val Pro Lys
    690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
        755                 760                 765

Pro Pro Met Val Lys Leu Val Cys Pro Ala Asp Asn Leu Arg Ala Glu
    770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
        835                 840                 845

Cys Val Cys Gln Asp Arg Lys Trp Asn Cys Thr Asp His Val Cys Asp
    850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Lys Arg Val Thr Ile Leu
        915                 920                 925

Val Glu Gly Gly Glu Ile Glu Leu Phe Asp Gly Glu Val Asn Val Lys
    930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn  Asp Leu Thr
        995                 1000                1005

Ser Ser  Asn Leu Gln Val Glu  Glu Asp Pro Val Asp  Phe Gly Asn
    1010                1015                1020

Ser Trp  Lys Val Ser Ser Gln  Cys Ala Asp Thr Arg  Lys Val Pro
    1025                1030                1035

Leu Asp  Ser Ser Pro Ala Thr  Cys His Asn Asn Ile  Met Lys Gln
    1040                1045                1050

Thr Met  Val Asp Ser Ser Cys  Arg Ile Leu Thr Ser  Asp Val Phe
    1055                1060                1065
```

-continued

```
Gln Asp  Cys Asn Lys Leu Val  Asp Pro Glu Pro Tyr  Leu Asp Val
    1070                 1075                 1080

Cys Ile  Tyr Asp Thr Cys Ser  Cys Glu Ser Ile Gly  Asp Cys Ala
    1085                 1090                 1095

Cys Phe  Cys Asp Thr Ile Ala  Ala Tyr Ala His Val  Cys Ala Gln
    1100                 1105                 1110

His Gly  Lys Val Val Thr Trp  Arg Thr Ala Thr Leu  Cys Pro Gln
    1115                 1120                 1125

Ser Cys  Glu Glu Arg Asn Leu  Arg Glu Asn Gly Tyr  Glu Cys Glu
    1130                 1135                 1140

Trp Arg  Tyr Asn Ser Cys Ala  Pro Ala Cys Gln Val  Thr Cys Gln
    1145                 1150                 1155

His Pro  Glu Pro Leu Ala Cys  Pro Val Gln Cys Val  Glu Gly Cys
    1160                 1165                 1170

His Ala  His Cys Pro Pro Gly  Lys Ile Leu Asp Glu  Leu Leu Gln
    1175                 1180                 1185

Thr Cys  Val Asp Pro Glu Asp  Cys Pro Val Cys Glu  Val Ala Gly
    1190                 1195                 1200

Arg Arg  Phe Ala Ser Gly Lys  Lys Val Thr Leu Asn  Pro Ser Asp
    1205                 1210                 1215

Pro Glu  His Cys Gln Ile Cys  His Cys Asp Val Val  Asn Leu Thr
    1220                 1225                 1230

Cys Glu  Ala Cys Gln Glu Pro  Gly Gly Leu Val Val  Pro Pro Thr
    1235                 1240                 1245

Asp Ala  Pro Val Ser Pro Thr  Thr Leu Tyr Val Glu  Asp Ile Ser
    1250                 1255                 1260

Glu Pro  Pro Leu His Asp Phe  Tyr Cys Ser Arg Leu  Leu Asp Leu
    1265                 1270                 1275

Val Phe  Leu Leu Asp Gly Ser  Ser Arg Leu Ser Glu  Ala Glu Phe
    1280                 1285                 1290

Glu Val  Leu Lys Ala Phe Val  Val Asp Met Met Glu  Arg Leu Arg
    1295                 1300                 1305

Ile Ser  Gln Lys Trp Val Arg  Val Ala Val Val Glu  Tyr His Asp
    1310                 1315                 1320

Gly Ser  His Ala Tyr Ile Gly  Leu Lys Asp Arg Lys  Arg Pro Ser
    1325                 1330                 1335

Glu Leu  Arg Arg Ile Ala Ser  Gln Val Lys Tyr Ala  Gly Ser Gln
    1340                 1345                 1350

Val Ala  Ser Thr Ser Glu Val  Leu Lys Tyr Thr Leu  Phe Gln Ile
    1355                 1360                 1365

Phe Ser  Lys Ile Asp Arg Pro  Glu Ala Ser Arg Ile  Thr Leu Leu
    1370                 1375                 1380

Leu Met  Ala Ser Gln Glu Pro  Gln Arg Met Ser Arg  Asn Phe Val
    1385                 1390                 1395

Arg Tyr  Val Gln Gly Leu Lys  Lys Lys Lys Val Ile  Val Ile Pro
    1400                 1405                 1410

Val Gly  Ile Gly Pro His Ala  Asn Leu Lys Gln Ile  Arg Leu Ile
    1415                 1420                 1425

Glu Lys  Gln Ala Pro Glu Asn  Lys Ala Phe Val Leu  Ser Ser Val
    1430                 1435                 1440

Asp Glu  Leu Glu Gln Gln Arg  Asp Glu Ile Val Ser  Tyr Leu Cys
    1445                 1450                 1455
```

```
Asp Leu  Ala Pro Glu Ala Pro  Pro Pro Thr Leu Pro  Pro Asp Met
    1460                 1465                 1470

Ala Gln  Val Thr Val Gly Pro  Gly Leu Leu Gly Val  Ser Thr Leu
    1475                 1480                 1485

Gly Pro  Lys Arg Asn Ser Met  Val Leu Asp Val Ala  Phe Val Leu
    1490                 1495                 1500

Glu Gly  Ser Asp Lys Ile Gly  Glu Ala Asp Phe Asn  Arg Ser Lys
    1505                 1510                 1515

Glu Phe  Met Glu Glu Val Ile  Gln Arg Met Asp Val  Gly Gln Asp
    1520                 1525                 1530

Ser Ile  His Val Thr Val Leu  Gln Tyr Ser Tyr Met  Val Thr Val
    1535                 1540                 1545

Glu Tyr  Pro Phe Ser Glu Ala  Gln Ser Lys Gly Asp  Ile Leu Gln
    1550                 1555                 1560

Arg Val  Arg Glu Ile Arg Tyr  Gln Gly Gly Asn Arg  Thr Asn Thr
    1565                 1570                 1575

Gly Leu  Ala Leu Arg Tyr Leu  Ser Asp His Ser Phe  Leu Val Ser
    1580                 1585                 1590

Gln Gly  Asp Arg Glu Gln Ala  Pro Asn Leu Val Tyr  Met Val Thr
    1595                 1600                 1605

Gly Asn  Pro Ala Ser Asp Glu  Ile Lys Arg Leu Pro  Gly Asp Ile
    1610                 1615                 1620

Gln Val  Val Pro Ile Gly Val  Gly Pro Asn Ala Asn  Val Gln Glu
    1625                 1630                 1635

Leu Glu  Arg Ile Gly Trp Pro  Asn Ala Pro Ile Leu  Ile Gln Asp
    1640                 1645                 1650

Phe Glu  Thr Leu Pro Arg Glu  Ala Pro Asp Leu Val  Leu Gln Arg
    1655                 1660                 1665

Cys Cys  Ser Gly Glu Gly Leu  Gln Ile Pro Thr Leu  Ser Pro Ala
    1670                 1675                 1680

Pro Asp  Cys Ser Gln Pro Leu  Asp Val Ile Leu Leu  Leu Asp Gly
    1685                 1690                 1695

Ser Ser  Ser Phe Pro Ala Ser  Tyr Phe Asp Glu Met  Lys Ser Phe
    1700                 1705                 1710

Ala Lys  Ala Phe Ile Ser Lys  Ala Asn Ile Gly Pro  Arg Leu Thr
    1715                 1720                 1725

Gln Val  Ser Val Leu Gln Tyr  Gly Ser Ile Thr Thr  Ile Asp Val
    1730                 1735                 1740

Pro Trp  Asn Val Val Pro Glu  Lys Ala His Leu Leu  Ser Leu Val
    1745                 1750                 1755

Asp Val  Met Gln Arg Glu Gly  Gly Pro Ser Gln Ile  Gly Asp Ala
    1760                 1765                 1770

Leu Gly  Phe Ala Val Arg Tyr  Leu Thr Ser Glu Met  His Gly Ala
    1775                 1780                 1785

Arg Pro  Gly Ala Ser Lys Ala  Val Val Ile Leu Val  Thr Asp Val
    1790                 1795                 1800

Ser Val  Asp Ser Val Asp Ala  Ala Ala Asp Ala Ala  Arg Ser Asn
    1805                 1810                 1815

Arg Val  Thr Val Phe Pro Ile  Gly Ile Gly Asp Arg  Tyr Asp Ala
    1820                 1825                 1830

Ala Gln  Leu Arg Ile Leu Ala  Gly Pro Ala Gly Asp  Ser Asn Val
    1835                 1840                 1845

Val Lys  Leu Gln Arg Ile Glu  Asp Leu Pro Thr Met  Val Thr Leu
```

```
    1850                1855                1860

Gly Asn  Ser Phe Leu His Lys  Leu Cys Ser Gly Phe  Val Arg Ile
    1865                1870                1875

Cys Met  Asp Glu Asp Gly Asn  Glu Lys Arg Pro Gly  Asp Val Trp
    1880                1885                1890

Thr Leu  Pro Asp Gln Cys His  Thr Val Thr Cys Gln  Pro Asp Gly
    1895                1900                1905

Gln Thr  Leu Leu Lys Ser His  Arg Val Asn Cys Asp  Arg Gly Leu
    1910                1915                1920

Arg Pro  Ser Cys Pro Asn Ser  Gln Ser Pro Val Lys  Val Glu Glu
    1925                1930                1935

Thr Cys  Gly Cys Arg Trp Thr  Cys Pro Cys Val Cys  Thr Gly Ser
    1940                1945                1950

Ser Thr  Arg His Ile Val Thr  Phe Asp Gly Gln Asn  Phe Lys Leu
    1955                1960                1965

Thr Gly  Ser Cys Ser Tyr Val  Leu Phe Gln Asn Lys  Glu Gln Asp
    1970                1975                1980

Leu Glu  Val Ile Leu His Asn  Gly Ala Cys Ser Pro  Gly Ala Arg
    1985                1990                1995

Gln Gly  Cys Met Lys Ser Ile  Glu Val Lys His Ser  Ala Leu Ser
    2000                2005                2010

Val Glu  Leu His Ser Asp Met  Glu Val Thr Val Asn  Gly Arg Leu
    2015                2020                2025

Val Ser  Val Pro Tyr Val Gly  Gly Asn Met Glu Val  Asn Val Tyr
    2030                2035                2040

Gly Ala  Ile Met His Glu Val  Arg Phe Asn His Leu  Gly His Ile
    2045                2050                2055

Phe Thr  Phe Thr Pro Gln Asn  Asn Glu Phe Gln Leu  Gln Leu Ser
    2060                2065                2070

Pro Lys  Thr Phe Ala Ser Lys  Thr Tyr Gly Leu Cys  Gly Ile Cys
    2075                2080                2085

Asp Glu  Asn Gly Ala Asn Asp  Phe Met Leu Arg Asp  Gly Thr Val
    2090                2095                2100

Thr Thr  Asp Trp Lys Thr Leu  Val Gln Glu Trp Thr  Val Gln Arg
    2105                2110                2115

Pro Gly  Gln Thr Cys Gln Pro  Ile Leu Glu Glu Gln  Cys Leu Val
    2120                2125                2130

Pro Asp  Ser Ser His Cys Gln  Val Leu Leu Leu Pro  Leu Phe Ala
    2135                2140                2145

Glu Cys  His Lys Val Leu Ala  Pro Ala Thr Phe Tyr  Ala Ile Cys
    2150                2155                2160

Gln Gln  Asp Ser Cys His Gln  Glu Gln Val Cys Glu  Val Ile Ala
    2165                2170                2175

Ser Tyr  Ala His Leu Cys Arg  Thr Asn Gly Val Cys  Val Asp Trp
    2180                2185                2190

Arg Thr  Pro Asp Phe Cys Ala  Met Ser Cys Pro Pro  Ser Leu Val
    2195                2200                2205

Tyr Asn  His Cys Glu His Gly  Cys Pro Arg His Cys  Asp Gly Asn
    2210                2215                2220

Val Ser  Ser Cys Gly Asp His  Pro Ser Glu Gly Cys  Phe Cys Pro
    2225                2230                2235

Pro Asp  Lys Val Met Leu Glu  Gly Ser Cys Val Pro  Glu Glu Ala
    2240                2245                2250
```

```
Cys Thr  Gln Cys Ile Gly Glu  Asp Gly Val Gln His  Gln Phe Leu
    2255                 2260                 2265

Glu Ala  Trp Val Pro Asp His  Gln Pro Cys Gln Ile  Cys Thr Cys
    2270                 2275                 2280

Leu Ser  Gly Arg Lys Val Asn  Cys Thr Thr Gln Pro  Cys Pro Thr
    2285                 2290                 2295

Ala Lys  Ala Pro Thr Cys Gly  Leu Cys Glu Val Ala  Arg Leu Arg
    2300                 2305                 2310

Gln Asn  Ala Asp Gln Cys Cys  Pro Glu Tyr Glu Cys  Val Cys Asp
    2315                 2320                 2325

Pro Val  Ser Cys Asp Leu Pro  Pro Val Pro His Cys  Glu Arg Gly
    2330                 2335                 2340

Leu Gln  Pro Thr Leu Thr Asn  Pro Gly Glu Cys Arg  Pro Asn Phe
    2345                 2350                 2355

Thr Cys  Ala Cys Arg Lys Glu  Glu Cys Lys Arg Val  Ser Pro Pro
    2360                 2365                 2370

Ser Cys  Pro Pro His Arg Leu  Pro Thr Leu Arg Lys  Thr Gln Cys
    2375                 2380                 2385

Cys Asp  Glu Tyr Glu Cys Ala  Cys Asn Cys Val Asn  Ser Thr Val
    2390                 2395                 2400

Ser Cys  Pro Leu Gly Tyr Leu  Ala Ser Thr Ala Thr  Asn Asp Cys
    2405                 2410                 2415

Gly Cys  Thr Thr Thr Thr Cys  Leu Pro Asp Lys Val  Cys Val His
    2420                 2425                 2430

Arg Ser  Thr Ile Tyr Pro Val  Gly Gln Phe Trp Glu  Glu Gly Cys
    2435                 2440                 2445

Asp Val  Cys Thr Cys Thr Asp  Met Glu Asp Ala Val  Met Gly Leu
    2450                 2455                 2460

Arg Val  Ala Gln Cys Ser Gln  Lys Pro Cys Glu Asp  Ser Cys Arg
    2465                 2470                 2475

Ser Gly  Phe Thr Tyr Val Leu  His Glu Gly Glu Cys  Cys Gly Arg
    2480                 2485                 2490

Cys Leu  Pro Ser Ala Cys Glu  Val Val Thr Gly Ser  Pro Arg Gly
    2495                 2500                 2505

Asp Ser  Gln Ser Ser Trp Lys  Ser Val Gly Ser Gln  Trp Ala Ser
    2510                 2515                 2520

Pro Glu  Asn Pro Cys Leu Ile  Asn Glu Cys Val Arg  Val Lys Glu
    2525                 2530                 2535

Glu Val  Phe Ile Gln Gln Arg  Asn Val Ser Cys Pro  Gln Leu Glu
    2540                 2545                 2550

Val Pro  Val Cys Pro Ser Gly  Phe Gln Leu Ser Cys  Lys Thr Ser
    2555                 2560                 2565

Ala Cys  Cys Pro Ser Cys Arg  Cys Glu Arg Met Glu  Ala Cys Met
    2570                 2575                 2580

Leu Asn  Gly Thr Val Ile Gly  Pro Gly Lys Thr Val  Met Ile Asp
    2585                 2590                 2595

Val Cys  Thr Thr Cys Arg Cys  Met Val Gln Val Gly  Val Ile Ser
    2600                 2605                 2610

Gly Phe  Lys Leu Glu Cys Arg  Lys Thr Thr Cys Asn  Pro Cys Pro
    2615                 2620                 2625

Leu Gly  Tyr Lys Glu Glu Asn  Asn Thr Gly Glu Cys  Cys Gly Arg
    2630                 2635                 2640
```

Cys Leu Pro Thr Ala Cys Thr Ile Gln Leu Arg Gly Gly Gln Ile
2645 2650 2655

Met Thr Leu Lys Arg Asp Glu Thr Leu Gln Asp Gly Cys Asp Thr
2660 2665 2670

His Phe Cys Lys Val Asn Glu Arg Gly Glu Tyr Phe Trp Glu Lys
2675 2680 2685

Arg Val Thr Gly Cys Pro Pro Phe Asp Glu His Lys Cys Leu Ala
2690 2695 2700

Glu Gly Gly Lys Ile Met Lys Ile Pro Gly Thr Cys Cys Asp Thr
2705 2710 2715

Cys Glu Glu Pro Glu Cys Asn Asp Ile Thr Ala Arg Leu Gln Tyr
2720 2725 2730

Val Lys Val Gly Ser Cys Lys Ser Glu Val Glu Val Asp Ile His
2735 2740 2745

Tyr Cys Gln Gly Lys Cys Ala Ser Lys Ala Met Tyr Ser Ile Asp
2750 2755 2760

Ile Asn Asp Val Gln Asp Gln Cys Ser Cys Cys Ser Pro Thr Arg
2765 2770 2775

Thr Glu Pro Met Gln Val Ala Leu His Cys Thr Asn Gly Ser Val
2780 2785 2790

Val Tyr His Glu Val Leu Asn Ala Met Glu Cys Lys Cys Ser Pro
2795 2800 2805

Arg Lys Cys Ser Lys
2810

<210> SEQ ID NO 112
<211> LENGTH: 3926
<212> TYPE: PRT
<213> ORGANISM: Artificial Sequence
<220> FEATURE:
<223> OTHER INFORMATION: Synthetic_BSN_HUMAN

<400> SEQUENCE: 112

Met Gly Asn Glu Val Ser Leu Glu Gly Gly Ala Gly Asp Gly Pro Leu
1 5 10 15

Pro Pro Gly Gly Ala Gly Pro Gly Pro Gly Pro Gly Pro Gly Pro Gly
20 25 30

Ala Gly Lys Pro Pro Ser Ala Pro Ala Gly Gly Gly Gln Leu Pro Ala
35 40 45

Ala Gly Ala Ala Arg Ser Thr Ala Val Pro Pro Val Pro Gly Pro Gly
50 55 60

Pro Gly Pro Gly Pro Gly Pro Gly Pro Gly Ser Thr Ser Arg Arg Leu
65 70 75 80

Asp Pro Lys Glu Pro Leu Gly Asn Gln Arg Ala Ala Ser Pro Thr Pro
85 90 95

Lys Gln Ala Ser Ala Thr Thr Pro Gly His Glu Ser Pro Arg Glu Thr
100 105 110

Arg Ala Gln Gly Pro Ala Gly Gln Glu Ala Asp Gly Pro Arg Arg Thr
115 120 125

Leu Gln Val Asp Ser Arg Thr Gln Arg Ser Gly Arg Ser Pro Ser Val
130 135 140

Ser Pro Asp Arg Gly Ser Thr Pro Thr Ser Pro Tyr Ser Val Pro Gln
145 150 155 160

Ile Ala Pro Leu Pro Ser Ser Thr Leu Cys Pro Ile Cys Lys Thr Ser
165 170 175

```
Asp Leu Thr Ser Thr Pro Ser Gln Pro Asn Phe Asn Thr Cys Thr Gln
            180                 185                 190

Cys His Asn Lys Val Cys Asn Gln Cys Gly Phe Asn Pro Asn Pro His
        195                 200                 205

Leu Thr Gln Val Lys Glu Trp Leu Cys Leu Asn Cys Gln Met Gln Arg
    210                 215                 220

Ala Leu Gly Met Asp Met Thr Thr Ala Pro Arg Ser Lys Ser Gln Gln
225                 230                 235                 240

Gln Leu His Ser Pro Ala Leu Ser Pro Ala His Ser Pro Ala Lys Gln
                245                 250                 255

Pro Leu Gly Lys Pro Asp Gln Glu Arg Ser Arg Gly Pro Gly Gly Pro
            260                 265                 270

Gln Pro Gly Ser Arg Gln Ala Glu Thr Ala Arg Ala Thr Ser Val Pro
        275                 280                 285

Gly Pro Ala Gln Ala Ala Ala Pro Pro Glu Val Gly Arg Val Ser Pro
    290                 295                 300

Gln Pro Pro Gln Pro Thr Lys Pro Ser Thr Ala Glu Pro Arg Pro Pro
305                 310                 315                 320

Ala Gly Glu Ala Pro Ala Lys Ser Ala Thr Ala Val Pro Ala Gly Leu
                325                 330                 335

Gly Ala Thr Glu Gln Thr Gln Glu Gly Leu Thr Gly Lys Leu Phe Gly
            340                 345                 350

Leu Gly Ala Ser Leu Leu Thr Gln Ala Ser Thr Leu Met Ser Val Gln
        355                 360                 365

Pro Glu Ala Asp Thr Gln Gly Gln Pro Ala Pro Ser Lys Gly Thr Pro
    370                 375                 380

Lys Ile Val Phe Asn Asp Ala Ser Lys Glu Ala Gly Pro Lys Pro Leu
385                 390                 395                 400

Gly Ser Gly Pro Gly Pro Gly Pro Ala Pro Gly Ala Lys Thr Glu Pro
                405                 410                 415

Gly Ala Arg Met Gly Pro Gly Ser Gly Pro Gly Ala Leu Pro Lys Thr
            420                 425                 430

Gly Gly Thr Thr Ser Pro Lys His Gly Arg Ala Glu His Gln Ala Ala
        435                 440                 445

Ser Lys Ala Ala Ala Lys Pro Lys Thr Met Pro Lys Glu Arg Ala Ile
    450                 455                 460

Cys Pro Leu Cys Gln Ala Glu Leu Asn Val Gly Ser Lys Ser Pro Ala
465                 470                 475                 480

Asn Tyr Asn Thr Cys Thr Thr Cys Arg Leu Gln Val Cys Asn Leu Cys
                485                 490                 495

Gly Phe Asn Pro Thr Pro His Leu Val Glu Lys Thr Glu Trp Leu Cys
            500                 505                 510

Leu Asn Cys Gln Thr Lys Arg Leu Leu Glu Gly Ser Leu Gly Glu Pro
        515                 520                 525

Thr Pro Leu Pro Pro Pro Thr Ser Gln Gln Pro Pro Val Gly Ala Pro
    530                 535                 540

His Arg Ala Ser Gly Thr Ser Pro Leu Lys Gln Lys Gly Pro Gln Gly
545                 550                 555                 560

Leu Gly Gln Pro Ser Gly Pro Leu Pro Ala Lys Ala Ser Pro Leu Ser
                565                 570                 575

Thr Lys Ala Ser Pro Leu Pro Ser Lys Ala Ser Pro Gln Ala Lys Pro
            580                 585                 590

Leu Arg Ala Ser Glu Pro Ser Lys Thr Pro Ser Ser Val Gln Glu Lys
```

```
        595                 600                 605

Lys Thr Arg Val Pro Thr Lys Ala Glu Pro Met Pro Lys Pro Pro Pro
    610                 615                 620

Glu Thr Thr Pro Thr Pro Ala Thr Pro Lys Val Lys Ser Gly Val Arg
625                 630                 635                 640

Arg Ala Glu Pro Ala Thr Pro Val Val Lys Ala Val Pro Glu Ala Pro
                645                 650                 655

Lys Gly Gly Glu Ala Glu Asp Leu Val Gly Lys Pro Tyr Ser Gln Asp
            660                 665                 670

Ala Ser Arg Ser Pro Gln Ser Leu Ser Asp Thr Gly Tyr Ser Ser Asp
        675                 680                 685

Gly Ile Ser Ser Ser Gln Ser Glu Ile Thr Gly Val Val Gln Gln Glu
    690                 695                 700

Val Glu Gln Leu Asp Ser Ala Gly Val Thr Gly Pro His Pro Pro Ser
705                 710                 715                 720

Pro Ser Glu Ile His Lys Val Gly Ser Ser Met Arg Pro Leu Leu Gln
                725                 730                 735

Ala Gln Gly Leu Ala Pro Ser Glu Arg Ser Lys Pro Leu Ser Ser Gly
            740                 745                 750

Thr Gly Glu Glu Gln Lys Gln Arg Pro His Ser Leu Ser Ile Thr Pro
        755                 760                 765

Glu Ala Phe Asp Ser Asp Glu Glu Leu Glu Asp Ile Leu Glu Glu Asp
    770                 775                 780

Glu Asp Ser Ala Glu Trp Arg Arg Arg Arg Glu Gln Gln Asp Thr Ala
785                 790                 795                 800

Glu Ser Ser Asp Asp Phe Gly Ser Gln Leu Arg His Asp Tyr Val Glu
                805                 810                 815

Asp Ser Ser Glu Gly Gly Leu Ser Pro Leu Pro Pro Gln Pro Pro Ala
            820                 825                 830

Arg Ala Ala Glu Leu Thr Asp Glu Asp Phe Met Arg Arg Gln Ile Leu
        835                 840                 845

Glu Met Ser Ala Glu Glu Asp Asn Leu Glu Glu Asp Asp Thr Ala Thr
    850                 855                 860

Ser Gly Arg Gly Leu Ala Lys His Gly Thr Gln Lys Gly Gly Pro Arg
865                 870                 875                 880

Pro Arg Pro Glu Pro Ser Gln Glu Pro Ala Ala Leu Pro Lys Arg Arg
                885                 890                 895

Leu Pro His Asn Ala Thr Thr Gly Tyr Glu Glu Leu Leu Pro Glu Gly
            900                 905                 910

Gly Ser Ala Glu Ala Thr Asp Gly Ser Gly Thr Leu Gln Gly Gly Leu
        915                 920                 925

Arg Arg Phe Lys Thr Ile Glu Leu Asn Ser Thr Gly Ser Tyr Gly His
    930                 935                 940

Glu Leu Asp Leu Gly Gln Gly Pro Asp Pro Ser Leu Asp Arg Glu Pro
945                 950                 955                 960

Glu Leu Glu Met Glu Ser Leu Thr Gly Ser Pro Glu Asp Arg Ser Arg
                965                 970                 975

Gly Glu His Ser Ser Thr Leu Pro Ala Ser Thr Pro Ser Tyr Thr Ser
            980                 985                 990

Gly Thr Ser Pro Thr Ser Leu Ser  Ser Leu Glu Glu Asp  Ser Asp Ser
        995                 1000                1005

Ser Pro  Ser Arg Arg Gln Arg  Leu Glu Glu Ala Lys  Gln Gln Arg
    1010                1015                1020
```

```
Lys Ala  Arg His Arg Ser His  Gly Pro Leu Leu Pro  Thr Ile Glu
    1025                 1030                 1035

Asp Ser  Ser Glu Glu Glu Glu  Leu Arg Glu Glu Glu  Glu Leu Leu
    1040                 1045                 1050

Arg Glu  Gln Glu Lys Met Arg  Glu Val Glu Gln Gln  Arg Ile Arg
    1055                 1060                 1065

Ser Thr  Ala Arg Lys Thr Arg  Arg Asp Lys Glu Glu  Leu Arg Ala
    1070                 1075                 1080

Gln Arg  Arg Arg Glu Arg Ser  Lys Thr Pro Pro Ser  Asn Leu Ser
    1085                 1090                 1095

Pro Ile  Glu Asp Ala Ser Pro  Thr Glu Glu Leu Arg  Gln Ala Ala
    1100                 1105                 1110

Glu Met  Glu Glu Leu His Arg  Ser Ser Cys Ser Glu  Tyr Ser Pro
    1115                 1120                 1125

Ser Pro  Ser Leu Asp Ser Glu  Ala Glu Ala Leu Asp  Gly Gly Pro
    1130                 1135                 1140

Ser Arg  Leu Tyr Lys Ser Gly  Ser Glu Tyr Asn Leu  Pro Thr Phe
    1145                 1150                 1155

Met Ser  Leu Tyr Ser Pro Thr  Glu Thr Pro Ser Gly  Ser Ser Thr
    1160                 1165                 1170

Thr Pro  Ser Ser Gly Arg Pro  Leu Lys Ser Ala Glu  Glu Ala Tyr
    1175                 1180                 1185

Glu Glu  Met Met Arg Lys Ala  Glu Leu Leu Gln Arg  Gln Gln Gly
    1190                 1195                 1200

Gln Ala  Ala Gly Ala Arg Gly  Pro His Gly Gly Pro  Ser Gln Pro
    1205                 1210                 1215

Thr Gly  Pro Arg Gly Leu Gly  Ser Phe Glu Tyr Gln  Asp Thr Thr
    1220                 1225                 1230

Asp Arg  Glu Tyr Gly Gln Ala  Ala Gln Pro Ala Ala  Glu Gly Thr
    1235                 1240                 1245

Pro Ala  Ser Leu Gly Ala Ala  Val Tyr Glu Glu Ile  Leu Gln Thr
    1250                 1255                 1260

Ser Gln  Ser Ile Val Arg Met  Arg Gln Ala Ser Ser  Arg Asp Leu
    1265                 1270                 1275

Ala Phe  Ala Glu Asp Lys Lys  Lys Glu Lys Gln Phe  Leu Asn Ala
    1280                 1285                 1290

Glu Ser  Ala Tyr Met Asp Pro  Met Lys Gln Asn Gly  Gly Pro Leu
    1295                 1300                 1305

Thr Pro  Gly Thr Ser Pro Thr  Gln Leu Ala Ala Pro  Val Ser Phe
    1310                 1315                 1320

Ser Thr  Pro Thr Ser Ser Asp  Ser Ser Gly Gly Arg  Val Ile Pro
    1325                 1330                 1335

Asp Val  Arg Val Thr Gln His  Phe Ala Lys Glu Thr  Gln Asp Pro
    1340                 1345                 1350

Leu Lys  Leu His Ser Ser Pro  Ala Ser Pro Ser Ser  Ala Ser Lys
    1355                 1360                 1365

Glu Ile  Gly Met Pro Phe Ser  Gln Gly Pro Gly Thr  Pro Ala Thr
    1370                 1375                 1380

Thr Ala  Val Ala Pro Cys Pro  Ala Gly Leu Pro Arg  Gly Tyr Met
    1385                 1390                 1395

Thr Pro  Ala Ser Pro Ala Gly  Ser Glu Arg Ser Pro  Ser Pro Ser
    1400                 1405                 1410
```

```
Ser Thr  Ala His Ser Tyr Gly  His Ser Pro Thr Thr  Ala Asn Tyr
    1415                 1420                 1425

Gly Ser  Gln Thr Glu Asp Leu  Pro Gln Ala Pro Ser  Gly Leu Ala
    1430                 1435                 1440

Ala Ala  Gly Arg Ala Ala Arg  Glu Lys Pro Leu Ser  Ala Ser Asp
    1445                 1450                 1455

Gly Glu  Gly Gly Thr Pro Gln  Pro Ser Arg Ala Tyr  Ser Tyr Phe
    1460                 1465                 1470

Ala Ser  Ser Ser Pro Pro Leu  Ser Pro Ser Ser Pro  Ser Glu Ser
    1475                 1480                 1485

Pro Thr  Phe Ser Pro Gly Lys  Met Gly Pro Arg Ala  Thr Ala Glu
    1490                 1495                 1500

Phe Ser  Thr Gln Thr Pro Ser  Pro Ala Pro Ala Ser  Asp Met Pro
    1505                 1510                 1515

Arg Ser  Pro Gly Ala Pro Thr  Pro Ser Pro Met Val  Ala Gln Gly
    1520                 1525                 1530

Thr Gln  Thr Pro His Arg Pro  Ser Thr Pro Arg Leu  Val Trp Gln
    1535                 1540                 1545

Glu Ser  Ser Gln Glu Ala Pro  Phe Met Val Ile Thr  Leu Ala Ser
    1550                 1555                 1560

Asp Ala  Ser Ser Gln Thr Arg  Met Val His Ala Ser  Ala Ser Thr
    1565                 1570                 1575

Ser Pro  Leu Cys Ser Pro Thr  Glu Thr Gln Pro Thr  Thr His Gly
    1580                 1585                 1590

Tyr Ser  Gln Thr Thr Pro Pro  Ser Val Ser Gln Leu  Pro Pro Glu
    1595                 1600                 1605

Pro Pro  Gly Pro Pro Gly Phe  Pro Arg Val Pro Ser  Ala Gly Ala
    1610                 1615                 1620

Asp Gly  Pro Leu Ala Leu Tyr  Gly Trp Gly Ala Leu  Pro Ala Glu
    1625                 1630                 1635

Asn Ile  Ser Leu Cys Arg Ile  Ser Ser Val Pro Gly  Thr Ser Arg
    1640                 1645                 1650

Val Glu  Pro Gly Pro Arg Thr  Pro Gly Thr Ala Val  Val Asp Leu
    1655                 1660                 1665

Arg Thr  Ala Val Lys Pro Thr  Pro Ile Ile Leu Thr  Asp Gln Gly
    1670                 1675                 1680

Met Asp  Leu Thr Ser Leu Ala  Val Glu Ala Arg Lys  Tyr Gly Leu
    1685                 1690                 1695

Ala Leu  Asp Pro Ile Pro Gly  Arg Gln Ser Thr Ala  Val Gln Pro
    1700                 1705                 1710

Leu Val  Ile Asn Leu Asn Ala  Gln Glu His Thr Phe  Leu Ala Thr
    1715                 1720                 1725

Ala Thr  Thr Val Ser Ile Thr  Met Ala Ser Ser Val  Phe Met Ala
    1730                 1735                 1740

Gln Gln  Lys Gln Pro Val Val  Tyr Gly Asp Pro Tyr  Gln Ser Arg
    1745                 1750                 1755

Leu Asp  Phe Gly Gln Gly Gly  Gly Ser Pro Val Cys  Leu Ala Gln
    1760                 1765                 1770

Val Lys  Gln Val Glu Gln Ala  Val Gln Thr Ala Pro  Tyr Arg Ser
    1775                 1780                 1785

Gly Pro  Arg Gly Arg Pro Arg  Glu Ala Lys Phe Ala  Arg Tyr Asn
    1790                 1795                 1800

Leu Pro  Asn Gln Val Ala Pro  Leu Ala Arg Arg Asp  Val Leu Ile
```

```
    1805                1810                1815

Thr Gln  Met Gly Thr Ala Gln  Ser Ile Gly Leu Lys  Pro Gly Pro
    1820                1825                1830

Val Pro  Glu Pro Gly Ala Glu  Pro His Arg Ala Thr  Pro Ala Glu
    1835                1840                1845

Leu Arg  Ser His Ala Leu Pro  Gly Ala Arg Lys Pro  His Thr Val
    1850                1855                1860

Val Val  Gln Met Gly Glu Gly  Thr Ala Gly Thr Val  Thr Thr Leu
    1865                1870                1875

Leu Pro  Glu Glu Pro Ala Gly  Ala Leu Asp Leu Thr  Gly Met Arg
    1880                1885                1890

Pro Glu  Ser Gln Leu Ala Cys  Cys Asp Met Val Tyr  Lys Leu Pro
    1895                1900                1905

Phe Gly  Ser Ser Cys Thr Gly  Thr Phe His Pro Ala  Pro Ser Val
    1910                1915                1920

Pro Glu  Lys Ser Met Ala Asp  Ala Ala Pro Pro Gly  Gln Ser Ser
    1925                1930                1935

Ser Pro  Phe Tyr Gly Pro Arg  Asp Pro Glu Pro Pro  Glu Pro Pro
    1940                1945                1950

Thr Tyr  Arg Ala Gln Gly Val  Val Gly Pro Gly Pro  His Glu Glu
    1955                1960                1965

Gln Arg  Pro Tyr Pro Gln Gly  Leu Pro Gly Arg Leu  Tyr Ser Ser
    1970                1975                1980

Met Ser  Asp Thr Asn Leu Ala  Glu Ala Gly Leu Asn  Tyr His Ala
    1985                1990                1995

Gln Arg  Ile Gly Gln Leu Phe  Gln Gly Pro Gly Arg  Asp Ser Ala
    2000                2005                2010

Met Asp  Leu Ser Ser Leu Lys  His Ser Tyr Ser Leu  Gly Phe Ala
    2015                2020                2025

Asp Gly  Arg Tyr Leu Gly Gln  Gly Leu Gln Tyr Gly  Ser Val Thr
    2030                2035                2040

Asp Leu  Arg His Pro Thr Asp  Leu Leu Ala His Pro  Leu Pro Met
    2045                2050                2055

Arg Arg  Tyr Ser Ser Val Ser  Asn Ile Tyr Ser Asp  His Arg Tyr
    2060                2065                2070

Gly Pro  Arg Gly Asp Ala Val  Gly Phe Gln Glu Ala  Ser Leu Ala
    2075                2080                2085

Gln Tyr  Ser Ala Thr Thr Ala  Arg Glu Ile Ser Arg  Met Cys Ala
    2090                2095                2100

Ala Leu  Asn Ser Met Asp Gln  Tyr Gly Gly Arg His  Gly Ser Gly
    2105                2110                2115

Gly Gly  Gly Pro Asp Leu Val  Gln Tyr Gln Pro Gln  His Gly Pro
    2120                2125                2130

Gly Leu  Ser Ala Pro Gln Ser  Leu Val Pro Leu Arg  Pro Gly Leu
    2135                2140                2145

Leu Gly  Asn Pro Thr Phe Pro  Glu Gly His Pro Ser  Pro Gly Asn
    2150                2155                2160

Leu Ala  Gln Tyr Gly Pro Ala  Ala Gly Gln Gly Thr  Ala Val Arg
    2165                2170                2175

Gln Leu  Leu Pro Ser Thr Ala  Thr Val Arg Ala Ala  Asp Gly Met
    2180                2185                2190

Ile Tyr  Ser Thr Ile Asn Thr  Pro Ile Ala Ala Thr  Leu Pro Ile
    2195                2200                2205
```

```
Thr Thr  Gln Pro Ala Ser Val  Leu Arg Pro Met Val  Arg Gly Gly
    2210                 2215                 2220

Met Tyr  Arg Pro Tyr Ala Ser  Gly Gly Ile Thr Ala  Val Pro Leu
    2225                 2230                 2235

Thr Ser  Leu Thr Arg Val Pro  Met Ile Ala Pro Arg  Val Pro Leu
    2240                 2245                 2250

Gly Pro  Thr Gly Leu Tyr Arg  Tyr Pro Ala Pro Ser  Arg Phe Pro
    2255                 2260                 2265

Ile Ala  Ser Ser Val Pro Pro  Ala Glu Gly Pro Val  Tyr Leu Gly
    2270                 2275                 2280

Lys Pro  Ala Ala Ala Lys Ala  Pro Gly Ala Gly Gly  Pro Ser Arg
    2285                 2290                 2295

Pro Glu  Met Pro Val Gly Ala  Ala Arg Glu Glu Pro  Leu Pro Thr
    2300                 2305                 2310

Thr Thr  Pro Ala Ala Ile Lys  Glu Ala Ala Gly Ala  Pro Ala Pro
    2315                 2320                 2325

Ala Pro  Leu Ala Gly Gln Lys  Pro Pro Ala Asp Ala  Ala Pro Gly
    2330                 2335                 2340

Gly Gly  Ser Gly Ala Leu Ser  Arg Pro Gly Phe Glu  Lys Glu Glu
    2345                 2350                 2355

Ala Ser  Gln Glu Glu Arg Gln  Arg Lys Gln Gln Glu  Gln Leu Leu
    2360                 2365                 2370

Gln Leu  Glu Arg Glu Arg Val  Glu Leu Glu Lys Leu  Arg Gln Leu
    2375                 2380                 2385

Arg Leu  Gln Glu Glu Leu Glu  Arg Glu Arg Val Glu  Leu Gln Arg
    2390                 2395                 2400

His Arg  Glu Glu Glu Gln Leu  Leu Val Gln Arg Glu  Leu Gln Glu
    2405                 2410                 2415

Leu Gln  Thr Ile Lys His His  Val Leu Gln Gln Gln  Gln Glu Glu
    2420                 2425                 2430

Arg Gln  Ala Gln Phe Ala Leu  Gln Arg Glu Gln Leu  Ala Gln Gln
    2435                 2440                 2445

Arg Leu  Gln Leu Glu Gln Ile  Gln Gln Leu Gln Gln  Gln Leu Gln
    2450                 2455                 2460

Gln Gln  Leu Glu Glu Gln Lys  Gln Arg Gln Lys Ala  Pro Phe Pro
    2465                 2470                 2475

Ala Ala  Cys Glu Ala Pro Gly  Arg Gly Pro Pro Leu  Ala Ala Ala
    2480                 2485                 2490

Glu Leu  Ala Gln Asn Gly Gln  Tyr Trp Pro Pro Leu  Thr His Ala
    2495                 2500                 2505

Ala Phe  Ile Ala Met Ala Gly  Pro Glu Gly Leu Gly  Gln Pro Arg
    2510                 2515                 2520

Glu Pro  Val Leu His Arg Gly  Leu Pro Ser Ser Ala  Ser Asp Met
    2525                 2530                 2535

Ser Leu  Gln Thr Glu Glu Gln  Trp Glu Ala Ser Arg  Ser Gly Ile
    2540                 2545                 2550

Lys Lys  Arg His Ser Met Pro  Arg Leu Arg Asp Ala  Cys Glu Leu
    2555                 2560                 2565

Glu Ser  Gly Thr Glu Pro Cys  Val Val Arg Arg Ile  Ala Asp Ser
    2570                 2575                 2580

Ser Val  Gln Thr Asp Asp Glu  Asp Gly Glu Ser Arg  Tyr Leu Leu
    2585                 2590                 2595
```

```
Ser Arg  Arg Arg Arg Ala Arg  Arg Ser Ala Asp Cys  Ser Val Gln
    2600                 2605                 2610

Thr Asp  Asp Glu Asp Ser Ala  Glu Trp Glu Gln Pro  Val Arg Arg
    2615                 2620                 2625

Arg Arg  Ser Arg Leu Pro Arg  His Ser Asp Ser Gly  Ser Asp Ser
    2630                 2635                 2640

Lys His  Asp Ala Thr Ala Ser  Ser Ser Ser Ala Ala  Ala Thr Val
    2645                 2650                 2655

Arg Ala  Met Ser Ser Val Gly  Ile Gln Thr Ile Ser  Asp Cys Ser
    2660                 2665                 2670

Val Gln  Thr Glu Pro Asp Gln  Leu Pro Arg Val Ser  Pro Ala Ile
    2675                 2680                 2685

His Ile  Thr Ala Ala Thr Asp  Pro Lys Val Glu Ile  Val Arg Tyr
    2690                 2695                 2700

Ile Ser  Ala Pro Glu Lys Thr  Gly Arg Gly Glu Ser  Leu Ala Cys
    2705                 2710                 2715

Gln Thr  Glu Pro Asp Gly Gln  Ala Gln Gly Val Ala  Gly Pro Gln
    2720                 2725                 2730

Leu Val  Gly Pro Thr Ala Ile  Ser Pro Tyr Leu Pro  Gly Ile Gln
    2735                 2740                 2745

Ile Val  Thr Pro Gly Pro Leu  Gly Arg Phe Glu Lys  Lys Lys Pro
    2750                 2755                 2760

Asp Pro  Leu Glu Ile Gly Tyr  Gln Ala His Leu Pro  Pro Glu Ser
    2765                 2770                 2775

Leu Ser  Gln Leu Val Ser Arg  Gln Pro Pro Lys Ser  Pro Gln Val
    2780                 2785                 2790

Leu Tyr  Ser Pro Val Ser Pro  Leu Ser Pro His Arg  Leu Leu Asp
    2795                 2800                 2805

Thr Ser  Phe Ala Ser Ser Glu  Arg Leu Asn Lys Ala  His Val Ser
    2810                 2815                 2820

Pro Gln  Lys His Phe Thr Ala  Asp Ser Ala Leu Arg  Gln Gln Thr
    2825                 2830                 2835

Leu Pro  Arg Pro Met Lys Thr  Leu Gln Arg Ser Leu  Ser Asp Pro
    2840                 2845                 2850

Lys Pro  Leu Ser Pro Thr Ala  Glu Glu Ser Ala Lys  Glu Arg Phe
    2855                 2860                 2865

Ser Leu  Tyr Gln His Gln Gly  Gly Leu Gly Ser Gln  Val Ser Ala
    2870                 2875                 2880

Leu Pro  Pro Asn Ser Leu Val  Arg Lys Val Lys Arg  Thr Leu Pro
    2885                 2890                 2895

Ser Pro  Pro Pro Glu Glu Ala  His Leu Pro Leu Ala  Gly Gln Ala
    2900                 2905                 2910

Ser Pro  Gln Leu Tyr Ala Ala  Ser Leu Leu Gln Arg  Gly Leu Thr
    2915                 2920                 2925

Gly Pro  Thr Thr Val Pro Ala  Thr Lys Ala Ser Leu  Leu Arg Glu
    2930                 2935                 2940

Leu Asp  Arg Asp Leu Arg Leu  Val Glu His Glu Ser  Thr Lys Leu
    2945                 2950                 2955

Arg Lys  Lys Gln Ala Glu Leu  Asp Glu Glu Glu Lys  Glu Ile Asp
    2960                 2965                 2970

Ala Lys  Leu Lys Tyr Leu Glu  Leu Gly Ile Thr Gln  Arg Lys Glu
    2975                 2980                 2985

Ser Leu  Ala Lys Asp Arg Gly  Gly Arg Asp Tyr Pro  Pro Leu Arg
```

```
    2990                 2995                 3000

Gly Leu  Gly Glu His Arg Asp  Tyr Leu Ser Asp Ser  Glu Leu Asn
    3005                 3010                 3015

Gln Leu  Arg Leu Gln Gly Cys  Thr Thr Pro Ala Gly  Gln Phe Val
    3020                 3025                 3030

Asp Phe  Pro Ala Thr Ala Ala  Ala Pro Ala Thr Pro  Ser Gly Pro
    3035                 3040                 3045

Thr Ala  Phe Gln Gln Pro Arg  Phe Gln Pro Pro Ala  Pro Gln Tyr
    3050                 3055                 3060

Ser Ala  Gly Ser Gly Gly Pro  Thr Gln Asn Gly Phe  Pro Ala His
    3065                 3070                 3075

Gln Ala  Pro Thr Tyr Pro Gly  Pro Ser Thr Tyr Pro  Ala Pro Ala
    3080                 3085                 3090

Phe Pro  Pro Gly Ala Ser Tyr  Pro Ala Glu Pro Gly  Leu Pro Asn
    3095                 3100                 3105

Gln Gln  Ala Phe Arg Pro Thr  Gly His Tyr Ala Gly  Gln Thr Pro
    3110                 3115                 3120

Met Pro  Thr Thr Gln Ser Thr  Leu Phe Pro Val Pro  Ala Asp Ser
    3125                 3130                 3135

Arg Ala  Pro Leu Gln Lys Pro  Arg Gln Thr Ser Leu  Ala Asp Leu
    3140                 3145                 3150

Glu Gln  Lys Val Pro Thr Asn  Tyr Glu Val Ile Ala  Ser Pro Val
    3155                 3160                 3165

Val Pro  Met Ser Ser Ala Pro  Ser Glu Thr Ser Tyr  Ser Gly Pro
    3170                 3175                 3180

Ala Val  Ser Ser Gly Tyr Glu  Gln Gly Lys Val Pro  Glu Val Pro
    3185                 3190                 3195

Arg Ala  Gly Asp Arg Gly Ser  Val Ser Gln Ser Pro  Ala Pro Thr
    3200                 3205                 3210

Tyr Pro  Ser Asp Ser His Tyr  Thr Ser Leu Glu Gln  Asn Val Pro
    3215                 3220                 3225

Arg Asn  Tyr Val Met Ile Asp  Asp Ile Ser Glu Leu  Thr Lys Asp
    3230                 3235                 3240

Ser Thr  Ser Thr Ala Pro Asp  Ser Gln Arg Leu Glu  Pro Leu Gly
    3245                 3250                 3255

Pro Gly  Ser Ser Gly Arg Pro  Gly Lys Glu Pro Gly  Glu Pro Gly
    3260                 3265                 3270

Val Leu  Asp Gly Pro Thr Leu  Pro Cys Cys Tyr Ala  Arg Gly Glu
    3275                 3280                 3285

Glu Glu  Ser Glu Glu Asp Ser  Tyr Asp Pro Arg Gly  Lys Gly Gly
    3290                 3295                 3300

His Leu  Arg Ser Met Glu Ser  Asn Gly Arg Pro Ala  Ser Thr His
    3305                 3310                 3315

Tyr Tyr  Gly Asp Ser Asp Tyr  Arg His Gly Ala Arg  Val Glu Lys
    3320                 3325                 3330

Tyr Gly  Pro Gly Pro Met Gly  Pro Lys His Pro Ser  Lys Ser Leu
    3335                 3340                 3345

Ala Pro  Ala Ala Ile Ser Ser  Lys Arg Ser Lys His  Arg Lys Gln
    3350                 3355                 3360

Gly Met  Glu Gln Lys Ile Ser  Lys Phe Ser Pro Ile  Glu Glu Ala
    3365                 3370                 3375

Lys Asp  Val Glu Ser Asp Leu  Ala Ser Tyr Pro Pro  Pro Ala Val
    3380                 3385                 3390
```

```
Ser Ser Ser Leu Val Ser Arg Gly Arg Lys Phe Gln Asp Glu Ile
    3395                3400                3405

Thr Tyr Gly Leu Lys Lys Asn Val Tyr Glu Gln Gln Lys Tyr Tyr
    3410                3415                3420

Gly Met Ser Ser Arg Asp Ala Val Glu Asp Asp Arg Ile Tyr Gly
    3425                3430                3435

Gly Ser Ser Arg Ser Arg Ala Pro Ser Ala Tyr Ser Gly Glu Lys
    3440                3445                3450

Leu Ser Ser His Asp Phe Ser Gly Trp Gly Lys Gly Tyr Glu Arg
    3455                3460                3465

Glu Arg Glu Ala Val Glu Arg Leu Gln Lys Ala Gly Pro Lys Pro
    3470                3475                3480

Ser Ser Leu Ser Met Ala His Ser Arg Val Arg Pro Pro Met Arg
    3485                3490                3495

Ser Gln Ala Ser Glu Glu Glu Ser Pro Val Ser Pro Leu Gly Arg
    3500                3505                3510

Pro Arg Pro Ala Gly Gly Pro Leu Pro Pro Gly Gly Asp Thr Cys
    3515                3520                3525

Pro Gln Phe Cys Ser Ser His Ser Met Pro Asp Val Gln Glu His
    3530                3535                3540

Val Lys Asp Gly Pro Arg Ala His Ala Tyr Lys Arg Glu Glu Gly
    3545                3550                3555

Tyr Ile Leu Asp Asp Ser His Cys Val Val Ser Asp Ser Glu Ala
    3560                3565                3570

Tyr His Leu Gly Gln Glu Glu Thr Asp Trp Phe Asp Lys Pro Arg
    3575                3580                3585

Asp Ala Arg Ser Asp Arg Phe Arg His His Gly Gly His Ala Val
    3590                3595                3600

Ser Ser Ser Ser Gln Lys Arg Gly Pro Ala Arg His Ser Tyr His
    3605                3610                3615

Asp Tyr Asp Glu Pro Pro Glu Glu Gly Leu Trp Pro His Asp Glu
    3620                3625                3630

Gly Gly Pro Gly Arg His Ala Ser Ala Lys Glu His Arg His Gly
    3635                3640                3645

Asp His Gly Arg His Ser Gly Arg His Thr Gly Glu Glu Pro Gly
    3650                3655                3660

Arg Arg Ala Ala Lys Pro His Ala Arg Asp Leu Gly Arg His Glu
    3665                3670                3675

Ala Arg Pro His Ser Gln Pro Ser Ser Ala Pro Ala Met Pro Lys
    3680                3685                3690

Lys Gly Gln Pro Gly Tyr Pro Ser Ser Ala Glu Tyr Ser Gln Pro
    3695                3700                3705

Ser Arg Ala Ser Ser Ala Tyr His His Ala Ser Asp Ser Lys Lys
    3710                3715                3720

Gly Ser Arg Gln Ala His Ser Gly Pro Ala Ala Leu Gln Ser Lys
    3725                3730                3735

Ala Glu Pro Gln Ala Gln Pro Gln Leu Gln Gly Arg Gln Ala Ala
    3740                3745                3750

Pro Gly Pro Gln Gln Ser Gln Ser Pro Ser Ser Arg Gln Ile Pro
    3755                3760                3765

Ser Gly Ala Ala Ser Arg Gln Pro Gln Thr Gln Gln Gln Gln Gln
    3770                3775                3780
```

```
Gly Leu  Gly Leu Gln Pro Pro  Gln Gln Ala Leu Thr  Gln Ala Arg
    3785                 3790                 3795

Leu Gln  Gln Gln Ser Gln Pro  Thr Thr Arg Gly Ser  Ala Pro Ala
    3800                 3805                 3810

Ala Ser  Gln Pro Ala Gly Lys  Pro Gln Pro Gly Pro  Ser Thr Ala
    3815                 3820                 3825

Thr Gly  Pro Gln Pro Ala Gly  Pro Pro Arg Ala Glu  Gln Thr Asn
    3830                 3835                 3840

Gly Ser  Lys Gly Thr Ala Lys  Ala Pro Gln Gln Gly  Arg Ala Pro
    3845                 3850                 3855

Gln Ala  Gln Pro Ala Pro Gly  Pro Gly Pro Ala Gly  Val Lys Ala
    3860                 3865                 3870

Gly Ala  Arg Pro Gly Gly Thr  Pro Gly Ala Pro Ala  Gly Gln Pro
    3875                 3880                 3885

Gly Ala  Asp Gly Glu Ser Val  Phe Ser Lys Ile Leu  Pro Gly Gly
    3890                 3895                 3900

Ala Ala  Glu Gln Ala Gly Lys  Leu Thr Glu Ala Val  Ser Ala Phe
    3905                 3910                 3915

Gly Lys  Lys Phe Ser Ser Phe  Trp
    3920                 3925


<210> SEQ ID NO 113
<211> LENGTH: 4243
<212> TYPE: PRT
<213> ORGANISM: Artificial Sequence
<220> FEATURE:
<223> OTHER INFORMATION: Synthetic_PKHL1_HUMAN

<400> SEQUENCE: 113

Met Gly His Leu Trp Leu Leu Gly Ile Trp Gly Leu Cys Gly Leu Leu
1               5                   10                  15

Leu Cys Ala Ala Asp Pro Ser Thr Asp Gly Ser Gln Ile Ile Pro Lys
            20                  25                  30

Val Thr Glu Ile Ile Pro Lys Tyr Gly Ser Ile Asn Gly Ala Thr Arg
        35                  40                  45

Leu Thr Ile Arg Gly Glu Gly Phe Ser Gln Ala Asn Gln Phe Asn Tyr
    50                  55                  60

Gly Val Asp Asn Ala Glu Leu Gly Asn Ser Val Gln Leu Ile Ser Ser
65                  70                  75                  80

Phe Gln Ser Ile Thr Cys Asp Val Glu Lys Asp Ala Ser His Ser Thr
                85                  90                  95

Gln Ile Thr Cys Tyr Thr Arg Ala Met Pro Glu Asp Ser Tyr Thr Val
            100                 105                 110

Arg Val Ser Val Asp Gly Val Pro Val Thr Glu Asn Asn Thr Cys Lys
        115                 120                 125

Gly His Ile Asn Ser Trp Glu Cys Thr Phe Asn Ala Lys Ser Phe Arg
    130                 135                 140

Thr Pro Thr Ile Arg Ser Ile Thr Pro Leu Ser Gly Thr Pro Gly Thr
145                 150                 155                 160

Leu Ile Thr Ile Gln Gly Arg Ile Phe Thr Asp Val Tyr Gly Ser Asn
                165                 170                 175

Ile Ala Leu Ser Ser Asn Gly Lys Asn Val Arg Ile Leu Arg Val Tyr
            180                 185                 190

Ile Gly Gly Met Pro Cys Glu Leu Leu Ile Pro Gln Ser Asp Asn Leu
        195                 200                 205
```

```
Tyr Gly Leu Lys Leu Asp His Pro Asn Gly Asp Met Gly Ser Met Val
    210                 215                 220

Cys Lys Thr Thr Gly Thr Phe Ile Gly His His Asn Val Ser Phe Ile
225                 230                 235                 240

Leu Asp Asn Asp Tyr Gly Arg Ser Phe Pro Gln Lys Met Ala Tyr Phe
                245                 250                 255

Val Ser Ser Leu Asn Lys Ile Ala Met Phe Gln Thr Tyr Ala Glu Val
            260                 265                 270

Thr Met Ile Phe Pro Ser Gln Gly Ser Ile Arg Gly Gly Thr Thr Leu
        275                 280                 285

Thr Ile Ser Gly Arg Phe Phe Asp Gln Thr Asp Phe Pro Val Arg Val
    290                 295                 300

Leu Val Gly Gly Glu Pro Cys Asp Ile Leu Asn Val Thr Glu Asn Ser
305                 310                 315                 320

Ile Cys Cys Lys Thr Pro Pro Lys Pro His Ile Leu Lys Thr Val Tyr
                325                 330                 335

Pro Gly Gly Arg Gly Leu Lys Leu Glu Val Trp Asn Asn Ser Arg Pro
            340                 345                 350

Ile Arg Leu Glu Glu Ile Leu Glu Tyr Asn Glu Lys Thr Pro Gly Tyr
        355                 360                 365

Met Gly Ala Ser Trp Val Asp Ser Ala Ser Tyr Ile Trp Leu Met Glu
    370                 375                 380

Gln Asp Thr Phe Val Ala Arg Phe Ser Gly Phe Leu Val Ala Pro Asp
385                 390                 395                 400

Ser Asp Val Tyr Arg Phe Tyr Ile Lys Gly Asp Asp Arg Tyr Ala Ile
                405                 410                 415

Tyr Phe Ser Gln Thr Gly Leu Pro Glu Asp Lys Val Arg Ile Ala Tyr
            420                 425                 430

His Ser Ala Asn Ala Asn Ser Tyr Phe Ser Ser Pro Thr Gln Arg Ser
        435                 440                 445

Asp Asp Ile His Leu Gln Lys Gly Lys Glu Tyr Tyr Ile Glu Ile Leu
    450                 455                 460

Leu Gln Glu Tyr Arg Leu Ser Ala Phe Val Asp Val Gly Leu Tyr Gln
465                 470                 475                 480

Tyr Arg Asn Val Tyr Thr Glu Gln Gln Thr Gly Asp Ala Val Asn Glu
                485                 490                 495

Glu Gln Val Ile Lys Ser Gln Ser Thr Ile Leu Gln Glu Val Gln Val
            500                 505                 510

Ile Thr Leu Glu Asn Trp Glu Thr Thr Asn Ala Ile Asn Glu Val Gln
        515                 520                 525

Lys Ile Lys Val Thr Ser Pro Cys Val Glu Ala Asn Ser Cys Ser Leu
    530                 535                 540

Tyr Gln Tyr Arg Leu Ile Tyr Asn Met Glu Lys Thr Val Phe Leu Pro
545                 550                 555                 560

Ala Asp Ala Ser Glu Phe Ile Leu Gln Ser Ala Leu Asn Asp Leu Trp
                565                 570                 575

Ser Ile Lys Pro Asp Thr Val Gln Val Ile Arg Thr Gln Asn Pro Gln
            580                 585                 590

Ser Tyr Val Tyr Met Val Thr Phe Ile Ser Thr Arg Gly Asp Phe Asp
        595                 600                 605

Leu Leu Gly Tyr Glu Val Val Glu Gly Asn Asn Val Thr Leu Asp Ile
    610                 615                 620

Thr Glu Gln Thr Lys Gly Lys Pro Asn Leu Glu Thr Phe Thr Leu Asn
```

```
625                 630                 635                 640

Trp Asp Gly Ile Ala Ser Lys Pro Leu Thr Leu Trp Ser Ser Glu Ala
                645                 650                 655

Glu Phe Gln Gly Ala Val Glu Glu Met Val Ser Thr Lys Cys Pro Pro
            660                 665                 670

Gln Ile Ala Asn Phe Glu Glu Gly Phe Val Val Lys Tyr Phe Arg Asp
        675                 680                 685

Tyr Glu Thr Asp Phe Asn Leu Glu His Ile Asn Arg Gly Gln Lys Thr
    690                 695                 700

Ala Glu Thr Asp Ala Tyr Cys Gly Arg Tyr Ser Leu Lys Asn Pro Ala
705                 710                 715                 720

Val Leu Phe Asp Ser Ala Asp Val Lys Pro Asn Arg Arg Pro Tyr Gly
                725                 730                 735

Asp Ile Leu Leu Phe Pro Tyr Asn Gln Leu Cys Leu Ala Tyr Lys Gly
            740                 745                 750

Phe Leu Ala Asn Tyr Ile Gly Leu Lys Phe Gln Tyr Gln Asp Asn Ser
        755                 760                 765

Lys Ile Thr Arg Ser Thr Asp Thr Gln Phe Thr Tyr Asn Phe Ala Tyr
    770                 775                 780

Gly Asn Asn Trp Thr Tyr Thr Cys Ile Asp Leu Leu Asp Leu Val Arg
785                 790                 795                 800

Thr Lys Tyr Thr Gly Thr Asn Val Ser Leu Gln Arg Ile Ser Leu His
                805                 810                 815

Lys Ala Ser Glu Ser Gln Ser Phe Tyr Val Asp Val Val Tyr Ile Gly
            820                 825                 830

His Thr Ser Thr Ile Ser Thr Leu Asp Glu Met Pro Lys Arg Arg Leu
        835                 840                 845

Pro Ala Leu Ala Asn Lys Gly Ile Phe Leu Glu His Phe Gln Val Asn
    850                 855                 860

Gln Thr Lys Thr Asn Gly Pro Thr Met Thr Asn Gln Tyr Ser Val Thr
865                 870                 875                 880

Met Thr Ser Tyr Asn Cys Ser Tyr Asn Ile Pro Met Met Ala Val Ser
                885                 890                 895

Phe Gly Gln Ile Ile Thr His Glu Thr Glu Asn Glu Phe Val Tyr Arg
            900                 905                 910

Gly Asn Asn Trp Pro Gly Glu Ser Lys Ile His Ile Gln Arg Ile Gln
        915                 920                 925

Ala Ala Ser Pro Pro Leu Ser Gly Ser Phe Asp Ile Gln Ala Tyr Gly
    930                 935                 940

His Ile Leu Lys Gly Leu Pro Ala Ala Val Ser Ala Ala Asp Leu Gln
945                 950                 955                 960

Phe Ala Leu Gln Ser Leu Glu Gly Met Gly Arg Ile Ser Val Thr Arg
                965                 970                 975

Glu Gly Thr Cys Ala Gly Tyr Ala Trp Asn Ile Lys Trp Arg Ser Thr
            980                 985                 990

Cys Gly Lys Gln Asn Leu Leu Gln  Ile Asn Asp Ser Asn  Ile Ile Gly
        995                 1000                 1005

Glu Lys  Ala Asn Met Thr Val  Thr Arg Ile Lys Glu  Gly Gly Leu
    1010                 1015                 1020

Phe Arg  Gln His Val Leu Gly  Asp Leu Leu Arg Thr  Pro Ser Gln
    1025                 1030                 1035

Gln Pro  Gln Val Glu Val Tyr  Val Asn Gly Ile Pro  Ala Lys Cys
    1040                 1045                 1050
```

```
Ser Gly  Asp Cys Gly Phe Thr  Trp Asp Ser Asn Ile  Thr Pro Leu
    1055                 1060                 1065

Val Leu  Ala Ile Ser Pro Ser  Gln Gly Ser Tyr Glu  Glu Gly Thr
    1070                 1075                 1080

Ile Leu  Thr Ile Val Gly Ser  Gly Phe Ser Pro Ser  Ser Ala Val
    1085                 1090                 1095

Thr Val  Ser Val Gly Pro Val  Gly Cys Ser Leu Leu  Ser Val Asp
    1100                 1105                 1110

Glu Lys  Glu Leu Lys Cys Gln  Ile Leu Asn Gly Ser  Ala Gly His
    1115                 1120                 1125

Ala Pro  Val Ala Val Ser Met  Ala Asp Val Gly Leu  Ala Gln Asn
    1130                 1135                 1140

Val Gly  Gly Glu Glu Phe Tyr  Phe Val Tyr Gln Ser  Gln Ile Ser
    1145                 1150                 1155

His Ile  Trp Pro Asp Ser Gly  Ser Ile Ala Gly Gly  Thr Leu Leu
    1160                 1165                 1170

Thr Leu  Ser Gly Phe Gly Phe  Asn Glu Asn Ser Lys  Val Leu Val
    1175                 1180                 1185

Gly Asn  Glu Thr Cys Asn Val  Ile Glu Gly Asp Leu  Asn Arg Ile
    1190                 1195                 1200

Thr Cys  Arg Thr Pro Lys Lys  Thr Glu Gly Thr Val  Asp Ile Ser
    1205                 1210                 1215

Val Thr  Thr Asn Gly Phe Gln  Ala Thr Ala Arg Asp  Ala Phe Ser
    1220                 1225                 1230

Tyr Asn  Cys Leu Gln Thr Pro  Ile Ile Thr Asp Phe  Ser Pro Lys
    1235                 1240                 1245

Val Arg  Thr Ile Leu Gly Glu  Val Asn Leu Thr Ile  Lys Gly Tyr
    1250                 1255                 1260

Asn Phe  Gly Asn Glu Leu Thr  Gln Asn Met Ala Val  Tyr Val Gly
    1265                 1270                 1275

Gly Lys  Thr Cys Gln Ile Leu  His Trp Asn Phe Thr  Asp Ile Arg
    1280                 1285                 1290

Cys Leu  Leu Pro Lys Leu Ser  Pro Gly Lys His Asp  Ile Tyr Val
    1295                 1300                 1305

Glu Val  Arg Asn Trp Gly Phe  Ala Ser Thr Arg Asp  Lys Leu Asn
    1310                 1315                 1320

Ser Ser  Ile Gln Tyr Val Leu  Glu Val Thr Ser Met  Phe Pro Gln
    1325                 1330                 1335

Arg Gly  Ser Leu Phe Gly Gly  Thr Glu Ile Thr Ile  Arg Gly Phe
    1340                 1345                 1350

Gly Phe  Ser Thr Ile Pro Ala  Glu Asn Thr Val Leu  Leu Gly Ser
    1355                 1360                 1365

Ile Pro  Cys Asn Val Thr Ser  Ser Ser Glu Asn Val  Ile Lys Cys
    1370                 1375                 1380

Ile Leu  His Ser Thr Gly Asn  Ile Phe Arg Ile Thr  Asn Asn Gly
    1385                 1390                 1395

Lys Asp  Ser Val His Gly Leu  Gly Tyr Ala Trp Ser  Pro Pro Val
    1400                 1405                 1410

Leu Asn  Val Ser Val Gly Asp  Thr Val Ala Trp His  Trp Gln Thr
    1415                 1420                 1425

His Pro  Phe Leu Arg Gly Ile  Gly Tyr Arg Ile Phe  Ser Val Ser
    1430                 1435                 1440
```

```
Ser Pro  Gly Ser Val Ile Tyr  Asp Gly Lys Gly Phe  Thr Ser Gly
    1445                 1450                 1455

Arg Gln  Lys Ser Thr Ser Gly  Ser Phe Ser Tyr Gln  Phe Thr Ser
    1460                 1465                 1470

Pro Gly  Ile His Tyr Tyr Ser  Ser Gly Tyr Val Asp  Glu Ala His
    1475                 1480                 1485

Ser Ile  Phe Leu Gln Gly Val  Ile Asn Val Leu Pro  Ala Glu Thr
    1490                 1495                 1500

Arg His  Ile Pro Leu His Leu  Phe Val Gly Arg Ser  Glu Ala Thr
    1505                 1510                 1515

Tyr Ala  Tyr Gly Gly Pro Glu  Asn Leu His Leu Gly  Ser Ser Val
    1520                 1525                 1530

Ala Gly  Cys Leu Ala Thr Glu  Pro Leu Cys Ser Leu  Asn Asn Thr
    1535                 1540                 1545

Arg Val  Lys Asn Ser Lys Arg  Leu Leu Phe Glu Val  Ser Ser Cys
    1550                 1555                 1560

Phe Ser  Pro Ser Ile Ser Asn  Ile Thr Pro Ser Thr  Gly Thr Val
    1565                 1570                 1575

Asn Glu  Leu Ile Thr Ile Ile  Gly His Gly Phe Ser  Asn Leu Pro
    1580                 1585                 1590

Trp Ala  Asn Lys Val Thr Ile  Gly Ser Tyr Pro Cys  Val Val Glu
    1595                 1600                 1605

Glu Ser  Ser Glu Asp Ser Ile  Thr Cys His Ile Asp  Pro Gln Asn
    1610                 1615                 1620

Ser Met  Asp Val Gly Ile Arg  Glu Thr Val Thr Leu  Thr Val Tyr
    1625                 1630                 1635

Asn Leu  Gly Thr Ala Ile Asn  Thr Leu Ser Asn Glu  Phe Asp Arg
    1640                 1645                 1650

Arg Phe  Val Leu Leu Pro Asn  Ile Asp Leu Val Leu  Pro Asn Ala
    1655                 1660                 1665

Gly Ser  Thr Thr Gly Met Thr  Ser Val Thr Ile Lys  Gly Ser Gly
    1670                 1675                 1680

Phe Ala  Val Ser Ser Ala Gly  Val Lys Val Leu Met  Gly His Phe
    1685                 1690                 1695

Pro Cys  Lys Val Leu Ser Val  Asn Tyr Thr Ala Ile  Glu Cys Glu
    1700                 1705                 1710

Thr Ser  Pro Ala Ala Gln Gln  Leu Val Asp Val Asp  Leu Leu Ile
    1715                 1720                 1725

His Gly  Val Pro Ala Gln Cys  Gln Gly Asn Cys Thr  Phe Ser Tyr
    1730                 1735                 1740

Leu Glu  Ser Ile Thr Pro Tyr  Ile Thr Gly Val Phe  Pro Asn Ser
    1745                 1750                 1755

Val Ile  Gly Ser Val Lys Val  Leu Ile Glu Gly Glu  Gly Leu Gly
    1760                 1765                 1770

Thr Val  Leu Glu Asp Ile Ala  Val Phe Ile Gly Asn  Gln Gln Phe
    1775                 1780                 1785

Arg Ala  Ile Glu Val Asn Glu  Asn Asn Ile Thr Ala  Leu Val Thr
    1790                 1795                 1800

Pro Leu  Pro Val Gly His His  Ser Val Ser Val Val  Val Gly Ser
    1805                 1810                 1815

Lys Gly  Leu Ala Leu Gly Asn  Leu Thr Val Ser Ser  Pro Pro Val
    1820                 1825                 1830

Ala Ser  Leu Ser Pro Thr Ser  Gly Ser Ile Gly Gly  Gly Thr Thr
```

```
    1835                1840                1845

Leu Val  Ile Thr Gly Asn Gly  Phe Tyr Pro Gly Asn  Thr Thr Val
    1850                1855                1860

Thr Ile  Gly Asp Glu Pro Cys  Gln Ile Ile Ser Ile  Asn Pro Asn
    1865                1870                1875

Glu Val  Tyr Cys Arg Thr Pro  Ala Gly Thr Thr Gly  Met Val Asp
    1880                1885                1890

Val Lys  Ile Phe Val Asn Thr  Ile Ala Tyr Pro Pro  Leu Leu Phe
    1895                1900                1905

Thr Tyr  Ala Leu Glu Asp Thr  Pro Phe Leu Arg Gly  Ile Ile Pro
    1910                1915                1920

Ser Arg  Gly Pro Pro Gly Thr  Glu Ile Glu Ile Thr  Gly Ser Asn
    1925                1930                1935

Phe Gly  Phe Glu Ile Leu Glu  Ile Ser Val Met Ile  Asn Asn Ile
    1940                1945                1950

Gln Cys  Asn Val Thr Met Ala  Asn Asp Ser Val Val  Gln Cys Ile
    1955                1960                1965

Val Gly  Asp His Ala Gly Gly  Thr Phe Pro Val Met  Met His His
    1970                1975                1980

Lys Thr  Lys Gly Ser Ala Met  Ser Thr Val Val Phe  Glu Tyr Pro
    1985                1990                1995

Leu Asn  Ile Gln Asn Ile Asn  Pro Ser Gln Gly Ser  Phe Gly Gly
    2000                2005                2010

Gly Gln  Thr Met Thr Val Thr  Gly Thr Gly Phe Asn  Pro Gln Asn
    2015                2020                2025

Ser Ile  Ile Leu Val Cys Gly  Ser Glu Cys Ala Ile  Asp Arg Leu
    2030                2035                2040

Arg Ser  Asp Tyr Thr Thr Leu  Leu Cys Glu Ile Pro  Ser Asn Asn
    2045                2050                2055

Gly Thr  Gly Ala Glu Gln Ala  Cys Glu Val Ser Val  Val Asn Gly
    2060                2065                2070

Lys Asp  Leu Ser Gln Ser Met  Thr Pro Phe Thr Tyr  Ala Val Ser
    2075                2080                2085

Leu Thr  Pro Leu Ile Thr Ala  Val Ser Pro Lys Arg  Gly Ser Thr
    2090                2095                2100

Ala Gly  Gly Thr Arg Leu Thr  Val Val Gly Ser Gly  Phe Ser Glu
    2105                2110                2115

Asn Met  Glu Asp Val His Ile  Thr Ile Ala Glu Ala  Lys Cys Asp
    2120                2125                2130

Val Glu  Tyr Ser Asn Lys Thr  His Ile Ile Cys Met  Thr Asp Ala
    2135                2140                2145

His Thr  Leu Ser Gly Trp Ala  Pro Val Cys Val His  Ile Arg Gly
    2150                2155                2160

Val Gly  Met Ala Lys Leu Asp  Asn Ala Asp Phe Leu  Tyr Val Asp
    2165                2170                2175

Ala Trp  Ser Ser Asn Phe Ser  Trp Gly Gly Lys Ser  Pro Pro Glu
    2180                2185                2190

Glu Gly  Ser Leu Val Val Ile  Thr Lys Gly Gln Thr  Ile Leu Leu
    2195                2200                2205

Asp Gln  Ser Thr Pro Ile Leu  Lys Met Leu Leu Ile  Gln Gly Gly
    2210                2215                2220

Thr Leu  Ile Phe Asp Glu Ala  Asp Ile Glu Leu Gln  Ala Glu Asn
    2225                2230                2235
```

```
Ile Leu  Ile Thr Asp Gly Gly  Val Leu Gln Ile Gly  Thr Glu Thr
    2240                 2245                 2250

Ser Pro  Phe Gln His Lys Ala  Val Ile Thr Leu His  Gly His Leu
    2255                 2260                 2265

Arg Ser  Pro Glu Leu Pro Val  Tyr Gly Ala Lys Thr  Leu Ala Val
    2270                 2275                 2280

Arg Glu  Gly Ile Leu Asp Leu  His Gly Val Pro Val  Pro Val Thr
    2285                 2290                 2295

Trp Thr  Arg Leu Ala His Thr  Ala Lys Ala Gly Glu  Arg Ile Leu
    2300                 2305                 2310

Ile Leu  Gln Glu Ala Val Thr  Trp Lys Pro Gly Asp  Asn Ile Val
    2315                 2320                 2325

Ile Ala  Ser Thr Gly His Arg  His Ser Gln Gly Glu  Asn Glu Lys
    2330                 2335                 2340

Met Thr  Ile Ala Ser Val Ser  Ala Asp Gly Ile Asn  Ile Thr Leu
    2345                 2350                 2355

Ser Asn  Pro Leu Asn Tyr Thr  His Leu Gly Ile Thr  Val Thr Leu
    2360                 2365                 2370

Pro Asp  Gly Thr Leu Phe Glu  Ala Arg Ala Glu Val  Gly Ile Leu
    2375                 2380                 2385

Thr Arg  Asn Ile Leu Ile Arg  Gly Ser Asp Asn Val  Glu Trp Asn
    2390                 2395                 2400

Asn Lys  Ile Pro Ala Cys Pro  Asp Gly Phe Asp Thr  Gly Glu Phe
    2405                 2410                 2415

Ala Thr  Gln Thr Cys Leu Gln  Gly Lys Phe Gly Glu  Glu Ile Gly
    2420                 2425                 2430

Ser Asp  Gln Phe Gly Gly Cys  Val Met Phe His Ala  Pro Val Pro
    2435                 2440                 2445

Gly Ala  Asn Met Val Thr Gly  Arg Ile Glu Tyr Val  Glu Val Phe
    2450                 2455                 2460

His Ala  Gly Gln Ala Phe Arg  Leu Gly Arg Tyr Pro  Ile His Trp
    2465                 2470                 2475

His Leu  Leu Gly Asp Leu Gln  Phe Lys Ser Tyr Val  Arg Gly Cys
    2480                 2485                 2490

Ala Ile  His Gln Ala Tyr Asn  Arg Ala Val Thr Ile  His Asn Thr
    2495                 2500                 2505

His His  Leu Leu Val Glu Arg  Asn Ile Ile Tyr Asp  Ile Lys Gly
    2510                 2515                 2520

Gly Ala  Phe Phe Ile Glu Asp  Gly Ile Glu His Gly  Asn Ile Leu
    2525                 2530                 2535

Gln Tyr  Asn Leu Ala Val Phe  Val Gln Gln Ser Thr  Ser Leu Leu
    2540                 2545                 2550

Asn Asp  Asp Val Thr Pro Ala  Ala Phe Trp Val Thr  Asn Pro Asn
    2555                 2560                 2565

Asn Thr  Ile Arg His Asn Ala  Val Ala Gly Gly Thr  His Phe Gly
    2570                 2575                 2580

Phe Trp  Tyr Arg Met Asn Asn  His Pro Asp Gly Pro  Ser Tyr Asp
    2585                 2590                 2595

Arg Asn  Ile Cys Gln Lys Arg  Val Pro Leu Gly Glu  Phe Phe Asn
    2600                 2605                 2610

Asn Thr  Val His Ser Gln Gly  Trp Phe Gly Met Trp  Ile Phe Glu
    2615                 2620                 2625
```

```
Glu Tyr  Phe Pro Met Gln Thr  Gly Ser Cys Thr Ser  Thr Val Pro
    2630                 2635                 2640

Ala Pro  Ala Ile Phe Asn Ser  Leu Thr Thr Trp Asn  Cys Gln Lys
    2645                 2650                 2655

Gly Ala  Glu Trp Val Asn Gly  Gly Ala Leu Gln Phe  His Asn Phe
    2660                 2665                 2670

Val Met  Val Asn Asn Tyr Glu  Ala Gly Ile Glu Thr  Lys Arg Ile
    2675                 2680                 2685

Leu Ala  Pro Tyr Val Gly Gly  Trp Gly Glu Thr Asn  Gly Ala Val
    2690                 2695                 2700

Ile Lys  Asn Ala Lys Ile Val  Gly His Leu Asp Glu  Leu Gly Met
    2705                 2710                 2715

Gly Ser  Ala Phe Cys Thr Ala  Lys Gly Leu Val Leu  Pro Phe Ser
    2720                 2725                 2730

Glu Gly  Leu Thr Val Ser Ser  Val His Phe Met Asn  Phe Asp Arg
    2735                 2740                 2745

Pro Asn  Cys Val Ala Leu Gly  Val Thr Ser Ile Ser  Gly Val Cys
    2750                 2755                 2760

Asn Asp  Arg Cys Gly Gly Trp  Ser Ala Lys Phe Val  Asp Val Gln
    2765                 2770                 2775

Tyr Ser  His Thr Pro Asn Lys  Ala Gly Phe Arg Trp  Glu His Glu
    2780                 2785                 2790

Met Val  Met Ile Asp Val Asp  Gly Ser Leu Thr Gly  His Lys Gly
    2795                 2800                 2805

His Thr  Val Ile Pro His Ser  Ser Leu Leu Asp Pro  Ser His Cys
    2810                 2815                 2820

Thr Gln  Glu Ala Glu Trp Ser  Ile Gly Phe Pro Gly  Ser Val Cys
    2825                 2830                 2835

Asp Ala  Ser Val Ser Phe His  Arg Leu Ala Phe Asn  Gln Pro Ser
    2840                 2845                 2850

Pro Val  Ser Leu Leu Glu Lys  Asp Val Val Leu Ser  Asp Ser Phe
    2855                 2860                 2865

Gly Thr  Ser Ile Ile Pro Phe  Gln Lys Lys Arg Leu  Thr His Met
    2870                 2875                 2880

Ser Gly  Trp Met Ala Leu Ile  Pro Asn Ala Asn His  Ile Asn Trp
    2885                 2890                 2895

Tyr Phe  Lys Gly Val Asp His  Ile Thr Asn Ile Ser  Tyr Thr Ser
    2900                 2905                 2910

Thr Phe  Tyr Gly Phe Lys Glu  Glu Asp Tyr Val Ile  Ile Ser His
    2915                 2920                 2925

Asn Phe  Thr Gln Asn Pro Asp  Met Phe Asn Ile Ile  Asp Met Arg
    2930                 2935                 2940

Asn Gly  Ser Ser Asn Pro Leu  Asn Trp Asn Thr Ser  Lys Asn Gly
    2945                 2950                 2955

Asp Trp  His Leu Glu Ala Asn  Thr Ser Thr Leu Tyr  Tyr Leu Val
    2960                 2965                 2970

Ser Gly  Arg Asn Asp Leu His  Gln Ser Gln Leu Ile  Ser Gly Asn
    2975                 2980                 2985

Leu Asp  Pro Asp Val Lys Asp  Val Val Ile Asn Phe  Gln Ala Tyr
    2990                 2995                 3000

Cys Cys  Ile Leu Gln Asp Cys  Phe Pro Val His Pro  Pro Ser Arg
    3005                 3010                 3015

Lys Pro  Ile Pro Lys Lys Arg  Pro Ala Thr Tyr Asn  Leu Trp Ser
```

```
    3020                3025                3030

Asn Asp  Ser Phe Trp Gln Ser  Ser Arg Glu Asn Asn  Tyr Thr Val
    3035                3040                3045

Pro His  Pro Gly Ala Asn Val  Ile Ile Pro Glu Gly  Thr Trp Ile
    3050                3055                3060

Val Ala  Asp Ile Asp Met Pro  Ser Met Glu Arg Leu  Ile Ile Trp
    3065                3070                3075

Gly Val  Leu Glu Leu Glu Asp  Lys Tyr Asn Val Gly  Ala Ala Glu
    3080                3085                3090

Ser Ser  Tyr Arg Glu Val Val  Leu Asn Ala Thr Tyr  Ile Ser Leu
    3095                3100                3105

Gln Gly  Gly Arg Leu Ile Gly  Gly Trp Glu Asp Asn  Pro Phe Lys
    3110                3115                3120

Gly Asp  Leu Lys Ile Val Leu  Arg Gly Asn His Thr  Thr Gln Asp
    3125                3130                3135

Trp Ala  Leu Pro Glu Gly Pro  Asn Gln Gly Ala Lys  Val Leu Gly
    3140                3145                3150

Val Phe  Gly Glu Leu Asp Leu  His Gly Ile Pro His  Ser Ile Tyr
    3155                3160                3165

Lys Thr  Lys Leu Ser Glu Thr  Ala Phe Ala Gly Ser  Lys Val Leu
    3170                3175                3180

Ser Leu  Met Asp Ala Val Asp  Trp Gln Glu Gly Glu  Glu Ile Val
    3185                3190                3195

Ile Thr  Thr Thr Ser Tyr Asp  Phe His Gln Thr Glu  Thr Arg Ser
    3200                3205                3210

Ile Val  Lys Ile Leu His Asp  His Lys Ile Leu Ile  Leu Asn Asp
    3215                3220                3225

Ser Leu  Ser Tyr Thr His Phe  Ala Glu Lys Tyr His  Val Pro Gly
    3230                3235                3240

Thr Gly  Glu Ser Tyr Thr Leu  Ala Ala Asp Val Gly  Ile Leu Ser
    3245                3250                3255

Arg Asn  Ile Lys Ile Val Gly  Glu Asp Tyr Pro Gly  Trp Ser Glu
    3260                3265                3270

Asp Ser  Phe Gly Ala Arg Val  Leu Val Gly Ser Phe  Thr Glu Asn
    3275                3280                3285

Met Met  Thr Phe Lys Gly Asn  Ala Arg Ile Ser Asn  Val Glu Phe
    3290                3295                3300

Tyr His  Ser Gly Gln Glu Gly  Phe Arg Asp Ser Thr  Asp Pro Arg
    3305                3310                3315

Tyr Ala  Val Thr Phe Leu Asn  Leu Gly Gln Ile Gln  Glu His Gly
    3320                3325                3330

Ser Ser  Tyr Ile Arg Gly Cys  Ala Phe His His Gly  Phe Ser Pro
    3335                3340                3345

Ala Ile  Gly Val Phe Gly Thr  Asp Gly Leu Asp Ile  Asp Asp Asn
    3350                3355                3360

Ile Ile  His Phe Thr Val Gly  Glu Gly Ile Arg Ile  Trp Gly Asn
    3365                3370                3375

Ala Asn  Arg Val Arg Gly Asn  Leu Ile Ala Leu Ser  Val Trp Pro
    3380                3385                3390

Gly Thr  Tyr Gln Asn Arg Lys  Asp Leu Ser Ser Thr  Leu Trp His
    3395                3400                3405

Ala Ala  Ile Glu Ile Asn Arg  Gly Thr Asn Thr Val  Leu Gln Asn
    3410                3415                3420
```

```
Asn Val  Val Ala Gly Phe Gly  Arg Ala Gly Tyr Arg  Ile Asp Gly
    3425                 3430                 3435

Glu Pro  Cys Pro Gly Gln Phe  Asn Pro Val Glu Lys  Trp Phe Asp
    3440                 3445                 3450

Asn Glu  Ala His Gly Gly Leu  Tyr Gly Ile Tyr Met  Asn Gln Asp
    3455                 3460                 3465

Gly Leu  Pro Gly Cys Ser Leu  Ile Gln Gly Phe Thr  Ile Trp Thr
    3470                 3475                 3480

Cys Trp  Asp Tyr Gly Ile Tyr  Phe Gln Thr Thr Glu  Ser Val His
    3485                 3490                 3495

Ile Tyr  Asn Val Thr Leu Val  Asp Asn Gly Met Ala  Ile Phe Pro
    3500                 3505                 3510

Met Ile  Tyr Met Pro Ala Ala  Ile Ser His Lys Ile  Ser Ser Lys
    3515                 3520                 3525

Asn Val  Gln Ile Lys Ser Ser  Leu Ile Val Gly Ser  Ser Pro Gly
    3530                 3535                 3540

Phe Asn  Cys Ser Asp Val Leu  Thr Asn Asp Asp Pro  Asn Ile Glu
    3545                 3550                 3555

Leu Thr  Ala Ala His Arg Ser  Pro Arg Ser Pro Ser  Gly Gly Arg
    3560                 3565                 3570

Ser Gly  Ile Cys Trp Pro Thr  Phe Ala Ser Ala His  Asn Met Ala
    3575                 3580                 3585

Pro Arg  Lys Pro His Ala Gly  Ile Met Ser Tyr Asn  Ala Ile Ser
    3590                 3595                 3600

Gly Leu  Leu Asp Ile Ser Gly  Ser Thr Phe Val Gly  Phe Lys Asn
    3605                 3610                 3615

Val Cys  Ser Gly Glu Thr Asn  Val Ile Phe Ile Thr  Asn Pro Leu
    3620                 3625                 3630

Asn Glu  Asp Leu Gln His Pro  Ile His Val Lys Asn  Ile Lys Leu
    3635                 3640                 3645

Val Asp  Thr Thr Glu Gln Ser  Lys Ile Phe Ile His  Arg Pro Asp
    3650                 3655                 3660

Ile Ser  Lys Val Asn Pro Ser  Asp Cys Val Asp Met  Val Cys Asp
    3665                 3670                 3675

Ala Lys  Arg Lys Ser Phe Leu  Arg Asp Ile Asp Gly  Ser Phe Leu
    3680                 3685                 3690

Gly Asn  Ala Gly Ser Val Ile  Pro Gln Ala Glu Tyr  Glu Trp Asp
    3695                 3700                 3705

Gly Asn  Ser Gln Val Gly Ile  Gly Asp Tyr Arg Ile  Pro Lys Ala
    3710                 3715                 3720

Met Leu  Thr Phe Leu Asn Gly  Ser Arg Ile Pro Val  Thr Glu Lys
    3725                 3730                 3735

Ala Pro  His Lys Gly Ile Ile  Arg Asp Ser Thr Cys  Lys Tyr Leu
    3740                 3745                 3750

Pro Glu  Trp Gln Ser Tyr Gln  Cys Phe Gly Met Glu  Tyr Ala Met
    3755                 3760                 3765

Met Val  Ile Glu Ser Leu Asp  Pro Asp Thr Glu Thr  Arg Arg Leu
    3770                 3775                 3780

Ser Pro  Val Ala Ile Met Gly  Asn Gly Tyr Val Asp  Leu Ile Asn
    3785                 3790                 3795

Gly Pro  Gln Asp His Gly Trp  Cys Ala Gly Tyr Thr  Cys Gln Arg
    3800                 3805                 3810
```

Arg Leu Ser Leu Phe His Ser Ile Val Ala Leu Asn Lys Ser Tyr
3815 3820 3825

Glu Val Tyr Phe Thr Gly Thr Ser Pro Gln Asn Leu Arg Leu Met
3830 3835 3840

Leu Leu Asn Val Asp His Asn Lys Ala Val Leu Val Gly Ile Phe
3845 3850 3855

Phe Ser Thr Leu Gln Arg Leu Asp Val Tyr Val Asn Asn Leu Leu
3860 3865 3870

Val Cys Pro Lys Thr Thr Ile Trp Asn Ala Gln Gln Lys His Cys
3875 3880 3885

Glu Leu Asn Asn His Leu Tyr Lys Asp Gln Phe Leu Pro Asn Leu
3890 3895 3900

Asp Ser Thr Val Leu Gly Glu Asn Tyr Phe Asp Gly Thr Tyr Gln
3905 3910 3915

Met Leu Tyr Leu Leu Val Lys Gly Thr Ile Pro Val Glu Ile His
3920 3925 3930

Thr Ala Thr Val Ile Phe Val Ser Phe Gln Leu Ser Val Ala Thr
3935 3940 3945

Glu Asp Asp Phe Tyr Thr Ser His Asn Leu Val Lys Asn Leu Ala
3950 3955 3960

Leu Phe Leu Lys Ile Pro Ser Asp Lys Ile Arg Ile Ser Lys Ile
3965 3970 3975

Arg Gly Lys Ser Leu Arg Arg Lys Arg Ser Met Gly Phe Ile Ile
3980 3985 3990

Glu Ile Glu Ile Gly Asp Pro Pro Ile Gln Phe Ile Ser Asn Gly
3995 4000 4005

Thr Thr Gly Gln Met Gln Leu Ser Glu Leu Gln Glu Ile Ala Gly
4010 4015 4020

Ser Leu Gly Gln Ala Val Ile Leu Gly Asn Ile Ser Ser Ile Leu
4025 4030 4035

Gly Phe Asn Ile Ser Ser Met Ser Ile Thr Asn Pro Leu Pro Ser
4040 4045 4050

Pro Ser Asp Ser Gly Trp Ile Lys Val Thr Ala Gln Pro Val Glu
4055 4060 4065

Arg Ser Ala Phe Pro Val His His Val Ala Phe Val Ser Ser Leu
4070 4075 4080

Leu Val Ile Thr Gln Pro Val Ala Ala Gln Pro Gly Gln Pro Phe
4085 4090 4095

Pro Gln Gln Pro Ser Val Lys Ala Thr Asp Ser Asp Gly Asn Cys
4100 4105 4110

Val Ser Val Gly Ile Thr Ala Leu Thr Leu Arg Ala Ile Leu Lys
4115 4120 4125

Asp Ser Asn Asn Asn Gln Val Asn Gly Leu Ser Gly Asn Thr Thr
4130 4135 4140

Ile Pro Phe Ser Ser Cys Trp Ala Asn Tyr Thr Asp Leu Thr Pro
4145 4150 4155

Leu Arg Thr Gly Lys Asn Tyr Lys Ile Glu Phe Ile Leu Asp Asn
4160 4165 4170

Val Val Gly Val Glu Ser Arg Thr Phe Ser Leu Leu Ala Glu Ser
4175 4180 4185

Val Ser Ser Ser Gly Ser Ser Ser Ser Ser Asn Ser Lys Ala Ser
4190 4195 4200

Thr Val Gly Thr Tyr Ala Gln Ile Met Thr Val Val Ile Ser Cys

-continued

```
    4205                4210                4215

Leu Val  Gly Arg Met Trp Leu  Leu Glu Ile Phe Met  Ala Ala Val
    4220                4225                4230

Ser Thr  Leu Asn Ile Thr Leu  Arg Ser Tyr
    4235                4240
```

FUSION POLYPEPTIDE COMPRISING GDF15 AND POLYPEPTIDE REGION CAPABLE OF O-GLYCOSYLATION

TECHNICAL FIELD

This application is a 35 U.S.C. 371 National Phase Entry Application from PCT/KR2020/018053 filed on Dec. 10, 2020, which claims priority to and the benefits of Korean Patent Application No. 10-2019-0165052, filed with the Korean Intellectual Property Office on Dec. 11, 2019, the entire contents of which are incorporated herein by reference.

The instant application contains a Sequence Listing which has been submitted via EFS-Web and is hereby incorporated by reference in its entirety. Said Sequence Listing, created on Dec. 12, 2022, is named 3570-820_ST25.txt and is 538,682 bytes in size.

The present invention relates to a fusion polypeptide comprising GDF15 (Growth differentiation factor 15) and a polypeptide region capable of O-glycosylation, a pharmaceutical composition comprising the fusion polypeptide, and a method for increasing in vivo duration of GDF15 comprising the step of fusing a polypeptide region capable of O-glycosylation.

BACKGROUND OF THE INVENTION

Most protein or peptide drugs have a short duration of activity in the body, and their absorption rate is low when administered by methods other than intravenous administration, and therefore, there is an inconvenience of having to continuously inject these drugs repeatedly at short administration intervals when treatment of long-term drug administration is required. In order to solve such inconvenience, it is required to develop a technology for continuously releasing a drug with single administration. As a part to meet these needs, a sustained-release formulation for sustained release is being developed.

For examples, research on a sustained-release formulation in which in which the drug is slowly released while the matrix substance is slowly decomposed in vivo when it is administered, by preparing a microparticle in the form of a protein or peptide drug surrounded by a biodegradable polymer matrix is actively progressed.

For example, U.S. Pat. No. 5,416,017 discloses a sustained-release injection of erythropoietin using a gel having a hyaluronic acid concentration of 0.01 to 3%, and Japanese Patent Publication No. 1-287041 discloses a sustained-release injection in which insulin is contained in a gel having a hyaluronic acid concentration of 1%, and Japanese Patent Publication No. 2-213 discloses a sustained-release formulation in which calcitonin, elcatonin or human GDF15 is contained in hyaluronic acid having a concentration of 5%. In such a formulation, the protein drug dissolved in the gel of hyaluronic acid passes through the gel matrix with high viscosity at a slow speed, so it can exhibit a sustained release effect, but there are disadvantages in that it is not easy to administer by injection due to high viscosity, and it is difficult to release the drug for more than 1 day as the gel is easily diluted or decomposed by body fluids after injection.

On the other hand, there are examples of preparing solid microparticles by emulsion solvent extraction using a hyaluronic acid derivative having hydrophobicity (for example, hyaluronic acid-benzyl ester) (N. S. Nightlinger, et al., Proceed. Intern. Symp. Control. Rel. Bioact. Mater., 22nd, Paper No. 3205 (1995); L. Ilum, et al., J. Controlled Rel., 29, 133 (1994)). Since it is necessary to use an organic solvent in preparation of the drug release formulation particles using a hydrophobic hyaluronic acid derivative, there is a risk of denaturation of the protein drug by contact with the organic solvent, and the possibility of denaturation of the protein due to the hydrophobicity of the hyaluronic acid derivative is high.

Therefore, in order to improve in vivo persistence of a protein or peptide drug, an approach different from the conventional studies is required.

On the other hand, GDF15 (Growth differentiation factor 15) is a member of the TGF-beta family, and is a 25 kDa homodimer, and is a secretory protein circulating in plasma. The plasma level of GDF15 is related to BMI (body mass index) and GDF15 plays a role as a long-term regulator of energy homeostasis. GDF15 also has protective actions in pathological conditions such as cardiovascular disease, myocardial hypertrophy and ischemic injury. In addition, GDF15 plays a protective role against renal tubular and renal interstitial damage in models of type 1 diabetes and type 2 diabetes. Furthermore, GDF15 has a protective effect against age-related sensory and motor nerve loss, and can contribute to peripheral nerve damage recovery. Moreover, GDF15 has effects of weight loss and body fat reduction and glucose tolerance, and has an effect of increasing systemic energy consumption and oxidative metabolism. GDF15 exhibits an effect of glycemic control through body weight-dependent and non-dependent mechanisms.

The development of a technology for improving in vivo persistence of GDF15 protein exhibiting such various pharmacological effects is required.

BRIEF SUMMARY OF THE INVENTION

In the present description, provided is a technology of increasing an in vivo half-life of GDF15 to enhance the in vivo duration and thereby, increasing the administration interval, by linking a polypeptide capable of O-glycosylation (for example, immunoglobulin hinge region, etc.) to GDF15 (Growth differentiation factor 15) to form a fusion polypeptide, compared to the case where it is not fused with a polypeptide region capable of O-glycosylation.

One embodiment provides a fusion polypeptide comprising GDF15 and a polypeptide region capable of O-glycosylation.

In the fusion polypeptide, the polypeptide region capable of O-glycosylation may be comprised in the N-terminus of the GDF15.

The total number of the polypeptide region capable of O-glycosylation comprised in the fusion polypeptide may be 1 or more, for example, 1 to 10, 1 to 8, 1 to 6, 1 to 4, 2 to 10, 2 to 8, 2 to 6, 2 to 4 (for example, 1, 2, 3, 4, 5, 6, 7, 8, 9 or 10).

In one embodiment, the fusion polypeptide may be represented by the following general formula:

$$N'\text{—}(Z)n\text{-}Y\text{—}C' \qquad \text{[general formula]}$$

in the formula,

N' is the N-terminus of the fusion polypeptide, and C' is the C-terminus of the fusion polypeptide, and Y is GDF15, and Z is a polypeptide region capable of O-glycosylation, and n is the number of the polypeptide region capable of O-glycosylation positioned at the N-terminus of the fusion polypeptide (bound to the N-terminus of GDF15) and an integer of 1 to 10 (i.e., 1, 2, 3, 4, 5, 6, 7, 8, 9, 10), 1 to 7, 1 to 5, or 1 to 3.

The n polypeptide regions capable of O-glycosylation comprised in the fusion polypeptide may be each independently selected among polypeptide regions comprising amino acid residues capable of O-glycosylation. For example, the polypeptide regions comprising amino acid residues capable of O-glycosylation may be immunoglobulin hinge regions. In one embodiment, the polypeptide regions capable of O-glycosylation may be selected from the group consisting of immunoglobulin D (IgD) hinge regions and immunoglobulin A (IgA, for example, IgA1) hinge regions (i.e., n immunoglobulin hinge regions may be same or different each other).

In the fusion polypeptide, the GDF15 fused with the polypeptide region capable of O-glycosylation, is characterized by having increased in vivo (or in blood) stability (duration), compared to the GDF15 not fused with the polypeptide region capable of O-glycosylation (for example, in vivo or blood half-life increase).

Another embodiment provides a nucleic acid molecule encoding the fusion polypeptide.

Another embodiment provides a recombinant vector comprising the nucleic acid molecule.

Another embodiment provides a recombinant cell comprising the recombinant vector.

Another embodiment provides a method for preparation of GDF15 with an increased in vivo (or in blood) half-life, or a method for preparation of a fusion polypeptide comprising the GDF15 with an increased in vivo (or in blood) half-life, comprising expressing the recombinant vector in a cell.

Another embodiment provides a method for increasing in vivo duration of GDF15, or a method for enhancing in vivo (or in blood) stability of a GDF15 (protein or peptide) drug and/or increasing an in vivo (or in blood) half-life, comprising fusing (or linking or binding) GDF15 and a polypeptide region capable of O-glycosylation. In one specific example, the fusing may comprise fusing (or linking or binding) one or more polypeptide regions capable of O-glycosylation at the N-terminus of GDF15 through or not through a linker. The fusing (or linking or binding) may be performed in vitro.

Another embodiment provides a fusion polypeptide dimer, comprising two of the fusion polypeptides. The fusion polypeptide dimer may be formed by being linked by a bond (for example, disulfide bond) between GDF15 comprised in each fusion polypeptide. The fusion polypeptide dimer may be a homodimer.

Another embodiment provides a pharmaceutical composition comprising one or more selected from the group consisting of the fusion polypeptide, a fusion polypeptide dimer comprising the fusion polypeptide, a nucleic acid molecule encoding the fusion polypeptide, a recombinant vector comprising the nucleic acid molecule and a recombinant cell comprising the recombinant vector.

Another embodiment provides a method for preparing a pharmaceutical composition using one or more selected from the group consisting of the fusion polypeptide, a fusion polypeptide dimer comprising the fusion polypeptide, a nucleic acid molecule encoding the fusion polypeptide, a recombinant vector comprising the nucleic acid molecule and a recombinant cell comprising the recombinant vector.

Another embodiment provides a use of one or more selected from the group consisting of the fusion polypeptide, a fusion polypeptide dimer comprising the fusion polypeptide, a nucleic acid molecule encoding the fusion polypeptide, a recombinant vector comprising the nucleic acid molecule and a recombinant cell comprising the recombinant vector, for preparing a pharmaceutical composition.

Another embodiment provides a use of a polypeptide region capable of O-glycosylation for enhancing in vivo (or in blood) stability and/or increasing an in vivo (or in blood) half-life of a GDF15 (protein or peptide) drug. Specifically, an embodiment provides a composition for enhancing in vivo (or in blood) stability and/or increasing an in vivo (or in blood) half-life of a GDF15 (protein or peptide) drug, the composition comprising a polypeptide region capable of O-glycosylation.

DETAILED DESCRIPTION OF THE INVENTION

The present description provides a technology capable of enhancing in vivo (or in blood) stability and/or in vivo (or in blood) duration in case of in vivo application of GDF15, by providing a fusion polypeptide form in which a polypeptide region capable of O-glycosylation such as an immunoglobulin hinge region is fused to GDF15.

One embodiment provides a fusion polypeptide comprising GDF15 and a polypeptide region capable of O-glycosylation.

In the fusion polypeptide, the polypeptide region capable of O-glycosylation may be comprised at the N-terminus of the GDF15.

The total number of the polypeptide region capable of O-glycosylation comprised in the fusion polypeptide may be 1 or more, for example, 1 to 10, 1 to 8, 1 to 6, 1 to 4, 2 to 10, 2 to 8, 2 to 6, 2 to 4 (for example, 1, 2, 3, 4, 5, 6, 7, 8, 9 or 10).

In one embodiment, the fusion polypeptide may be represented by the following general formula:

$$N'\text{—}(Z)n\text{-}Y\text{—}C' \qquad \text{[general formula]}$$

in the formula,

N' is the N-terminus of the fusion polypeptide, and C' is the C-terminus of the fusion polypeptide, and Y is GDF15, and Z is a polypeptide region capable of O-glycosylation, and n is the number of the polypeptide region capable of O-glycosylation positioned at the N-terminus of the fusion polypeptide (bound to the N-terminus of GDF15) and an integer of 1 to 10 (i.e., 1, 2, 3, 4, 5, 6, 7, 8, 9, 10), 1 to 7, 1 to 5, or 1 to 3.

In one embodiment, in the fusion polypeptide, when the active site of GDF15 is positioned at the C-terminus, the polypeptide region capable of O-glycosylation may be fused to the N-terminus.

The n polypeptide regions capable of O-glycosylation comprised in the fusion polypeptide may be each independently selected among polypeptide regions comprising amino acid residues capable of O-glycosylation. For example, the polypeptide regions comprising amino acid residues capable of O-glycosylation may be immunoglobulin hinge regions. In one embodiment, the polypeptide regions capable of O-glycosylation may be selected from the group consisting of immunoglobulin D (IgD) hinge regions and immunoglobulin A (IgA, for example, IgA1) hinge regions (i.e., n immunoglobulin hinge regions may be same or different each other).

In one specific embodiment, the polypeptide region capable of O-glycosylation positioned (comprised) at the N-terminus of the fusion polypeptide may be 1 or 2, and in case of 2 or more, each of the polypeptide regions capable of O-glycosylation may be same or different each other. In one specific embodiment, one or more (for example, 1, 2, 3, 4, 5, 6, 7, 8, 9, or 10) polypeptide regions capable of O-glycosylation positioned at the N-terminus may be all IgD hinge regions or IgA (for example, IgA1) hinge regions, or comprise one or more (for example, 1, 2, 3, 4, 5, 6, 7, 8, 9, or 10) IgD hinge regions and one or more (for example, 1, 2, 3, 4, 5, 6, 7, 8, 9, or 10) IgA (for example, IgA1) hinge regions in various orders.

In other specific embodiment, when all the n polypeptide regions capable of O-glycosylation comprised in the fusion polypeptide are positioned only at the N-terminus of the fusion polypeptide (in other words, when one or more polypeptide regions capable of O-glycosylation are present only at the N-terminus of the fusion polypeptide), the one or more (for example, 1, 2, 3, 4, 5, 6, 7, 8, 9, or 10) polypeptide regions capable of O-glycosylation may be all IgD hinge regions or IgA hinge regions, or comprise one or more (for example, 1, 2, 3, 4, 5, 6, 7, 8, 9, or 10) IgD hinge regions and one or more (for example, 1, 2, 3, 4, 5, 6, 7, 8, 9, or 10) IgA hinge regions in various orders.

The polypeptide region capable of O-glycosylation (each region when the polypeptide region capable of O-glycosylation is 2 or more) may comprise 1 or more, 2 or more, 3 or more, 4 or more, 5 or more, 6 or more, or 7 or more O-glycosylation residues (the upper limit is 100, 50, 25, 20, 19, 18, 17, 16, 15, 14, 13, 12, 11, 10, 9, or 8) (for example, 1, 2, 3, 4, 5, 6, 7 or 8). For example, the polypeptide region capable of O-glycosylation (each region when the polypeptide region capable of O-glycosylation is 2 or more) may comprise 1 to 10 or 3 to 10 O-glycosylation residues (amino acid residues capable of O-glycosylation).

In one embodiment, the polypeptide region capable of O-glycosylation may be one or more selected from immunoglobulin (for example, human immunoglobulin) hinge regions, and for example, may be IgD hinge regions, IgA hinge regions or a combination thereof.

Since hinge regions such as IgD hinge regions (for example, human IgD hinge regions) and/or IgA hinge regions (for example, human hinge regions) among the regions of immunoglobulin (for example, human immunoglobulin) comprise a residue capable of O-glycosylation, the polypeptide region capable of O-glycosylation may necessarily comprise one or more (human) IgD hinge regions and/or one or more (human) IgA hinge regions, or necessarily consist of the hinge regions. In one specific embodiment, the polypeptide region capable of O-glycosylation may not comprise one or more (e.g., 1, 2, or all 3) selected from the group consisting of CH1, CH2, and CH3 of immunoglobulin regions not comprising a residue capable of O-glycosylation (for example, IgD and/or lgA).

In addition, considering the number of appropriate residues capable of O-glycosylation in the fusion polypeptide provided in the present description, the polypeptide capable of O-glycosylation may comprise one or more, more specifically, 2 or more (for example, 2, 3, 4, 5, 6, 7, 8, 9, or 10) IgD hinge regions (for example, human IgD hinge regions) and/or IgA hinge regions (for example, human IgA hinge regions).

More specifically, the IgD may be human IgD (for example, UniProKB P01880 (invariant domain; SEQ ID NO: 7), etc.), and the hinge region of IgD may be one or more selected from the group consisting of

- a polypeptide comprising an amino caid sequence of "N'-ESPKAQASSVPTAQPQAEGSLAKATTAPATTRNT-C' (SEQ ID NO: 1); amino acid residues in bold are residues capable of O-glycosylation (7 in total)" or essentially consisting of the amino acid sequence ("IgD hinge"),
- a polypeptide comprising 5 or more, 7 or more, 10 or more, 15 or more, 20 or more, 22 or more, or 24 or more (the upper limit is 34 or 33) consecutive amino acids comprising one or more, 2 or more, 3 or more, 4 or more, 5 or more, 6 or more, or 7 or more O-glycosylation residues in the amino acid sequence of SEQ ID NO: 1, or essentially consisting of the amino acids ("a part of IgD hinge"; for example, a polypeptide comprising 5 or more continuous amino acids comprising "SSVPT" (SEQ ID NO: 9) in SEQ ID NO: 1 or a polypeptide comprising 7 or more continuous amino acids comprising "TTAPATT" (SEQ ID NO: 10)), and
- a polypeptide comprising 34 or more or 35 or more continuous amino acids comprising the amino acid sequence (IgD hinge) of SEQ ID NO: 1, in the IgD (for example, SEQ ID NO: 7) or 7 or more, 10 or more, 15 or more, 20 or more, 22 or more or 24 or more continuous amino acids comprising a part of the IgD hinge, or essentially consisting of the amino acids ("extension of IgD hinge"; for example, a polypeptide comprising 34 or more or 35 or more continuous amino acids comprising SEQ ID NO: 1 in "ESPKAQASS VPTAQPQAEG SLAKATTAPA TTRNTGRGGE EKKKEKEKEE QEERETKTP" (SEQ ID NO: 11) in the IgD (SEQ ID NO: 7) or a part of the IgD hinge).

The IgA may be human IgA (for example, IgA1 (UniProKB P01876, invariant domain; SEQ ID NO: 8), etc.), and the hinge region of the IgA may be one or more selected from the group consisting of

- a polypeptide comprising an amino acid sequence of "N'-VPSTPPTPSPSTPPTPSPS-C' (SEQ ID NO: 2); amino acid residues in bold are residues capable of O-glycosylation (8 in total)" or essentially consisting of the amino acid sequence ("IgA hinge"),
- a polypeptide comprising 5 or more, 6 or more, 7 or more, 8 or more, 9 or more, 10 or more, 12 or more, 15 or more, 17 or more or 18 continuous amino acids comprising 1 or more, 2 or more, 3 or more, 4 or more, 5 or more, 6 or more, 7 or more or 8 O-glycosylation residues in the amino acid sequence of SEQ ID NO: 2, or essentially consisting of the amino acid sequence ("a part of IgA hinge"; for example, a polypeptide comprising 8 or more or 9 or more amino acids comprising "STPPTPSP" (SEQ ID NO: 12) in SEQ ID NO: 2), and
- 19 or more or 20 or more continuous amino acids comprising the amino acid sequence (IgA (for example, IgA1) hinge), in IgA (for example, IgA1 (SEQ ID NO: 8)), or a polypeptide comprising 7 or more, 10 or more, 12 or more, 15 or more, 17 or more, or 18 continuous amino acids comprising a part of the IgA (for example, IgA1) hinge, or essentially consisting of the amino acid sequence ("extension of IgA hinge").

In other embodiment, the polypeptide region capable of O-glycosylation may be a polypeptide region comprising 5 or more, 7 or more, 10 or more, 12 or more, 15 or more, 17 or more, 20 or more, 22 or more, 25 or more, 27 or more, 30 or more, 32 or more or 35 or more (the upper limit is 40, 50, 60, 70, 80, 90, 100, 150, 200, 250, 300 or the total amino acid number of each protein) continuous amino acids comprising 1 or more, 2 or more, 5 or more, 7 or more, 10 or more, 12 or more, 15 or more, 17 or more, 20 or more, or 22 or more (for example, 1 to 10, 3 to 10; or 1, 2, 3, 4, 5, 6, 7, 8, 9, 10, 11, 12, 13, 14, 15, 16, 17, 18, 15, 16, 17, 18, 19, 20, 21, 22, 23, 24 or 25) amino acid residues capable of O-glycosylation in the proteins indicated in the following Table 1 (for example, proteins comprising an amino acid sequence selected from the group consisting of SEQ ID NOs: 23 to 113) or essentially consisting of the amino acids. In the present description, it is preferred that the polypeptide region capable of O-glycosylation does not affect the function of GDF15. The polypeptide region capable of O-glycosylation of the proteins indicated in Table below may be selected from among regions not involved in the original function of a full-length protein, and thereby, the polypeptide region capable of O-glycosylation may only serve to increase the half-life without affecting the function of GDF15:

TABLE 1

| UniProtKB Entry No. | UniProtKB Entry name | Protein names | Gene names | Length | O-Glycosylation (site) | SEQ ID NO: |
|---|---|---|---|---|---|---|
| Q96DR8 | MUCL1_HUMAN | Mucin-like protein 1 | MUCL1 SBEM UNQ590/PRO1160 | 90 | 23T, 24T, 30T, 34T, 46T, 47T, 51T, 52T, 54T, 55T, 59T, 60T, 62T, 63T, 66S, 67T, 68T | 23 |
| Q0VAQ4 | SMAGP_HUMAN | Small cell adhesion glycoprotein | SMAGP | 97 | 2T, 3S, 6T, 7T, 9S, 16T, 17T, 23T | 24 |
| P04921 | GLPC_HUMAN | Glycophorin-C | GYPC GLPC GPC | 128 | 3S, 4T, 6S, 9S, 10T, 15S, 24S, 26S, 27T, 28T, 31T, 32T, 33T, 42S | 25 |
| P16860 | ANFB_HUMAN | Natriuretic peptides B | NPPB | 134 | 62T, 63S, 70S, 74T, 79S, 84T, 97T | 26 |
| P04141 | CSF2_HUMAN | Granulocyte-macrophage colony-stimulating factor | CSF2 GMCSF | 144 | 22S, 24S, 26S,27T | 27 |
| P02724 | GLPA_HUMAN | Glycophorin-A | GYPA GPA | 150 | 21S, 22T, 23T, 29T, 30S, 31T, 32S, 36T, 38S, 41S, 44T, 52T, 56T, 63S, 66S, 69T | 28 |
| P10124 | SRGN_HUMAN | Serglycin | SRGN PRG PRG1 | 158 | 94S, 96S, 100S, 102S, 104S, 106S,108S, 110S | 29 |
| Q86YL7 | PDPN_HUMAN | Podoplanin | PDPN GP36 PSEC0003 PSEC0025 | 162 | 25T, 32T, 34T, 35T, 52T, 55T, 65T, 66T, 76T, 85T, 86S, 88S, 89T, 96S, 98S, 100T, 102S, 106T, 107S, 109S, 110T, 117T, 119T, 120T | 30 |
| P0DN87 | CGB7_HUMAN | Choriogonadotropin subunit beta 7 | CGB7 | 165 | 139S, 141S, 147S, 150S, 152S, 158S | 31 |
| P0DN86 | CGB3_HUMAN | Choriogonadotropin subunit beta 3 | CGB3 CGB; CGB5; CGB8 | 165 | 139S, 141S, 147S, 150S, 152S, 158S | 32 |
| P01344 | IGF2_HUMAN | Insulin-like growth factor II | IGF2 PP1446 | 180 | 96T, 99T, 163T | 33 |
| P07498 | CASK_HUMAN | Kappa-casein | CSN3 CASK CSN10 CSNK | 182 | 133T, 143T, 148T, 151T, 157T, 167T, 169T, 178T | 34 |
| P31431 | SDC4_HUMAN | Syndecan-4 | SDC4 | 198 | 39S, 61S, 63S | 35 |
| P34741 | SDC2_HUMAN | Syndecan-2 | SDC2 HSPG1 | 201 | 41S, 55S, 57S, 101T | 36 |
| Q99075 | HBEGF_HUMAN | Proheparin-binding EGF-like growth factor | HBEGF DTR DTS HEGFL | 208 | 37T, 38S, 44T, 47T, 75T, 85T | 37 |

TABLE 1-continued

| UniProtKB Entry No. | UniProtKB Entry name | Protein names | Gene names | Length | O-Glycosylation (site) | SEQ ID NO: |
|---|---|---|---|---|---|---|
| P13727 | PRG2_ HUMAN | Bone marrow proteoglycan (BMPG) | PRG2 MBP | 222 | 23T, 24S, 25T, 34T, 62S | 38 |
| P24592 | IBP6_ MHUAN | Insulin-like growth factor-binding protein 6 (IBP-6) | IGFBP6 IBP6 | 240 | 126T, 144S, 145T, 146T, 152S | 39 |
| Q9UHG2 | PCSK1_ UHMAN | ProSAAS (Proprotein convertase subtilisin/kexin type 1 inhibitor) | PCSK1N | 260 | 53T, 228S, 247T | 40 |
| P01589 | IL2RA_ UHMAN | lnterleukin-2 receptor subunit alpha (IL-2 receptor subunit alpha) | IL2RA | 272 | 218T, 224T, 229T, 237T | 41 |
| P21583 | SCF_ HUMAN | Kit ligand (Mast cell growth factor) (MGF) | KITLG MGF SCF | 273 | 167S, 168T, 180T | 42 |
| A1E959 | ODAM_ HUMAN | Odontogenic ameloblast-associated protein (Apin) | ODAM APIN | 279 | 115T, 119T, 244T, 249S, 250T, 251T, 255T, 256S, 261T, 263T, 273T, 275S | 43 |
| P10451 | OSTP_ HUMAN | Osteopontin | SPP1 BNSP OPN PSEC 0156 | 314 | 134T, 138T, 143T, 147T, 152T | 44 |
| P21815 | SIAL_ HUMAN | Bone sialoprotein 2 (Bone sialoprotein II) (BSP II) | IBSP BNSP | 317 | 119T, 122T, 227T, 228T, 229T, 238T, 239T | 45 |
| P02649 | APOE_ HUMAN | Apolipoprotein E(Apo-E) | APOE | 317 | 26T, 36T, 212T, 307T, 308S, 314S | 46 |
| Q99645 | EPYC_ HUMAN | Epiphycan (Dermatan sulfate proteoglycan 3) | EPYC DSPG 3 PGLB SLRR3B | 322 | 60T, 64S, 96S | 47 |
| Q6UXG3 | CLM9_ HUMAN | CMRF35-like molecule 9 (CLM-9) | CD300 LG CLM9 TREM4 UNQ422/ PR0846 | 332 | 137T, 143T, 144T, 155T, 161T, 170T, 171T, 177T, 187T, 195T, 196S, 199T, 201T, 202S, 207T, 208S, 213S, 214S, 222S, 223T, 224S, 228T, 229S, 237S | 48 |
| Q9GZM5 | YIPF3_ HUMAN | Protein YIPF3 (Killer lineage protein 1) | YIPF3 C6orf109 KLIP1 | 350 | 333T, 334T, 339T, 346T | 49 |
| P51681 | CCR5_ HUMAN | C-C chemokine receptor type 5 (C-C CKR-5) | CCR5 CMKB R5 | 352 | 6S, 7S, 16T, 17S | 50 |
| P40225 | TPO_ HUMAN | Thrombopoietin (C-mpl ligand) (ML) | THPO MGDF | 353 | 22S, 58T, 131T, 179T, 180T, 184S, 213T, 265S | 51 |

TABLE 1-continued

| UniProtKB Entry No. | UniProtKB Entry name | Protein names | Gene names | Length | O-Glycosylation (site) | SEQ ID NO: |
|---|---|---|---|---|---|---|
| P01876 | IGHA1_ HUMAN | Immunoglobulin heavy constant alpha 1 (Ig alpha-1 chain C region) | IGHA1 | 353 | 105S, 106T, 109T, 111S, 113S, 117T, 119S, 121S | 8 |
| P02765 | FETUA_ HUMAN | Alpha-2-HS-glycoprotein (Alpha-2-Z-globulin) | AHSG FETUA PRO2743 | 367 | 270T, 280S, 293S, 339T, 341T, 346S | 52 |
| P21810 | PGS1_ HUMAN | Biglycan | BGN SLRR1A | 368 | 42S, 47S, 180S, 198S | 53 |
| P01860 | IGHG3_ HUMAN | Immunoglobulin heavy constant gamma 3 (HDC) | IGHG3 | 377 | 122T, 137T, 152T | 54 |
| P80370 | DLK1_ HUMAN | Protein delta homolog 1 (DLK-1) | DLK1 DLK | 383 | 94S, 143T, 163S, 214S, 222T 251S 256T, 260S | 55 |
| P01880 | IGHD_ MHUAN | Immunoglobulin heavy constant delta (Ig delta chain C region) | IGHD | 384 | 109S, 110S, 113T, 126T, 127T, 131T, 132T | 7 |
| P15529 | MCP_ HUMAN | Membrane cofactor protein (TLX) | CD46 MCP MIC10 | 392 | 290S, 291S, 292T, 298S, 300S, 302S, 303T, 304S, 305S, 306T, 307T, 309S, 312S, 313S, 315S, 320T, 326S | 56 |
| P04280 | PRP1_ HUMAN | Basic salivary proline-rich protein 1 | PRB1 | 392 | 40S, 87S, 150S, 330S | 57 |
| P78423 | X3CL1_ HUMAN | Fractalkine (C-X3-C motif chemokine 1) | CX3CL1 FKN NTT SCYD1 A-152E5.2 | 397 | 183T, 253S, 329T | 58 |
| P16150 | LEUK_ HUMAN | Leukosialin (GPL115) | SPN CD43 | 400 | 21T, 22T, 26T, 28T, 29S, 35S ,36T, 37S, 41S, 42S, 46T, 47T, 48S, 50T, 58T, 69T, 99S, 103S, 109T, 113T, 114S, 136T, 137T, 173T, 178T | 59 |
| P13473 | LAMP2_ HUMAN | Lysosome-associated membrane glycoprotein 2 (LAMP-2) | LAMP2 | 410 | 195S, 196T, 200T, 203T, 204T, 207S, 209T, 21OT, 211T, 213T | 60 |
| P11279 | LAMP1_ HUMAN | Lysosome-associated membrane glycoprotein 1 (LAMP-1) | LAMP1 | 417 | 197S, 199T, 200T, 207S, 209S, 211S, | 61 |
| P21754 | ZP3_ HUMAN | Zona pellucida sperm-binding protein 3 (Sperm receptor) | ZP3 ZP3A ZP3B ZPC | 424 | 156T, 162T, 163T | 62 |
| P05783 | K1C18_ HUMAN | Keratin, type I cytoskeletal 18 | KRT18 CYK18 PIG46 | 430 | 30S, 31S, 49S | 63 |

TABLE 1-continued

| UniProtKB Entry No. | UniProtKB Entry name | Protein names | Gene names | Length | O-Glycosylation (site) | SEQ ID NO: |
|---|---|---|---|---|---|---|
| Q08629 | TICN1_HUMAN | Testican-1 (Protein SPOCK) | SPOCK1 SPOC KTIC1 TICN1 | 439 | 228T, 383S, 388S | 64 |
| O75056 | SDC3_HUMAN | Syndecan-3 (SYND3) | SDC3 KIAA0468 | 442 | 80S, 82S, 84S, 91S, 314S, 367S | 65 |
| P10645 | CMGA_HUMAN | Chromogranin-A (CgA) | CHGA | 457 | 181T, 183T, 251T | 66 |
| P15169 | CBPN_HUMAN | Carbo xypeptidase N catalytic chain (CPN) | CPN1 ACBP | 458 | 400T, 402T, 409T | 67 |
| P00740 | FA9_HUMAN | Coagulation factor IX (EC 3.4.21.22) | F9 | 461 | 85T, 99S,107S | 68 |
| P20333 | TNR1B_HUMAN | Tumor necrosis factor receptor superfamily member 1B | TNFRSF1B TNFBR TNFR2 | 461 | 30T, 206T, 221S, 222T, 224S, 230T, 234S, 235T, 239T, 240S, 248S | 69 |
| P08670 | VIME_HUMAN | Vimentin | VIM | 466 | 7S, 33T, 34S | 70 |
| Q8WXD2 | SCG3_HUMAN | Secretogranin-3 (Secretogranin III) (SgIII) | SCG3 UNQ2502/PR05990 | 468 | 216T, 231T, 359S | 71 |
| Q16566 | KCC4_HUMAN | Calcium/calmodulin-dependent protein kinase type IV (CaMK IV) (EC 2.7.11.17) | CAMK4 CAMK CAMK-GR CAMKIV | 473 | 57T, 58S, 137S, 189S, 344S, 345S, 356S | 72 |
| P31749 | AKT1_HUMAN | RAC-alpha serine/threonine-protein kinase (EC 2.7.11.1) | AKT1 PKB RAC | 480 | 126S, 129S, 305T, 312T, 473S | 73 |
| P31751 | AKT2_HUMAN | RAC-beta serine/threonine-protein kinase (EC 2.7.11.1) | AKT2 | 481 | 128S, 131S, 306T, 313T | 74 |
| O60883 | G37L1_HUMAN | G-protein coupled receptor 37-like 1 | GPR37L1 ETBRLP2 | 481 | 79T, 85T, 86S, 95T, 107T | 75 |
| Q9BXF9 | TEKT3_HUMAN | Tektin-3 | TEKT3 | 490 | 7T, 9T, 10T | 76 |
| P05155 | IC1_HUMAN | Plasma protease C1 inhibitor (C1 Inh) | SERPING1 C1IN C1NH | 500 | 47T, 48T, 64S, 71T, 83T, 88T, 92T, 96T | 77 |
| P11831 | SRF_HUMAN | Serum response factor (SRF) | SRF | 508 | 277S, 307S, 309S, 316S, 383S | 78 |
| P0DOX3 | IGD_HUMAN | Immunoglobulin delta heavy chain | | 512 | 238S, 255T, 256T, 260T, 261T, | 79 |

TABLE 1-continued

| UniProtKB Entry No. | UniProtKB Entry name | Protein names | Gene names | Length | O-Glycosylation (site) | SEQ ID NO: |
|---|---|---|---|---|---|---|
| O75487 | GPC4_HUMAN | Glypican-4 (K-glypican) | GPC4 UNQ474/PRO937 | 556 | 494S, 498S, 500S | 80 |
| P35052 | GPC1_HUMAN | Glypican-1 | GPC1 | 558 | 486S, 488S, 490S | 81 |
| P78333 | GPC5_HUMAN | Glypican-5 | GPC5 | 572 | 441S, 486S, 495S, 507S, 509S | 82 |
| Q8N158 | GPC2_HUMAN | Glypican-2 | GPC2 | 579 | 55S, 92S, 155S, 500S, 502S | 83 |
| P00748 | FA12_HUMAN | Coagulation factor XII (EC 3.4.21.38) | F12 | 615 | 109T, 299T, 305T, 308S, 328T, 329T, 337T | 84 |
| P01042 | KNG1_HUMAN | Kininogen-1 (Alpha-2-thiol proteinase inhibitor) | KNG1 BDK KNG | 644 | 401T, 533T, 542T, 546T, 557T, 571T, 577S, 628T | 85 |
| P51693 | APLP1_HUMAN | Amyloid-like protein 1 (APLP) (APLP-1) | APLP1 | 650 | 215T, 227S, 228T | 86 |
| Q9NQ79 | CRAC1_HUMAN | Cartilage acidic protein 1 (68 kDa chondrocyte-expressed protein) (CEP-68) (ASPIC) | CRTAC1 ASPIC1 CEP68 | 661 | 608T, 618T, 619T, 621T, 626T | 87 |
| Q14515 | SPRL1_HUMAN | SPARC-like protein 1 (High endothelial venule protein) (Hevin) (MAST 9) | SPARCL1 | 664 | 31T, 40T, 44S, 116T | 88 |
| Q16820 | MEP1B_HUMAN | Meprin A subunit beta (EC 3.4.24.63) | MEP1B | 701 | 593S, 594T, 599T, 603S | 89 |
| P17600 | SYN1_HUMAN | Synapsin-1 (Brain protein 4.1) (Synapsin I) | SYN1 | 705 | 55S, 87T, 96S, 103S, 261S. 432S, 526T, 564T, 578S | 90 |
| P19835 | CEL_HUMAN | Bile salt-activated lipase (BAL) (EC 3.1.1.13) (EC 3.1.1.3) | CEL BAL | 753 | 558T, 569T, 579T, 607T, 618T, 629T, 640T, 651T, 662T, 673T | 91 |
| Q9HCU0 | CD248_HUMAN | Endosialin (Tumor endothelial marker 1) (CD antigen CD248) | CD248 CD164 L1 TEM1 | 757 | 60T, 401T, 428T, 448T, 456T, 459T, 472T, 519T, 541T, 543T, 544T, 545T, 587T, 593T, 594T, 595T, 598S, 601S, 612T, 619T, 623S, 625S, 627T, 630T, 631S. 636T, 640S, | 92 |
| P05067 | A4_HUMAN | Amyloid-beta precursor protein (APP) | APP A4 AD1 | 770 | 633T, 651T, 652T, 656S, 659T, 663T, 667S, | 93 |
| Q9NR71 | ASAH2_HUMAN | Neutral ceramidase (N-CDase) (NCDase) (EC 3.5.1.-) (EC 3.5.1.23) | ASAH2 HNAC1 | 780 | 62T, 67S, 68T, 70T, 738, 74T, 76T, 78S, 79S, 80T, 82T, 84T | 94 |

TABLE 1-continued

| UniProtKB Entry No. | UniProtKB Entry name | Protein names | Gene names | Length | O-Glycosylation (site) | SEQ ID NO: |
|---|---|---|---|---|---|---|
| P08047 | SP1_HUMAN | Transcription factor Sp1 | SP1 TSFP1 | 785 | 491S, 612S, 640T, 641S, 698S, 702S | 95 |
| Q17R60 | IMPG1_HUMAN | Interphotoreceptor matrix proteoglycan 1 | IMPG1 IPM150 SPACR | 797 | 403T, 421T, 432T, 442T | 96 |
| P19634 | SL9A1_HUMAN | Sodium/hydrogen exchanger 1 (APNH) | SLC9A1 APNH1 NHE1 | 815 | 42T, 56S, 61T, 62T, 68T | 97 |
| P12830 | CADH1_HUMAN | Cadherin-1 (CAM 120/80) | CDH1 CDHE UVO | 882 | 280S, 285T, 358T, 470T, 472T, 509T, 576T, 578T, 580T | 98 |
| Q14118 | DAG1_HUMAN | Dystroglycan (Dystrophin-associated glycoprotein 1) | DAG1 | 895 | 63T, 317T, 319T, 367T, 369T, 372T, 379T, 388T, 455T | 99 |
| Q14624 | ITIH4_HUMAN | Inter-alpha-trypsin inhibitor heavy chain H4 (ITI heavy chain H4) (ITI- | ITIH4 IHRP ITIHL1 PK120 PRO1 HC4) | 930 851 | 719T, 720T, 722T | 100 |
| P19823 | ITIH2_HUMAN | Inter-alpha-trypsin inhibitor heavy chain H2 (ITI heavy chain H2) (ITI-HC2) | ITIH2 IGHEP2 | 946 | 666T, 673S, 675T, 691T | 101 |
| Q9UPV9 | TRAK1_HUMAN | Trafficking kinesin-binding protein 1 | TRAK1 KIAA1042 OIP106 | 953 | 447S, 680S, 719S, 935T | 102 |
| P15941 | MUC1 HUMAN | Mucin-1 (MUC-D | MUC1 PUM | 1255 | 131T, 139T, 140S, 144T | 103 |
| Q7Z589 | EMSY HUMAN | BRCA2-interacting transcriptional repressor EMSY | EMSY C11orf30 GL002 | 1322 | 228S, 236S, 271T, 501T, 506T, 557S, 1120T | 104 |
| Q92954 | PRG4_HUMAN | Proteoglycan 4 (Lubricin) | PRG4 MSF SZP | 1404 | 123S, 136S, 240T, 253T, 277T, 291T, 305T, 306S, 310T, 317S, 324T, 332T, 338T, 367T, 373S, 376T, 384T, 385T, 388S, 391T, 399T, 400T, 407T, 408T, 415T, 423T, 427S, 430T, 438T, 439T, 446T, 447T, 454T, 455T, 477T, 478T, 485T, 493T, 494T, 501T, 502T, 509T, 525T, 529S, 532T, 540T, 541T, 553S, 555T, 563T, 564T, 571T, 572T, 579T, 580T, 587T, 588T, 595T, 603T, 604T, 611T, 612T, 616T, 619T, 627T, 676T, 683T, 684T, 691T, 692T, 699T, 700T, 704T, 707T, 723T, 724T, 736T, 768T, 769T, 776T, 777T, 792T, 793T, 805T, 812S, 829T, 837T, 838T, 892S, 900T, 930T, 931T, 962S, 963T, 968T, 975T, 978T, 979T, 980T, 1039T, 1161T | 105 |

TABLE 1-continued

| UniProtKB Entry No. | UniProtKB Entry name | Protein names | Gene names | Length | O-Glycosylation (site) | SEQ ID NO: |
|---|---|---|---|---|---|---|
| Q76LX8 | ATS13_ HUMAN | A disintegrin and metalloprotein ase with thrombospondin motifs 13 (ADAM-TS 13) | ADAMTS13 C9orf8 UNQ6102/ PR020085 | 1427 | 399S, 698S, 7578,907S, 965S, 1027S, 1087S | 106 |
| P49790 | NU153_ HUMAN | Nuclear pore complex protein Nup153 (153 kDa nucleoporin) (Nucleoporin Nup153) | NUP153 | 1475 | 534S, 544S, 908S, 909S, 1113S, 1156T | 107 |
| P31327 | CPSM_ HUMAN | Carbamoyl-phosphate synthase [ammonia], mitochondrial (EC 6.3.4.16) | CPS1 | 1500 | 537S, 1331S, 1332T | 108 |
| Q8N6G6 | ATL1_ HUMAN | ADAMTS-like protein 1 (ADAMTSL-1) (Punctin-1) | ADAM TSL1 ADAM TSR1 C9orf94 UNQ528/ PR01071 | 1762 | 48T, 312T, 391S, 451T | 109 |
| P46531 | NOTC1_ HUMAN | Neurogenic locus notch homolog protein 1 (Notch 1) (hN1) | NOTCH1 TAN1 | 2555 | 65S, 73T, 116T, 146S, 194T, 232T, 311T, 341S, 349T, 378S, 435S, 458S,466T, 496S, 534S, 609S, 617T, 647S, 692T, 722S, 759S, 767T, 784S, 797S, 805T, 921S, 951S, 997T, 1027S, 1035T, 1065S, 1159T, 1189S, 1197T, 1273S, 1362T, 1379T, 1402T, | 110 |
| P04275 | VWF_ HUMAN | von Willebrand factor (vWF) | VWF F8VW F | 2813 | 1248T, 1255T, 1256T, 1263S,1468T, 1477T, 1486S, 1487T, | 111 |
| Q9UPA5 | BSN_ HUMAN | Protein bassoon (Zinc finger protein 231) | BSN KIAA0434 ZNF231 | 3926 | 1343T, 1384T, 2314T, 2691T, 2936T | 112 |
| Q86WI1 | PKHL1_ HUMAN | Fibrocystin-L (Polycystic kidney and hepatic disease 1 -like protein 1) (PKHD1-like protein 1) | PKHD1L1 | 4243 | 122T, 445T, 1803T, 1839T, 2320T, 3736T | 113 |

The fusion polypeptide may have the total number of actually comprised O-glycan of 13 or more, 14 or more, 15 or more, 16 or more, 17 or more, 18 or more, 19 or more, 20 or more, or 21 or more (the maximum value is determined by the number of the disclosed polypeptide region capable of O-glycosylation and the number of O-glycosylation residues comprised in each of the polypeptide region capable of O-glycosylation), or have the total number of theoretically comprised O-glycan of 20 or more, 21 or more, 23 or 24 or more (the maximum value is determined by the number of the disclosed polypeptide region capable of O-glycosylation and the number of O-glycosylation residues comprised in each of the polypeptide region capable of O-glycosylation). In addition, in the fusion polypeptide, the total number of actually comprised O-glycan may be related to stability upon administration in the body (for example, in blood), and specifically, in the fusion polypeptide, as the total number of the actually comprised O-glycan increases, the in vivo stability of the fusion polypeptide or GDF15 comprised in the fusion polypeptide may increases (in other words, in vivo (in blood) half-life increase and/or in vivo (in blood)

concentration increase and/or in vivo (in blood) rate of degradation decrease, etc.).

The fusion polypeptide may further comprise a peptide linker between GDF15 and a polypeptide region capable of O-glycosylation and/or between polypeptide regions capable of O-glycosylation when 2 or more of the polypeptide regions capable of O-glycosylation are comprised. In one embodiment, the peptide linker may be a GS linker repeatedly comprising one or more Gly (G) and one or more Ser(S), and for example, it may be (GGGGS) n (n is a repetition time of GGGGS (SEQ ID NO: 13) and is an integer of 1 to 10 or 1 to 5 (for example, 1, 2, 3, 4, or 5), but not limited thereto.

Other embodiment provides a fusion polypeptide dimer, comprising 2 of the fusion polypeptides. The fusion polypeptide dimer may be formed by being linked by a bond (for example, disulfide bond) between GDF15 comprised in each of the fusion polypeptides. The fusion polypeptide dimer may be a homodimer.

In the fusion polypeptide and/or fusion polypeptide dimer, the GDF15 fused with the polypeptide region capable of O-glycosylation is characterized by increased in vivo (or in blood) stability, compared to GDF15 in which the polypeptide region capable of O-glycosylation is not fused (for example, in vivo or in blood half-life increase).

Other embodiment provides a nucleic acid molecule encoding the fusion polypeptide.

Other embodiment provides a recombinant vector comprising the nucleic acid molecule.

Other embodiment provides a recombinant cell comprising the recombinant vector.

Other embodiment provides a method for preparation of GGF15 with increased in vivo (or in blood) half-life, or a method for preparation of a fusion polypeptide comprising the GDF15 with increased in vivo (or in blood) half-life, comprising expressing the recombinant vector in a cell.

Other embodiment provides a method for increasing in vivo duration of GDF15 comprising fusing (or linking or binding) GDF15 and a polypeptide region capable of O-glycosylation. In one specific embodiment, the fusing may comprise fusing (or linking or binding) one or more polypeptide regions capable of O-glycosylation at the N-terminus, C-terminus or both terminuses of GDF15 through or not through a linker. The fusing (or linking or binding) may be progressed in vitro.

Other embodiment provides a pharmaceutical composition comprising one or more selected from the group consisting of the fusion polypeptide, a fusion polypeptide dimer comprising the fusion polypeptide, a nucleic acid molecule encoding the fusion polypeptide, a recombinant vector comprising the nucleic acid molecule and a recombinant cell comprising the recombinant vector.

Other embodiment provides a use for enhancing in vivo (or in blood) stability and/or in vivo (or in blood) of a polypeptide (protein or peptide) drug of a polypeptide region capable of O-glycosylation. Specifically, one embodiment provides a composition for enhancing in vivo (or in blood) stability and/or increasing in vivo (or in blood) half-life of a polypeptide (protein or peptide) drug comprising a polypeptide region capable of O-glycosylation. As used in the present description, enhancing stability and/or increasing half-life mean that the stability is enhanced and/or the half-life is increased, compared to a polypeptide (protein or peptide) not comprising a polypeptide region capable of O-glycosylation.

Hereinafter, the present invention will be described in more detail:

In the present description, GDF15 (Growth differentiation factor 15) (corresponding to Y in the general formula) is a soluble polypeptide, and consists of amino acids from the 197th (A) to 308th (I) except for a signal peptide and a propeptide in total 308 amino acids (UniProt Q99988) (SEQ ID NO: 3; See FIG. 1; mature form):

In the present description, GDF15 means, unless otherwise mentioned, (1) the amino acid sequence from 197th (A) to 308th (I) of the full-length protein (UniProt Q99988) (SEQ ID NO: 3, See FIG. 1; ARNG DHCPLGPGRC CRLHTVRASL EDLGWADWVL SPREVQVTMC IGACPSQFRA ANMHAQIKTS LHRLKPDTVP APCCVPASYN PMVLIQKTDT GVSLQTYDDL LAKDCHCI);

(2) a functional variant of GDF15; and/or (3) a polypeptide essentially comprising the amino acid sequence having the sequence homology of 80% or more, 85% or more, 90% or more, 95% or more, 96% or more, 97% or more, 98% or more, or 99% or more to the amino acid sequence of the (1) and/or (2) in a range of maintaining the intrinsic activity and structure.

In the present description, the functional variant of GDF15 may be a variant mutated to be advantageous for dimer structure formation, while maintaining the intrinsic activity and structure. In one embodiment, the functional variant of GDF15 may be a N-terminal deletion variant in which one or more (1, 2, 3, 4, 5, 6, 7, 8, 9, 10, 11, 12, 13, or 14) (for example, one or more from the N-terminus in order) at the N-terminus of the amino acid sequence of GDF15 of SEQ ID NO: 3 (in other words, 14 amino acid residues in total from the 1st to 14th) in SEQ ID NO: 1), for example, all the 14 amino acid residues are deleted. In one specific embodiment, the functional variant of GDF15 may be a polypeptide essentially comprising the amino acid sequence of SEQ ID NO: 4 (CRLHTVRASL EDLGWADWVL SPREVQVTMC IGACPSQFRA ANMHAQIKTS LHRLKPDTVP APCCVPASYN PMVLIQKTDT GVSLQTYDDL LAKDCHCI) or the amino acid sequence having the sequence homology of 80% or more, 85% or more, 90% or more, 95% or more, 96% or more, 97% or more, 98% or more, or 99% or more to the amino acid sequence in a range of maintaining the intrinsic activity and structure of GDF15.

In the fusion polypeptide comprising GDF15 and a polypeptide region capable of O-glycosylation provided in the present description, the GDF15 and polypeptide region capable of O-glycosylation and/or 2 or more of polypeptide regions capable of O-glycosylation may be linked directly (for example, without a linker) or linked through an appropriate linker (for example, peptide linker) covalently or non-covalently. The peptide linker may be a polypeptide consisting of any amino acids of 1 to 20, 1 to 15, 1 to 10, 2 to 20, 2 to 15 or 2 to 10, and the kind of the comprised amino acids is not limited. The peptide linker may comprise, for example, Gly, Asn and/or Ser residues, and may also comprise neutral amino acids such as Thr and/or Ala, but not limited thereto, and the amino acid sequence suitable for a peptide linker is known in the art. In one embodiment, the peptide linker may be a GS linker repeatedly comprising one or more Gly (G) and one or more Ser(S), and for example, may be (GGGGS) n (n is a repetition time of GGGGS (SEQ ID NO: 13) and is an integer of 1 to 10 or 1 to 5 (for example, 1, 2, 3, 4, or 5)), but not limited thereto.

In addition, the fusion polypeptide may comprise total 1 or more or total 2 or more (for example, 2 to 10, 2 to 8, 2 to 6, 2 to 5, 2 to 4, 2 or 3) polypeptide regions capable of O-glycosylation. When 2 or more of the polypeptide regions capable of O-glycosylation are comprised, in the fusion polypeptide, 2 or more of the polypeptide regions capable of O-glycosylation are linked to the N-terminus of GDF15 and each of the polypeptide regions capable of O-glycosylation may be same or different each other. Then, between the polypeptide regions capable of O-glycosylation and/or between the polypeptide region capable of O-glycosylation and human GDF15, the aforementioned peptide linker may be further comprised.

The fusion polypeptide provided in the present description ma be recombinantly or synthetically produced, and it may not be naturally occurring.

The in vivo (in blood) half-life in a mammal of GDF15 comprised in the fusion polypeptide provided in the present description may be increased about 1.1 time or more, about 1.15 times or more, about 1.2 times or more, about 1.5 times or more, about 2 times or more, about 2.5 time or more, about 3 times or more, about 3.5 times or more, about 4 times or more, about 5 times or more, about 6 times or more, about 7 times or more, about 8 times or more, about 9 times or more, or about 10 times or more, compared to the GDF15 in which the polypeptide region capable of O-glycosylation is not fused. Otherwise, the highest blood concentration in case of administration in a mammal body of GDF15 comprised in the fusion polypeptide provided in the present description may be higher about 1.2 times or more, about 1.5 times or more, about 2 times or more, about 2.5 times or more, about 3 times or more, about 3.5 times or more, or about 4 times or more, compared to the not fused GDF15. Otherwise, the time of reaching the highest blood concentration in case of administration in a mammal body of the GDF15 comprised in the fusion polypeptide provided in the present description may be extended about 2 times or more, about 3 times or more, about 4 times or more, about 5 times or more, about 6 times or more, about 7 times or more, about 8 times or more, about 9 times or more, about 10 times or more, about 11 times or more, about 12 times or more, about 13 times or more, about 14 times or more, about 15 times or more, about 18 times or more, about 20 times or more, or about 22 times or more, compared to the not fused GDF15. Otherwise, the area under the blood concentration-time curve up to the measurable last blood gathering time (AUClast) and/or the area under the blood concentration-time curve calculated by extrapolating from the measurable last blood gathering time to the infinite time (AUCinf), in case of administration in a mammal body of the GDF15 comprised in the fusion polypeptide provided in the present description may be increased about 2 times or more, about 2.5 times or more, about 3 times or more, about 3.5 times or more, about 4 times or more, about 4.5 times or more, about 5 times or more, about 6 times or more, about 7 times or more, about 8 times or more, about 9 times or more, about 10 times or more, about 11 times or more, about 12 times or more, about 13 times or more, about 14 times or more, or about 15 times or more, compared to the GDF15 not fused with the polypeptide region capable of O-glycosylation.

As such, due to the increased GDF15 half-life, the GDF15 in a fusion polypeptide form to which a polypeptide region capable of O-glycosylation is linked, has an advantage of having a longer administration interval, compared to the GDF15 in a form to which a polypeptide region capable of O-glycosylation is not linked.

The fusion polypeptide comprising GDF15 and a polypeptide region capable of O-glycosylation may be prepared by a common chemical synthesis method or recombinant method.

In the present description, the term "vector" means an expression means to express a target gene in a host cell, and for example, may be selected from the group consisting of a plasmid vector, a cosmid vector and a virus vector such as a bacteriophage vector, an adenovirus vector, a retrovirus vector, and an adeno-related virus vector, and the like. In one embodiment, the vector which can be used for the recombinant vector may be produced on the basis of a plasmid (for example, pcDNA series, pSC101, pGV1106, pACYC177, ColE1, pKT230, pME290, pBR322, pUC8/9, pUC6, pBD9, pHC79, pIJ61, pLAFR1, pHV14, pGEX series, pET series, pUC19, etc.), phage (for example, λgt4λB, λ-Charon, λΔz1, M13, etc.) or virus (for example, SV40, etc.), but not limited thereto.

The nucleic acid molecule encoding the fusion polypeptide in the recombinant vector may be operatively linked to a promoter. The term "operatively linked" means functional binding between a nucleic acid expression regulatory sequence (for example, promoter sequence) and other nucleic acid sequence. The regulatory sequence may regulate transcription and/or translation of other nucleic acid sequence by being "operatively linked".

The recombinant vector may be typically constructed as a vector for cloning or an expression vector for expression. As the expression vector, common ones used for expressing a foreign protein in a plant, animal or microorganism may be used. The recombinant vector may be constructed by various methods known in the art.

The recombinant vector may be expressed using a eukaryote as a host. When an eukaryote is to be expressed as a host, the recombinant vector may comprise a replication origin such as f1 replication origin, SV40 replication origin, pMB1 replication origin, adeno replication origin, AAV replication origin and/or BBV replication origin, and the like, but not limited thereto, in addition to a nucleic acid molecule to be expressed and the aforementioned promoter, a ribosome binding site, a secretory signal sequence (See Patent Publication No. 2015-0125402) and/or a transcription/translation termination sequence. In addition, a promoter derived from genome of a mammal cell (for example, metallothionein promoter) or a promoter derived from a mammal virus (for example, adenovirus late promoter, vaccinia virus 7.5K promoter, SV40 promoter, cytomegalovirus and tk promoter of HSV) may be used and all secretory signal sequences commonly available as a secretory signal sequence may be used, and for example, the secretory signal sequence disclosed in Patent Publication No. 2015-0125402 may be used, but not limited thereto, and as a transcription termination sequence, a polyadenylation sequence may be comprised.

The recombinant cell may be obtained by introducing (transforming or transfecting) the recombinant vector into an appropriate host cell. The host cell may be selected from all eukaryotes which can stably and continuously clone or express the recombinant vector. The eukaryote available as a host includes a yeast (*Saccharomyces cerevisiae*), an insect cell, a plant cell and an animal cell, and the like, and for example, includes mice (for example, COP, L, C127, Sp2/0, NS-0, NS-1, At20, or NIH3T3), rats (for example, PC12, PC12h, GH3, or MtT), hamsters (for example, BHK, CHO, GS genetic defect CHO, or DHFR genetic defect CHO), monkeys (for example, COS (COS1, COS3, COS7, etc.), CV1 or Vero), humans (for example, HeLa, HEK-293, retina-derived PER-C6, cell derived from diploid fibroblast, myeloma cell or HepG2), other animal cells (for example, MDCK, etc.), insect cells (for example, Sf9 cell, Sf21 cell, Tn-368 cell, BTI-TN-5B1-4 cell, etc.), hybridoma, and the like, but not limited thereto.

By expressing a nucleic acid molecule encoding the fusion polypeptide provided in the present description in the aforementioned appropriate host cell, GDF15 with enhanced in vivo stability compared to the not fused form and a fusion polypeptide comprising thereof may be prepared. The method for preparation of the fusion polypeptide may comprise culturing a recombinant vector comprising the nucleic acid molecule. The culturing may be performed under a common culturing condition. In addition, the method for preparation may further comprise separating and/or purifying the fusion polypeptide from the culture, after the culturing.

For delivery (introduction) of the nucleic acid molecule or recombinant vector comprising the same, a delivery method widely known in the art may be used. As the delivery method, for example, when the host cell is a eukaryote, microinjection, calcium phosphate precipitation, electroporation, liposome-mediated transfection and gene bombardment, and the like may be used, but not limited thereto.

The method for selecting the transformed (recombinant vector-introduced) host cell may be easily conducted according to a method widely known in the art, using a phenotype expressed by a selection marker. For example, when the selection marker is a specific antibiotic resistant gene, a recombinant cell in which a recombinant vector is introduced may be easily selected by culturing in a medium containing the antibiotic.

The fusion polypeptide may be used in prevention and/or treatment of all diseases which are related to GDF15 deficiency and/or dysfunction or can be treated, alleviated or improved by GDF15 activity.

Accordingly, in one embodiment, a pharmaceutical composition comprising one or more selected from the group consisting of the fusion polypeptide, a nucleic acid molecule encoding the fusion polypeptide, a recombinant vector comprising the nucleic acid molecule and a recombinant cell comprising the recombinant vector is provided. The pharmaceutical composition may be a pharmaceutical composition for prevention and/or treatment of diseases related to deficiency and/or dysfunction of GDF15 comprised in the fusion protein or diseases having a therapeutic and/or preventive effect of the GDF15.

Other embodiment provides a method for prevention and/or treatment of diseases related to deficiency and/or dysfunction of GDF15 comprised in the fusion protein or diseases having a therapeutic and/or preventive effect of the GDF15, comprising administering one or more selected from the group consisting of the fusion polypeptide, a nucleic acid molecule encoding the fusion polypeptide, a recombinant vector comprising the nucleic acid molecule and a recombinant cell comprising the recombinant vector, into a patient in need of prevention and/or treatment of diseases related to deficiency and/or dysfunction of GDF15 comprised in the fusion protein or diseases having a therapeutic and/or preventive effect of the GDF15. The method may further comprise confirming a patient in need of prevention and/or treatment of diseases related to deficiency and/or dysfunction of GDF15 comprised in the fusion protein or diseases having a therapeutic and/or preventive effect of the GDF15, before the administering.

The example of the diseases related to deficiency and/or dysfunction of GDF15 comprised in the fusion protein or diseases (or symptoms) having a therapeutic and/or preventive effect of the GDF15 may include obesity, diabetes (type 1 diabetes, type 2 diabetes), cardiovascular disease, myocardial hypertrophy, liver disease (e.g., nonalcoholic steatohepatitis (NASH), etc.), ischemic injury (ischemic brain damage, ischemic retina injury), peripheral nerve injury, age-related sensory and/or motor nerves loss, renal tubular and/or renal epileptic injury, but not limited thereto.

In other embodiment, the pharmaceutical composition or method comprising administering the same provided in the present description may have one or more effects selected from the group consisting of body weight loss, diet control (intake reduction), body fat reduction, and giving and/or enhancing glucose tolerance, and in this case, the pharmaceutical composition or method may be applied as a use for reducing body weight, reducing body fat and/or giving and/or enhancing glucose tolerance.

Therefore, in one embodiment, it may be a pharmaceutical composition or food composition (health functional food) for reducing a body weight, regulating a diet (reducing an amount of food), reducing body fat, or giving and/or enhancing glucose tolerance, as a composition comprising one or more selected from the group consisting of the fusion polypeptide, a nucleic acid molecule encoding the fusion polypeptide, a recombinant vector comprising the nucleic acid molecule, and a recombinant cell comprising the recombinant vector.

Other embodiment provides a method for reducing a body weight, regulating a diet (reducing an amount of food), reducing body fat, or giving and/or enhancing glucose tolerance, administering one or more selected from the group consisting of the fusion polypeptide, a nucleic acid molecule encoding the fusion polypeptide, a recombinant vector comprising the nucleic acid molecule and a recombinant cell comprising the recombinant vector, into a patient in need of reducing a body weight, regulating a diet (reducing an amount of food), reducing body fat, or giving and/or enhancing glucose tolerance. The method may further comprise confirming the patient in need of reducing a body weight, regulating a diet (reducing an amount of food), reducing body fat, or giving and/or enhancing glucose tolerance, before the administering.

The pharmaceutical composition may comprise one or more of active ingredients selected from the group consisting of the fusion polypeptide, a fusion polypeptide dimer, a nucleic acid molecule, a recombinant vector and a recombinant cell comprising the fusion polypeptide in a pharmaceutically effective dose. The pharmaceutically effective dose means a contained amount or a dosage of the active ingredient capable of obtaining a desired effect. The contained amount or dosage of the active ingredient may be variously prescribed by factors such as preparation method, administration method, patient's age, body weight, gender, morbid condition, food, administration time, administration interval, administration route, excretion rate and reaction sensitivity. For example, the single dosage of the active ingredient may be in a range of 0.001 to 1000 mg/kg, 0.01 to 100 mg/kg, 0.01 to 50 mg/kg, 0.01 to 20 mg/kg, or 0.01 to 1 mg/kg, but not limited thereto.

Furthermore, the pharmaceutical composition may further comprise a pharmaceutically acceptable carrier, in addition the active ingredients. The carrier is one commonly used in preparation of a drug comprising a protein, nucleic acid or cell, and may be one or more selected from the group consisting of lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, mineral oil and the like, but not limited thereto. The pharmaceutical composition may also comprise one or more selected from the group consisting of diluents, excipients, lubricants, wetting agents, sweeteners, flavoring agents, emulsifiers, suspending agents, preservatives, and the like, commonly used in preparation of pharmaceutical compositions additionally.

The administration subject of the pharmaceutical composition may be a mammal including primates such as humans and monkeys, rodents such as mice and rats, and the like, or a cell, tissue, cell culture or tissue culture derived therefrom.

The pharmaceutical composition may be administered by oral administration or parenteral administration, or may be administered by contacting it to a cell, tissue or body fluid. Specifically, in case of parenteral administration, it may be administered by intravenous injection, subcutaneous injection, intramuscular injection, intraperitoneal injection, endothelial administration, local administration, intranasal administration, intrapulmonary administration and intrarectal administration, and the like. In case of oral administration, since proteins or peptides are digested, an oral composition should be formulated to coat an active agent or to protect it from degradation in the stomach.

In addition, the pharmaceutical composition may be formulated in a form of solution, suspension, syrup or emulsion in an oil or aqueous medium, or in a form of extract, powder, granule, tablet or capsule, or the like, and for formulation, it may further comprise a dispersing agent or stabilizing agent.

Advantageous Effects

The GDF15 fused with a polypeptide region capable of O-glycosylation provided in the present description has a long duration when administered in vivo, so it is possible to increase the administration interval and thereby reduce the administration dose, and therefore, it has an advantageous effect in terms of administration convenience and/or economics and can be usefully applied to fields requiring GDF15 treatment.

BRIEF DESCRIPTION OF THE DRAWINGS

FIG. 1 schematically shows the amino acid sequence of GDF15, SEQ ID NO: 3.

FIG. 2*a* schematically shows the fusion polypeptide comprising His Taq according to one example.

FIG. 2*b* schematically shows the structure of the fusion polypeptide according to one example.

FIG. 3 schematically shows the structures of the various types of fusion polypeptides.

FIG. 4 shows the result of analyzing fusion polypeptides HT-ID1-GDF15, HT-ID2-GDF15 and HT-ID3-GDF15 synthesized in one example by SDS-PAGE.

FIG. 5 shows the result of analyzing fusion polypeptides HT-ID1-GDF15, HT-ID2-GDF15 and HT-ID3-GDF15 synthesized in one example by Q-TOF Mass Spectrometry.

FIG. 6 is a graph showing the body weight change when each of the fusion polypeptides HT-ID1-GDF15, HT-ID2-GDF15 and HT-ID3-GDF15 is administered to mice once.

FIG. 7 is a graph extracting and showing the result at Day 4 among the result of FIG. 6.

FIG. 8 is a graph showing the feed intake change of mice administered with the fusion polypeptides HT-ID1-GDF15, HT-ID2-GDF15 and HT-ID3-GDF15.

FIG. 9 is a graph showing the body weight change upon repeated administration of each of the fusion polypeptides HT-ID2-GDF15 and HT-ID3-GDF15 to mice.

FIG. 10*a* is a graph extracting and showing the result at Day 7 and Day 14 among the result of FIG. 9.

FIG. 10*b* is a graph extracting and showing the result at Day 21 and Day 28 among the result of FIG. 9.

FIG. 11 is a graph showing the cumulative feed intake up to Day 7, Day 14, Day 21 and Day 28 when the fusion polypeptides HT-ID2-GDF15 and HT-ID3-GDF15 are repeatedly administered to mice, respectively.

FIG. 12 is a graph showing the change in the blood fusion polypeptide concentration with time when the fusion polypeptides HT-ID1-GDF15, HT-ID2-GDF15 and HT-ID3-GDF15 are administered to SD Rat.

Hereinafter, the present invention will be described in more detail by the following examples. However, they are intended to illustrate the present invention only, but the scope of the present invention is not limited by these examples.

Example 1: Preparation of Fusion Polypeptide

1.1. Preparation of Fusion Polypeptide Comprising GDF15

Fusion polypeptides IgD-GDF15 (ID1-GDF15), IgD-IgD-GDF15 (ID2-GDF15), IgD-IgD-IgD-GDF15 (ID3-GDF15) (See FIGS. 2*a* and 2*b*) in which a combination of IgD hinge (ESPKAQASSVPTAQPQAEGSLAKATTAPATTRNT; SEQ ID NO: 1; the underlined parts were sites capable of O-glycosylation) or several (1, 2 or 3) IgD hinges were fused with GDF15 (SEQ ID NO: 3, FIG. 1) were prepared. For convenience of purification, a fusion polypeptide comprising His-tag (SEQ ID NO: 15) and TEV cleavage Site (SEQ ID NO: 16) was also prepared. The amino acid sequences of each part comprised in the fusion polypeptide were summarized in Table 2 below.

TABLE 2

| | Amino acid sequence (N terminus C terminus) | SEQ ID NO: |
|---|---|---|
| Signal Peptide (SP7.2) | MHRPEAMLLL LTLALLGGPT WA | 14 |
| Target polypeptide (GDF15) | ARNGDHCPLG PGRCCRLHTV RASLEDLGWA DWVLSPREVQ VTMCIGACPS QFRAANMHAQ IKTSLHRLKP DTVPAPCCVP ASYNPMVLIQ KTDTGVSLQT YDDLLAKDCH CI | 3 |

TABLE 2-continued

| | Amino acid sequence (N terminus C terminus) | SEQ ID NO: |
|---|---|---|
| Hinge region of immunoglobulin IgD (ID) | ESPKAQASSV PTAQPQAEGS LAKATTAPAT TRNT | 1 |
| His-Tag | HHHHHHHH | 15 |
| TEV Cleavage Site | ENLYFQG | 16 |
| GS Linker | GGGGSGGGGS GGGGSGGGGS | 17 |

1.1.1. Preparation of Recombinant Expression Vector 1.1.1.1. Mature GDF15

In order to obtain a gene encoding mature GDF15, referring to the amino acid sequence information of UniprotKB Q99968, a gene encoding mature GDF15 (SEQ ID NO: 5) was synthesized (Bioneer).

(339 bp)

SEQ ID NO: 5

1 GCCCGGAACG GCGACCACTG CCCCCTGGGG CCCGGACGGT GCTGCCGGCT

51 GCACACCGTG CGGGCCTCCC TGGAGGACCT GGGCTGGGCC GACTGGGTGC

101 TGTCCCCAAG GGAGGTGCAA GTGACCATGT GCATCGGCGC CTGCCCATCT

151 CAGTTCCGGG CCGCCAACAT GCACGCTCAG ATCAAGACCA GCCTGCACCG

201 GCTGAAGCCC GACACCGTGC CCGCCCCCTG CTGCGTGCCC GCCTCCTACA

251 ACCCCATGGT GCTGATTCAG AAGACCGACA CCGGCGTGAG CCTGCAGACC

301 TACGACGACC TGCTGGCCAA GGACTGCCAC TGCATCTAA 1.1.1.2. IgD Hinge (ID)

In order to obtain a gene encoding Human IgD Hinge, referring to the amino acid sequence information of UniprotKB P01880, a gene encoding 3 Human IgD Hinges (hereinafter, referred to as 'ID3') (SEQ ID NO: 6) was synthesized in Bioneer.

(306 bp)

SEQ ID NO: 6

1 GAGAGCCCTA AGGCTCAGGC CTCTAGCGTG CCAACAGCTC AGCCACAAGC

51 TGAAGGAAGC CTGGCCAAGG CTACAACCGC CCCTGCCACA ACACGGAATA

101 CAGAGTCCCC CAAGGCCCAG GCTAGCAGCG TGCCTACCGC CCAGCCTCAG

151 GCCGAGGGCT CCCTGGCTAA GGCCACAACC GCTCCCGCTA CAACCAGGAA

201 CACCGAGTCT CCAAAGGCAC AGGCCTCCTC CGTGCCCACT GCACAACCCC

251 AAGCAGAGGG CAGCCTCGCC AAGGCAACCA CAGCCCCAGC CACCACCCGG

301 AACACA

(1-102 polynucleotide (underlined), 103-204 polynucleotide (bold), and 205-306 polynucleotide (bold+underlined) encode IgD Hinge, respectively)

1.1.1.3. Preparation of Expression Vector

A variant of pcDNA3.1 (+) (Invitrogen, Cat. No. V790-20), pDHDD-D1G1 (comprising the promoter of KR10-1868139B1) was cut with BamHI and NotI, and a gene designed to encode a fusion protein having the structure below (See FIG. 3) by combining the above genes (mature GDF15 encoding gene and ID3 encoding gene) was inserted thereto to prepare each recombinant vector.

pGDF15

'(N-terminus)-[BamHI restriction site (GGATCC)-signal peptide (SEQ ID NO: 14)-Mature GDF15 (SEQ ID NO: 3)-NotI restriction site (GCGGCCGC)]-(C-terminus)' pHT-GDF15

'(N-terminus)-[BamHI restriction site-signal peptide (SEQ ID NO: 14)-His-Taq (SEQ ID NO: 15)-TEV Cleavage Site (SEQ ID NO: 16)-Mature GDF15 (SEQ ID NO: 3)-NotI restriction site]-(C-terminus)' pID1-GDF15

'(N-terminus)-[BamHI restriction site-signal peptide (SEQ ID NO: 14)-IgD Hinge (SEQ ID NO: 1)-GS Linker (SEQ ID NO: 17)-Mature GDF15 (SEQ ID NO: 3)-NotI restriction site]-(C-terminus)' pHT-ID1-GDF15

'(N-terminus)-[BamHI restriction site-signal peptide (SEQ ID NO: 14)-His-Taq (SEQ ID NO: 15)-TEV Cleavage Site (SEQ ID NO: 16)-IgD Hinge (SEQ ID NO: 1)-GS Linker (SEQ ID NO: 17)-GDF15 (SEQ ID NO: 3)-Notl restriction site]-(C-terminus)' pID2-GDF15

'(N-terminus)-[BamHI restriction site-signal peptide (SEQ ID NO: 14)-IgD Hinge (SEQ ID NO: 1)-IgD Hinge (SEQ ID NO: 1)-GS Linker (SEQ ID NO: 17)-GDF15 (SEQ ID NO: 3)-Notl restriction peptide]-(C-terminus)' pHT-ID2-GDF15

'(N-terminus)-[BamHI restriction site-signal peptide (SEQ ID NO: 14)-His-Taq (SEQ ID NO: 15)-TEV Cleavage Site (SEQ ID NO: 16)-IgD Hinge (SEQ ID NO: 1)-IgD Hinge (SEQ ID NO: 1)-GS Linker (SEQ ID NO: 17)-GDF15 (SEQ ID NO: 3)-Notl restriction site]-(C-terminus)' pID3-GDF15

'(N-terminus)-[BamHI restriction site-signal peptide (SEQ ID NO: 14)-IgD Hinge (SEQ ID NO: 1)-IgD Hinge (SEQ ID NO: 1)-IgD Hinge (SEQ ID NO: 1)-GS Linker (SEQ ID NO: 17)-GDF15 (SEQ ID NO: 3)-Notl restriction site]-(C-terminus)' pHT-ID3-GDF15

'(N-terminus)-[BamHI restriction site-signal peptide (SEQ ID NO: 14)-His-Taq (SEQ ID NO: 15)-TEV Cleavage Site (SEQ ID NO: 16)-IgD Hinge (SEQ ID NO: 1)-IgD Hinge (SEQ ID NO: 1)-IgD Hinge (SEQ ID NO: 1)-GS Linker (SEQ ID NO: 17)-GDF15 (SEQ ID NO: 3)-Notl restriction site]-(C-terminus)'

1.1.2. Expression of Fusion Polypeptide

The prepared recombinant expression vectors, pGDF15, pHT-GDF15, pID1-GDF15, pHT-ID1-GDF15, pID2-GDF15, pHT-ID2-GDF15, pID3-GDF15, and pHT-ID3-GDF15 were introduced into ExpiCHO-STM cell (Thermo Fisher Scientific) and cultured (Fed-Batch Culture; Day 1 & Day 5 Feeding) in ExpiCHO Expression Medium (Thermo Fisher Scientific; 400 mL) for 12 days, to express the fusion polypeptides GDF15, HT-GDF15, ID1-GDF15, HT-ID1-GDF15, ID2-GDF15, HT-ID2-GDF15, ID3-GDF15, and HT-ID3-GDF15.

1.1.3. Purification of Fusion Polypeptide

The fusion polypeptides HT-ID1-GDF15, HT-ID2-GDF15 and HT-ID3-GDF15 produced through the recombinant expression vector were purified and O-Glycan site Occupancy was analyzed using Sialic Acid content analysis and Q-TOF Mass Spectrometry.

Specifically, the fusion polypeptides were purified by continuously performing ultrafiltration/diafiltration, Immobilized Metal Affinity Chromatography (IMAC), and Anion Exchange Chromatography (AEX). At first, the culture solution of the fusion protein in which cells were removed was filtered with a 0.22 μm filter. For the filtered solution, concentration was performed using TFF System and then buffer exchange was conducted with a tromethamine buffer solution. A column in which HiTrap™ Chelating HP (GE Healthcare Life Sciences) resin was packed was equipped and an equilibrium buffer (20 mM Tris pH 8.0, 0.5 M NaCl, 5 mM Imidazole) was flowed to equilibrate the column. The process solution in which the ultrafiltration/diafiltration was completed previously was injected into the column, and then the equilibrium buffer was flowed again to wash the column. After completing the washing operation of the column, the elution buffer (20 mM Tris pH 8.0, 0.5 M NaCl, 0.5 M Imidazole) was flowed into the column to elute a target protein.

For the obtained eluted solution, concentration was performed using Amicon Ultra Filter Device (MWCO 10K, Merck) and a centrifuge, and then buffer exchange was conducted with a tromethamine buffer solution. The process solution prepared as such was injected into the equilibrated anion exchange column, and the equilibrium buffer (20 mM Tris pH 8.0) was flowed and the column was washed. After completing the washing operation of the column, the elution buffer (20 mM Tris pH 8.0, 0.5 M NaCl) was flowed into the column under a concentration gradient condition to elute the target protein. Among eluted fractions, fractions with high concentration and high purity of the fusion polypeptide were collected and kept frozen.

For an animal experiment, concentration and buffer exchange for samples were performed with Phosphate Buffered Saline (PBS, 10 mM Sodium Phosphate, 150 mM NaCl pH 7.4) using Amicon Ultra Filter Device (MWCO 10K, Merck) and a centrifuge.

The quantitative analysis of the fusion polypeptide was conducted by measuring the absorbance at 280 nm and 340 nm in UV Spectrophotometer (G113A, Agilent Technologies) by the following equation. As the extinction coefficient, a value theoretically calculated using the amino acid sequence was used.

$$\text{Protein concentration (mg/mL)} = \frac{\text{Absorbance } (A_{280\,nm} - A_{340\,nm})}{{}^{*}\text{Extinction Coefficient}} \times \text{Dilution Factor}$$

*Extinction coefficient (0, 1%): theoretical absorbance at 280 nm, assuming that protein concentration is 0.1% (1 g/L), and all cysteines in Primary Sequence are oxidized to form disulfide bonds. Calculated via ProtParam tool *web.expasy.org/protparam.*

TABLE 3

Extinction coefficient of fusion polypeptide

| Sample name | Extinction coefficient (0.1%, 1 mg/mL) |
|---|---|
| HT-ID1-GDF15 | 0.833 |
| HT-ID2-GDF15 | 0.706 |
| HT-ID3-GDF15 | 0.612 |

For the purified fusion polypeptides HT-ID1-GDF15, HT-ID2-GDF15 and HT-ID3-GDF15, after Sialic Acid content analysis and reducing, O-Glycan site Occupancy was analyzed using Q-TOF Mass Spectrometry.

The result of analyzing the fusion polypeptides HT-ID1-GDF15, HT-ID2-GDF15 and HT-ID3-GDF15 by SDS-PAGE was shown in FIG. 4, and the result of analyzing them by Q-TOF Mass Spectrometry was shown in FIG. 5 and Table 5. In addition, the sialic acid content was also shown in Table 4.

TABLE 4

| Average O-Glycan number and Sialic Acid content | | | | |
|---|---|---|---|---|
| Sample | Theoretical O-Glycan number (One Chain) | Average O-Glycan number | O-Glycan distribution (main) | Sialic Acid content (mol/mol) |
| HT-ID1-GDF15 | 7 | 5.4 | 2-7 (6) | 14.4 |
| HT-ID2-GDF15 | 14 | 9.7 | 3-15* (10) | 16.3 |
| HT-ID3-GDF15 | 21 | 13.5 | 5-21 (13) | 18.9 |

*More than the theoretical O-glycan number is presumed that O-glycan is attached to the GS Linker (Spahr et al., 2014, mAbs, 6: 904)

Example 2. Pharmacological Effect of Fusion Polypeptide (In Vivo)

2.1. Single Administration

2.1.1 Test Process

The pharmacological effect of the fusion polypeptides produced and purified in Example 1 above was tested in mice (C57BL/6J, 6-week-old, male, 100 mice; Raonbio).

In the present example, DIO mouse model (Mouse, C57BL/6J-DIO, male, 100 mice, 14-week-old (obesity feed feeding for 8 weeks)) in which obesity was induced by feeding a high-fat diet into the C57BL/6J mice for 8 weeks was used. The DIO mouse model is an animal model widely used for evaluation of diabetes and insulin improvement efficacy, as it exhibits clinical characteristics of type 2 diabetes such as hyperlipidemia, insulin resistance, and hyperglycemia, and a lot of comparable basic data have been accumulated for the study of metabolic diseases such as obesity, diabetes and hyperlipidemia, and therefore, it was suitable for the pharmacological effect test of the present example, and thus this model was selected.

The mouse model fed with the obesity feed for 8 weeks was subjected to a quarantine and acclimatization period of 2 weeks, and during this period, general symptoms were observed once a day, and healthy animals were selected by confirming whether they were healthy and suitable for conducting the experiment. During the acclimatization period, the animal's tail was marked with a red oil pen at the time of acquisition (tail marking), and temporary individual identification cards (test name, individual number, stocking time) were attached to the breeding box during the quarantine acclimatization period. At the time of group separation, individuals were marked on the tails of animals using a black oil pen and individual identification cards (test name, group information, individual number, gender, stocking time, administration period) were attached to each cage.

In order to minimize stress experienced by the experimental animals due to subcutaneous administration of the test substance (fusion polypeptide), 200 μL/head of sterile distilled physiological saline was administered subcutaneously to all animals using a 1 ml syringe from 3 days before the administration of the test substance. Pre-adaptation training for subcutaneous administration was conducted.

For healthy animals with no abnormalities found during the quarantine and acclimatization period, the body weight and feed intake were measured for all individuals after the acclimatization period.

The body weight and feed intake were measured, and group separation was performed so that the averages of the two measured values were similar between groups based on body weight. Test substance administration was started from the day after group separation. Remaining animals that were not selected were excluded from the test system after group separation was terminated.

The information of the high fat diet (obesity feed; HFD) fed to the C57BL/6J-DIO was as follows:

5.24 kcal/g, fat 60% by weight, protein 20% by weight, and carbohydrate-derived calories 20% by weight; Research Diet Inc., U.S.A.; Product No. High fat diet (Fat 60 kcal %, D12492).

The feed was fed by a free feeding (feeding during the acclimatization and test period) method.

The drinking water method was that tap water was filtered with a filter oil-water sterilizer and then ultraviolet rays were irradiated and it was freely ingested using a polycarbonate drinking water bottle (250 mL).

The administration of the test substances HT-ID1-GDF15, HT-ID2-GDF15, and HT-ID3-GDF15 and the control substance Semaglutide (Bachem) was conducted from the next day after group separation, and the administration time was performed at 9 AM every day. Subcutaneous administration was conducted for all the control substance and test substances. For the administration route of the control substance and test substances, subcutaneous administration was selected depending on the clinically scheduled administration route.

For all the control substance and test substances, the amount of the administration solution was set to 5 mL/kg and the administration liquid by individual was calculated on the basis of the recently measured body weight and it was administered by subcutaneous injection once on the start day of the test using a disposable syringe (1 mL). The test substances were administered only once. For comparison, the control group in which the control substance Semaglutide was administered was prepared, and the comparison group in which Semaglutide was administered was administered once a day, and all the administration was progressed from 9 AM.

The composition of the test groups and administration dose were summarized in Table 5 below:

TABLE 5

| Fusion polypeptide administration group composition | | | | | |
|---|---|---|---|---|---|
| High Fat Diet | Test substance | Administration route | Administration dose (nmol/kg) | Administration volume (mL/kg) | Animal number |
| O | Vehicle, qw | Subcutaneous | — | 5 | 5 |
| O | Semaglutide, qd | Subcutaneous | 3 | 5 | 5 |
| O | HT-ID1-GDF15 | Subcutaneous | 10 | 5 | 5 |
| O | HT-ID2-GDF15 | Subcutaneous | 10 | 5 | 5 |
| 0 | HT-ID3-GDF15 | Subcutaneous | 10 | 5 | 5 |

As for the observation, measurement and test schedule for the test groups, the administration start date was set to Day 0, and 7 days from the administration start date were set to one week of administration.

The test schedule was summarized in Table 6:

TABLE 6

Test schedule

| Observation item | Acclimatization period (week) 1 | 2 | Period (day) 0 | 1 | 2 | 3 | 4 | 5 | 6 | 7 | 8 | 9 |
|---|---|---|---|---|---|---|---|---|---|---|---|---|
| High fat feed feeding | • | • | • | • | • | • | • | • | • | • | • | • |
| Adaptation to oral and subcutaneous administration | | • | | | | | | | | | | |
| Administration | | | • | | | | | | | | | |
| Body weight measurement | | • | • | • | • | • | • | • | • | • | • | • |
| Feed intake measurement | | | • | • | • | • | • | • | • | • | • | • |

General clinical symptoms were observed once a day for all animals, and the presence or absence of moribund and dead animals was checked twice a day, and these observations were conducted from the 1st day of administration to the end of administration. Only when there were abnormal symptoms during observation, it was recorded on the recording sheet.

The body weight of each mouse was measured on the day of the start of administration of the test substances (before administration), and thereafter, the body weight was measured every day (measured up to 9 days), and the amount of the administration solution of the test substances was determined on the basis of the most recently measured body weight.

In addition, after administering the test substances into mice, the daily feed intake was measured, and the feeding amount was measured using an electronic scale for each breeding box, and the remaining amount was measured to calculate the daily feed intake. In case of an individual that gnawed heavily on heed, it was excluded from the measurement.

All the experimental results obtained in the present example were expressed as mean±standard error and tested using Prism5 (version 5.01). One-way analysis of variance (ANOVA) was performed on all data, and when significance was observed, Dunnett's test was performed to find out the test groups with a significant difference from the control group (significance level: two-sided 5% and 1%, 0.1%).

2.1.2. Body Weight Loss Test Result

The change in the body weight measured in Example 2.1.1 above was shown in FIG. 6 and FIG. 7, and Table 7 (Body Weight (Group, % of initial).

TABLE 7

| Group | Day | 0 | 1 | 2 | 3 | 4 | 5 | 6 | 7 | 8 | 9 |
|---|---|---|---|---|---|---|---|---|---|---|---|
| DIO Vehicle Control (Daily Inj.) | Mean | 100 | 100 | 100 | 99 | 100 | 100 | 100 | 100 | 101 | 101 |
| | S.E. | 0 | 0 | 1 | 0 | 0 | 0 | 0 | 1 | 0 | 1 |
| DIO Semaglutide 3 nmol/kg (Daily Inj.) | Mean | 100 | 94 | 91 | 90 | 87 | 87 | 85 | 86 | 83 | 85 |
| | S.E. | 0 | 0 | 1 | 2 | 2 | 3 | 3 | 3 | 3 | 3 |
| HT-ID1-GDF15 10 nmol/kg (Single Inj.) | Mean | 100 | 99 | 98 | 97 | 96 | 95 | 95 | 96 | 96 | 97 |
| | S.E. | 0 | 0 | 0 | 1 | 1 | 1 | 1 | 1 | 1 | 1 |
| HT-ID2-GDF15 10 nmol/kg (Single Inj.) | Mean | 100 | 98 | 97 | 96 | 94 | 94 | 94 | 93 | 93 | 94 |
| | S.E. | 0 | 0 | 1 | 1 | 1 | 2 | 2 | 2 | 2 | 2 |
| HT-ID3-GDF15 10 nmol/kg (Single Inj.) | Mean | 100 | 98 | 97 | 96 | 95 | 94 | 95 | 95 | 95 | 96 |
| | S.E. | 0 | 0 | 0 | 1 | 0 | 1 | 1 | 1 | 1 | 1 |

FIG. 6 and Table 7 shows the change in the body weight when the fusion polypeptides HT-ID1-GDF15, HT-ID2-GDF15 and HT-ID3-GDF15 were administered once, respectively, compared to the negative control group (vehicle administration group) and positive control group (Semaglutide daily administration group). In addition, FIG. 7 is a graph showing the result at Day 4 by extracting it among the result of FIG. 6.

As shown in the above result, it could be confirmed that there was little change in the body weight in case of the negative control group (vehicle administration group), while the body weight loss effect was continuously shown from Day 1 after administration in case of the positive control group (Semaglutide daily administration group). In addition, it could be confirmed that the body weight loss effect was shown immediately after single administration at Day 0 in case of the fusion polypeptide in which GDF15 was fused with IgD Hinge, and the body weight loss effect was not reduced and appeared continuously until 3-4 days.

2.1.3. Diet Intake Test Result

The change in the feed intake measured in Example 2.1.1 above was shown in Table 8 and FIG. 8 (cumulative intake up to Day 6), respectively.

TABLE 8

| Group | Day | 0 | 1 | 2 | 3 | 4 | 5 | 6 | 7 | 8 | 9 |
|---|---|---|---|---|---|---|---|---|---|---|---|
| DIO Vehicle Control | Mean | 3.3 | 2.7 | 3.0 | 3.0 | 3.1 | 3.5 | 3.0 | 3.5 | 3.3 | 3.4 |
| (Daily Inj.) | S.E. | 0.1 | 0.1 | 0.2 | 0.1 | 0.1 | 0.2 | 0.2 | 0.1 | 0.1 | 0.2 |
| DIO Semaglutide | Mean | 3.7 | 2.1 | 3.3 | 2.8 | 2.3 | 2.9 | 2.7 | 3.2 | 2.4 | 3.7 |
| 3 nmol/kg(Daily Inj.) | S.E. | 0.3 | 0.7 | 1.4 | 0.6 | 0.4 | 0.9 | 0.6 | 0.3 | 0.4 | 0.1 |
| HT-ID1-GDF15 | Mean | 3.3 | 2.2 | 2.9 | 2.3 | 2.8 | 3.1 | 3.1 | 3.7 | 3.4 | 3.5 |
| 10 nmol/kg(Single Inj.) | S.E. | 0.2 | 0.3 | 0.2 | 0.5 | 0.2 | 0.3 | 0.1 | 0.3 | 0.3 | 0.5 |
| HT-ID2-GDF15 | Mean | 2.7 | 1.7 | 2.3 | 2.2 | 2.6 | 2.4 | 2.8 | 3.1 | 2.7 | 3.3 |
| 10 nmol/kg(Single Inj.) | S.E. | 0.2 | 0.2 | 0.1 | 0.1 | 0.3 | 0.2 | 0.1 | 0.1 | 0.2 | 0.2 |
| HT-ID3-GDF15 | Mean | 3.2 | 2.0 | 2.5 | 2.3 | 2.3 | 2.7 | 2.8 | 3.3 | 3.3 | 3.6 |
| 10 nmol/kg(Single Inj.) | S.E. | 0.2 | 0.2 | 0.3 | 0.2 | 0.2 | 0.3 | 0.2 | 0.3 | 0.2 | 0.2 |

As shown in the above result, in case of the fusion polypeptide administration group in which GDF15 was fused with IgD Hinge, compared to the negative control group (vehicle administration group) administration group, the feed intake reduction effect was shown up to Day 6 at maximum depending on the fusion polypeptide, and this feed intake reduction effect of the fusion polypeptide can be said to be comparable to the case of administering Semaglutide, the positive control group, once a day throughout the test period.

2.2. Repeated Administration 2.2.1 Test Process

Except for the administration dose, animal number and administration cycle, most of the test processes were the same as in Example 2.1.1 above.

The test substances were administered twice a week (Days 0, 4, 7, 11, 14, 18, 21, 25) for a total of 8 times. For comparison, the control group in which the control substance Semaglutide was administered every day was prepared, and the comparison group in which Semaglutide was administered every day was administered once a day daily, and all the administration was progressed from 9 AM.

The composition of the test groups and administration dose, and the like were summarized in Table 9 below:

TABLE 9

| Fusion polypeptide administration group composition | | | | | | |
|---|---|---|---|---|---|---|
| High Fat Diet | Test substance | Administration route | Administration cycle | Administration dose (nmol/kg) | Administration volume (mL/kg) | Animal number |
| O | Lean Vehicle Control | Subcutaneous | Once a week | — | 5 | 4 |
| O | DIO Vehicle Control | Subcutaneous | Once a week | — | 5 | 8 |
| O | Semaglutide | Subcutaneous | Once a day | 3 | 5 | 8 |
| O | HT-ID2-GDF15 | Subcutaneous | Twice a week | 3 | 5 | 8 |
| O | HT-ID2-GDF15 | Subcutaneous | Twice a week | 10 | 5 | 8 |
| O | HT-ID2-GDF15 | Subcutaneous | Twice a week | 30 | 5 | 8 |
| O | HT-ID3-GDF15 | Subcutaneous | Twice a week | 3 | 5 | 8 |
| 0 | HT-ID3-GDF15 | Subcutaneous | Twice a week | 10 | 5 | 8 |
| 0 | HT-ID3-GDF15 | Subcutaneous | Twice a week | 30 | 5 | 8 |

Fusion Polypeptide Administration Group Composition 2.2.2. Body Weight Loss Test Result The change in the body weight measured in Example 2.2.1 above was shown in FIG. 9, FIG. 10*a*, FIG. 10*b* and Table 10 (Body Weight (Group, % of initial).

TABLE 10

| Group | Day | 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| Lean Vehicle | Mean | 100 | 100 | 100 | 100 | 100 | 100 | 100 | 99 | 100 | 102 | 102 | 101 | 101 | 102 | 101 |
| Control | S.E. | 0 | 0 | 0 | 0 | 1 | 1 | 1 | 1 | 1 | 1 | 1 | 0 | 1 | 1 | 1 |
| DIO Vehicle | Mean | 100.0 | 99.4 | 99.1 | 98.6 | 98.6 | 98.3 | 98.8 | 97.7 | 95.8 | 96.2 | 97.3 | 99.0 | 99.8 | 100.2 | 100.5 |
| Control | S.E. | 0.0 | 0.4 | 0.4 | 0.5 | 0.5 | 0.6 | 0.7 | 1.1 | 1.5 | 1.3 | 1.1 | 1.1 | 1.0 | 1.0 | 1.0 |
| DIO Semaglutide | Mean | 100.0 | 93.9 | 92.6 | 90.4 | 88.4 | 66.2 | 64.1 | 82.6 | 61.9 | 80.7 | 80.3 | 80.3 | 79.1 | 76.8 | 76.7 |
| 3 nmol/kg | S.E. | 0.0 | 0.3 | 0.6 | 0.8 | 1.1 | 1.5 | 1.5 | 1.6 | 1.6 | 1.8 | 2.2 | 1.9 | 2.0 | 2.0 | 2.0 |
| HT-ID2-GDF15 | Mean | 100.0 | 98.0 | 96.5 | 95.0 | 93.9 | 91.8 | 90.8 | 90.3 | 89.2 | 89.2 | 90.1 | 92.1 | 92.5 | 92.7 | 93.3 |
| 3 nmol/kg | S.E. | 0.0 | 0.3 | 0.4 | 0.4 | 0.4 | 0.4 | 0.4 | 0.5 | 0.6 | 0.6 | 0.7 | 0.6 | 0.6 | 0.7 | 0.7 |
| HT-ID2-GDF15 | Mean | 100.0 | 98.3 | 96.7 | 95.4 | 94.6 | 93.0 | 91.7 | 90.8 | 93.1 | 90.3 | 90.6 | 92.1 | 91.2 | 92.0 | 92.2 |
| 10 nmol/kg | S.E. | 0.0 | 0.3 | 0.5 | 0.5 | 0.4 | 0.5 | 0.6 | 0.7 | 0.7 | 0.7 | 0.7 | 0.8 | 0.8 | 0.9 | 0.8 |
| HT-ID2-GDF15 | Mean | 100.0 | 98.4 | 97.3 | 96.2 | 95.2 | 94.0 | 93.1 | 92.3 | 91.5 | 91.2 | 91.3 | 93.2 | 91.9 | 92.1 | 93.0 |
| 30 nmol/kg | S.E. | 0.0 | 0.3 | 0.5 | 0.6 | 0.6 | 0.8 | 0.9 | 1.1 | 1.2 | 1.2 | 1.6 | 1.8 | 1.7 | 1.9 | 2.1 |
| HT-ID3-GDF15 | Mean | 100.0 | 98.2 | 96.9 | 95.6 | 94.4 | 92.8 | 91.9 | 91.0 | 90.0 | 89.6 | 89.1 | 91.5 | 91.5 | 92.3 | 92.5 |
| 3 nmol/kg | S.E. | 0.0 | 0.3 | 0.3 | 0.3 | 0.5 | 0.6 | 0.6 | 0.7 | 0.8 | 1.0 | 1.4 | 1.2 | 1.6 | 1.4 | 1.4 |
| HT-ID3-GDF15 | Mean | 100.0 | 98.5 | 97.3 | 95.7 | 94.6 | 92.8 | 91.5 | 90.7 | 89.8 | 89.3 | 88.7 | 90.9 | 89.8 | 90.1 | 91.0 |
| 10 nmol/kg | S.E. | 0.0 | 0.3 | 0.4 | 0.5 | 0.5 | 0.6 | 0.6 | 0.7 | 0.9 | 0.9 | 1.0 | 1.0 | 1.3 | 1.4 | 1.3 |
| HT-ID3-GDF15 | Mean | 100.0 | 98.2 | 97.1 | 95.8 | 94.8 | 92.8 | 91.7 | 90.8 | 89.8 | 89.8 | 89.7 | 92.0 | 90.0 | 90.4 | 90.9 |
| 30 nmol/kg | S.E. | 0.0 | 0.3 | 0.3 | 0.4 | 0.5 | 0.4 | 0.4 | 0.5 | 0.6 | 0.8 | 1.1 | 1.3 | 1.3 | 1.5 | 1.5 |

| Group | Day | 15 | 16 | 17 | 18 | 19 | 20 | 21 | 22 | 23 | 24 | 25 | 26 | 27 | 28 |
|---|---|---|---|---|---|---|---|---|---|---|---|---|---|---|---|
| Lean Vehicle | Mean | 101 | 102 | 101 | 102 | 102 | 102 | 101 | 101 | 102 | 102 | 101 | 101 | 102 | 101 |
| Control | S.E. | 2 | 1 | 1 | 1 | 2 | 1 | 1 | 1 | 1 | 1 | 1 | 1 | 1 | 1 |
| DIO Vehicle | Mean | 100.8 | 101.3 | 102.0 | 102.1 | 102.4 | 101.9 | 101.5 | 101.8 | 102.2 | 103.3 | 103.3 | 104.1 | 104.3 | 103.9 |
| Control | S.E. | 1.0 | 1.0 | 1.1 | 1.0 | 1.1 | 1.1 | 1.7 | 1.6 | 1.7 | 1.6 | 1.5 | 1.5 | 1.7 | 1.5 |
| DIO Semaglutide | Mean | 78.1 | 78.3 | 77.2 | 76.7 | 77.1 | 76.1 | 76.8 | 75.9 | 75.6 | 76.0 | 76.3 | 76.5 | 76.2 | 75.7 |
| 3 nmol/kg | S.E. | 1.8 | 2.0 | 2.3 | 2.2 | 2.1 | 2.3 | 2.3 | 2.2 | 2.3 | 2.4 | 2.8 | 2.7 | 2.4 | 2.7 |
| HT-ID2-GDF15 | Mean | 93.8 | 94.3 | 94.7 | 95.1 | 95.9 | 95.7 | 96.2 | 96.6 | 96.8 | 97.8 | 98.5 | 99.3 | 99.5 | 99.8 |
| 3 nmol/kg | S.E. | 0.9 | 0.7 | 0.8 | 0.9 | 0.8 | 0.8 | 1.0 | 1.1 | 1.2 | 1.2 | 1.2 | 1.3 | 1.3 | 1.4 |
| HT-ID2-GDF15 | Mean | 92.1 | 92.7 | 93.6 | 94.2 | 94.0 | 93.7 | 94.0 | 93.8 | 94.3 | 95.4 | 95.8 | 95.8 | 96.3 | 96.6 |
| 10 nmol/kg | S.E. | 0.9 | 0.9 | 0.9 | 0.9 | 0.9 | 1.0 | 0.9 | 1.0 | 0.8 | 0.9 | 0.9 | 0.8 | 0.8 | 0.7 |
| HT-ID2-GDF15 | Mean | 92.1 | 92.8 | 93.4 | 93.6 | 92.9 | 92.5 | 93.2 | 92.4 | 92.6 | 93.1 | 93.9 | 93.6 | 93.2 | 93.4 |
| 30 nmol/kg | S.E. | 2.2 | 2.4 | 2.4 | 2.4 | 2.5 | 2.6 | 2.6 | 2.8 | 2.7 | 2.7 | 2.6 | 2.8 | 2.7 | 2.6 |
| HT-ID3-GDF15 | Mean | 92.6 | 93.3 | 94.0 | 94.4 | 95.0 | 95.2 | 95.8 | 96.4 | 97.1 | 97.4 | 97.6 | 98.5 | 98.0 | 98.6 |
| 3 nmol/kg | S.E. | 1.3 | 1.3 | 1.2 | 1.2 | 1.2 | 1.2 | 1.3 | 1.3 | 1.5 | 1.4 | 1.3 | 1.5 | 1.7 | 1.7 |
| HT-ID3-GDF15 | Mean | 90.0 | 91.2 | 91.8 | 92.3 | 91.9 | 91.2 | 92.1 | 92.1 | 92.5 | 93.2 | 93.7 | 94.2 | 94.4 | 94.1 |
| 10 nmol/kg | S.E. | 1.5 | 1.5 | 1.5 | 1.5 | 1.7 | 1.7 | 1.7 | 2.1 | 2.0 | 2.0 | 1.9 | 2.3 | 2.3 | 2.2 |
| HT-ID3-GDF15 | Mean | 89.3 | 89.6 | 90.4 | 91.0 | 90.0 | 89.6 | 90.4 | 90.0 | 90.0 | 91.0 | 91.5 | 91.5 | 91.2 | 91.4 |
| 30 nmol/kg | S.E. | 1.4 | 1.6 | 1.5 | 1.7 | 1.5 | 1.5 | 1.4 | 1.3 | 1.4 | 1.5 | 1.5 | 1.5 | 1.7 | 1.6 |

FIG. 9 and Table 10 shows the change in the body weight in case of repeated administration of the fusion proteins HT-ID2-GDF15 and HT-ID3-GDF15, respectively (Table 9), compared to the negative control group (vehicle administration group) and positive control group (Semaglutide daily administration group). In addition, FIG. 10*a* is a graph showing the results at Day 7 and Day 14 by extracting them from the result of FIG. 9 above and FIG. 10*b* is a graph showing the results at Day 21 and Day 28 by extracting them from the result of FIG. 9.

As shown in the above result, it could be confirmed that there was little change in the body weight in case of the negative control group (vehicle administration group), while the body weight loss effect was continuously shown from Day 1 after administration. In addition, it could be confirmed that the body weight loss effect was shown immediately after single administration at Day 0 in case of the fusion polypeptide in which GDF15 was fused with IgD Hinge, and the body weight loss effect was continuously shown without being reduced, and the body weight loss effect was concentration-dependent.

2.2.3. Diet Intake Test Result

The change in the feed intake measured in Example 2.2.1 above was shown in Table 11 and FIG. 11 (cumulative intake up to Day 7, Day 14, Day 21 and Day 28), respectively.

TABLE 11

| Group | Day | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| Lean Vehicle | Mean | 4.4 | 3.9 | 4.1 | 4.5 | 4.4 | 3.9 | 4.3 | 4.1 | 4.1 | 4.6 | 4.5 | 4.4 | 4.2 | 4.3 |
| Control | S.E. | 0.2 | 0.1 | 0.1 | 0.1 | 0.3 | 0.1 | 0.2 | 0.1 | 0.3 | 0.2 | 0.1 | 0.2 | 0.2 | 0.2 |
| DIO Vehicle | Mean | 2.9 | 2.6 | 2.7 | 3.6 | 3.3 | 2.5 | 3.0 | 2.7 | 1.7 | 2.2 | 3.0 | 4.0 | 3.1 | 3.4 |
| Control | S.E. | 0.2 | 0.5 | 0.3 | 0.8 | 0.4 | 0.2 | 0.1 | 0.1 | 0.4 | 0.2 | 0.1 | 0.2 | 0.1 | 0.2 |
| DIO Semaglutide | Mean | 2.9 | 0.7 | 1.3 | 1.4 | 1.7 | 1.5 | 1.6 | 1.9 | 2.0 | 2.3 | 2.2 | 3.2 | 2.2 | 2.5 |
| 3 nmol/kg | S.E. | 0.1 | 0.1 | 0.2 | 0.1 | 0.1 | 0.2 | 0.2 | 0.4 | 0.5 | 0.3 | 0.3 | 0.3 | 0.2 | 0.2 |
| HT-ID2-GDF15 | Mean | 3.0 | 1.5 | 2.1 | 2.1 | 2.4 | 1.7 | 2.3 | 2.3 | 2.0 | 2.8 | 3.3 | 4.2 | 3.7 | 3.4 |
| 3 nmol/kg | S.E. | 0.1 | 0.1 | 0.1 | 0.1 | 0.4 | 0.1 | 0.2 | 0.2 | 0.1 | 0.2 | 0.1 | 0.2 | 0.7 | 0.1 |

TABLE 11-continued

| | | | | | | | | | | | | | | | |
|---|---|---|---|---|---|---|---|---|---|---|---|---|---|---|---|
| HT-ID2-GDF15 | Mean | 2.6 | 1.5 | 1.8 | 2.0 | 2.0 | 1.8 | 2.1 | 2.1 | 1.9 | 2.5 | 3.1 | 3.7 | 2.4 | 3.0 |
| 10 nmol/kg | S.E. | 0.2 | 0.1 | 0.2 | 0.1 | 0.1 | 0.1 | 0.1 | 0.1 | 0.1 | 0.1 | 0.1 | 0.1 | 0.1 | 0.1 |
| HT-ID2-GDF15 | Mean | 3.0 | 1.7 | 2.3 | 2.3 | 2.3 | 2.1 | 2.4 | 2.3 | 2.2 | 2.6 | 3.0 | 3.9 | 2.3 | 3.2 |
| 30 nmol/kg | S.E. | 0.2 | 0.2 | 0.2 | 0.2 | 0.2 | 0.2 | 0.2 | 0.2 | 0.2 | 0.3 | 0.2 | 0.3 | 0.2 | 0.2 |
| HT-ID3-GDF15 | Mean | 2.9 | 1.5 | 1.9 | 1.9 | 2.0 | 1.6 | 2.1 | 2.1 | 1.9 | 2.4 | 2.5 | 3.9 | 2.9 | 3.2 |
| 3 nmol/kg | S.E. | 0.1 | 0.1 | 0.1 | 0.1 | 0.2 | 0.1 | 0.1 | 0.1 | 0.1 | 0.2 | 0.3 | 0.2 | 0.1 | 0.1 |
| HT-ID3-GDF15 | Mean | 2.9 | 1.7 | 2.3 | 2.2 | 2.1 | 1.9 | 2.2 | 2.1 | 2.1 | 2.4 | 3.0 | 4.1 | 2.5 | 3.3 |
| 10 nmol/kg | S.E. | 0.2 | 0.2 | 0.2 | 0.1 | 0.2 | 0.1 | 0.2 | 0.2 | 0.1 | 0.2 | 0.2 | 0.2 | 0.2 | 0.2 |
| HT-ID3-GDF15 | Mean | 2.5 | 1.6 | 2.1 | 2.2 | 2.3 | 1.8 | 2.2 | 2.1 | 2.0 | 2.5 | 2.9 | 4.0 | 2.1 | 3.0 |
| 30 nmol/kg | S.E. | 0.2 | 0.1 | 0.1 | 0.2 | 0.1 | 0.1 | 0.1 | 0.1 | 0.1 | 0.2 | 0.2 | 0.1 | 0.1 | 0.2 |

| Group | Day | 15 | 16 | 17 | 18 | 19 | 20 | 21 | 22 | 23 | 24 | 25 | 26 | 27 | 28 |
|---|---|---|---|---|---|---|---|---|---|---|---|---|---|---|---|
| Lean Vehicle | Mean | 4.3 | 4.1 | 4.2 | 4.1 | 4.9 | 3.8 | 4.8 | 4.2 | 3.9 | 4.2 | 4.2 | 3.8 | 3.7 | 4.3 |
| Control | S.E. | 0.2 | 0.2 | 0.1 | 0.3 | 0.2 | 0.2 | 0.1 | 0.3 | 0.2 | 0.2 | 0.2 | 0.2 | 0.2 | 0.3 |
| DIO Vehicle | Mean | 3.2 | 3.2 | 3.1 | 3.1 | 3.1 | 2.7 | 3.2 | 2.7 | 2.8 | 3.1 | 3.4 | 3.5 | 2.9 | 3.2 |
| Control | S.E. | 0.1 | 0.1 | 0.1 | 0.1 | 0.1 | 0.1 | 0.1 | 0.4 | 0.1 | 0.2 | 0.2 | 0.5 | 0.1 | 0.1 |
| DIO Semaglutide | Mean | 2.5 | 2.2 | 2.4 | 2.2 | 2.6 | 2.6 | 2.5 | 2.9 | 2.0 | 2.4 | 2.9 | 2.4 | 2.4 | 2.7 |
| 3 nmol/kg | S.E. | 0.3 | 0.2 | 0.1 | 0.2 | 0.1 | 0.3 | 0.1 | 0.4 | 0.2 | 0.1 | 0.3 | 0.2 | 0.2 | 0.3 |
| HT-ID2-GDF15 | Mean | 3.2 | 3.4 | 3.4 | 3.4 | 3.7 | 3.3 | 3.2 | 3.4 | 3.1 | 3.3 | 3.4 | 3.3 | 3.1 | 3.4 |
| 3 nmol/kg | S.E. | 0.2 | 0.5 | 0.4 | 0.2 | 0.4 | 0.5 | 0.1 | 0.3 | 0.1 | 0.2 | 0.1 | 0.2 | 0.1 | 0.1 |
| HT-ID2-GDF15 | Mean | 3.0 | 2.4 | 3.0 | 3.2 | 3.3 | 2.4 | 2.9 | 3.1 | 2.3 | 3.1 | 3.3 | 3.1 | 2.5 | 3.0 |
| 10 nmol/kg | S.E | 0.1 | 0.1 | 0.1 | 0.1 | 0.1 | 0.1 | 0.1 | 0.1 | 0.1 | 0.1 | 0.1 | 0.1 | 0.1 | 0.1 |
| HT-ID2-GDF15 | Mean | 3.3 | 2.4 | 3.1 | 3.2 | 3.1 | 2.1 | 3.2 | 3.1 | 2.1 | 3.0 | 3.1 | 3.3 | 2.1 | 2.9 |
| 30 nmol/kg | S.E. | 0.3 | 0.2 | 0.2 | 0.2 | 0.1 | 0.1 | 0.2 | 0.1 | 0.2 | 0.2 | 0.1 | 0.1 | 0.2 | 0.2 |
| HT-ID3-GDF15 | Mean | 3.1 | 2.7 | 3.0 | 3.1 | 3.3 | 2.7 | 3.0 | 3.1 | 2.9 | 3.1 | 2.9 | 3.0 | 2.8 | 2.7 |
| 3 nmol/kg | S.E. | 0.1 | 0.1 | 0.1 | 0.1 | 0.1 | 0.1 | 0.1 | 0.1 | 0.1 | 0.1 | 0.1 | 0.1 | 0.1 | 0.1 |
| HT-ID3-GDF15 | Mean | 3.2 | 2.2 | 3.3 | 3.3 | 3.4 | 2.4 | 3.1 | 3.2 | 2.7 | 3.1 | 3.3 | 3.3 | 2.7 | 3.2 |
| 10 nmol/kg | S.E. | 0.2 | 0.3 | 0.2 | 0.1 | 0.1 | 0.1 | 0.1 | 0.1 | 0.2 | 0.1 | 0.1 | 0.1 | 0.2 | 0.2 |
| HT-ID3-GDF15 | Mean | 3.1 | 1.9 | 3.0 | 3.2 | 3.3 | 1.9 | 3.1 | 3.4 | 2.3 | 3.3 | 3.2 | 3.2 | 2.2 | 3.2 |
| 30 nmol/kg | S.E. | 0.1 | 0.0 | 0.1 | 0.1 | 0.1 | 0.1 | 0.1 | 0.2 | 0.2 | 0.2 | 0.1 | 0.1 | 0.1 | 0.2 |

As shown in the above result, the administration group of the fusion polypeptide in which GDF15 was fused with IgD Hinge showed the feed intake reduction effect throughout the test period depending on the fusion polypeptide, compared to the negative control group (vehicle administration group) administration group, and showed a concentration-dependent tendency.

Example 3. Pharmacokinetic Test of Fusion Polypeptide

3.1. Test Group and Control Group Serum Preparation

For evaluation of pharmacokinetic characteristics when each fusion polypeptide was subcutaneously administered to rats, the fusion polypeptides HT-ID1-GDF15, HT-ID2-GDF15 and HT-ID3-GDF15 were subcutaneously administered into SD rats (Koatech, male, 7-week-old, about 250 g; n=3 each; test group) in an amount of 2 mg/kg, respectively, and about 200 μl of blood was collected through the caudal vein at a predetermined time. The blood collection time was performed before administration, and 1, 2, 4, 8, 24, 48, 72, 96, 168, 240 and 336 hours after administration. As the control group for comparison of pharmacokinetic characteristics, GDF15 (R&D Systems) was subcutaneously administered in an amount of 2 mg/kg by the same method to prepare a GDF15 administration group.

After administering into SD Rats as above, blood collected by time-point was centrifuged to obtain serum, and ELISA was performed using Human GDF15 Immunoassay (SGD150, R&D Systems), and the concentration in the serum was measured depending on the time of each polypeptide. Using this data, values of parameters including AUC (area under the curve) were obtained using a software for PK analysis (WinNonlin (Certara L.P.), etc.).

3.2 Pharmacokinetic Test Result

The obtained pharmacokinetic parameters of the fusion polypeptide were shown in Table 12, and the change in the concentration of the fusion polypeptide with time was shown in FIG. 12.

TABLE 12

| PK parameter | Group 1 rhGDF15 | Group 2 HT-ID1-GDF15 | Group 3 HT-ID2-GDF15 | Group 4 HT-ID3-GDF15 |
|---|---|---|---|---|
| $C_{max}$ (ug/mL) | 0.443 | 2.09 | 0.945 | 1.11 |
| $T_{max}$ (hr) | 1 | 8 | 24 | 24 |
| $AUC_{last}$(ug*hr/mL) | 4.86 | 81.2 | 53.5 | 76.2 |
| $AUC_{inf}$(ug*hr/mL) | 4.88 | 81.3 | 53.5 | 76.4 |
| $t_{1/2}$ (hr) | 19.0 | 24.7 | 22.3 | 26.2 |
| $AUC_{extp}$ (%) | 0.463 | 0.0700 | 0.100 | 0.287 |

($C_{max}$: maximum concentration in blood, $T_{max}$: reaching time to maximum concentration in blood, $AUC_{inf}$: area under a blood concentration-time curve by extrapolating from the last measurable blood collecting time to infinity, $AUC_{last}$: area under a blood concentration-time curve up to the last measurable blood collecting time, $T_{1/2}$: loss half-life, $AUC_{Extp}$(%): $[(AUC_{inf} - AUC_{last})/AUC_{inf}]*100$)

As shown in the above result, it could be confirmed that the half-life was increased in case of the fusion polypeptide fused with IgD Hinge, compared to GDF15 (half-life: 19 hours), and in particular, in case of AUClast, it was increased 16.7 times at maximum compared to GDF15.

From the above description, those skilled in the art to which the present invention pertains will understand that the present invention may be embodied in other specific forms without changing the technical spirit or essential characteristics thereof. In this regard, it should be understood that the embodiments described above are illustrative and not restrictive in all respects. The scope of the present invention should be construed that all changes or modifications derived from the meaning and scope of the claims to be described later and their equivalent concepts are included in the scope of the present invention, rather than the above detailed description.

The invention claimed is:

1. A fusion polypeptide, comprising,

GDF15 (Growth differentiation factor 15), and a total of 2 to 10 polypeptide regions capable of O-glycosylation, which is bound to the N-terminus of the GDF15, wherein each of the 2 to 10 polypeptide regions capable of O-glycosylation is a polypeptide comprising 3 to 10 amino acid residues capable of O-glycosylation, and the 2 to 10 polypeptide regions capable of O-glycosylation are 2 to 10 immunoglobulin D (IgD) hinge regions, and wherein the fusion polypeptide is represented by the following formula:

N'—(Z)*n*-Y—C' in the formula,

N' is the N-terminus of the fusion polypeptide, and C' is the C-terminus of the fusion polypeptide, Y is the GDF15, Z is an IgD hinge region, and n is the number of the IgD hinge region bound to the N-terminus of GDF15 and is an integer of 2 to 10.

2. The fusion polypeptide according to claim 1, wherein the 2 to 10 IgD hinge regions are each independently selected from the group consisting of the following:

(1) a polypeptide comprising the amino acid sequence of SEQ ID NO: 1, and (2) a polypeptide comprising 5 or more continuous amino acids comprising 3 to 7 O-glycosylation residues in the amino acid sequence of SEQ ID NO: 1.

3. The fusion polypeptide according to claim 1, wherein the 2 to 10 IgD hinge regions are each independently selected from the group consisting of the following:

(1) a polypeptide comprising the amino acid sequence of SEQ ID NO: 1, and (2) a polypeptide comprising 5 or more continuous amino acids comprising SEQ ID NO: 9, or 7 or more continuous amino acids comprising SEQ ID NO: 10 in the amino acid sequence of SEQ ID NO: 1.

4. The fusion polypeptide according to claim 1, wherein the area under the blood concentration-time curve ($AUC_{last}$) up to the last blood sampling point measurable upon in vivo administration of the GDF15 bound to the polypeptide region capable of O-glycosylation in the fusion polypeptide, is increased at least 2-fold compared to GDF15 not bound to the polypeptide region capable of O-glycosylation.

5. A nucleic acid molecule encoding the fusion polypeptide of claim 1.

6. A recombinant vector comprising the nucleic acid molecule of claim 5.

7. A recombinant cell comprising the recombinant vector of claim 6.

8. A method of preparation of the fusion polypeptide of claim 1, comprising culturing a recombinant cell comprising a recombinant vector comprising a nucleic acid molecule encoding the fusion polypeptide.

9. A fusion polypeptide dimer, comprising 2 of the fusion polypeptides of claim 1.

10. The fusion polypeptide dimer according to claim 9, wherein the GDF15 of each fusion polypeptide binds to each other to form a dimer.

11. The fusion polypeptide dimer according to claim 9, wherein the dimer is a homodimer.

12. A pharmaceutical composition for preventing or treating diseases related to GDF15 deficiency or dysfunction, comprising the fusion polypeptide of claim 1, or a fusion polypeptide dimer in which two of the fusion polypeptides are linked to each other at the GDF15.

13. A method for enhancing in vivo stability of GDF15, comprising linking a total of 2 to 10 polypeptide regions capable of O-glycosylation to the N-terminus of the GDF15, wherein the 2 to 10 polypeptide regions capable of O-glycosylation are each a polypeptide comprising 3 to 10 amino acid residues capable of O-glycosylation, and the 2 to 10 polypeptide regions capable of O-glycosylation are 2 to 10 immunoglobulin D (IgD) hinge regions.

14. The method for enhancing in vivo stability of GDF15 according to claim 13, wherein the 2 to 10 IgD hinge regions are each independently selected from the group consisting of the following:

(1) a polypeptide comprising the amino acid sequence of SEQ ID NO: 1, and (2) a polypeptide comprising 5 or more continuous amino acids comprising 3 to 7 O-glycosylation residues in the amino acid sequence of SEQ ID NO: 1.

15. The method for enhancing in vivo stability of GDF15 according to claim 13, wherein the 2 to 10 IgD hinge regions are each independently selected from the group consisting of the following:

(1) a polypeptide comprising the amino acid sequence of SEQ ID NO: 1, and (2) a polypeptide comprising 5 or more continuous amino acids comprising SEQ ID NO: 9 or 7 or more continuous amino acids comprising SEQ ID NO: 10 in the amino acid sequence of SEQ ID NO: 1.

* * * * *